(12) United States Patent
Buchanan et al.

(10) Patent No.: US 7,442,698 B2
(45) Date of Patent: Oct. 28, 2008

(54) SUBSTITUTED HETEROCYCLIC COMPOUNDS AND METHODS OF USE

(75) Inventors: John L. Buchanan, Brookline, MA (US); Daniel Elbaum, Newton, MA (US); Matthew W. Martin, Cambridge, MA (US); David C. McGowan, Arlington, MA (US); Perry M. Novak, Milford, MA (US); Joseph J. Nunes, Andover, MA (US)

(73) Assignee: Amgen Inc., Thousand Oaks, CA (US)

( * ) Notice: Subject to any disclaimer, the term of this patent is extended or adjusted under 35 U.S.C. 154(b) by 388 days.

(21) Appl. No.: 10/891,636

(22) Filed: Jul. 13, 2004

(65) Prior Publication Data

US 2005/0026914 A1  Feb. 3, 2005

Related U.S. Application Data

(60) Provisional application No. 60/490,220, filed on Jul. 24, 2003.

(51) Int. Cl.
C07D 239/48 (2006.01)
C07D 403/12 (2006.01)
A61K 31/505 (2006.01)

(52) U.S. Cl. .............. 514/235.8; 514/252.14; 514/275; 544/122; 544/295; 544/323

(58) Field of Classification Search ............. 544/122, 544/295, 323; 514/235.8, 252.14, 275
See application file for complete search history.

(56) References Cited

U.S. PATENT DOCUMENTS 3,331,845 A  7/1967 Tomcufcik

FOREIGN PATENT DOCUMENTS

| EP | 0039051 | 7/1985 |
|---|---|---|
| EP | 0486948 B2 | 10/2000 |
| WO | WO9749710 A1 | 12/1997 |
| WO | WO98/41512 | 9/1998 |
| WO | WO03/004492 | 1/2003 |
| WO | WO 03/018021 | 3/2003 |
| WO | WO03/048133 | 6/2003 |
| WO | WO 2005/009443 | * 2/2005 |

OTHER PUBLICATIONS

Casanova et al., PubMed Abstract (Rev Neurol. 28(9):909-15) May 1999.*
Kane, LP et al. "Signal Transduction by the TCR for Antigen," Current Opinion in Immunol. 12: 242 (2000).
Bolen, JB, and Brugge, "Leukocyte protein Tyrosine Kinases:Potential Targets for Drug Discovery" JS Annu. Rev. Immunol. 15: 371 (1997).
Soriano, P. Cell, "Targeted disruption of the c-src proto-oncogene leads to osteopetrosis in mice" 64: 693 (1991).
Anderson, SJ et al. "Involvement of the Protein Tyrosine Kinase p56$^{lck}$ in T Cell Signaling and Thymocyte Development" Adv. Immunol. 56: 151 (1994).
Goldman, FD et al. "Defective Expression of p56lck in an Infant with Severe Combined Immunodeficiency" J. Clin. Invest. 102: 421 (1998).
Manser et.al., "A non-receptor tyrosine kinase that inhibits the GTPase activity of p21cdc42" Nature 363(6427): 364-367, (1993).
Appleby, MW et al. "Defective T Cell Receptor Signaling in Mice Lacking the Thymic Isoform of p59$^{fyn}$" Cell 70: 751 (1992).
Vicentini, L. et al. "Fgr Deficiency Results in Defective Eosinophil Recruitment to the Lung During Allergic Airway Inflammation" J. Immunol. 168: 6446 (2002).
Turner, H. and Kinet, J-P "Signalling through the high-affinity IgE receptor Fc epsilon RI" Nature 402: B24 (1999).
Abram, CL and Courtneidge, SA "Src Family Tyrosine Kinases and Growth Factor Signaling" Exp. Cell Res. 254: 1 (2000).
Paul, R. et al. "Src deficiency or blockade of Src activity in mice provides cerebral protection following stroke" Nature Medicine 7: 222 (2001).
Snow, RJ et al. "Discovery of 2-Phenylamino-imidazo[4,5-h]isoquinolin-9-ones: A New Class of Inhibitors of Lck Kinase" J. Med. Chem. 45: 3394 (2002).
Burchat, AF et al. "Design, synthesis and brief SAR of pyrazolo(3,4-d) and pyrrolo(2,3-d)pyrimidines as potent inhibitors of lck" et al. Bioorganic and Med. Chem. Letters 12: 1687 (2002).

(Continued)

*Primary Examiner*—Deepak Rao
(74) *Attorney, Agent, or Firm*—G. Prabhaker Reddy

(57) ABSTRACT

The present invention relates to pyrimidine or pyridine carbamate compounds having the general Formula I:

I and pharmaceutically acceptable salts or derivatives thereof. Also included are methods of treatment of various diseases and conditions, including inflammation, inhibition of T cell activation and proliferation, arthritis, organ transplant, ischemic or reperfusion injury, myocardial infarction, stroke, multiple sclerosis, inflammatory bowel disease, Crohn's disease, lupus, hypersensitivity, type 1 diabetes, psoriasis, dermatitis, Hashimoto's thyroiditis, Sjogren's syndrome, autoimmune hyperthyroidism, Addison's disease, autoimmune diseases, glomerulonephritis, allergic diseases, asthma, hayfever, eczema, cancer, colon carcinoma, thymoma, just to name a few, in a mammal, the methods comprising administering a therapeutically-effective amount a compound of Formula I, or a salt or derivative form thereof, as described above.

12 Claims, No Drawings

OTHER PUBLICATIONS

Hanke, JH et al. "Discovery of a Novel, Potent, and Src Family-selective Tyrosine Kinase Inhibitor" J. Biol. Chem. 271: 695 (1996).

Altmann, E et al. "7-Pyrrolidinyl- and 7-piperidinyl-5-aryl-pyrrolo(2,3-d)-pyrimidines: Potent inhibitors of the tyrosine kinase c-Src" Bioorganic and Med. Chem. Letters 11: 853 (2001).

Wang, YD et al. "Inhibitors of Src Tyrosine Kinase: The Preparation and Structure-Activity Relationship of 4-Anilino-3-cyanoquinolines and 4-Anilinoquinazoles" Bioorganic and Med. Chem. Letters 10: 2477 (2000).

Chen, P. et al. "Synthesis and SAR of novel imidazoquinoxaline-based Lck inhibitors: Improvement of cell potency" Bioorganic and Med. Chem. Letters 12: 3153 (2002).

Berge et al., J. Pharm. Sci. 66:1 (1977).

Bundgaard, H. et al. "A Novel Solution-Stable Water-Soluble Prodrug Type For Drugs Containing A Hydroxyl Or An Amino-Acidic Group" J. Med. Chem. 32(12): 2503 (1989).

Terashima, K. et al. "Studies on Antiulcer Agents.II. 1) Antiulcer Protperties of N-(1H-Tetrazol-5-yl)-2-anilino-5-pyrimidinecarboxamides Inhibiting Release of Histamine from Passively Sensitized Rat Peritoneal Mast Cells" Chem. Pharm. Bull. 43(6): 1042-1044 (1995).

* cited by examiner

SUBSTITUTED HETEROCYCLIC COMPOUNDS AND METHODS OF USE

This application claims the benefit of U.S. Provisional Application No. 60/490,220 filed Jul. 24, 2003, which disclosure is hereby incorporated by reference in its entirety.

BACKGROUND OF THE INVENTION

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR) which is expressed on the cell surface. This activation triggers a series of intracellular signaling cascades mediated by enzymes expressed within the cell (Kane, L P et al. Current Opinion in Immunol. 200, 12, 242). These cascades lead to gene regulation events that result in the production of cytokines, like interleukin-2 (IL-2). IL-2 is a critical cytokine in T cell activation, leading to proliferation and amplification of specific immune responses.

One class of enzymes shown to be important in signal transduction is the kinase enzymes Members of the Src-family of tyrosine kinases include, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the src family of kinases would potentially lead to therapeutic benefit. Src(−/−) mice have abnormalities in bone remodeling or osteopetrosis (Soriano, P. Cell 1991, 64, 693), suggesting that inhibition of this kinase might be useful in diseases of bone resorption, such as osteoporosis. Lck(−/−) mice have defects in T cell maturation and activation (Anderson, S J et al. Adv. Immunol. 1994, 56, 151), suggesting that inhibition of this kinase might be useful in diseases of T cell mediated inflammation. In addition, (Goldman, F D et al. J. Clin. Invest. 1998, 102, 421). These patients suffer from a severe combined immunodeficiency disorder (SCID).

Ack, a gene containing a tyrosine kinase domain, is also reported to possess tyrosine kinase activity, lending to the belief that it is involved in the regulatory mechanism that sustains the GTP-bound active form of cdc42Hs, which is directly linked to a tyrosine phosphorylation signal transduction pathway (Manser et. Al., Nature 363(6427), 364-367, 1994). More specifically, the activated p21cdc42Hs kinase gene encodes an intracellular, non-receptor tyrosine kinase that binds cdc42Hs in its GTP-bound form and inhibits the GTPase activity of p21cdc42, a Ras-like protein involved in cell growth. Accordingly, Ack is a target believed to be useful in the regulation of cancer.

Without wishing to imply that the compounds disclosed in the present invention possess pharmacological activity only by virtue of an effect on a single biological process, it is believed that the compounds modulate T cell activation by way of inhibition of one or more of the multiple protein tyrosine kinases involved in early signal transduction steps leading to T cell activation, for example by way of inhibition of Lck kinase.

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Ihmmunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

Src kinases have also been found to be activated in tumors including sarcoma, melanoma, breast, and colon cancers suggesting that Src kinase inhibitors may be useful anti-cancer agents (Abram, C L and Courtneidge, S A Exp. Cell Res. 2000, 254, 1).

Src kinase inhibitors have also been reported to be effective in an animal model of cerebral ischemia (R. Paul et al. Nature Medicine 2001, 7, 222), suggesting that Src kinase inhibitors may be effective at limiting brain damage following stroke.

Several groups have published on inhibitors of Src family kinase and the activities of these inhibitors in various in vitro and in vivo biological systems. These include the 2-phenylamino-imidazo [4,5-h]isoquinolin-9-ones (Snow, R J et al. J. Med. Chem. 2002, 45, 3394), the pyrazolo [3,4-d]pyrimidines (Burchat, A F et al. Bioorganic and Med. Chem. Letters 2002, 12, 1687. Hanke, J H et al. J. Biol. Chem. 1996, 271, 695), the pyrrolo [2,3-d]pyrimidines (Altmann, E et al. Bioorganic and Med. Chem. Letters 2001, 11, 853), the anilino-quinazolines (Wang, Y D et al. Bioorganic and Med. Chem. Letters 2000, 10, 2477), and the imidazoquinoxalines (Chen, P. et al. Bioorganic and Med. Chem. Letters 2002, 12, 3153). However, none of these groups describe the compounds of the present invention, and in particular, as modulators of kinase enzymes such as Lck in general, and useful for the regulation of T-cell mediated immune response, autoimmune disease, organ transplantation, allergies, asthma and cancer. Further, there is a need to develop novel modulators of kinase enzymes useful to treat inflammation and related conditions and diseases.

BRIEF DESCRIPTION OF EXEMPLARY EMBODIMENTS OF THE INVENTION

The present invention provides compounds represented by Formula I:

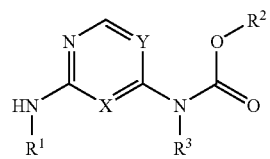

and pharmaceutically-acceptable salts thereof, wherein X, Y, $R^1$, $R^2$ and $R^3$ are defined in the Detailed Description below, which are capable of modulating protein tyrosine kinases, such as Lck, Fyn(B), Fyn(T), Lyn, Src, Yes, Hck, Fgr and Blk, as well as other protein tyrosine kinases including Ack. Accordingly, these compounds are useful in the treatment, including preventative, prophylactic and therapeutic treatment, of protein tyrosine kinase-associated disorders such as immunologic disorders.

"Protein tyrosine kinase-associated disorders" are disorders which result from aberrant tyrosine kinase activity, and/or which are alleviated by the regulation, and inhibition in particular, of one or more of these enzymes. For example, Lck inhibitors are of value in the treatment of a number of such disorders (for example, the treatment of autoimmune diseases), as Lck inhibition blocks T cell activation. In one embodiment of the invention, the compounds are useful for the treatment of T cell mediated diseases, including inhibition of T cell activation and proliferation. In another embodiment, the invention provides compounds which selectively block T cell activation and proliferation. Further, the compounds may block the activation of endothelial cell protein tyrosine kinase by oxidative stress thereby limiting surface expression of adhesion molecules that induce neutrophil binding, and they also can inhibit protein tyrosine kinase necessary for neutrophil activation. The compounds would be useful, therefore, in the treatment of ischemia and reperfusion injury.

In another embodiment of the invention, there are provided methods for the treatment of protein tyrosine kinase-associated disorders, comprising administering to a subject at least one compound of Formula I in an amount effective to treat the disorder. To this end, another embodiment of the invention provides a composition comprising a compound of Formula I and a pharmaceutically acceptable carrier. Such a composition can be administered to the subject, such as a mammal, for the purpose of treating the disorder. Other therapeutic agents such as those described below may be employed in combination with the inventive compounds, such as in a composition, in the present methods. Such other therapeutic agent(s) may be administered prior to, simultaneously with, or following the administration of the compound(s) of the present invention.

The compound(s) of the present invention may be used in treating various protein tyrosine kinase-associated disorders and related conditions including, without limitation, arthritis (such as rheumatoid arthritis, psoriatic arthritis or osteoarthritis); transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracielma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides methods for treating the aforementioned disorders such as atopic dermatitis by administration of a therapeutically effective amount of a compound of the present invention, which is an inhibitor of protein tyrosine kinase, to a patient suffering from dermatitis and potentially in need of such treatment.

Src-family kinases other than Lck, such as Hck and Fgr, are important in the Fcγ receptor induced respiratory burst of neutrophils as well as the Fcγ receptor responses of monocytes and macrophages. The compounds of the present invention may inhibit the Fcγ induced respiratory burst response in neutrophils, and may also inhibit the Fcγ dependent production of TNFα. The ability to inhibit Fcγ receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease. The present compounds may also be of value for the treatment of autoimmune glomerulonephritis and other instances of glomerulonephritis induced by deposition of immune complexes in the kidney that trigger Fcγ receptor responses and which can lead to kidney damage.

In addition, certain Src family kinases, such as Lyn and Fyn(B), may be important in the Fcε receptor induced degranulation of mast cells and basophils that plays an important role in asthma, allergic rhinitis, and other allergic disease. Fcε receptors are stimulated by IgE-antigen complexes. The compounds of the present invention may inhibit the Fcε induced degranulation responses. The ability to inhibit Fcε receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders.

In another embodiment, the compounds are useful for the treatment of the aforementioned exemplary disorders irrespective of their etiology, for example, for the treatment of rheumatoid arthritis, transplant rejection, multiple sclerosis, inflammatory bowel disease, lupus, graft v. host disease, T cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The foregoing merely summarizes certain aspects of the invention and is not intended, nor should it be construed, as limiting the invention in any way. All patents and other publications recited herein are hereby incorporated by reference in their entireties.

DETAILED DESCRIPTION OF THE
EXEMPLARY EMBODIMENTS OF THE
INVENTION

In one embodiment, the present invention provides a compound of Formula I

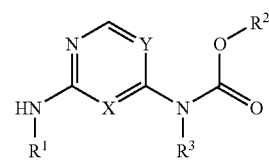

I or a pharmaceutically-acceptable salt thereof, wherein

X is N or CH;

Y is N or CH; wherein at least one of X and Y is CH;

$R^1$ is selected from —$R^{11}$, —$R^{11}$—$R^{12}$, —$R^{11}$—$R^{14}$, —$R^{12}$—$R^{14}$, —$R^{11}$—$R^{12}$—$R^{14}$, —$R^{11}$—$R^{13}$—$R^{14}$, —$R^{12}$—$R^{13}$—$R^{14}$, —$R^{11}$—$R^{13}$—$R^{12}$—$R^{14}$ and —$R^{11}$—$R^{12}$—$R^{13}$—$R^{14}$, any of which is substituted by 0, 1, 2, 3 or 4 substituents independently selected from $R^c$;

$R^2$ is selected from —$R^{21}$, —$R^{21}$—$R^{22}$, —$R^{21}$—$R^{24}$, —$R^{22}$—$R^{24}$, —$R^{21}$—$R^{22}$—$R^{24}$, —$R^{21}$—$R^{23}$—$R^{24}$, —$R^{22}$—$R^{23}$—$R^{24}$, —$R^{21}$—$R^{23}$—$R^{22}$—$R^{24}$, and —$R^{21}$—$R^{22}$—$R^{23}$—$R^{24}$, any of which is substituted by 0, 1, 2, 3 or 4 substituents independently selected from $R^c$;

$R^3$ is selected from —$R^{31}$, —$R^{31}$—$R^{32}$, —$R^{31}$—$R^{34}$, —$R^{32}$—$R^{34}$, —$R^{31}$—$R^{32}$—$R^{34}$, —$R^{31}$—$R^{33}$—$R^{34}$, —$R^{32}$—$R^{33}$—$R^{34}$, —$R^{31}$—$R^{33}$—$R^{32}$—$R^{34}$ and —$R^{31}$—$R^{32}$—$R^{33}$—$R^{34}$, any of which is substituted by 0, 1, 2, 3 or 4 substituents independently selected from $R^c$;

$R^{11}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{12}$ is independently at each instance $C_{1-8}$alkyl;

$R^{13}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

$R^{14}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{21}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{22}$ is independently at each instance $C_{1-8}$alkyl;

$R^{23}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)N(R$^a$)—N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

$R^{24}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{31}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{32}$ is independently at each instance $C_{1-8}$alkyl;

$R^{33}$ is independently at each instance —C(=O)—, —(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O), —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

$R^{34}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^a$ is independently at each instance H or $R^b$;

$R^b$ is independently at each instance $C_{1-8}$alkyl, phenyl or benzyl; and $R_c$ is independently at each instance $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$.

In one embodiment, X is N or CH.

In another embodiment, in conjunction with any of the above or below embodiments, X is N.

In another embodiment, in conjunction with any of the above or below embodiments, Y is N.

In another embodiment, in conjunction with any of the above or below embodiments, X is CH and Y is CH.

In another embodiment, in conjunction with any of the above or below embodiments, X is N and Y is CH.

Embodiment A: In another embodiment, in conjunction with any of the above or below embodiments, $R^1$ is selected from —$R^{11}$, —$R^{11}$—$R^{14}$, —$R^{11}$—$R^{12}$, —$R^{12}$—$R^{14}$, —$R^{11}$—$R^{12}$—$R^{14}$, —$R^{11}$—$R^{13}$—$R^{14}$, —$R^{12}$—$R^{13}$—$R^{14}$, —$R^{11}$—$R^{13}$—$R^{12}$—$R^{14}$ and —$R^{11}$—$R^{12}$—$R^{13}$—$R^{14}$, any of which is substituted by 0, 1, 2, 3 or 4 substituents independently selected from $R^c$.

In another embodiment, in conjunction with any of the above or below embodiments, $R^1$ is selected from —$R^{11}$, —$R^{11}$—$R^{14}$, —$R^{11}$—$R^{12}$, —$R^{11}$—$R^{12}$—$R^{14}$, —$R^{11}$—$R^{13}$—$R^{14}$, —$R^{11}$—$R^{13}$—$R^{12}$—$R^{14}$ and —$R^{11}$—$R^{12}$—$R^{13}$—$R^{14}$, any of which is substituted by 0, 1, 2, 3 or 4 substituents independently selected from $R^c$.

Embodiment A would include, in conjunction with any of the above or below embodiments, compounds wherein $R^1$ is $R^{11}$, substituted by 0, 1, 2, 3 or 4 substituents independently selected from $R^c$.

Embodiment A would also include, for example and in conjunction with any of the above or below embodiments, compounds wherein $R^{11}$ is phenyl or pyridine, either of which is substituted by 0, 1, 2, 3 or 4 substituents independently selected from $R^c$.

Embodiment B: In another embodiment, in conjunction with any of the above or below embodiments, $R^1$ is —$R^{11}$—$R^{14}$, which is substituted by 0, 1, 2, 3 or 4 substituents independently selected from $R^c$.

Embodiment C: In another embodiment, in conjunction with any of the above or below embodiments, $R^1$ is —$R^{11}$—$R^{12}$, which is substituted by 0, 1, 2, 3 or 4 substituents independently selected from $R^c$.

In another embodiment, in conjunction with any of the above or below embodiments, $R^1$ is —$R^{11}$—$R^{12}$—$R^{14}$, which is substituted by 0, 1, 2, 3 or 4 substituents independently selected from $R^c$.

In another embodiment, in conjunction with any of the above or below embodiments, $R^1$ is —$R^{11}$—$R^{13}$—$R^{14}$, which is substituted by 0, 1, 2, 3 or 4 substituents independently selected from $R^c$.

Embodiment D: In another embodiment, in conjunction with any of the above or below embodiments, $R^1$ is —$R^{11}$—$R^{13}$—$R^{12}$—$R^{14}$, which is substituted by 0, 1, 2, 3 or 4 substituents independently selected from $R^c$.

In another embodiment, in conjunction with any of the above or below embodiments, $R^1$ is —$R^{11}$—$R^{12}$—$R^{13}$—$R^{14}$, which is substituted by 0, 1, 2, 3 or 4 substituents independently selected from $R^c$.

Embodiments A-D, independently, in conjunction with any of the above or below embodiments, include compounds wherein $R^{11}$ is phenyl or pyridine; $R^{13}$ is, independently at each instance, —C(=O)NR$^a$—, —O—, —OC$_{2-6}$alkyl-NR$^a$—, —OC$_{2-6}$alkylO—, —S—, —S(=O)$_2$NR$^a$—, —N(R$^a$)—, —N(R$^a$)C(=O)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—; and $R^{14}$ is, independently at each instance, a saturated or unsaturated 5-, 6- or 7-membered monocyclic ring containing 0, 1, 2, 3 or 4 atoms selected from N, O and S.

Embodiments A-D, independently, in conjunction with any of the above or below embodiments, further include compounds wherein $R^1$ is selected from 3,4-bismethoxy-5-(3-(4-methyl-1-piperizinyl)propyl)oxy phenyl, 3-fluoro-4-(1-methyl-3-piperidinyl)methyloxy phenyl, 3-fluoro-4-(4-(1-methylethyl)-1-piperizinyl)ethyloxy phenyl, 3-chloro-4-(4-(1-methylethyl)-1-piperizinyl)phenyl, 3-methoxy-4-(4-(1-methylethyl)-1-piperizinyl)propyloxyphenyl, 4-(2-diethylamino)ethyl)-(N-methyl)aminocarbonyl phenyl, 4-(2-diethylamino)ethyl)-aminocarbonyl phenyl, 3-(2-diethylamino)ethyl)-aminocarbonyl phenyl, 4-(2-dimethylamino)ethyl)-aminocarbonyl phenyl, 4-(2-diethylamino)propyl)-aminocarbonyl phenyl, 3-(2-diethylamino)propyl)-aminocarbonyl phenyl, 3-(2-dimethylamino)hexyl)-aminocarbonyl phenyl, 4-(2-dimethylamino)hexyl)-aminocarbonyl phenyl, 3-(2-diethylamino)butyl)-aminocarbonyl phenyl, 3-(2-diethylamino)butyl)-aminocarbonyl phenyl, 3-(1-piperidinyl)propyloxy phenyl, 3-fluoro-4-(1-piperidinyl) propyloxy phenyl, 3-fluoro-4-(1-methyl-3-piperidinyl) propyloxy phenyl, 3-(1-piperidinyl)propyloxy phenyl, 3-fluoro-4-(1-piperidinyl)propyloxyphenyl, 4-(4-amino-1-piperidinyl)phenyl, 3,5-difluoro-4-(2-(1-piperidinyl)ethyl) oxy phenyl, 3-fluoro-4-(4-methyl-1-piperizinyl)propyloxy phenyl, 4-(3,4-dimethyl-1-piperizinyl)-3-fluorophenyl, 4-(4-methyl-1-piperizinyl)ethylphenyl, 3-fluoro-4-(3,4,5-trimethyl-1-piperizinyl) phenyl, 4-(3,4-dimethyl-1-piperizinyl) phenyl, 3-(4-methyl-1-piperizinyl)phenyl, 4-(3-dimethylaminopropyl-1-piperizinyl)phenyl, 3-difluoromethoxy-4-(4-methyl-1-piperizinyl)phenyl, 3,5-bismethoxy-4-(4-methyl-1-piperizinyl)ethyloxy phenyl, 3-(4-methyl-1-piperizinyl)propyloxy pyridine, 3-methoxy-4-(2-pyrrolinidyl)methyloxy phenyl, 3-acetylaminophenyl and 2-aminomethylphenyl, 3-aminophenyl.

In another embodiment, in conjunction with any of the above or below embodiments, $R^2$ is selected from —$R^{21}$, —$R^{21}$—$R^{24}$, —$R^{21}$—$R^{22}$, —$R^{22}$—$R^{24}$, —$R^{21}$—$R^{22}$—$R^{24}$, —$R^{21}$—$R^{23}$—$R^{24}$, —$R^{22}$—$R^{23}$—$R^{24}$, —$R^{21}$—$R^{23}$—$R^{22}$—$R^{24}$ and —$R^{21}$—$R^{22}$—$R^{23}$—$R^{24}$, any of which is substituted by 0, 1, 2, 3 or 4 substituents independently selected from $R^c$.

Embodiment E: In another embodiment, in conjunction with any of the above or below embodiments, $R^2$ is selected from —$R^{21}$, —$R^{21}$—$R^{24}$, —$R^{21}$—$R^{22}$, —$R^{21}$—$R^{22}$—$R^{24}$, —$R^{21}$—$R^{23}$—$R^{24}$, —$R^{21}$—$R^{23}$—$R^{22}$—$R^{24}$ and —$R^{21}$—$R^{22}$—$R^{23}$—$R^{24}$, any of which is substituted by 0, 1, 2, 3 or 4 substituents independently selected from $R^c$.

Embodiment F: In another embodiment, in conjunction with any of the above or below embodiments, $R^2$ is $R^{21}$, which is substituted by 0, 1, 2, 3 or 4 substituents independently selected from $R^c$.

Embodiment F, in conjunction with any of the above or below embodiments, includes compounds wherein $R^{21}$ is phenyl, cyclohexyl or $C_{1-8}$alkyl, each of which is substituted by 0, 1, 2, 3 or 4 substituents independently selected from $R^c$.

In another embodiment, in conjunction with any of the above or below embodiments, $R^2$ is —$R^{21}$—$R^{24}$, which is substituted by 0, 1, 2, 3 or 4 substituents independently selected from $R^c$.

In another embodiment, in conjunction with any of the above or below embodiments, $R^2$ is —$R^{21}$—$R^{22}$, which is substituted by 0, 1, 2, 3 or 4 substituents independently selected from $R^c$.

In another embodiment, in conjunction with any of the above or below embodiments, $R^2$ is —$R^{21}$—$R^{22}$—$R^{24}$, which is substituted by 0, 1, 2, 3 or 4 substituents independently selected from $R^c$.

In another embodiment, in conjunction with any of the above or below embodiments, $R^2$ is —$R^{21}$—$R^{23}$—$R^{24}$, which is substituted by 0, 1, 2, 3 or 4 substituents independently selected from $R^c$.

Embodiment G: In another embodiment, in conjunction with any of the above or below embodiments, $R^2$ is —$R^{21}$—$R^{23}$—$R^{22}$—$R^{24}$, which is substituted by 0, 1, 2, 3 or 4 substituents independently selected from $R^c$.

In another embodiment, in conjunction with any of the above or below embodiments, $R^2$ is —$R^{21}$—$R^{22}$—$R^{23}$—$R^{24}$, which is substituted by 0, 1, 2, 3 or 4 substituents independently selected from $R^c$.

Embodiments E-G, in conjunction with any of the above or below embodiments, include compounds wherein $R^2$ is phenyl substituted by 1, 2, 3 or 4 substituents independently selected from $R^c$.

In another embodiment, in conjunction with any of the above or below embodiments, $R^2$ is a 2,5-disubstituted phenyl, wherein the two substituents are independently selected from $R^c$.

In another embodiment, in conjunction with any of the above or below embodiments, $R^2$ is a 2,5-disubstituted phenyl, wherein the two substituents are independently selected from $C_{1-2}$alkyl, halo and $C_{1-2}$haloalkyl.

In another embodiment, in conjunction with any of the above or below embodiments, $R^2$ is a 2,5-disubstituted phenyl, wherein the two substituents are independently selected from $CH_3$ and Cl.

In another embodiment, in conjunction with any of the above or below embodiments, $R^2$ is 2,5-dichlorophenyl.

In another embodiment, in conjunction with any of the above or below embodiments, $R^2$ is 2,5-dimethylphenyl.

Embodiments E-G, in conjunction with any of the above or below embodiments, further include compounds wherein $R^2$ is selected from 2-methylphenyl, 3-methylphenyl, 4-methylphenyl, 2-methoxyphenyl, 3-methoxyphenyl, 4-methoxyphenyl, 2-chlorophenyl, 2,5-dimethylphenyl, 2,6-dimethylphenyl, 2,4-dimethylphenyl, 3,5-dimethylphenyl, 2,5-dimethoxyphenyl, 2,4-dimethoxyphenyl, 2,6-dimethoxyphenyl, 3,5-dimethoxyphenyl, 2,6-difluorophenyl, 2,5-difluorophenyl, 2,4-difluorophenyl, 3,5-difluorophenyl, 4-fluoro-2,6-dimethylphenyl, 2,4,6-trimethylphenyl, 2,4,6-trimethoxyphenyl, 2-(methoxy)methylphenyl, 3-(methoxy)methylphenyl, 4-(methoxy)methylphenyl, 2-(methoxy)methyl-5-methylphenyl, 2-methylsulfanylphenyl, 3-methylsulfanylphenyl, 4-methylsulfanylphenyl, 2,6-dimethylcyclohexyl, 2,5-dimethylcyclohexyl, 2,4-dimethylcyclohexyl, 3,5-dimethylcyclohexyl, 3,5-dimethoxycyclohexyl, 2-methyl-1-(1-methylethyl)propyl, 1-isopropyl-2-methylbutyl, 1-phenylethyl, 2-methanoylphenyl, 2-methyl-6-(2-propenyl)phenyl, 5-methyl-2-methyloxyphenyl and 4-chloro-2-methoxyphenyl.

In another embodiment, in conjunction with any of the above or below embodiments, $R^3$ is selected from —$R^{31}$, —$R^{31}$—$R^{34}$, —$R^{31}$—$R^{32}$, —$R^{32}$—$R^{34}$, —$R^{31}$—$R^{32}R^{34}$, —$R^{31}$—$R^{33}$—$R^{34}$, —$R^{32}$—$R^{33}$—$R^{34}$, —$R^{31}$—$R^{33}$—$R^{32}$—$R^{34}$ and —$R^{31}$—$R^{32}$—$R^{33}$—$R^{34}$, any of which is substituted by 0, 1, 2, 3 or 4 substituents independently selected from $R^c$.

Embodiment H: In another embodiment, in conjunction with any of the above or below embodiments, $R^3$ is selected from —$R^{31}$, —$R^{31}$—$R^{34}$, —$R^{31}$—$R^{32}$, —$R^{31}$—$R^{32}R^{34}$, —$R^{31}$—$R^{33}$—$R^{34}$, —$R^{31}$—$R^{33}$—$R^{32}$—$R^{34}$ and —$R^{31}$—$R^{32}$—$R^{33}$—$R^{34}$, any of which is substituted by 0, 1, 2, 3 or 4 substituents independently selected from $R^c$.

Embodiment I: In another embodiment, in conjunction with any of the above or below embodiments, $R^3$ is $R^{31}$, which is substituted by 0, 1, 2, 3 or 4 substituents independently selected from $R^c$.

Embodiment I, in conjunction with any of the above or below embodiments, includes compounds wherein $R^{31}$ is phenyl or cyclohexyl, either of which is substituted by 0, 1, 2, 3 or 4 substituents independently selected from $R^c$.

Embodiment J: In another embodiment, in conjunction with any of the above or below embodiments, $R^3$ is —$R^{31}$—$R^{34}$, which is substituted by 0, 1, 2, 3 or 4 substituents independently selected from $R^c$.

Embodiment K: In another embodiment, in conjunction with any of the above or below embodiments, $R^3$ is —$R^{31}$—$R^{32}$, which is substituted by 0, 1, 2, 3 or 4 substituents independently selected from $R^c$.

In another embodiment, in conjunction with any of the above or below embodiments, $R^3$ is —$R^{31}$—$R^{32}$—$R^{34}$, which is substituted by 0, 1, 2, 3 or 4 substituents independently selected from $R^c$.

In another embodiment, in conjunction with any of the above or below embodiments, $R^3$ is —$R^{31}$—$R^{33}$—$R^{34}$, which is substituted by 0, 1, 2, 3 or 4 substituents independently selected from $R^c$.

Embodiment L: In another embodiment, in conjunction with any of the above or below embodiments, $R^3$ is —$R^{31}$—$R^{33}$—$R^{32}$—$R^{34}$, which is substituted by 0, 1, 2, 3 or 4 substituents independently selected from $R^c$.

In another embodiment, in conjunction with any of the above or below embodiments, $R^3$ is —$R^{31}$—$R^{32}$—$R^{33}$—$R^{34}$, which is substituted by 0, 1, 2, 3 or 4 substituents independently selected from $R^c$.

Embodiments H-L, in conjunction with any of the above or below embodiments, include compounds wherein $R^{31}$ is phenyl or cyclohexyl; $R^{33}$ is independently at each instance —C(=O)—, —C(=O)NR$^a$—, —O—, —OC$_{2-6}$alkylNR$^a$—, —OC$_{2-6}$alkylO—, —S—, —S(=O)$_2$NR$^a$—, —N(R$^a$)—, —N(R$^a$)C(=O)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—; and $R^{34}$ is independently at each instance a saturated or unsaturated 5-, 6- or 7-membered monocyclic ring or 6-, 7-, 8-, 9-, 10-containing 0, 1, 2, 3 or 4 atoms selected from N, O and S.

Embodiments H-L, in conjunction with any of the above or below embodiments, include compounds wherein $R^3$ is selected from 2,4-dimethoxyphenyl, 2,4-dimethylphenyl, 2-(2-methoxyphenyl)ethyl, 3-phenylpropyl, 2-(4-morpholinyl)ethyl, (2-(trifluoromethyloxy)phenyl) methyl, 2-ethyloxyphenyl, 4-fluoro-2-(1-methylethyloxy)phenyl, 2,5-dichlorophenyl methyl, 3,5-dichlorophenyl methyl, 3,5-difluorophenyl methyl, 3,4-difluorophenyl methyl, 2-chloro-3,6-difluorophenyl methyl, 3,5-(bis)trifluoromethylphenyl methyl, 2,5-dimethylphenyl methyl, 3,5-dimethylphenyl methyl, 2,5-dimethoxyphenyl methyl, 2,3-dimethoxyphenyl methyl, 1,1'-biphenyl, 2-ethyl-4-methoxyphenyl, 4-methyl-2-methoxyphenyl, 4-butyl-2-methoxyphenyl, 2-(1,3-oxazole)phenyl, (5-chloro-2-methylphenyl)methyl, 2-chloro-5-trifluoromethyl phenyl methyl, 5-chloro-2-fluorophenyl methyl, 2-chlorophenyl, 3-chlorophenyl methyl, 3-methoxyphenyl methyl, cyclohexyl, 2-methoxy-4-(2-(1-methylpropylamino)-2-oxoethyl)phenyl, 2-methoxy-4-(2-(diethylamino)-2-oxoethyl)phenyl, 3-(2-(1-methylpropylamino)-3-oxopropyl)phenyl, 3-(3-(2-methyloxyethylamino)-3-oxopropyl)phenyl, 3-(2-(diethylamino)-3-oxopropyl)phenyl, 2-methoxy-4-(2-(diethylamino)-2-methyl-3-oxopropyl)phenyl, 2-methoxy-4-(1-methylpropylamino)carbonylphenyl, 4-methoxyphenyl ethyl, 3-(2-(3-methyl-1,2,4-oxodiazole-5-yl)ethyl)phenyl, 3-(5-methyl-1,2,4-oxodiazole-3-yl)phenyl methyl, 4-(5-methyl-1,2,4-oxodiazole-3-yl)phenyl methyl, 2-phenyl-1,3-thiazole-4-yl methyl, 2-ethyl-[1,2-a]imidazole, benzodioxo-5-yl-methyl, 6-fluoro-4H-1,3-benzodioxin-8-yl methyl, (3-(1H-pyrazole-1-yl)methyl)phenyl methyl, 2-methoxy-4-(1H-pyrazole-1-yl) phenyl, 2,3-dihydro-1H-inden-1-yl, 4-(1H-1,2,4-triazole-1-yl)methyl)phenyl methyl and 2,3-dihydro-1,4-benzodioxin-6-yl methyl.

In another embodiment, in conjunction with any of the above or below embodiments, $R^{11}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 5- or 6-membered monocyclic or 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 5- or 6-membered monocyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 5-membered monocyclic ring containing 1, 2 or 3 atoms selected from N, O and S.

In another embodiment, in conjunction with any of the above or below embodiments, $R^{11}$ is independently at each instance an unsaturated 6-membered monocyclic ring containing 0, 1 or 2 N atoms.

Embodiment M: In another embodiment, in conjunction with any of the above or below embodiments, $R^{11}$ is phenyl.

Embodiment N: In another embodiment, in conjunction with any of the above or below embodiments, $R^{11}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 6-membered monocyclic ring containing 1 or 2 N atoms.

In another embodiment, in conjunction with any of the above or below embodiments, $R^{11}$ is pyridinyl, pyrimidinyl or pyridazinyl.

In another embodiment, in conjunction with any of the above or below embodiments, $R^{12}$ is independently at each instance $C_{1-8}$alkyl.

In another embodiment, in conjunction with any of the above or below embodiments, $R^{12}$ is independently at each instance $C_{1-4}$alkyl.

In another embodiment, in conjunction with any of the above or below embodiments, $R^{12}$ is independently at each instance $C_{2-4}$alkyl.

Embodiment O: In another embodiment, in conjunction with any of the above or below embodiments, $R^{13}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{13}$ is independently at each instance —C(=O)—, —C(=O)O—, —C(=O)NR$^a$—, —C(=NR$^a$)NR$^a$—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{13}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{13}$ is —O—.

In another embodiment, in conjunction with any of the above or below embodiments, $R^{13}$ is —N(R$^a$)—.

In another embodiment, in conjunction with any of the above or below embodiments, $R^{13}$ is —N(R$^1$)C(=O)—, —C(=O)NR$^a$—, —C(=O)O— or —OC(=O)—.

In another embodiment, in conjunction with any of the above or below embodiments, $R^{13}$ is —O—, —N(R$^a$)—, —N(R$^a$)C(=O)—, —C(=O)NR$^a$—, —C(=O)O— or —OC(=O)—.

Embodiment P: In another embodiment, in conjunction with any of the above or below embodiments, $R^{14}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{14}$ is phenyl.

In another embodiment, in conjunction with any of the above or below embodiments, $R^{14}$ is naphthyl.

In another embodiment, in conjunction with any of the above or below embodiments, $R^{14}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{14}$ is independently at each instance a saturated or unsaturated 5-, 6- or 7-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{14}$ is independently at each instance a saturated 5- or 6-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{14}$ is independently at each instance a saturated 5- or 6-membered monocyclic ring containing 1 or 2 N atoms, wherein the carbon atoms of the ring are substituted by 0 or 1 oxo groups.

In another embodiment, in conjunction with any of the above or below embodiments, $R^{14}$ is piperidinyl, piperazinyl or pyrrolidinyl.

In another embodiment, in conjunction with any of the above or below embodiments, $R^{21}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 5- or 6-membered monocyclic or 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 5- or 6-membered monocyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 5-membered monocyclic ring containing 1 atom selected from N, O and S.

In another embodiment, in conjunction with any of the above or below embodiments, $R^{21}$ is independently at each instance an unsaturated 6-membered monocyclic ring containing 0, 1 or 2 N atoms.

Embodiment Q: In another embodiment, in conjunction with any of the above or below embodiments, $R^{21}$ is phenyl or cyclohexyl.

Embodiment R: In another embodiment, in conjunction with any of the above or below embodiments, $R^{21}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 6-membered monocyclic ring containing 1 or 2 N atoms.

In another embodiment, in conjunction with any of the above or below embodiments, $R^{21}$ is pyridinyl, pyrimidinyl or pyridazinyl.

In another embodiment, in conjunction with any of the above or below embodiments, $R^{22}$ is independently at each instance $C_{1-8}$alkyl.

In another embodiment, in conjunction with any of the above or below embodiments, $R^{22}$ is independently at each instance $C_{1-4}$alkyl.

In another embodiment, in conjunction with any of the above or below embodiments, $R^{22}$ is independently at each instance $C_{2-4}$alkyl.

Embodiment S: In another embodiment, in conjunction with any of the above or below embodiments, $R^{23}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{23}$ is independently at each instance —C(=O)—, —C(=O)O—, —C(=O)NR$^a$—, —C(=NR$^a$)NR$^a$—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{23}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{23}$ is —O—.

In another embodiment, in conjunction with any of the above or below embodiments, $R^{23}$ is —N(R$^a$)—.

In another embodiment, in conjunction with any of the above or below embodiments, $R^{23}$ is —N(R$^a$)C(=O)—, —C(=O)NR$^a$—, —C(=O)O— or —OC(=O)—.

In another embodiment, in conjunction with any of the above or below embodiments, $R^{23}$ is —O—, —N(R$^a$)—, —N(R$^a$)C(=O)—, —C(=O)NR$^a$—, —C(=O)O— or —OC(=O)—.

Embodiment T: In another embodiment, in conjunction with any of the above or below embodiments, $R^{24}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{24}$ is phenyl.

In another embodiment, in conjunction with any of the above or below embodiments, $R^{24}$ is naphthyl.

In another embodiment, in conjunction with any of the above or below embodiments, $R^{24}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{24}$ is independently at each instance a saturated or unsaturated 5-, 6- or 7-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{24}$ is independently at each instance a saturated 5- or 6-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{24}$ is independently at each instance a saturated 5- or 6-membered monocyclic ring containing 1 or 2 N atoms, wherein the carbon atoms of the ring are substituted by 0 or 1 oxo groups.

In another embodiment, in conjunction with any of the above or below embodiments, $R^{24}$ is piperidinyl, piperazinyl or pyrrolidinyl.

In another embodiment, in conjunction with any of the above or below embodiments, $R^{31}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 5- or 6-membered monocyclic or 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 5- or 6-membered monocyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 5-membered monocyclic ring containing 1 atom selected from N, O and S.

In another embodiment, in conjunction with any of the above or below embodiments, $R^{31}$ is independently at each instance an unsaturated 6-membered monocyclic ring containing 0, 1 or 2 N atoms.

Embodiment U: In another embodiment, in conjunction with any of the above or below embodiments, $R^{31}$ is phenyl or cyclohexyl.

Embodiment V: In another embodiment, in conjunction with any of the above or below embodiments, $R^{31}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 6-membered monocyclic ring containing 1 or 2 N atoms.

In another embodiment, in conjunction with any of the above or below embodiments, $R^{31}$ is pyridinyl, pyrimidinyl or pyridazinyl.

In another embodiment, in conjunction with any of the above or below embodiments, $R^{32}$ is independently at each instance $C_{1-8}$alkyl.

In another embodiment, in conjunction with any of the above or below embodiments, $R^{32}$ is independently at each instance $C_{1-4}$alkyl.

In another embodiment, in conjunction with any of the above or below embodiments, $R^{32}$ is independently at each instance $C_{1-3}$alkyl.

Embodiment W: In another embodiment, in conjunction with any of the above or below embodiments, $R^{33}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{33}$ is independently at each instance —C(=O)—, —C(=O)O—, —C(=O)NR$^a$—, —C(=NR$^a$)NR$^a$—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{33}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{33}$ is —O—.

In another embodiment, in conjunction with any of the above or below embodiments, $R^{33}$ is —N(R$^a$)—.

In another embodiment, in conjunction with any of the above or below embodiments, $R^{33}$ is —N(R$^a$)C(=O)—, —C(=O)NR$^a$—, —C(=O)O— or —OC(=O)—.

In another embodiment, in conjunction with any of the above or below embodiments, $R^{33}$ is —O—, —N(R$^a$)—, —N(R$^a$)C(=O)—, —C(=O)NR$^a$—, —C(=O)O— or —OC(=O)—.

Embodiment X: In another embodiment, in conjunction with any of the above or below embodiments, $R^{34}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{34}$ is phenyl.

In another embodiment, in conjunction with any of the above or below embodiments, $R^{34}$ is naphthyl.

In another embodiment, in conjunction with any of the above or below embodiments, $R^{34}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{34}$ is independently at each instance a saturated or unsaturated 5-, 6- or 7-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{34}$ is independently at each instance a saturated 5- or 6-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{34}$ is independently at each instance a saturated 5- or 6-membered monocyclic ring containing 1 or 2 N atoms, wherein the carbon atoms of the ring are substituted by 0 or 1 oxo groups.

In another embodiment, in conjunction with any of the above or below embodiments, $R^{34}$ is piperidinyl, piperazinyl, pyrrolidinyl, oxodiazolyl, thiazolyl, imidazolyl, benzodioxinyl, pyrazolyl, 2,3-dihydro-indenyl, 1,2,4-triazolyl or 2,3-dihydro-benzodioxinyl.

As stated above, the above embodiments may be used in conjunction with other embodiments listed. The following table is a non-exclusive, non-limiting list of some of the combinations of embodiments of the compounds of the present invention. For the structure

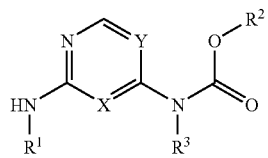

wherein

X is N or CH, $R^{12}$, $R^{22}$ and $R^{32}$ are independently selected from $C_{1-6}$alkyl; $R^{13}$, $R^{23}$ and $R^{33}$ are independently selected from Embodiments O, S and W, respectively; and $R^{14}$, $R^{24}$ and $R^{34}$ are independently selected from Embodiments P, T and X, respectively.

| No. | $R^1$ | $R^{11}$ | $R^2$ | $R^{21}$ | $R^3$ | $R^{31}$ |
|---|---|---|---|---|---|---|
| 1001 | A | M | E | Q | H | U |
| 1002 | A | M | E | Q | H | V |
| 1003 | A | M | E | Q | I | U |
| 1004 | A | M | E | Q | I | V |
| 1005 | A | M | E | Q | J | U |
| 1006 | A | M | E | Q | J | V |
| 1007 | A | M | E | Q | K | U |
| 1008 | A | M | E | Q | K | V |
| 1009 | A | M | E | Q | L | U |
| 1010 | A | M | E | Q | L | V |
| 1011 | A | M | E | R | H | U |
| 1012 | A | M | E | R | H | V |
| 1013 | A | M | E | R | I | U |
| 1014 | A | M | E | R | I | V |
| 1015 | A | M | E | R | J | U |
| 1016 | A | M | E | R | J | V |
| 1017 | A | M | E | R | K | U |
| 1018 | A | M | E | R | K | V |
| 1019 | A | M | E | R | L | U |
| 1020 | A | M | E | R | L | V |
| 1021 | A | M | F | Q | H | U |
| 1022 | A | M | F | Q | H | V |
| 1023 | A | M | F | Q | I | U |
| 1024 | A | M | F | Q | I | V |
| 1025 | A | M | F | Q | J | U |
| 1026 | A | M | F | Q | J | V |
| 1027 | A | M | F | Q | K | U |
| 1028 | A | M | F | Q | K | V |
| 1029 | A | M | F | Q | L | U |
| 1030 | A | M | F | Q | L | V |
| 1031 | A | M | F | R | H | U |
| 1032 | A | M | F | R | H | V |
| 1033 | A | M | F | R | I | U |
| 1034 | A | M | F | R | I | V |
| 1035 | A | M | F | R | J | U |
| 1036 | A | M | F | R | J | V |
| 1037 | A | M | F | R | K | U |
| 1038 | A | M | F | R | K | V |
| 1039 | A | M | F | R | L | U |
| 1040 | A | M | F | R | L | V |
| 1041 | A | M | G | Q | H | U |
| 1042 | A | M | G | Q | H | V |
| 1043 | A | M | G | Q | I | U |
| 1044 | A | M | G | Q | I | V |
| 1045 | A | M | G | Q | J | U |
| 1046 | A | M | G | Q | J | V |
| 1047 | A | M | G | Q | K | U |
| 1048 | A | M | G | Q | K | V |
| 1049 | A | M | G | Q | L | U |
| 1050 | A | M | G | Q | L | V |
| 1051 | A | M | G | R | H | U |
| 1052 | A | M | G | R | H | V |
| 1053 | A | M | G | R | I | U |
| 1054 | A | M | G | R | I | V |
| 1055 | A | M | G | R | J | U |
| 1056 | A | M | G | R | J | V |
| 1057 | A | M | G | R | K | U |
| 1058 | A | M | G | R | K | V |
| 1059 | A | M | G | R | L | U |
| 1060 | A | M | G | R | L | V |
| 1061 | A | N | E | Q | H | U |
| 1062 | A | N | E | Q | H | V |
| 1063 | A | N | E | Q | I | U |
| 1064 | A | N | E | Q | I | V |
| 1065 | A | N | E | Q | J | U |
| 1066 | A | N | E | Q | J | V |
| 1067 | A | N | E | Q | K | U |
| 1068 | A | N | E | Q | K | V |
| 1069 | A | N | E | Q | L | U |
| 1070 | A | N | E | Q | L | V |
| 1071 | A | N | E | R | H | U |
| 1072 | A | N | E | R | H | V |
| 1073 | A | N | E | R | I | U |
| 1074 | A | N | E | R | I | V |
| 1075 | A | N | E | R | J | U |
| 1076 | A | N | E | R | J | V |
| 1077 | A | N | E | R | K | U |
| 1078 | A | N | E | R | K | V |
| 1079 | A | N | E | R | L | U |
| 1080 | A | N | E | R | L | V |
| 1081 | A | N | F | Q | H | U |
| 1082 | A | N | F | Q | H | V |
| 1083 | A | N | F | Q | I | U |

| No. | R$^1$ | R$^{11}$ | R$^2$ | R$^{21}$ | R$^3$ | R$^{31}$ | No. | R$^1$ | R$^{11}$ | R$^2$ | R$^{21}$ | R$^3$ | R$^{31}$ |
|---|---|---|---|---|---|---|---|---|---|---|---|---|---|
| 1084 | A | N | F | Q | I | V | 1161 | B | M | G | Q | H | U |
| 1085 | A | N | F | Q | J | U | 1162 | B | M | G | Q | H | V |
| 1086 | A | N | F | Q | J | V | 1163 | B | M | G | Q | I | U |
| 1087 | A | N | F | Q | K | U | 1164 | B | M | G | Q | I | V |
| 1088 | A | N | F | Q | K | V | 1165 | B | M | G | Q | J | U |
| 1089 | A | N | F | Q | L | U | 1166 | B | M | G | Q | J | V |
| 1090 | A | N | F | Q | L | V | 1167 | B | M | G | Q | K | U |
| 1091 | A | N | F | R | H | U | 1168 | B | M | G | Q | K | V |
| 1092 | A | N | F | R | H | V | 1169 | B | M | G | Q | L | U |
| 1093 | A | N | F | R | I | U | 1170 | B | M | G | Q | L | V |
| 1094 | A | N | F | R | I | V | 1171 | B | M | G | R | H | U |
| 1095 | A | N | F | R | J | U | 1172 | B | M | G | R | H | V |
| 1096 | A | N | F | R | J | V | 1173 | B | M | G | R | I | U |
| 1097 | A | N | F | R | K | U | 1174 | B | M | G | R | I | V |
| 1098 | A | N | F | R | K | V | 1175 | B | M | G | R | J | U |
| 1099 | A | N | F | R | L | U | 1176 | B | M | G | R | J | V |
| 1100 | A | N | F | R | L | V | 1177 | B | M | G | R | K | U |
| 1101 | A | N | G | Q | H | U | 1178 | B | M | G | R | K | V |
| 1102 | A | N | G | Q | H | V | 1179 | B | M | G | R | L | U |
| 1103 | A | N | G | Q | I | U | 1180 | B | M | G | R | L | V |
| 1104 | A | N | G | Q | I | V | 1181 | B | N | E | Q | H | U |
| 1105 | A | N | G | Q | J | U | 1182 | B | N | E | Q | H | V |
| 1106 | A | N | G | Q | J | V | 1183 | B | N | E | Q | I | U |
| 1107 | A | N | G | Q | K | U | 1184 | B | N | E | Q | I | V |
| 1108 | A | N | G | Q | K | V | 1185 | B | N | E | Q | J | U |
| 1109 | A | N | G | Q | L | U | 1186 | B | N | E | Q | J | V |
| 1110 | A | N | G | Q | L | V | 1187 | B | N | E | Q | K | U |
| 1111 | A | N | G | R | H | U | 1188 | B | N | E | Q | K | V |
| 1112 | A | N | G | R | H | V | 1189 | B | N | E | Q | L | U |
| 1113 | A | N | G | R | I | U | 1190 | B | N | E | Q | L | V |
| 1114 | A | N | G | R | I | V | 1191 | B | N | E | R | H | U |
| 1115 | A | N | G | R | J | U | 1192 | B | N | E | R | H | V |
| 1116 | A | N | G | R | J | V | 1193 | B | N | E | R | I | U |
| 1117 | A | N | G | R | K | U | 1194 | B | N | E | R | I | V |
| 1118 | A | N | G | R | K | V | 1195 | B | N | E | R | J | U |
| 1119 | A | N | G | R | L | U | 1196 | B | N | E | R | J | V |
| 1120 | A | N | G | R | L | V | 1197 | B | N | E | R | K | U |
| 1121 | B | M | E | Q | H | U | 1198 | B | N | E | R | K | V |
| 1122 | B | M | E | Q | H | V | 1199 | B | N | E | R | L | U |
| 1123 | B | M | E | Q | I | U | 1200 | B | N | E | R | L | V |
| 1124 | B | M | E | Q | I | V | 1201 | B | N | F | Q | H | U |
| 1125 | B | M | E | Q | J | U | 1202 | B | N | F | Q | H | V |
| 1126 | B | M | E | Q | J | V | 1203 | B | N | F | Q | I | U |
| 1127 | B | M | E | Q | K | U | 1204 | B | N | F | Q | I | V |
| 1128 | B | M | E | Q | K | V | 1205 | B | N | F | Q | J | U |
| 1129 | B | M | E | Q | L | U | 1206 | B | N | F | Q | J | V |
| 1130 | B | M | E | Q | L | V | 1207 | B | N | F | Q | K | U |
| 1131 | B | M | E | R | H | U | 1208 | B | N | F | Q | K | V |
| 1132 | B | M | E | R | H | V | 1209 | B | N | F | Q | L | U |
| 1133 | B | M | E | R | I | U | 1210 | B | N | F | Q | L | V |
| 1134 | B | M | E | R | I | V | 1211 | B | N | F | R | H | U |
| 1135 | B | M | E | R | J | U | 1212 | B | N | F | R | H | V |
| 1136 | B | M | E | R | J | V | 1213 | B | N | F | R | I | U |
| 1137 | B | M | E | R | K | U | 1214 | B | N | F | R | I | V |
| 1138 | B | M | E | R | K | V | 1215 | B | N | F | R | J | U |
| 1139 | B | M | E | R | L | U | 1216 | B | N | F | R | J | V |
| 1140 | B | M | E | R | L | V | 1217 | B | N | F | R | K | U |
| 1141 | B | M | F | Q | H | U | 1218 | B | N | F | R | K | V |
| 1142 | B | M | F | Q | H | V | 1219 | B | N | F | R | L | U |
| 1143 | B | M | F | Q | I | U | 1220 | B | N | F | R | L | V |
| 1144 | B | M | F | Q | I | V | 1221 | B | N | G | Q | H | U |
| 1145 | B | M | F | Q | J | U | 1222 | B | N | G | Q | H | V |
| 1146 | B | M | F | Q | J | V | 1223 | B | N | G | Q | I | U |
| 1147 | B | M | F | Q | K | U | 1224 | B | N | G | Q | I | V |
| 1148 | B | M | F | Q | K | V | 1225 | B | N | G | Q | J | U |
| 1149 | B | M | F | Q | L | U | 1226 | B | N | G | Q | J | V |
| 1150 | B | M | F | Q | L | V | 1227 | B | N | G | Q | K | U |
| 1151 | B | M | F | R | H | U | 1228 | B | N | G | Q | K | V |
| 1152 | B | M | F | R | H | V | 1229 | B | N | G | Q | L | U |
| 1153 | B | M | F | R | I | U | 1230 | B | N | G | Q | L | V |
| 1154 | B | M | F | R | I | V | 1231 | B | N | G | R | H | U |
| 1155 | B | M | F | R | J | U | 1232 | B | N | G | R | H | V |
| 1156 | B | M | F | R | J | V | 1233 | B | N | G | R | I | U |
| 1157 | B | M | F | R | K | U | 1234 | B | N | G | R | I | V |
| 1158 | B | M | F | R | K | V | 1235 | B | N | G | R | J | U |
| 1159 | B | M | F | R | L | U | 1236 | B | N | G | R | J | V |
| 1160 | B | M | F | R | L | V | 1237 | B | N | G | R | K | U |

-continued

| No. | R¹ | R¹¹ | R² | R²¹ | R³ | R³¹ |
|---|---|---|---|---|---|---|
| 1238 | B | N | G | R | K | V |
| 1239 | B | N | G | R | L | U |
| 1240 | B | N | G | R | L | V |
| 1241 | C | M | E | Q | H | U |
| 1242 | C | M | E | Q | H | V |
| 1243 | C | M | E | Q | I | U |
| 1244 | C | M | E | Q | I | V |
| 1245 | C | M | E | Q | J | U |
| 1246 | C | M | E | Q | J | V |
| 1247 | C | M | E | Q | K | U |
| 1248 | C | M | E | Q | K | V |
| 1249 | C | M | E | Q | L | U |
| 1250 | C | M | E | Q | L | V |
| 1251 | C | M | E | R | H | U |
| 1252 | C | M | E | R | H | V |
| 1253 | C | M | E | R | I | U |
| 1254 | C | M | E | R | I | V |
| 1255 | C | M | E | R | J | U |
| 1256 | C | M | E | R | J | V |
| 1257 | C | M | E | R | K | U |
| 1258 | C | M | E | R | K | V |
| 1259 | C | M | E | R | L | U |
| 1260 | C | M | E | R | L | V |
| 1261 | C | M | F | Q | H | U |
| 1262 | C | M | F | Q | H | V |
| 1263 | C | M | F | Q | I | U |
| 1264 | C | M | F | Q | I | V |
| 1265 | C | M | F | Q | J | U |
| 1266 | C | M | F | Q | J | V |
| 1267 | C | M | F | Q | K | U |
| 1268 | C | M | F | Q | K | V |
| 1269 | C | M | F | Q | L | U |
| 1270 | C | M | F | Q | L | V |
| 1271 | C | M | F | R | H | U |
| 1272 | C | M | F | R | H | V |
| 1273 | C | M | F | R | I | U |
| 1274 | C | M | F | R | I | V |
| 1275 | C | M | F | R | J | U |
| 1276 | C | M | F | R | J | V |
| 1277 | C | M | F | R | K | U |
| 1278 | C | M | F | R | K | V |
| 1279 | C | M | F | R | L | U |
| 1280 | C | M | F | R | L | V |
| 1281 | C | M | G | Q | H | U |
| 1282 | C | M | G | Q | H | V |
| 1283 | C | M | G | Q | I | U |
| 1284 | C | M | G | Q | I | V |
| 1285 | C | M | G | Q | J | U |
| 1286 | C | M | G | Q | J | V |
| 1287 | C | M | G | Q | K | U |
| 1288 | C | M | G | Q | K | V |
| 1289 | C | M | G | Q | L | U |
| 1290 | C | M | G | Q | L | V |
| 1291 | C | M | G | R | H | U |
| 1292 | C | M | G | R | H | V |
| 1293 | C | M | G | R | I | U |
| 1294 | C | M | G | R | I | V |
| 1295 | C | M | G | R | J | U |
| 1296 | C | M | G | R | J | V |
| 1297 | C | M | G | R | K | U |
| 1298 | C | M | G | R | K | V |
| 1299 | C | M | G | R | L | U |
| 1300 | C | M | G | R | L | V |
| 1301 | C | N | E | Q | H | U |
| 1302 | C | N | E | Q | H | V |
| 1303 | C | N | E | Q | I | U |
| 1304 | C | N | E | Q | I | V |
| 1305 | C | N | E | Q | J | U |
| 1306 | C | N | E | Q | J | V |
| 1307 | C | N | E | Q | K | U |
| 1308 | C | N | E | Q | K | V |
| 1309 | C | N | E | Q | L | U |
| 1310 | C | N | E | Q | L | V |
| 1311 | C | N | E | R | H | U |
| 1312 | C | N | E | R | H | V |
| 1313 | C | N | E | R | I | U |
| 1314 | C | N | E | R | I | V |
| 1315 | C | N | E | R | J | U |
| 1316 | C | N | E | R | J | V |
| 1317 | C | N | E | R | K | U |
| 1318 | C | N | E | R | K | V |
| 1319 | C | N | E | R | L | U |
| 1320 | C | N | E | R | L | V |
| 1321 | C | N | F | Q | H | U |
| 1322 | C | N | F | Q | H | V |
| 1323 | C | N | F | Q | I | U |
| 1324 | C | N | F | Q | I | V |
| 1325 | C | N | F | Q | J | U |
| 1326 | C | N | F | Q | J | V |
| 1327 | C | N | F | Q | K | U |
| 1328 | C | N | F | Q | K | V |
| 1329 | C | N | F | Q | L | U |
| 1330 | C | N | F | Q | L | V |
| 1331 | C | N | F | R | H | U |
| 1332 | C | N | F | R | H | V |
| 1333 | C | N | F | R | I | U |
| 1334 | C | N | F | R | I | V |
| 1335 | C | N | F | R | J | U |
| 1336 | C | N | F | R | J | V |
| 1337 | C | N | F | R | K | U |
| 1338 | C | N | F | R | K | V |
| 1339 | C | N | F | R | L | U |
| 1340 | C | N | F | R | L | V |
| 1341 | C | N | G | Q | H | U |
| 1342 | C | N | G | Q | H | V |
| 1343 | C | N | G | Q | I | U |
| 1344 | C | N | G | Q | I | V |
| 1345 | C | N | G | Q | J | U |
| 1346 | C | N | G | Q | J | V |
| 1347 | C | N | G | Q | K | U |
| 1348 | C | N | G | Q | K | V |
| 1349 | C | N | G | Q | L | U |
| 1350 | C | N | G | Q | L | V |
| 1351 | C | N | G | R | H | U |
| 1352 | C | N | G | R | H | V |
| 1353 | C | N | G | R | I | U |
| 1354 | C | N | G | R | I | V |
| 1355 | C | N | G | R | J | U |
| 1356 | C | N | G | R | J | V |
| 1357 | C | N | G | R | K | U |
| 1358 | C | N | G | R | K | V |
| 1359 | C | N | G | R | L | U |
| 1360 | C | N | G | R | L | V |
| 1361 | D | M | E | Q | H | U |
| 1362 | D | M | E | Q | H | V |
| 1363 | D | M | E | Q | I | U |
| 1364 | D | M | E | Q | I | V |
| 1365 | D | M | E | Q | J | U |
| 1366 | D | M | E | Q | J | V |
| 1367 | D | M | E | Q | K | U |
| 1368 | D | M | E | Q | K | V |
| 1369 | D | M | E | Q | L | U |
| 1370 | D | M | E | Q | L | V |
| 1371 | D | M | E | R | H | U |
| 1372 | D | M | E | R | H | V |
| 1373 | D | M | E | R | I | U |
| 1374 | D | M | E | R | I | V |
| 1375 | D | M | E | R | J | U |
| 1376 | D | M | E | R | J | V |
| 1377 | D | M | E | R | K | U |
| 1378 | D | M | E | R | K | V |
| 1379 | D | M | E | R | L | U |
| 1380 | D | M | E | R | L | V |
| 1381 | D | M | F | Q | H | U |
| 1382 | D | M | F | Q | H | V |
| 1383 | D | M | F | Q | I | U |
| 1384 | D | M | F | Q | I | V |
| 1385 | D | M | F | Q | J | U |
| 1386 | D | M | F | Q | J | V |
| 1387 | D | M | F | Q | K | U |
| 1388 | D | M | F | Q | K | V |
| 1389 | D | M | F | Q | L | U |
| 1390 | D | M | F | Q | L | V |
| 1391 | D | M | F | R | H | U |

| No. | R$^1$ | R$^{11}$ | R$^2$ | R$^{21}$ | R$^3$ | R$^{31}$ |
|---|---|---|---|---|---|---|
| 1392 | D | M | F | R | H | V |
| 1393 | D | M | F | R | I | U |
| 1394 | D | M | F | R | I | V |
| 1395 | D | M | F | R | J | U |
| 1396 | D | M | F | R | J | V |
| 1397 | D | M | F | R | K | U |
| 1398 | D | M | F | R | K | V |
| 1399 | D | M | F | R | L | U |
| 1400 | D | M | F | R | L | V |
| 1401 | D | M | G | Q | H | U |
| 1402 | D | M | G | Q | H | V |
| 1403 | D | M | G | Q | I | U |
| 1404 | D | M | G | Q | I | V |
| 1405 | D | M | G | Q | J | U |
| 1406 | D | M | G | Q | J | V |
| 1407 | D | M | G | Q | K | U |
| 1408 | D | M | G | Q | K | V |
| 1409 | D | M | G | Q | L | U |
| 1410 | D | M | G | Q | L | V |
| 1411 | D | M | G | R | H | U |
| 1412 | D | M | G | R | H | V |
| 1413 | D | M | G | R | I | U |
| 1414 | D | M | G | R | I | V |
| 1415 | D | M | G | R | J | U |
| 1416 | D | M | G | R | J | V |
| 1417 | D | M | G | R | K | U |
| 1418 | D | M | G | R | K | V |
| 1419 | D | M | G | R | L | U |
| 1420 | D | M | G | R | L | V |
| 1421 | D | N | E | Q | H | U |
| 1422 | D | N | E | Q | H | V |
| 1423 | D | N | E | Q | I | U |
| 1424 | D | N | E | Q | I | V |
| 1425 | D | N | E | Q | J | U |
| 1426 | D | N | E | Q | J | V |
| 1427 | D | N | E | Q | K | U |
| 1428 | D | N | E | Q | K | V |
| 1429 | D | N | E | Q | L | U |
| 1430 | D | N | E | Q | L | V |
| 1431 | D | N | E | R | H | U |
| 1432 | D | N | E | R | H | V |
| 1433 | D | N | E | R | I | U |
| 1434 | D | N | E | R | I | V |
| 1435 | D | N | E | R | J | U |
| 1436 | D | N | E | R | J | V |
| 1437 | D | N | E | R | K | U |
| 1438 | D | N | E | R | K | V |
| 1439 | D | N | E | R | L | U |
| 1440 | D | N | E | R | L | V |
| 1441 | D | N | F | Q | H | U |
| 1442 | D | N | F | Q | H | V |
| 1443 | D | N | F | Q | I | U |
| 1444 | D | N | F | Q | I | V |
| 1445 | D | N | F | Q | J | U |
| 1446 | D | N | F | Q | J | V |
| 1447 | D | N | F | Q | K | U |
| 1448 | D | N | F | Q | K | V |
| 1449 | D | N | F | Q | L | U |
| 1450 | D | N | F | Q | L | V |
| 1451 | D | N | F | R | H | U |
| 1452 | D | N | F | R | H | V |
| 1453 | D | N | F | R | I | U |
| 1454 | D | N | F | R | I | V |
| 1455 | D | N | F | R | J | U |
| 1456 | D | N | F | R | J | V |
| 1457 | D | N | F | R | K | U |
| 1458 | D | N | F | R | K | V |
| 1459 | D | N | F | R | L | U |
| 1460 | D | N | F | R | L | V |
| 1461 | D | N | G | Q | H | U |
| 1462 | D | N | G | Q | H | V |
| 1463 | D | N | G | Q | I | U |
| 1464 | D | N | G | Q | I | V |
| 1465 | D | N | G | Q | J | U |
| 1466 | D | N | G | Q | J | V |
| 1467 | D | N | G | Q | K | U |
| 1468 | D | N | G | Q | K | V |
| 1469 | D | N | G | Q | L | U |
| 1470 | D | N | G | Q | L | V |
| 1471 | D | N | G | R | H | U |
| 1472 | D | N | G | R | H | V |
| 1473 | D | N | G | R | I | U |
| 1474 | D | N | G | R | I | V |
| 1475 | D | N | G | R | J | U |
| 1476 | D | N | G | R | J | V |
| 1477 | D | N | G | R | K | U |
| 1478 | D | N | G | R | K | V |
| 1479 | D | N | G | R | L | U |
| 1480 | D | N | G | R | L | V |

Another embodiment of the invention relates to a pharmaceutical composition comprising a compound according to any one of the above embodiments and a pharmaceutically acceptable carrier.

Another embodiment of the invention relates to a method of treatment of inflammation comprising administering a therapeutically effective amount of a compound according to any one of the above embodiments.

Another embodiment of the invention relates to a method of inhibition of T cell activation and proliferation in a mammal, comprising administering to the mammal a therapeutically effective amount of a compound according to any one of the above embodiments.

Another embodiment of the invention relates to a method of treatment of arthritis, rheumatoid arthritis, psoriatic arthritis, or osteoarthritis in a mammal comprising administering to the mammal a therapeutically effective amount of a compound according to any one of the above embodiments.

Another embodiment of the invention relates to a method of treatment of organ transplant, acute transplant or heterograft or homograft rejection, or transplantation tolerance induction in a mammal comprising administering to the mammal a therapeutically effective amount of a compound according to any one of the above embodiments.

Another embodiment of the invention relates to a method of treatment of ischemic or reperfusion injury, myocardial infarction, or stroke in a mammal, comprising administering to the mammal a therapeutically-effective amount of a compound according to any one of the above embodiments.

Another embodiment of the invention relates to a method of treatment of multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal comprising administering to the mammal a therapeutically effective amount of a compound according to any one of the above embodiments.

Another embodiment of the invention relates to a method of treatment of colon carcinoma or thymoma in a mammal comprising administering to the mammal a therapeutically-effective amount of a compound according to any one of the above embodiments.

Another embodiment of the invention relates to the manufacture of a medicament comprising a compound according to any one of the above embodiments.

Another embodiment of the invention relates to the manufacture of a medicament for the treatment of inflammation comprising a therapeutically effective amount of a compound according to any one of the above embodiments.

Another embodiment of the invention relates to the manufacture of a medicament for the inhibition of T cell activation and proliferation in a mammal, comprising a therapeutically effective amount of a compound according to any one of the above embodiments.

Another embodiment of the invention relates to the manufacture of a medicament for the treatment of arthritis, rheumatoid arthritis, psoriatic arthritis, or osteoarthritis in a mammal comprising a therapeutically-effective amount of a compound according to any one of the above embodiments.

Another embodiment of the invention relates to the manufacture of a medicament for the treatment of organ transplant, acute transplant or heterograft or homograft rejection, or transplantation tolerance induction in a mammal comprising a therapeutically effective amount of a compound according to any one of the above embodiments.

Another embodiment of the invention relates to the manufacture of a medicament for the treatment of ischemic or reperfusion injury, myocardial infarction, or stroke in a mammal, comprising a therapeutically effective amount of a compound according to any one of the above embodiments.

Another embodiment of the invention relates to the manufacture of a medicament for the treatment of multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal comprising a therapeutically effective amount of a compound according to any one of the above embodiments.

Another embodiment of the invention relates to the manufacture of a medicament for the treatment of colon carcinoma or thymoma in a mammal comprising a therapeutically effective amount of a compound according to any one of the above embodiments.

Another embodiment of the invention relates to a method of making a compound as described herein, comprising the steps of:

reacting a compound having the structure

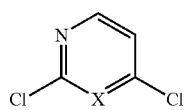

with $R^3NH_2$ to give a chloroaniline of structure

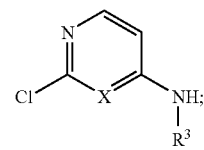

reacting the formed chloroanaline with $R^2O(C=O)Cl$ to give a carbamate of structure

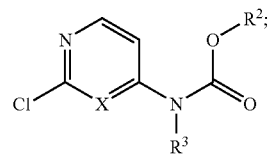

and reacting the formed carbamate with $R^1NH_2$ in the presence of an acid to give

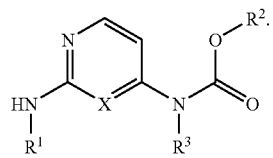

The compounds of this invention may have in general several asymmetric centers and are typically depicted in the form of racemic mixtures. This invention is intended to encompass racemic mixtures, partially racemic mixtures and separate enantiomers and diasteromers.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

Unless otherwise specified, the following definitions apply to terms found in the specification and claims:

"Aryl" means a phenyl or naphthyl radical, wherein the phenyl may be fused with a $C_{3-4}$cycloalkyl bridge, wherein the bridge optionally includes 1, 2 or 3 heteroatoms selected from N, O and S.

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

"$C_{\alpha-\beta}$alkyl" means an alkyl group comprising from α to β carbon atoms in a branched, cyclical or linear relationship or any combination of the three. The alkyl groups described in this section may also contain double or triple bonds. Examples of $C_{1-8}$alkyl include, but are not limited to the following:

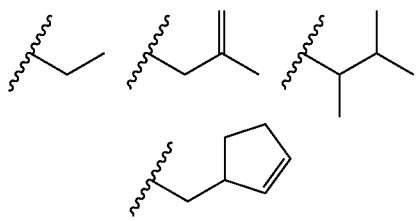

"Halogen" and "halo" mean a halogen atoms selected from F, Cl, Br and I.

"$C_{\alpha-\beta}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

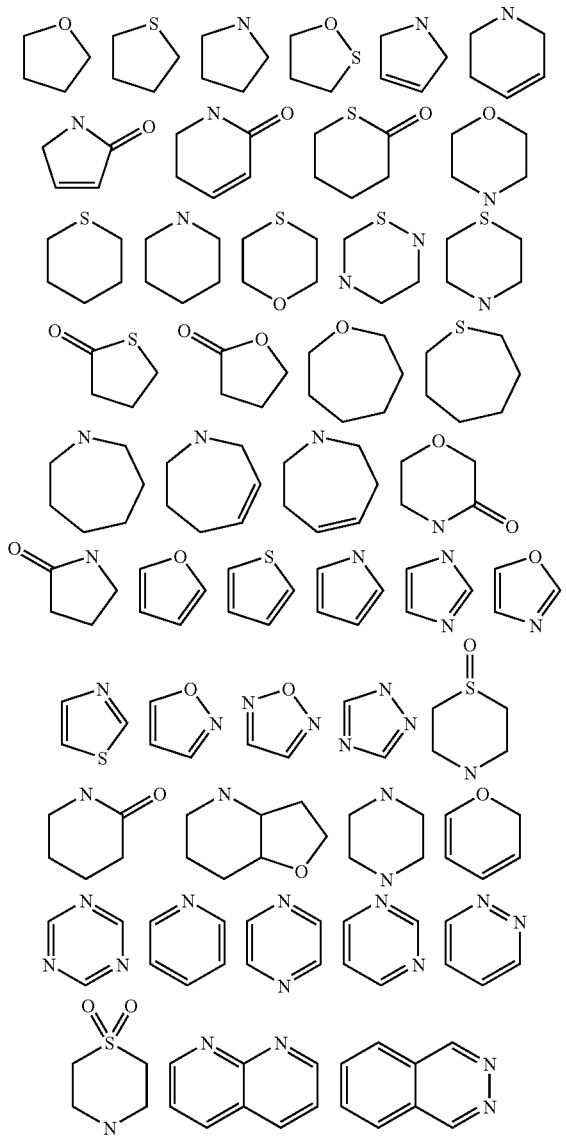

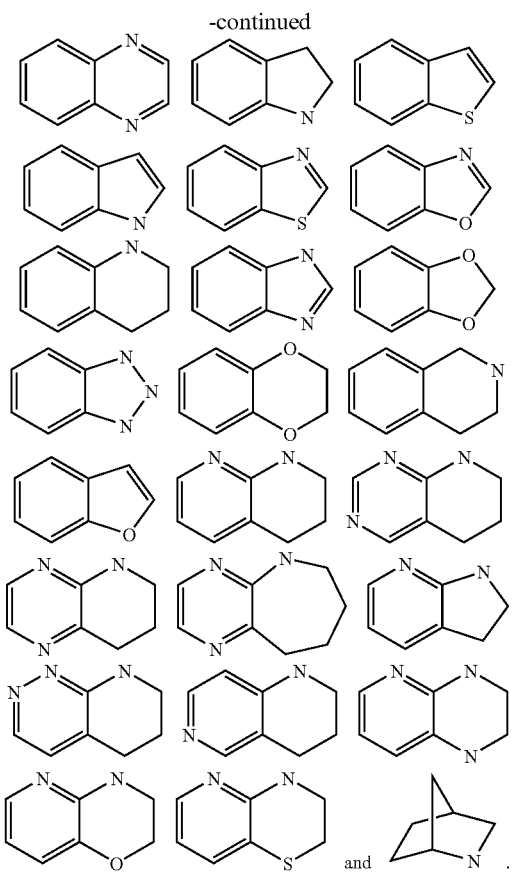

"Saturated or unsaturated" means a substituent that is completely saturated, completely unsaturated, or has any degree of unsaturation in between. Examples of a saturated or unsaturated 6-membered ring carbocycle would include phenyl, cyclohexyl, cyclohexenyl and cyclohexadienyl.

Substituents, including rings and alkyl groups, may be either monovalent or polyvalent depending on the context of their usage. For example, if description contained the group $R^\alpha$—$R^\beta$—$R^\gamma$ and $R^\beta$ was defined as $C_{1-6}$alkyl, then the $R^\beta$ alkyl would be considered polyvalent because it must be bonded to at least $R^\alpha$ and $R^\gamma$. Alternatively, if $R^\gamma$ was defined as $C_{1-6}$alkyl, then the $R^\gamma$ alkyl would be monovalent (excepting any further substitution language).

"Pharmaceutically-acceptable salt" means a salt form of a free base compound of the present invention. "Pharmaceutically acceptable" used with reference to a salt, means a salt that is pharmacologically safe for consumption, generally as determined by a governmental or authorized regulatory body. Salts may be prepared by conventional means, which are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, flimaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977). The term, "salt" as used herein, is contemplated to include pharmaceutically acceptable derivatives of compounds of Formula I.

"Derivative" generally refers to simple modifications, readily apparent to those of ordinary skill in the art, on the parent core structure of Formula I, which does not significantly affect (generally decrease) the activity of the compound in-vitro as well as in vivo, in a subject. For example, a pro-drug is encompassed within the term "derivative". A prodrug is a compound, which when administered to the body of subject, breaks down in the subject's metabolic pathway to provide an active compound of Formula I.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups, including aralkyl groups for example, are also suitable for protecting carboxy, hydroxy and mercapto groups. Alkyl groups are also suitable groups for protecting hydroxy and mercapto groups, such as tert-butyl.

Silyl protecting groups are groups containing silicon atoms which are optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

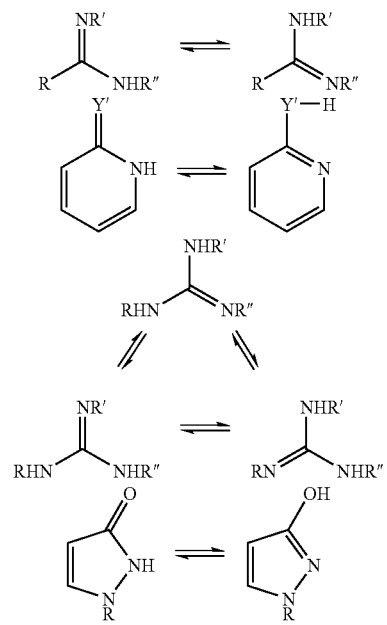

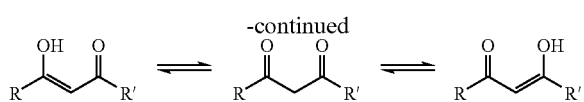

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a subject or patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

"Cytokine" means a secreted protein that affects the functions of other cells, particularly as it relates to the modulation of interactions between cells of the immune system or cells involved in the inflammatory-response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

"TNF, IL-1, IL-6, and/or IL-8 mediated disease or disease state" means all disease states wherein TNF, IL-1, IL-6, and/or IL-8 plays a role, either directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of or action of IL-1 is a result of TNF, would be considered mediated by TNF.

Synthesis

Compounds provided by the invention can be synthesized according to one or more of the following methods. It should be noted that the general procedures are shown as they relate to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

The following Examples are presented for illustrative purposes only and are not intended, nor should they be construed, as limiting the invention in any manner. Those skilled in the art will appreciate that modifications and variations of the compounds, procedures, methods, and the like, disclosed herein can be made without violating the spirit or scope of the present invention.

Aniline Synthesis

General schemes A-I describe various exemplary methods of synthesizing anilines and substituted anilines. General scheme J describes the synthesis of substituted nitrobenzenes, which can be converted to the corresponding aniline by various of the methods described in schemes A-I.

General Scheme A

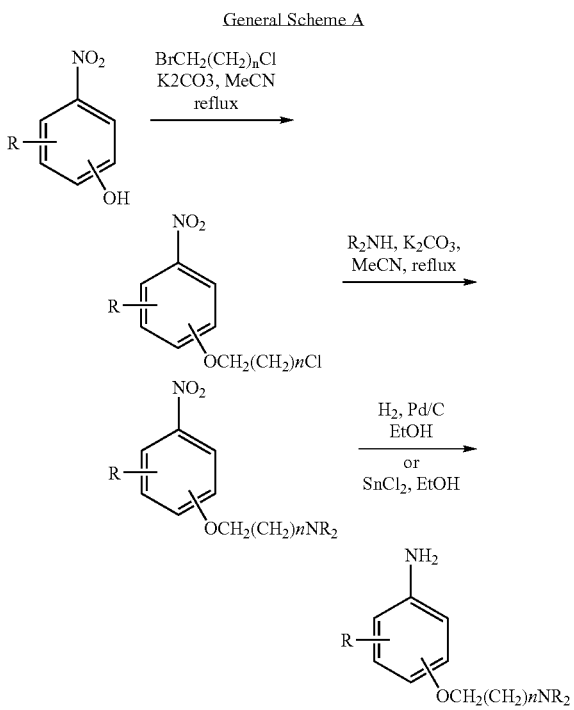

General Method A 3-(4-Nitrophenoxy)propyl chloride

Nitrophenol (10 g, 72 mmol) was dissolved in acetonitrile (100 mL) and potassium carbonate (24.9 g, 180 mmol) added followed by bromochloropropane (113.2 g, 720 mmol). The mixture was heated and stirred under reflux overnight. The reaction was cooled to room temperature, the solid was then filtered off and the solvent evaporated under reduced pressure, taking care to remove all excess alkylating agent, to give the title compound.

N,N-dimethyl-3-(4-nitrophenoxy)propylamine

A mixture of 3-(4-nitrophenoxy)propyl chloride (2 g, 9.27 mmol), potassium carbonate (7.69 g, 46.4 mmol) and acetonitrile (15 mL) were stirred in a sealed tube and dimethylamine hydrochloride (3.78 g, 46.4 mmol) added quickly. The mixture was stirred and heated overnight at 80° C. The mixture was cooled well before opening the pressure tube, then water and dichloromethane were added and the aqueous layer was extracted with dichloromethane. The combined organics were dried and evaporated giving the title product. $^1$H NMR (400 MHz, CDCl$_3$): 1.95 (2H, t, J 7 Hz); 2.2 (6H, s); 2.35-2.45 (2H, m); 4.05 (2H, t, J 7 Hz); 6.9 (2H, d, J 8 Hz); 8.1 (2H, d, J 8 Hz).

N,N-dimethyl-3-(4-aminophenoxy)propylamine

N,N-dimethyl-3-(4-nitrophenoxy)propylamine (4.4 g, 19.6 mmol) was hydrogenated over Pd (10% on C, 0.4 g) in ethanol (ca 50 mL) for 16 h. The catalyst was filtered off and the solvent removed under reduced pressure to afford the title compound as a brown oil. $^1$H NMR (400 MHz, dmso-d6): 1.95 (2H, t, J 6.5 Hz); 2.25 (6H, s); 2.35-2.45 (2H, m); 3.95 (2H, t, J 6.5 Hz); 4.7 (2H, bs); 6.9 (2H, d, J 8 Hz); 8.1 (2H, d, J 8 Hz); 6.65 (2H, d, J 8 Hz); 6.75 (2H, d, J 8 Hz).

General Scheme B

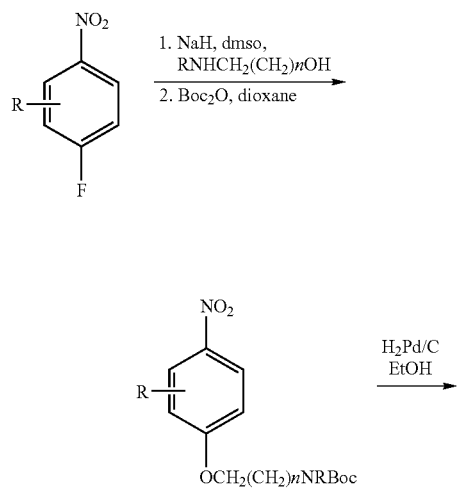

General Method B

Isopropyl-[2-(4-nitrophenoxy)ethyl]amine

Deprotonation of DMSO (anhydrous, 5 mL) was effected with NaH (0.40 g, 60 wt % in mineral oil, 10 mmol) over 30 min at 40° C. with stirring under a nitrogen atmosphere. When 2-isopropylaminoethanol (1.15 mL, 10 mmol) was added to the solution of the DMSO anion at room temperature, some effervescence occurred. 4-Fluoronitrobenzene (1.06 mL, 10 mmol) was added after 10 min and the dark red solution was then stirred at room temperature for further 20 min. The reaction was diluted with dichloromethane (100 mL), washed with water (50 mL) and then extrected twice with 3M HCl (100 mL). The combined acidic extracts were washed once with dichloromethane (50 mL). Ethyl acetate (125 mL) was then added and the mixture was cooled to 6-8° C. before the aqueous layer was adjusted to pH 11 by gradual addition of 5M aq. NaOH (ca. 150 mL), with vigorous stirring. The organic layer was separated and washed twice with water (50 mL) dried over magnesium sulfate, and concentrated in vacuo at 35° C. to afford the title compound as a yellow oil. $^1$H NMR (400 MHz, CDCl$_3$): 1.10 (6H, d, J 6.25), 2.88 (1H, m, J 6.25), 3.04 (2H, t, J 5.2), 4.16 (2H, t, J 5.2), 6.96 (2H, d, J 9.3), 8.18 (2H, d, J 9.3); MS: 225 Isopropyl-[2-(4-nitrophenoxy)ethyl]carbamic acid tert-butyl ester Isopropyl-[2-(4-nitrophenoxy)ethyl]amine (1.80 g, 8.05 mmol) was dissolved in 1,4-dioxane (containing 1% water, 20 mL) and cooled to 0-5° C. Di-tert-butyldicarbonate (1.76 g, 8.05 mmol) was added slowly with vigorous stirring. The reaction was stirred at 0° C. for 0.5 h, then at room temperature for 20 h. The solvent was removed in vacuo and the residue taken up into EtOAc. The organic layer was washed twice with water (25 mL), the aqueous washes are extracted back with EtOAc (25 mL). The combined organic extracts were washed twice with 0.3 M HCl (25 mL), then brine and are dried over sodium sulfate. The solvent was removed in vacuo to afford a yellow solid, which was recrystallised from hot n-hexane to give the crystalline title compound as fine, light-yellow needles. $^1$H NMR: (400 MHz, CDCl$_3$): 1.06 (6H, d, J 6.8), 1.37 (9H, s), 3.90 (2H, bm, 2H), 4.06 (2H, bm), 4.26 (1H, bm), 6.86 (2H, d, J 9.0), 8.09 (2H, d, J 9.2). MS: 225 [M+H$^+$-Boc]). Isopropyl-[2-(4-aminophenoxy)ethyl]carbamic acid tert-butyl ester A solution of isopropyl-[2-(4-aminophenoxy)ethyl]carbamic acid tert-butyl ester (2.09 g, 6.45 mmol) in ethanol/tetrahydrofuran (30 mL, 2:1) was reduced over palladium on carbon (10 wt %, 50% wet, 0.4 g) with hydrogen under atmospheric pressure at room temperature for 20 h. The catalyst was separated by filtration through celite. The solvent was removed in vacuo to afford the title compound as a red oil. $^1$H NMR: (400 MHz, CDCl$_3$): 1.08 (6H, d, J 6.7), 1.39 (9H, s), 3.34 (2H, bm), 3.90 (2H, bm), 4.26 (1H, bm), 6.56 (2H, d, J 8.9), 6.67 (2H, d, J 8.9); MS: 195 [M+H$^+$-Boc], 295 [M+H$^+$].

General Scheme C

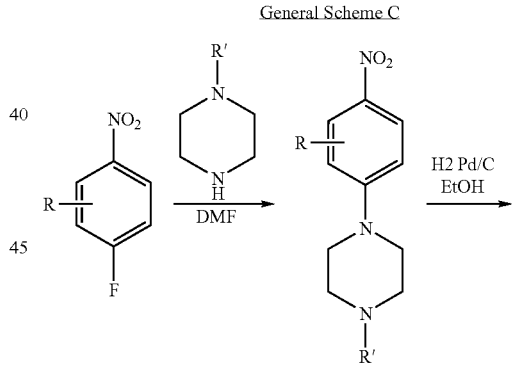

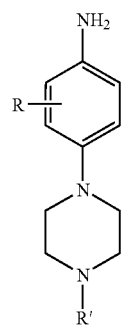

General Method C

1-(2-Fluoro-4-nitrophenyl)-4-methylpiperazine

N-Methylpiperazine (30 mL, 27.1 g, 0.268 mol) was cooled in ice/water while adding 3,4-difluoronitrobenzene (2.0 g, 0.0126 mol) with stirring. The mixture was then heated at 100° C. overnight, evaporated to remove all excess N-methyl-piperazine and the residue dissolved in 1M hydrochloric acid (30 mL). After washing twice with 20 mL portions of dichloromethane the solution was basified with 5M sodium hydroxide (10 mL). The product was extracted into dichloromethane (twice with 20 mL), dried over sodium sulphate and evaporated giving a yellow oil which solidified on standing. $^1$H NMR (CDCl$_3$) 8.00 (m, 1H) 7.91 (m, 1H) 6.92 (m, 1H) 3.33 (m, 4H) 2.63 (m, 4H) 2.39 (s, 3H).

1-(2-Fluoro-4-aminophenyl)-4-methylpiperazine

Obtained by hydrogenation over Pd-10% C of the corresponding nitro compound in ethanol. $^1$H NMR (CDCl$_3$) 6.75 (m, 1H) 6.33 (m, 2H) 3.48 (m, 2H) 2.94 (m, 4H) 2.53 (m, 4H) 2.29 (s, 3H).

Specific Syntheses:

tert-Butyl 4-(2-difluoromethoxy-4-nitrophenyl)piperazine-1-carboxylate 1-(2-Difluoromethoxy-4-nitrophenyl)piperazine A stirred mixture of 1-bromo-2-difluoromethoxy-4-nitrobenzene (prepared from the corresponding phenol following the procedure outlined in WO9749710A1; 2.68 g, 10 mmol), piperazine (1.12 g, 13 mmol), potassium carbonate (2.07 g, 15 mmol), tetrabutylammonium bromide (0.03 g, 0.1 mmol) and dry dimethyl sulphoxide (20 mL) was heated under nitrogen at 120° C. for 3 h. The product was added to water (100 mL) and 6M hydrochloric acid (10 mL, 60 mmol), washed with ethyl acetate until washings colourless and the aqueous layer basified with 5M sodium hydroxide solution (20 mL, 100 mmol). Extraction with ethyl acetate (3× with 50 mL), drying (sodium sulphate) and evaporating gave product as viscous orange oil.

$^1$H NMR (CDCl$_3$) 8.00 (m, 1H) 7.92 (m, 1H) 6.93 (m,1H) 6.47 (t, J=73.6, 1H) 3.18 (m, 2H) 2.98 (m, 2H) 2.54 (s, 1H).

tert-Butyl 4-(2-difluoromethoxy-4-nitrophenyl)piperazine-1-carboxylate

The above product (1.64 g, 6 mmol) was dissolved in dry tetrahydrofuran (25 mL) and di-tert-butyl dicarbonate (1.26 g, 6 mmol) added. After stirring overnight the mixture was evaporated and the resulting orange solid recrystallised from ethyl acetate giving the final product. $^1$H NMR (CDCl$_3$) 8.03 (m, 1H) 7.93 (m, 1H) 6.48 (t, 1H) 3.53 (m, 2H) 3.15 (m, 2H) 1.42 (s, 9H).

tert-Butyl 4-(2-difluoromethoxy-4-aminophenyl)piperazine-1-carboxylate

Obtained by hydrogenation over Pd-10% C of the corresponding nitro compound in ethanol. $^1$H NMR (CDCl$_3$) 7.73 (m, 1H) 6.56 (t, 1H) 6.42 (m, 2H) 3.46 (m, 2H) 2.80 (m, 2H) 1.40 (s, 9H).

4-(4-Amino-2-fluorophenyl)-1 2-dimethylpiperazine 4-(2-Fluoro-4-nitrophenyl)-2-methylpiperazine To rac-2-methylpiperazine (2.64 g, 23.1 mmol) in acetonitrile (50 mL) was added triethylamine (1.95 g, 2.7 mL, 19.2 mmol) followed by 3,4-difluoronitrobenzene (1 g, 7.7 mmol) dropwise over 5 min under a nitrogen atmosphere. The resulting yellow solution was allowed to stir at room temperature for 3 days. Excess acetonitrile was removed by evaporation under reduced pressure and the residue reconstituted in DCM (50 mL), washed with water (2×50 mL), dried (MgSO$_4$) and concentrated to afford the title compound as a yellow solid. LC-MS (UV 215 nm): 100%; m/z 240.19; 0.91 min. $^1$H NMR (CDCl$_3$): 1.13 (3H, d, J 6.4), 2.56 (1H, dd, J 10.2 11.7), 2.91-2.99 (1H, m), 3.00-3.13 (3H, m), 3.52-3.59 (2H, m), 6.91 (1H, t, J 8.8), 7.85-8.01 (2H, m).

1 2-Dimethyl-4-(2-fluoro-4-nitrophenyl)piperazine

To a solution of 4-(2-fluoro-4-nitrophenyl)-2-methylpiperazine (1 g, 4.2 mmol) in formic acid (10 mL) was added paraformaldehyde (1.2 mL, 15.8 mmol of a 36.5% v/v aqueous solution). The resulting yellow solution was heated at 100° C. for 18 h. Upon cooling, excess formic acid/paraformaldehyde was removed under reduced pressure and the residue basified with 1M KOH solution. The resulting yellow precipitate was extracted into DCM (3×25 mL), dried (MgSO$_4$) and concentrated to afford the title compound as a yellow solid. LC-MS (UV 215nm): 100%; m/z 254.40; 1.93 min. $^1$H NMR (CDCl$_3$): 1.13 (3H, d, J 6.4), 2.28-2.34 (1H, m), 2.35 (3H, s), 2.43-2.52 (1H, m), 2.73 (1H, dd, J 10.0 12.0), 2.87-2.91 (1H, m), 3.07-3.14 (1H, m), 3.47-3.51 (1H, m), 3.55-3.57 (1H, m), 6.90 (1H, t, J 8.8), 7.84-7.92 (1H, m), 7.96-8.01 (1H, m).

4-(4-Amino-2-fluorophenyl)-1,2-dimethylpiperazine

Absolute ethanol (2 mL) was added to a two-necked round-bottomed flask containing palladium on carbon (0.09 g, 0.42 mmol). The reaction vessel was evacuated and purged with nitrogen three times. 1,2-Dimethyl-4-(2-fluoro-4-nitrophenyl)piperazine (1.06 g, 4.2 mmol) in absolute ethanol (10 mL) was added and the vessel purged thrice more with nitrogen. After purging thrice with hydrogen, the reaction was left to stir under a hydrogen atmosphere at room temperature for 18 h. The reaction mixture was filtered through a pad of Celite washing with additional ethanol. Excess ethanol was removed under reduced pressure to afford the title compound as an off-white oil. LC-MS (UV 215nm): 93%; m/z 224.35; 0.58 min.

$^1$H NMR (DMSO-d$_6$): 1.08 (3H, d, J 5.8, —CH(CH$_3$)), 2.37 (3H, s, —NCH$_3$), 2.43-2.59 (3H, m, —NCH(H) CH$_2$N—), 2.73-2.83 (1H, m, —NCH(H)), 2.90-3.06 (3H, m, —NCH(H)), 5.01 (2H, br, ArNH$^2$), 6.25-6.49 (2H, m, ArH), 6.69-6.81 (1H, m, ArH).

General Scheme D

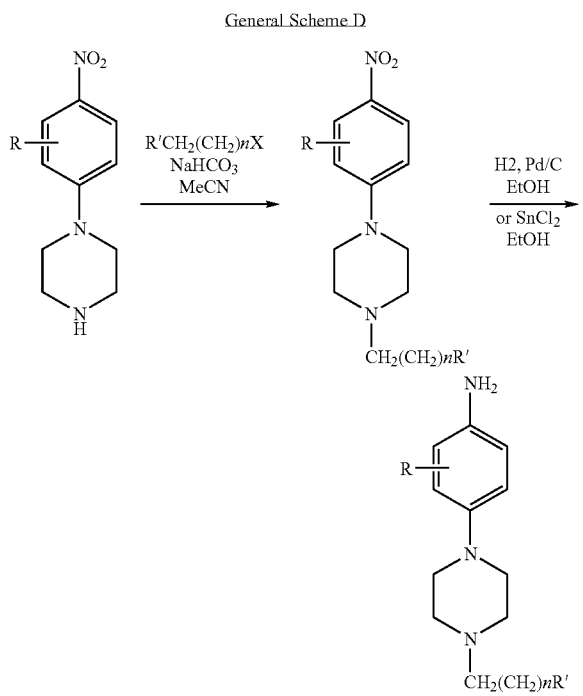

General Method D

4-(4-(3-Dimethylaminopropyl)piperazino)nitrobenzene

Prepared according to a slightly modified procedure from U.S. Pat. No. 3,331,845. A mixture of 4-nitrophenylpiperazine (2.1 g, 10 mmol), sodium hydrogen carbonate (2.5 g, 30 mmol), N,N-dimethyl-N-(3-chloropropyl)amine hydrochloride (1.9 g, 12 mmol) in isopropanol (80 mL) was heated at 80° C. for 18 h. The mixture was then allowed to cool, the solid filtered off and the solvent removed under reduced pressure. Ethyl acetate (ca. 200 mL) was added and the residue was washed with saturated brine twice (50 mL each time). The organic layer was dried over sodium sulphate and the solvent evaporated under reduced pressure. The crude compound was purified by column, eluting with dichloromethane/methanol 9/1 (containing 1% N,N-dimethylethylamine) to give the title compound as a yellow solid. $^1$H NMR (CDCl$_3$, 400 MHz): 1.6 (2H, m); 2.15 (6H, s); 2.25 (2H, m); 2.35 (2H, m); 2.5-2.55 (4H, m); 3.35-3.4 (4H, m); 6.75 (2H, d, J 8 Hz); 8.05 (2H, d, J 8 Hz) MS: 293, 248.

4-(4-(3-Dimethylaminopropyl)piperazino)aniline

A solution of 4-(4-(3-dimethylaminopropyl)piperazino)nitrobenzene (1.5 g) in methanol (50 mL) was hydrogenated at atmospheric pressure over Pd (5% on carbon) (0.3 g; 50% water content) for 4 h. The catalyst was filtered off and the solvent removed under reduced pressure to give the title compound as a brown solid $^1$H NMR (CDCl$_3$, 400 MHz): 1.65 (2H, m); 2.15 (6H, s); 2.25 (2H, m); 2.35 (2H, m); 2.5-2.55 (4H, m); 2.95-3.05 (4H, m); 6.55 (2H, d, J 7 Hz); 6.75 (2H, d, J 7 Hz) MS: 263, 218.

4-(4-(3-Chlorobenzyl)piperazino)aniline 4-(4-(3-chlorobenzyl)piperazino)nitrobenzene (3 g, 9 mmol, prepared as in the general method) was dissolved in ethanol (100 mL). Tin (II) chloride dihydrate (10.1 g, 45 mmol) was added and the reaction heated to 80° C. for 66 h. The reaction mixture was concentrated under reduced pressure. A saturated solution (200 mL) of Rochelle's salt (sodium potassium tartrate) was prepared, and solid NaHCO$_3$ was added to this until no more would dissolve. Ethyl acetate (200 mL) was added to the vessel, followed by the reaction mixture. The solution was then stirred until clear. The phases were separated, and the aqueous layer washed with ethyl acetate (50 mL). The organic layers were combined, washed with saturated brine, dried over magnesium sulphate, and evaporated to give the title compound. $^1$H NMR (CDCl$_3$, 400 MHz): 2.5-2.55 (4H, m); 2.95-3.05 (4H, m); 3.47 (2H, s); 6.5-6.6 (2H, m); 6.7-6.8 (4H, m); 7.15-7.25 (4H,m); MS: 302, 304.

4-(4-Aminophenyl)-1-(2-tert-butoxycarbonylaminoethyl)ipiperazine 1-(2-Hydroxyethyl)-4-(4-nitrophenyl)piperazine 1-(4-Nitrophenyl)piperazine (12.0 g, 0.058 mol) and 2-bromoethanol (8.7 g, 0.070 mol) were dissolved in acetonitrile (175 mL) and treated with Hunig's base (9.0 g, 0.070 mol). The mixture was refluxed overnight, then the solvent evaporated and the residue redissolved in dichloromethane. The organic layer was washed with water and brine, dried over Na$_2$SO$_4$ and evaporated under reduced pressure to give the title compound.

1-(2-Chloroethyl)-4-(4-nitrophenyl)piperazine 1-(2-Hydroxyethyl)-4-(4-nitrophenyl)piperazine (5 g, 0.02 mol) was dissolved in 50 mL of DCM and treated with HCl (40 mL of a 1M solution in Et$_2$O) under a drying tube for 90 min. The solvent was evaporated, the residue dissolved in thionyl chloride (60 mL) and the mixture refluxed at 80° C. After 5 h, the reaction was complete as shown by LCMS and the thionyl chloride was removed under reduced pressure redissolving in DCM and evaporating three times to give the title compound as the HCl salt. LCMS: 93%, t=0.88 min, [MH+]=270.23.

1-(2-Azidoethyl)-4-(4-nitrophenyl)piperazine 1-(2-Chloroethyl)-4-(4-nitrophenyl)piperazine (1 g, 0.0033 mol) was dissolved in dimethylsulphoxide (30 mL) and sodium azide (0.34 g, 0.0052 mol) was added followed by Hunig's base (0.84 g, 0.0065 mol). The mixture was stirred at 80° C. overnight in a sealed tube, then diluted with ethyl acetate and washed with water, dried and evaporated to yield the title compound. LCMS: 90%, t=0.85 min, [MH+]= 277.26.

1-(2-Tert-butoxycarbonylaminoethyl)-4-(4-nitrophenyl)piperazine 1-(2-Azidoethyl)-4-(4-nitrophenyl)piperazine (0.8 g, 0.0029 mol) was dissolved in anhydrous ethyl ether (35 mL) under nitrogen, and tributyl phosphine (0.76 mL, 0.0032 mol) was added dropwise. The mixture was stirred at room temperature for 1 h then cooled to −50° C. before adding di-tert-butyldicarbonate (0.63 g, 0.0032 mol dissolved in little ether) and stirring for a further hour. Saturated sodium hydrogen carbonate (2 mL) was added and the flask was allowed to warm to room temperature. Further 20 mL of saturated sodium hydrogen carbonate and 20 mL ethyl acetate were added, the organic phase separated and the aqueous layer extracted with ethyl acetate. The organic layers were combined, dried and evaporated. The crude material was purified on silica (2% MeOH:DCM) to give the title compound. LCMS: 91%, t=1.25 min, [M-56]+=295.32 4-(4-Aminophenyl)-1-(2-tert-butoxycarbonylaminoethyl)piperazine 1-(2-Tert-butoxycarbonylaminoethyl)-4-(4-nitrophenyl)piperazine (0.8 g, 0.0023 mol) was dissolved in ethanol (40 mL) and stirred with Pd/C (10%, 100 mg) under a hydrogen atmosphere overnight. The catalyst was filtered off and solvent evaporated to yield the title compound. LCMS: 90%, t=0.82 min. $^1$H NMR (CDCl$_3$) 6.85 (2H, d); 6.65 (2H, d); 5.0 (1H, s); 3.3 (2H, t); 3.05 (4H, m); 2.6 (4H, m); 2.5 (2H, t); 1.5 (9H, s).

4-(4-Aminophenyl)-1-((2-N-tert-butoxycarbonyl-ethylamino)ethyl)piperazine 1-((2-Ethylamino)ethyl)-4-(4-nitrophenyl)piperazine 1-(2-Chloroethyl)-4-(4-nitrophenyl)piperazine (2.5 g, 0.0082 mol), ethylamine (20 mL, 0.041 mol) and Hunig's base (2.1 g, 0.016 mol) were dissolved in ethanol (150 mL) and stirred at 80° C. in a pressure tube for 48 h. The solvent evaporated and the residue dissolved in DCM; the organic layer was washed with brine to form a precipitate which was collected and combined with the material recovered from evaporation of the organic layer to give the title compound as the HCl salt
LCMS: 86%, t=0.92 min, [MH+]=270.23.

1-((2-N-Tert-butoxycarbonylethylamino)ethyl)-4-(4-nitrophenyl)piperazine 1-((2-Ethylamino)ethyl)-4-(4-nitrophenyl)piperazine (1.7 g, 0.0061 mol) was dissolved in dioxane/water 1/1 (70 mL) and di-tert-butyldicarbonate (1.47 g, 0.0067 mol) added. The reaction was stirred overnight at room temperature under nitrogen, the organic solvent was evaporated and the aqueous layer extracted into DCM, dried over Na$_2$SO$_4$ and evaporated. The residue was purified on silica eluting with 5% MeOH:DCM to give the title compound. LCMS: 87%, t=1.20min, [MH+]=379.35, [M-56]+=323.31.

4-(4-Aminophenyl)-1-((2-N-tert-butoxycarbonyl-ethylamino)ethyl)piperazine 1-((2-N-tert-Butoxycarbonylethylamino)ethyl)-4-(4-nitrophenyl)piperazine (1.0 g, 0.0027 mol) was hydrogenated overnight over Pd—C (10%, 100 mg) in ethanol (50 mL) to yield the the title aniline. LCMS: 94%, t=1.10min, [MH+]=349.41, [M-56]+=293.35. $^1$H NMR (CDCl$_3$) 6.8 (2H, d); 6.65 (2H, d); 5 (1H, s); 3.35 (2H, t); 3.25 (2H, t); 3.05 (4H, m); 2.65 (4H, t); 2.5 (2H, t); 1.45 (9H, s); 1.15 (3H, t).

General Scheme E

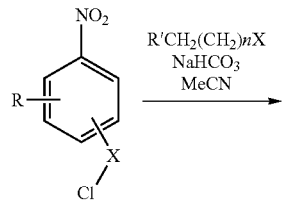

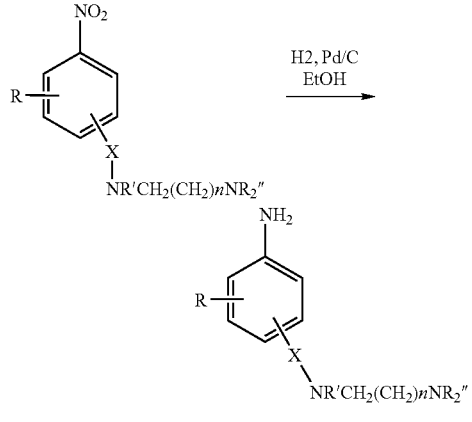

x = CO, SO$_2$

General Method E

N-(2-Dimethylaminoethyl)-3-nitrobenzamide

3-Nitrobenzoyl chloride (2 g, 10.77 mmol) was loaded into a round bottomed flask, placed under a N$_2$ atmosphere and dissolved in anhydrous dichloromethane (10 mL). The mixture was cooled to 0° C. and N,N-dimethylethylenediamine (0.98 mL, 8.98 mmol) was added to the reaction. The reaction was allowed to warm to room temperature and left to stir for 18 h. After 18 h the reaction had given a precipitate which was isolated by filtration and washed with dichloromethane to give 2.28 g of a white solid, which was partitioned between dichloromethane and a saturated aqueous NaHCO$_3$ solution. The organic layer was removed under eduosed pressure and the aqueous layer was then re-extracted dichloromethane. The organic layers were combined, dried over Na$_2$SO$_4$ and the solvent was removed under reduced pressure to afford the title compound as a yellow solid. MS: 193, 238; $^1$H NMR (400 MHz, dmso-d6): 2.19 (6H, s), 2.42 (2H, t, J 6.8 Hz), 3.39 (2H, q, J 12.4 Hz, 6.7 Hz), 7.78 (1H, t, J 7.9 Hz), 8.29 (1H, ddd, J 7.9 1.8, 1.1 Hz), 8.38 (1H, ddd, J 8.1 Hz, 2.3, 1.0 Hz), 8.68 (1H, t, J 1.8 Hz), 8.81 (1H, t, J 5.7 Hz).

3-(7-(2-Dimethylaminoethylcarbamoyl))aniline

Palladium on carbon (200 mg, 10% w/w) was loaded to a three-necked flask and ethanol (1 mL) was added. This was then fitted with a three-way tap with balloon. The flask was then placed under vacuum then purged with nitrogen, this was repeated twice more. The amide (2.0 g, 8.4 mmol) was dissolved in ethanol (20 mL), this was then added to the reaction. The reaction was then placed under vacuum and purged with nitrogen three more times. It was then placed under vacuum again then purged with hydrogen, this was repeated once more leaving the balloon filled with hydrogen. The reaction was left at room temperature overnight under a hydrogen atmosphere. The reaction solution was then filtered through a celite plug washing with ethanol. The filtrates were combined and solvent removed to give a clear colourless oil. MS: 208; $^1$H NMR (400 MHz, CDCl$_3$): 2.22 (6H, s), 2.27 (2H, t, J 5.9 Hz), 3.45 (2H, q, J 11.6, 5.3 Hz), 6.71 (1H, ddd, J 7.9, 2.4, 1.0 Hz), 6.85 (1H, bs), 7.0-7.15 (3H, m).

General Scheme F

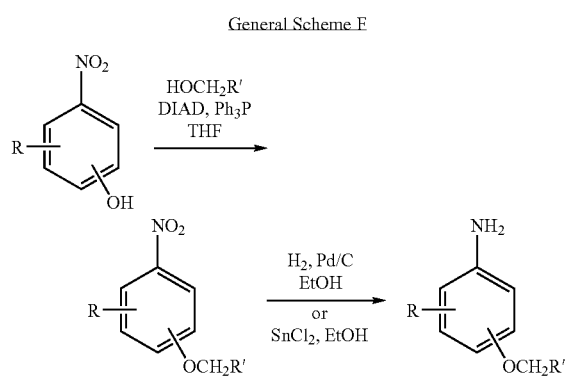

General method F

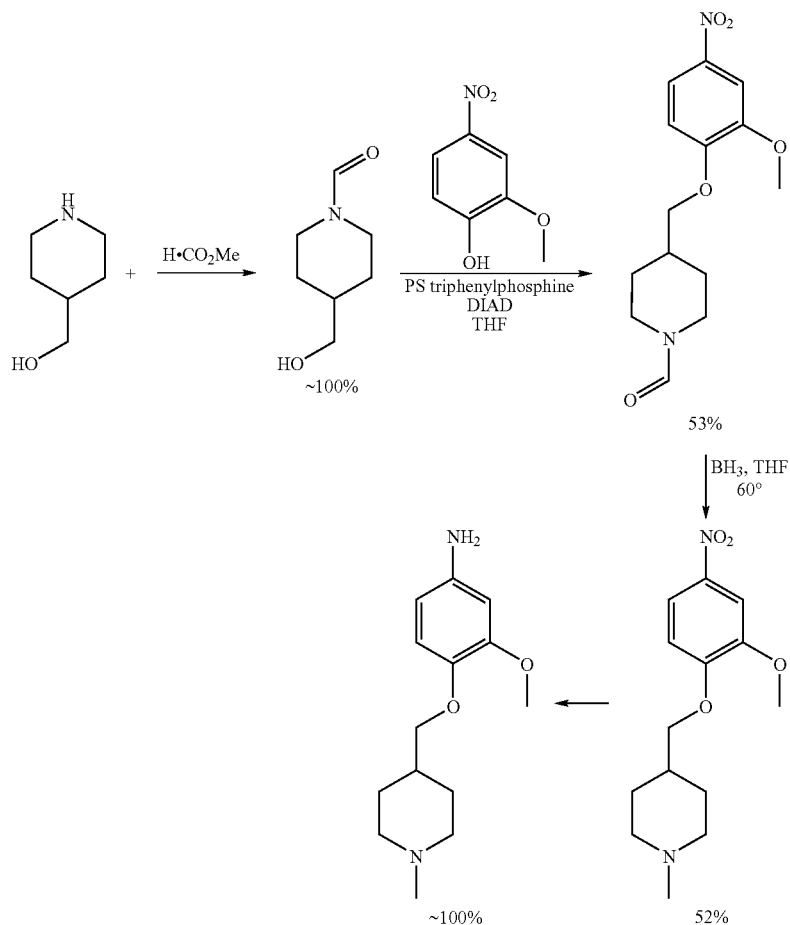

N-Formyl-4-piperidinemethanol

4-Piperidinemethanol (10 g, 87 mmol) was dissolved in methyl formate (7 mL, 113 mmol) 0° C., and maintained at that temperature for 30 min, then allowed to reach 20° C. and stirred 90 min. Solid sodium hydroxide was added (0.87 g, pellets) and the mixture was left overnight. Dichloromethane was added, the NaOH removed by filtration and the solution treated with 1M HCl in ether (10 mL). The mixture was filtered through Celite and the solvent was removed under reduced pressure to afford the crude title compound. $^1$H NMR (400 MHz, CDCl$_3$): 0.85-1.1 (2H, m); 1.55-1.85 (3H, m); 2.5-2.7 (1H, m); 2.95-3.1 (1H, m); 3.3 (2H, d, J 7 Hz); 3.6-3.7 (1H, m); 4.1-4.3 (1H, m); 8 (1H, s).

N-Formyl-4-(2-methoxy-4-nitrophenoxymethyl) piperidine

4-Nitroguaiacol (2 g, 11.8 mmol), N-formyl 4-piperidinemethanol (1.13 g, 7.89 mmol) and polymer-supported triphenylphosphine (3 mmol/g, 3.94 g, 11.8 mmol) were dissolved in tetrahydrofuran (30 mL). The mixture was cooled to 0° C. and diisopropyl azodicarboxylate (2.33 mL, 11.8 mmol) was added dropwise. The mixture was stirred at 0° C. for 30 min then at 20° C. overnight. The resin was filtered off, washed with dichloromethane then methanol and the filtrate evaporated to give a deep orange oil. The oil was taken up in dichloromethane, washed with 2M NaOH, 2M HCl then brine, dried and evaporated giving a pale brown oil. This was taken up in 50:50 ethyl acetate : hexane, filtered through celite, filtrate evaporated, taken up in ethyl acetate and washed further with 1M NaOH. The organic layer was separated, dried over Na$_2$SO$_4$, the solvent removed under reduced pressure and the residue columned in 50:50 ethyl acetate:

hexane to remove impurities. The product was then eluted with 9:1 dichloromethane : methanol to give a yellow oil, which crystallised on cooling. $^1$H NMR (400 MHz, CDCl$_3$): 1.15-1.3 (2H, m); 1.85-1.9 (1H, m); 2.6-2.7 (1H, m); 3-3.1 (1H, m); 3.7-3.8 (1H, m); 4.0 (2H, d, J 7 Hz); 4.15-4.25 (1H, m); 7.2 (1H, d, J 8 Hz); 7.75 (1H, d, J 2 Hz); 7.9 (1H, dd, J 2 and 8 Hz); 8 (1H, s).

N-Methyl-4-(2-methoxy-4-nitrophenoxymethyl) piperidine

A suspension of N-formyl-4-(2-methoxy-4-nitrophenoxymethyl)piperidine (1.24 g, 4.2 mmol) in tetrahydrofuran (5 mL) under nitrogen was stirred while adding the borane solution (8.4 mL of a 1M soln in THF) then heated to 60° C. for 2 h. Further borane solution (to a total of 5 equivalents) and 20 mL tetrahydrofuran (20 mL) were added and the mixture was heated overnight. The mixture was cooled, methanol (25 mL) was added carefully followed by dichloromethane. The mixture was then washed with brine, 2M NaOH, dried over Na$_2$SO$_4$ and solvent evaporated. The residue was dissolved in methanol, a few drops of acetic acid added and the mixture was heated under reflux for 3 days. Evaporation of the solvent and chromatography in 9:1 dichloromethane:methanol containing 1% triethylamine afforded the product as a brown solid. $^1$H NMR (400 MHz, dmso-d$_6$): 1.4-1.5 (2H, m); 1.85-2 (3H, m); 2-2.1 (2H, m); 2.8-3 (2H, m); 4.05 (3H, s); 4.15 (2H, d, J 7 Hz); 7.35 (1H, d, J 8 Hz); 7.9 (1H, d, J 2 Hz); 8.05 (1H, dd, J 2 and 8 Hz).

N-Methyl-4-(2-methoxy-4-nitrophenoxymethyl) piperidine

Catalytic reduction over Pd (10% C) in EtOH gave the aniline as a red-brown solid.

$^1$H NMR (400 MHz, CDCl$_3$): 1.3-1.5 (2H, m); 1.7-1.9 (3H, m); 2-2.1 (2H, m); 2.9-3 (2H, m); 3.4 (2H, broad s); 3.7 (2H, d, J 7 Hz); 3.75 (3H, s); 6.15 (1H, dd, J 1 and 7 Hz); 6.25 (1H, d, J 1 Hz); 6.65 (1H, d, J 7 Hz).

General Scheme G

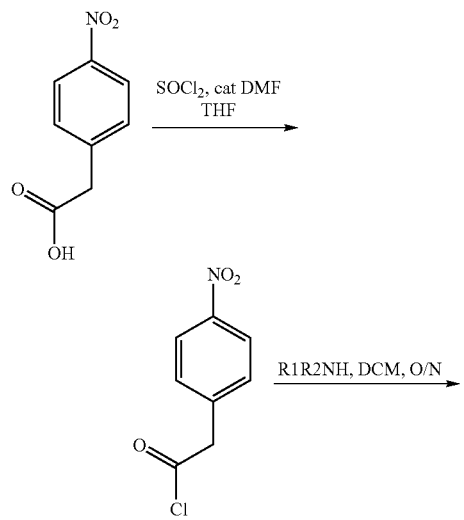

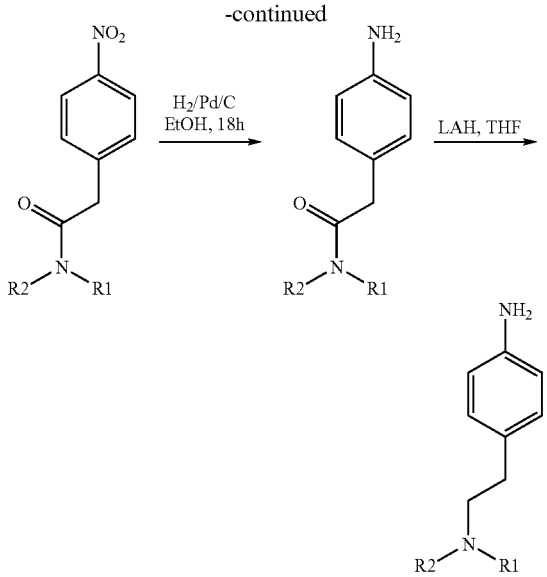

General Method G

1-Methyl-4-[(4-nitrophenyl)acetyl]piperazine

4-Nitrophenylacetic acid (2.00 g, 0.011 mol) was dissolved in anhydrous THF (20 mL) with gradual addition of thionyl chloride (1.03 mL, 0.0143 mol) and a catalytic amount of DMF (2 drops) at room temperature and stirred for 24 h. On completion, the reaction was quenched in situ with N-methylpiperazine (3.85 g, 0.038 mol) added dropwise in a solution of DCM (20 mL) at room temperature and stirred overnight to give a beige suspension. The solvent was removed in vacuo and the residue partitioned between DCM (30 mL) and sodium hydroxide (1N, 30 mL). The organic layer was washed twice, dried over sodium sulfate and filtered. Removal of the solvent in vacuo the title compound as an amber oil, which solidified on standing. LCMS:2.5 min; Rt 0.82 (m/z 264, M+H$^+$) 98%

$^1$H NMR: (400 MHz, CDCl$_3$); 2.28 (3H, s), 2.32 (2H, dd, J 5.03, 5.08), 2.39 (2H, t, J 5.13), 3.49 (2H, t, J 5.08), 3.67 (2H, t, J 5.03), 3.82 (2H, s), 7.42 (2H, d, J 8.78), 8.19 (2H, d, J 8.78).

4-(4-Methylpiperazin-1-yl)carbonylmethylaniline

A solution of 1-methyl-4-[(4-nitrophenyl)acetyl]piperazine(1.5 g, 5.70 mmol) in ethanol (30 mL) was reduced over palladium/charcoal (10% wt, 50% wet, 150 mg) with hydrogen under atmospheric pressure and room temperature for 18 h. The catalyst was separated by filtration through celite and the solvent evaporated to the title compound as a brown oil.
$^1$H NMR: (400 MHz, CDCl$_3$); 2.21 (2H, t, J 5.01), 2.24 (3H, s), 2.34(2H, t, J 5.13), 3.45 (2H, t, J 5.13), 3.61 (2H, s), 3.63-3.66 (2H, m), 6.64 (2H, d, J 8.56), 7.01 (2H, d, J 8.31).

4-[2-(4-Methyl-piperazin-1-yl)ethyl]aniline 4-(4-Methylpiperazin-1-yl)carbonylmethylaniline (596 mg, 2.55 mmol) was treated in anhydrous THF (20 mL) under nitrogen with lithium aluminium hydride (291 mg, 2.67 mmol) overnight. The reaction was quenched with water (3×0.29 mL), 15% sodium hydroxide (3×0.29 mL) and again water (3×0.29 mL). The resulting precipitate was removed by filtration. Evaporation of the filtrate afforded the title compound as an orange oil. LC:2.5 min; Rt 0.21(m/z 220, M+H+) 90%, $^1$HNMR: (400MHz, CDCl$_3$); 2.30 (3H, s), 2.40-2.73 (2H +8H, m), 2.69 (2H, m); 6.62 (2H, d, J 8.31), 6.99 (2H, d, J 8.31).

General Scheme H

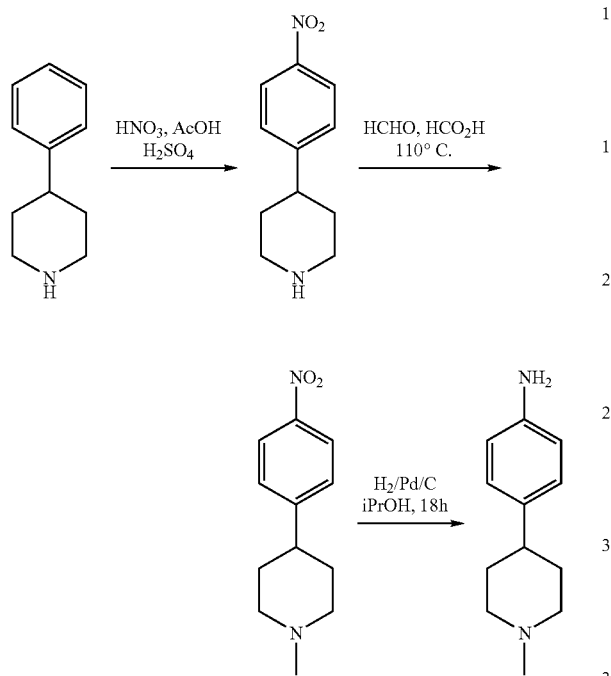

General Method H 4-(4-Nitrophenyl)piperidine

4-Phenylpiperidine (8 g, 49 mmol) was dissolved in 40 mL acetic acid and stirred with cooling below 25° C. while adding a solution of 2.64 mL sulphuric acid in 40 mL acetic acid. The solution was stirred at 20° C. while adding a solution of 2.08 mL 99% nitric acid in 20 mL acetic acid. Sulphuric acid (40 mL) was added without cooling, the temperature peaking at 58° C. When the solution had cooled to 25° C. it was added to 100 g ice/water and basified with a total of 150 g sodium hydrogen carbonate at 40° C. The mixture was then brought to pH 14 with 5M-sodium hydroxide solution. The mixture was extracted with dichloromethane (3×150 mL), dried with sodium sulphate and evaporated giving a pale yellow solid. Recrystallisation from a total of 180 mL cyclohexane (hot filtration) gave the product as pale beige solid. NMR δ 8.18 (d,2H), 7.40(d,2H), 3.21(m,2H), 2.77(m,3H), 1.82(m,3H), 1.68(m,2H).

1-Methyl-4-(4-nitrophenyl)piperidine 4-(4-Nitrophenyl)piperidine (515 mg) was added to 4 mL 90% formic acid and 1.5 mL formalin added. The solution was stirred and heated at 110° C. for 17 h, evaporated and the solids dissolved in 20 mL water. After basification to pH 14 with 5M sodium hydroxide solution the precipitated solid was extracted into t-butyl methyl ether (3×30 mL). Drying (sodium sulphate) and evaporating gave pure product as pale cream solid. NMR δ 8.15(d,2H), 7.39(d, 2H), 3.00(m,2H), 2.60(m,1H), 2.31(s, 3H), 2.08 (m, 2H), 1.86 (m, 4H).

4-(4-Aminophenyl)-1-methylpiperidine

Hydrogenation of the above compound in 30 mL isopropanol over 100 mg of 10% palladium on charcoal for 5 h, filtration and evaporation gave the pure product as cream solid. NMR δ 7.00(d, 2H), 6.63(d, 2H), 3.57(s, 2H), 2.98(m, 2H), 2.38(m, 1H), 2.30(s, 3H), 2.02(m, 2H),1.78(m, 4H).

General Scheme I

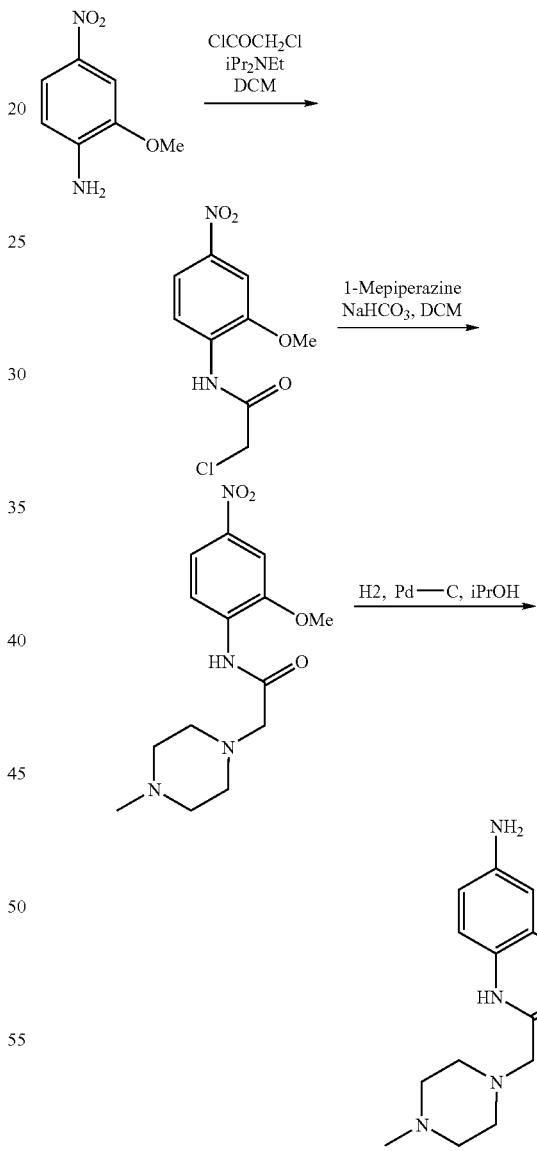

General Method I

N-(2-methoxy-4-nitrophenyl)chloroacetamide

2-Methoxy-4-nitroaniline (8.40 g, 50 mmol) was dissolved in 200 mL dichloromethane and stirred at 0° C. while adding diisopropylethylamine (6.45 g, 50 mmol) then a solution of chloroacetyl chloride (5.65 g, 50 mmol) in 50 mL dichloromethane. The mixture was stirred for 17 h at 20-25° C., evaporated and 300 mL ethyl acetate added. The solution was washed with 2×100 mL 2M hydrochloric acid then brine, dried (sodium sulphate) and evaporated. The residue dissolved in 200 mL warm toluene, charcoaled then chromatographed on 300 mL flash silica in a 10 cm sinter funnel. Elution with toluene and evaporation afforded a bright yellow oil which solidified on standing. NMR showed an 11:4 mixture of product and starting aniline—product δ 9.17(s, 1H), 8.56(m,1H), 7.94(m, 1H), 7.79(m, 1H), 4.22(s, 2H), 4.03(s, 3H). Used without further purification.

1-[(2-Methoxy-4-nitrophenyl)carbamoyl]methyl-4-methylpiperazine

The above product (3.06 g, containing 10 mmol of the chloroacetamide) was dissolved in 20 mL dichloromethane and 100 mL isopropanol. 1-Methylpiperazine (1.00 g, 10 mmol) was added followed by 4.20 g sodium hydrogen carbonate (50 mmol). The mixture was stirred at 20° C. for 4 h then left overnight. Next day the mixture was heated under reflux for 4 h, evaporated and the residue treated with 200 mL water/200 mL ethyl acetate. Further ethyl acetate was added to dissolve all the product. The ethyl acetate extracts were washed well with water then with 2M citric acid solution (3×40 mL). The acid extracts were washed with ethyl acetate (2×50 mL) then brought to pH 12 with 5M sodium hydroxide solution. The solid was collected and washed with water then dried in air giving the product as pale yellow needles. NMR δ 10.18(s, 1H), 8.59(m, 1H), 7.93(m, 1H), 7.78(m, 1H), 4.01(s, 3H), 3.20(s, 2H), 2.40-2.80(m, 8H), 2.50(s, 3H).

1-[(2-Methoxy-4-aminophenyl)carbamoyl]methyl-4-methylpiperazine

The above product was dissolved in 120 mL isopropanol, 300 mg 10% palladium on charcoal added and stirred under hydrogen for 6 h. Filtration and evaporation gave the product as cream solid. NMR δ 9.47(s, 1H), 8.09(m, 1H), 6.30(m, 2H), 3.83(s, 3H), 3.58(s 2H), 3.11(s, 2H), 2.30-2.70(m, 8H), 2.30(s, 3H).

General Scheme J

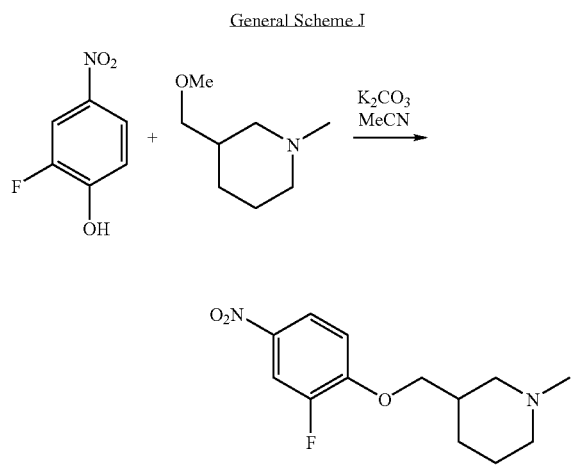

General Method J

Preparation of 3-(2-Fluoro-4-nitrophenoxymethyl)-1-methylpiperidine

3-Hydroxymethyl-1-methylpiperidine (2 g, 9.66 mmol) was dissolved in DCM (15 mL), the solution was cooled to 0° C. and methanesulfonyl chloride (0.9 mL, 11.6 mmol) was added dropwise. The reaction was then allowed to warm up to room temperature and left stirring for 24 h. After this time water (20 mL) was added to the reaction and the organic layer was separated, dried over $Na_2SO_4$, filtered and solvent removed to give a colourless oil. $^1$H NMR indicated a mixture of the starting piperidine and the desired product. This was then dissolved in acetonitrile (30 mL) along with 2-fluoro-4-nitrophenol (1.52 g., 9.66 mmol); potassium carbonate (2.67 g., 19.32 mmol) was added and the reaction was heated at 90° C. for 18 h, then allowed to cool to room temperature. The solids were filtered and solvent removed from the filtrate. This gave 3.5 g of an orange oil. Column chromatography (5% MeOH/DCM) gave a yellow solid which was shown to be a mixture of 2-fluoro-4-nitrophenol and 3-(2-fluoro-4-nitrophenoxymethyl)-1-methylpiperidine. The material was partitioned between DCM (30 mL) and saturated potassium carbonate solution (30 mL). The DCM layer was removed and washed with 5M HCl (20 mL). The acidic layer was then basified to pH 10 and extracted twice with DCM (30 mL). The organics combined, dried over $Na_2SO_4$, filtered and solvent removed to give 3-(2-fluoro-4-nitrophenoxymethyl)-1-methylpiperidine as a yellow oil. $^1$NMR (400 MHz, $CD_3OD$) 8.16-8.06 (2 H, m), 7.33 (1 H, t, J 8.8), 4.17 (1 H, m), 4.09 (1 H, m), 3.32 (1 H, d, J 10.8), 3.02 (1 H, t, J 11.5), 2.47 (3 H, s), 2.22 (3 H, m), 1.89 (3 H, m), 1.75 (1 H, m), 1.28 (1 H, m).

Alternatively, the nitro derivative was prepared as follows: 3,4-Difluoronitro phenol (3 g, 18.7 mmol) and 3-hydroxy-1-methylpiperidine (2.5 g, 19.3 mmol) were dissolved in dry THF (100 mL) under nitrogen. Sodium hydride (60%, 1 g, 25 mmol) was slowly added under positive nitrogen pressure. The resulting light yellow solution was heated at 60° C. for 2.5 h. The dark-red solution was left to cool to room temperature and quenched with a solution of acetic acid (0.3 mL, 5.2 mmol) in methanol (10 mL). Solvent was removed under reduced pressure to yield an orange solid that was purified by column chromatography using DCM: MeOH (75: 25) as eluent to yield 3-(2-fluoro-4-nitro phenoxymethyl)-1-methylpiperidine as an orange oil.

Catalytic hydrogenation as in general Method A afforded the aniline derivative.

Further examples of anilines include the following (NMR spectra at 400 MHz, in $CDCl_3$ unless otherwise stated):

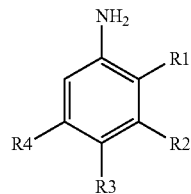

| Ex. | Method | R1 | R2 | R3 | R4 | MS | NMR |
|---|---|---|---|---|---|---|---|
| 1 | A (chloroalkyl phenol displacement) | H | H | 3-(dimethylamino)-ethoxy | H | 181 | 2.25 (6H, s); 2.65 (2H, t, J 7 Hz); 3.9 (2H, t, J 7 Hz); 6.5-7 (2H, m); 6.65-6.75 (2H, m) |
| 2 | A (chloroalkyl phenol displacement) | H | H | 3-(dimethylamino)-propoxy | | | See specific example |
| 3 | A (chloroalkyl phenol displacement) | H | OCH$_3$ | 2-((4-CH$_3$)piperazin-1-yl)ethoxy | OCH$_3$ | 296 | 2.25 (3H, s); 2.4-2.7 (8H, m); 2.75 (2H, t, J 7 Hz); 3.7 (6H, s); 3.9 (2H, t, J 7 Hz); 5.9 (2H, s) |
| 4 | A (chloroalkyl phenol displacement) | H | OCH$_3$ | 3-((4-CH$_3$)piperazin-1-yl)propoxy | OCH$_3$ | 310 | 1.8-1.9 (2H, m); 2.2 (3H, s); 2.3-2.6 (10H, m); 3.7 (6H, s); 3.85 (2H, t, J 7 Hz); 5.9 (2H, s) |
| 5 | A (chloroalkyl phenol displacement) | H | OCH$_3$ | 2-((4-CH$_3$)piperazin-1-yl)ethoxy | H | 266 | 2.35 (3H, s); 2.55-2.8 (10H, m); 3.7 (3H, s); 4 (2H, t, J 7 Hz); 6.1 (1H, dd, J 2 and 8 Hz); 6.2 (1H, d, J 2 Hz); 7.7 (1H, d, J 8 Hz) |
| 6 | A (chloroalkyl phenol displacement) | H | OCH$_3$ | 3-((4-CH$_3$)piperazin-1-yl)propoxy | H | 280 | 1.9-2.1 (2H, m); 2.35 (3H, s); 2.4-2.6 (10H, m); 3.8 (3H, s); 4 (2H, t, J 7 Hz); 6.2 (1H, dd, J 2 and 8 Hz); 6.3 (1H, d, J 2 Hz); 6.8 (1H, d, J 8 Hz) |
| 7 | A (chloroalkyl phenol displacement) | H | OCH$_3$ | OCH$_3$ | 2-((4-CH$_3$)piperazin-1-yl)ethoxy | 296 | 2.2 (3H, s); 2.3-2.5 (4H, m); 2.5-2.7 (4H, m); 2.8 (2H, t, J 7 Hz); 3.65 (3H, s); 3.75 (3H, s); 4 (2H, t, J 7 Hz); 5.8-5.85 (2H, m) |
| 8 | A (chloroalkyl phenol displacement) | H | OCH$_3$ | OCH$_3$ | 3-((4-CH$_3$)piperazin-1-yl)propoxy | 310 | 1.85-1.95 (2H, m); 2.2 (3H, s); 2.3-2.5 (10H, m); 3.65 (3H, s); 3.75 (3H, s); 3.95 (2H, t, J 7 Hz); 6.85-6.9 (2H, m) |

-continued

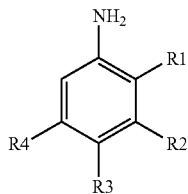

| Ex. | Method | R1 | R2 | R3 | R4 | MS | NMR |
|---|---|---|---|---|---|---|---|
| 9 | A (chloroalkyl phenol displacement) | H | OCH$_3$ | 2-(piperidino)-ethoxy | OCH$_3$ | 281 | 1.3-1.4 (2H, m) 1.5-1.6 (4H, m); 2.45-2.6 (4H, m), 2.75 (2H, t, J 7 Hz); 3.65 (6H, s); 3.95 (2H, t, J 7 Hz); 5.85 (2H, s) |
| 10 | A (phenol alkylation) | H | H | 2-(morpholino)ethoxy | H | 223 | 2.45-2.55 (4H, m); 2.7 (2H, t, J 7 Hz); 3.65-3.7 (4H, m), 3.95 (2H, t, J 7 Hz); 6.5-6.6 (2H, m); 6.65-6.7 (2H, m) |
| 11 | A (chloroalkyl phenol displacement) | H | OCH$_3$ | 2-(morpholino)ethoxy | OCH$_3$ | 283 | 2.5-2.55 (4H, m); 2.7 (2H, t, J 7 Hz); 3.6-3.7 (4H, m); 3.7 (6H, s); 4.95 (2H, t, J 7 Hz); 5.8 (2H, s) |
| 12 | A (chloroalkyl phenol displacement) | H | H | (S)-((1-CH$_3$)pyrrolidin-2-yl)methoxy | H | 207 | (dmso-d$_6$) 1.5-1.6 (1H, m); 1.6-1.65 (2H, m); 1.9-2 (1H, m); 2.15-2.25 (1H, m); 2.35 (3H, s); 2.5-2.6 (1H, m); 2.9-3 (1H, m); 4.65-4.7 (1H, m); 4.7-4.75 (1H, m); 6.45-6.5 (2H, m); 6.6-6.65 (2H, m) |
| 13 | A (chloroalkyl phenol displacement) | H | F | 3-((4-CH$_3$)piperazin-1-yl)propoxy | H | 268 | 1.8-1.9 (2H, m); 2.2 (3H, s); 2.3-2.55 (10H, m); 3.9 (2H, t, J 7 Hz); 6.3 (1H, m); 6.4 (1H, m); 6.7 (1H, m) |
| 14 | A (chloroalkyl phenol displacement) | H | F | 3-(piperidino)propoxy | H | 253 | 1.3-1.4 (2H, m); 1.4-1.5 (4H, m); 1.7-1.8 (2H, m); 2.25-2.4 (6H, m); 3.9 (2H, t, J 7 Hz); 6.25-6.3 (1H, m); 6.35-6.4 (1H, m); 6.75-6.85 (1H, m) |
| 15 | A (chloroalkyl phenol displacement) | H | F | 3-(diethylamino)-propoxy | H | 241 | 1.05 (6H, t, J 7 Hz); 1.9-2 (2H, m); 2.5-2.7 (6H, m); 4 (2H, t, J 7 Hz); 6.35-6.4 (1H, |

-continued

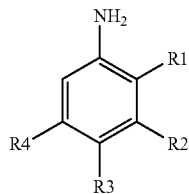

| Ex. | Method | R1 | R2 | R3 | R4 | MS | NMR |
|---|---|---|---|---|---|---|---|
| | | | | | | | m); 6.4-6.45 (1H, m); 6.8-6.9 (1H, m) |
| 16 | A (chloro-alkyl phenol displace-ment) | H | F | 2-((4-CH₃)-piper-azin-1-yl)ethoxy | H | 254 | 2.2 (3H, s); 2.3-2.4 (4H, m); 2.4-2.65 (4H, m), 2.75 (2H, t, J 7 Hz); 4 (2H, t, J 7 Hz); 6.25-6.3 (1H, m); 6.3-6.35 (1H, m); 6.75-6.85 (1H, m) |
| 17 | A (chloroal-kyl phenol displace-ment) | H | 3-(piper-idino)pro-poxy | H | H | 235 | 1.3-1.4 (2H, m); 1.45-1.55 (4H, m); 2.3-2.5 (6H, m); 3.9 (2H, t, J 7 Hz); 6.1-6.3 (3H, m); 6.9-7 (1H, m) |
| 18 | A (chloroal-kyl phenol displace-ment) | H | 3-((4-CH₃)-piperazin-1-yl)pro-poxy | H | H | 250 | 1.9-2 (2H, m); 2.3 (3H, s); 2.4-2.7 (10H, m); 4 (2H, m); 6.2-6.4 (3H, m); 7-7.1 (1H, m) |
| 19 | F (Mitsu-nobu) | H | OCH₃ | (R)-(pyrroli-din-2-yl)-methoxy | 323, 223 (as N-Boc pro-tected) | | (as N-Boc protected); (dmso-d₆): 1.4 (9H, broad s); 1.7-1.8 (2H, m); 1.8-2 (3H, m); 3.2-3.25 (2H, m); 3.65 (3H, s); 3.75-3.85 (2H, m); 4.7-4.8 (2H, broad s); 6 (1H, dd, J 2 and 8 Hz); 6.25 (1H, d, J 2 Hz); 6.65 (1H, d, J 8 Hz) |
| 20 | A (chloro-alkyl phenol displace-ment) | H | Cl | 2-(piper-idino)eth-oxy | H | 255 257 | 1.3-1.4 (2H, m); 1.5-1.6 (4H, m); 2.4-2.6 (4H, m); 2.8 (2H, t, J 7 Hz); 4.1 (2H, t, J 7 Hz); 6.55 (1H, dd, J 2 and 8 Hz); 7.7 (1H, d, J 2 Hz); 7.8 (1H, d, J 8 Hz) |
| 21 | A (chloro-alkyl phenol displace-ment) | H | F | 2-((4-iso-propyl)pi-perazin-1-yl)-ethoxy | H | 282 | 1.05 (6H, d, J 7 Hz); 2.5-2.7 (9H, m); 2.8 (2H, t, J 7 Hz), 4.1 (2H, t, J 7 Hz); 6.35-6.4 (1H, m); 6.45 (1H, m); 6.8-6.9 (1H, m) |

-continued

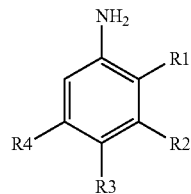

| Ex. | Method | R1 | R2 | R3 | R4 | MS | NMR |
|---|---|---|---|---|---|---|---|
| 22 | A (chloroalkyl phenol displacement) | H | OCH₃ | 2-((4-isopropyl)piperazin-1-yl)ethoxy | H | 294 | 1.05 (6H, d, J 7 Hz); 2.5-2.7 (9H, m); 2.8 (2H, t, J 7 Hz); 3.8 (3H, s); 4.1 (2H, t, J 7 Hz); 6.2 (1H, d, J 2 and 8 Hz); 6.3 (1H, d, J 2 Hz); 6.75 (1H, d, J 8 Hz) |
| 23 | A (chloroalkyl phenol displacement) | H | OCH₃ | 3-((4-isopropyl)-piperazin-1-yl)propoxy | H | 308 | 1.05 (6H, d, J 7 Hz); 1.9-2 (2H, m); 2.5-2.7 (11H, m); 3.4 (2H, broad s); 3.8 (3H, s); 4 (2H, t, J 7 Hz); 6.2 (1H, d; J 2 and 8 Hz); 6.3 (1H, d, J 2 Hz); 6.75 (1H, d, J 8 Hz) |
| 24 | A (chloroalkyl phenol displacement) | CH₃ | H | 3-((4-CH₃)piperazin-1-yl)propoxy | H | 264 | 1.9-2 (2H, m); 2.1 (3H, s); 2.35 (3H, s); 2.4-2.7 (10H, m); 4 (2H, t, J 7 Hz); 6.25-6.4 (2H, m); 6.9-7 (1H, m) |
| 25 | A (chloroalkyl phenol displacement) | CH₃ | H | 3-(piperidino)propoxy | H | 249 | 1.4-1.55 (2H, m); 1.6-1.7 (4H, m); 1.95-2.05 (2H, m); 2.1 (3H, s), 2.4-2.6 (6H, m); 4 (2H, t, J 7 Hz); 6.3-6.4 (2H, m); 6.9-7 (1H, m) |
| 26 | F (Mitsunobu) | H | OCH₃ | ((1-CH₃)-piperidin-4-yl)-methoxy | H | 251 | See specific example |
| 27 | F (Mitsunobu) | H | OCH₃ | 2-((1-CH₃)piperidin-4-yl)ethoxy | H | 265 | 1.2-1.35 (2H, m); 1.4-1.55 (1H, m); 1.65-1.75 (4H, m), 1.85-1.95 (2H, m); 2.2 (3H, s); 2.8-2.9 (2H, m); 3.7 (3H, s); 3.9 (2H, t, J 7 Hz); 6.15 (1H, dd, J 2 and 8 Hz); 6.2 (1H, d, J 2 Hz); 6.65 (1H, d, J 8 Hz) |
| 28 | F (Mitsunobu) | H | H | 2-((1-CH₃)piperidin-4-yl)ethoxy | H | 235 | 1.2-1.35 (2H, m); 1.4-1.55 (1H, m); 1.6-1.7 (4H, m); 1.85-1.95 (2H, |

-continued

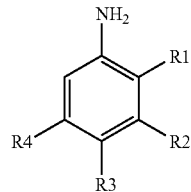

| Ex. | Method | R1 | R2 | R3 | R4 | MS | NMR |
|---|---|---|---|---|---|---|---|
|  |  |  |  |  |  |  | m); 2.2 (3H, s); 2.8-2.9 (2H, m); 3.8-3.9 (2H, m); 6.5-6.6 (2H, m); 6.7-6.8 (2H, m) |
| 29 | F (Mitsunobu) | H | H | (S)-(pyrrolidin-2-yl)methoxy | H | 293 193 | (as N-Boc protected); (dmso-d$_6$): 1.15 (9H, s), 1.4-1.7 (4H, m); 3-3.05 (2H, m); 3.4-3.45 (1H, m); 3.5-3.55 (2H, m); 4.4 (2H, broad s); 6.2-6.3 (2H, m); 6.4-6.5 (2H, m) |
| 30 | B (Halide displacement via alkoxy anion) | H | OCH$_3$ | 2-(isopropylamino)ethoxy | H |  | (as N-Boc protected) 1.15 (6H, d, J 7 Hz); 1.45 (9H, s); 3.35-3.5 (2H, m); 3.8 (3H, s); 3.9-4.1 (2H, m); 4.3-4.45 (1H, m); 6.2 (1H, dd, J 2 and 8 Hz); 6.3 (1H, d, J 2 Hz); 6.8 (1H, m) |
| 31 | B (Halide displacement via alkoxy anion) | H | Cl | 2-(isopropyl-amino)-ethoxy | H |  | (as N-Boc protected) 1.15 (6H, broad d, J 7 Hz); 1.45 (9H, s); 3.35-3.5 (2H, m); 3.9-4.1 (2H, m); 4.3-4.45 (1H, m); 6.5 (1H, dd, J 2 and 8 Hz); 6.7 (1H, d, J 2 Hz), 6.8 (1H, d, J 8 Hz) |
| 32 | C (Halide displacement) | ₐ——(H?) | OCH$_3$ | (4-CH$_3$)-piperazin-1-yl | H | 222 | 2.4 (3H, s); 2.5-2.7 (4H, m); 2.9-3.1 (4H, m); 3.8 (3H, s); 6.2-6.4 (2H, m); 6.8-6.9 (1H, m) |
| 33 | C (Halide displacement) | H | OCH$_3$ | 4-(tert-butoxycarbonyl)piperazin-1-yl | H |  | (as N-Boc protected) 1.4 (9H, s); 2.8-2.9 (4H, m); 3.5-3.6 94H, m); 3.75 (3H, s); 6.1- |

-continued

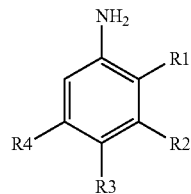

| Ex. | Method | R1 | R2 | R3 | R4 | MS | NMR |
|---|---|---|---|---|---|---|---|
| | | | | | | | 6.25 (2H, m); 6.65-6.8 (1H, m) |
| 34 | C (Halide displacement) | H | H | 4-(tert-butoxy-carbonyl)piperazin-1-yl | H | 278 | (as N-Boc protected) 1.4 (9H, s); 2.85-2.95 (4H, m); 3.4 (2H, broad s); 3.45-3.55 (4H, m); 6.6 (2H, d, J 8 Hz); 6.75 (2H, d, J 8 Hz) |
| 35 | C (Halide displacement) | H | H | 4-(iso-propyl)-piperazin-1-yl | H | 220 | 1.0 (6H, d, J 7 Hz); 2.55-2.7 (6H, m); 2.95-3.05 (4H, m, 3.35 (2H, broad s); 6.5-6.65 (2H, m); 6.7-6.8 (2H, m) |
| 36 | D (piperazine alkylation) | H | H | 4-(carb-amoyl-methyl)piperazin-1-yl | H | 235 | 2.6-2.7 (4H, m); 2.9-3.1 (4H, m); 3.4 (2H, broad s); 5.4 (1H, broad s); 6.55 (2H, d, J 8 Hz); 66.7 (2H, d, J 8 Hz); 7 (1H, broad s) |
| 37 | D (piperazine alkylation) | H | H | 4-(cyclo-hexyl-methyl)-piperazin-1-yl | H | 274 | 0.7-0.9 (2H, m); 1.1-1.3 (3H, m); 1.4-1.5 (1H, m); 1.6-1.8 (5H, m); 2.1 (2H, d, J 7 Hz); 2.4-2.55 (4H, m); 2.9-3 (4H, m); 3.35 (2H, broad s); 6.5-6.65 (2H, m); 7.8-7.9 (2H, m) |
| 38 | D (piperazine alkylation) | H | H | 4-(((3-Cl)-phenyl)-methyl)-piperazin-1-yl | H | 302/304 | See specific example |
| 39 | D (piperazine alkylation) | H | H | 4-(((3-cyano)-phenyl)-methyl)-piperazin-1-yl | H | 293 | 2.5-2.6 (4H, m); 2.9-3.1 (4H, m); 3.5 (2H, s); 6.5-6.6 (2H, m); 6.7-6.8 (2H, m); 7.3-7.4 (1H, m); 7.5-7.6 (2H, m); 7.6 (1H, m) |
| 40 | D (piperazine alkylation) | H | H | 4-(((3-OCH$_3$)-phenyl)-methyl)-piperazin-1-yl | H | | 2.5-2.6 (4H, m); 2.9-3.1 (4H, m); 3.45 (2H, s); 3.75 (3H, s); 6.5-6.6 (2H, m); 6.7-6.8 (3H, |

-continued

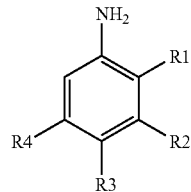

| Ex. | Method | R1 | R2 | R3 | R4 | MS | NMR |
|---|---|---|---|---|---|---|---|
| 41 | C (Halide displacement) | H | Cl | (4-CH₃)-piperazin-1-yl | H | 2.35 | m); 6.8-6.9 (2H, m); 7.2-7.3 (1H, m) (3H, s); 2.5-2.7 (4H, m), 2.9-3 (4H, m); 3.5 (2H, broad s); 6.5 (1H, dd, J 2 and 8 Hz); 6.7 (1H, d, J 2 hz); 6.9 (1H, d, J 8 Hz) |
| 42 | C (Halide displacement) | H | OCH₃ | 4-(iso-propyl)-piperazin-1-yl | H | | 1.1 (6H, d, J 7 Hz); 2.6-2.7 (6H, m); 2.9-3.1 (4H,m); 3.75 (3H, s); 6.15-6.3 (2H, m); 6.7 (1H, d, J 8 Hz) |
| 43 | C (Halide displacement) | H | F | 4-(iso-propyl)-piperazin-1-yl | H | | 1.1 (6H, d, J 7 Hz); 2.6-2.7 (6H, m); 2.9-3 (4H, m); 3.5 (H, broad s); 6.3-6.4 (2H, m); 6.7-6.8 (1H, m) |
| 44 | C (Halide displacement) | H | (4-CH₃)-piperazin-1-yl | H | H | 192 | 2.25 (3H, s); 2.45-2.5 (4H, m); 3.1-3.2 (4H, m), 3.6 (2H, broad s); 6.1 (1H, dd, J 2 and 8 Hz); 6.2 (1H, m; 6.3 (1H, d, J 2 and 8 Hz); 6.95 (1H, t, J 8 Hz) |
| 45 | C (Halide displacement) | CH₃ | H | (4-CH₃)-piperazin-1-yl | H | 206 | 2.1 (3H, s); 2.3 (3H, s); 2.5-2.6 (4H, m); 2.9-3.1 (4H, m); 6.5-6.6 (1H, m); 6.6-6.7 (2H, m) |
| 46 | D (piperazine alkylation) | H | H | (4-(2-dimethyl amino-ethyl))-piperazin-1-yl | H | 249 | 2.2 (6H, s); 2.3-2.4 (2H, m); 2.4-2.5 (2H, m); 2.5-2.6 (4H, m); 2.95-3.05 (4H, m); 6.55 (2H, d, J 8 Hz); 6.75 (2H, d, J 8 Hz) |
| 47 | D (piperazine alkylation) | H | H | (4-((2-methoxy)ethyl))-piperazin-1-yl | H | | 2.5-2.6 (6H, m); 2.95-3.05 (4H, m); 3.3 (3H, s); 3.5 (2H, t, J 7 Hz); 6.55 (2H, d, J 8 Hz); 6.75 (2H, d, J 8 Hz) |
| 48 | D (piperazine | H | H | (4-(3-dimethyl | H | | See specific example |

-continued

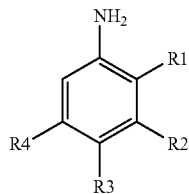

| Ex. | Method | R1 | R2 | R3 | R4 | MS | NMR |
|---|---|---|---|---|---|---|---|
| | alkylation) | | | aminopropyl))piperazin-1-yl | | | |
| 49 | E (amide formation) | H | H | (N-(2-diethyl-amino)-ethyl)-(N-methyl))carbamoyl | H | 250 | dmso-d$_6$: 0.8-1.0 (6H, m); 2.3-2.6 (6H, m); 3.0 (3H, broad s); 3.35-3.5 (2H, m); 5.45 (2H, broad s); 6.5 (2H, d, J 8 Hz); 7.1 (2H, d, J 8 Hz) |
| 50 | E (amide formation) | H | (N-(2-dimethyl amino)-ethyl)carbamoyl | H | H | 208 | See specific example |
| 51 | E (amide formation) | H | H | (N-(2-diethyl-amino)-ethyl)-(N-methyl))carbamoyl | H | 250 | dmso-d$_6$: 0.8-1.0 (6H, 2 broad m); 2.2-2.8 (4H, 2 broad m); 2.9-3.0 (3H, 2 broad s); 3.2-3.5 (2H, 2 broad m); 5.2 (2H, broad s); 6.4 (1H, d, J 8 Hz); 6.5 (1H, d, J 2 Hz); 6.6 (1H, dd, J 2 and 8 Hz); 7.05 (1H, m) |
| 52 | G (amide reduction) | H | H | 2-(diethylamino)ethyl | H | | 1.0-1.1 (6H, m); 2.5-2.75 (8H, m); 3.6 (2H, bs); 6.62 (2H, d, J 8.4); 6.98 (2H, d, J 8.4) |
| 53 | A | H | H | (2-(4-methylpiperazino)ethoxy | H | 236 | 2.3 (3H, s); 2.3-2.7 (8H, m); 2.75 (2H, t, J 7 Hz)); 3.95 (2H, t J 7 Hz); 6.5-6.6 (2H, m); 6.7-6.8 (2H, m) |
| 54 | C | H | F | (4-methylpiperazino) | H | 210 | 2.25 (3H, s); 2.45-2.55 (4H, m); 3.85-2.95 (4H, m), 3.55 (2H, bs); 6.25-6.35 (2H, m); 6.75-6.85 (1H, m) |
| 55 | A | H | F | 4-(2-(piperidino)ethoxy) | H | 239 | 1.35-1.45 (2H, m); 1.55-1.65 (4H, m); 2.45-2.5 (4H, m); 2.7 (2H, t, J 7 Hz); 3.4-3.5 (2H, bs); 4.0 (2H, t, J 7 Hz); 6.35-6.45 (1H, |

-continued

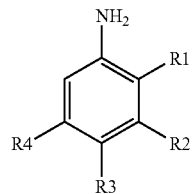

| Ex. | Method | R1 | R2 | R3 | R4 | MS | NMR |
|---|---|---|---|---|---|---|---|
| 56 | C | H | OCHF₂ | (4-methylpi-perazino) | H | 258 | m); 6.5-6.55 (1H, m); 6.7-6.8 (1H, m) 2.4-2.5 (4H, m); 3.85-3.95 (4H, m); 3.5 (2H, bs); 6.4-6.45 (2H, m); 6.6 (1H, t, J 65 Hz); 6.75-6.85 (1H, m) |
| 57 | F Boc deriv-ative | H | OCH₃ | 2-((1-tert-butoxycar-bonyl)pyr-rolidin-2-yl)metho-xy | H | 323 267 223 | (dmso-d₆) 1.3-1.4 (9H, m); 1.65-1.75 (1H, m), 1.8-1.95 (3H, m); 3.15-3.25 (1H, m); 3.65-3.75 (1H, m); 3.7 (3H, s); 3.8-3.9 (2H, m); 4.7 (2H, bs); 6.0 (1H, dd, J 2 and 8 Hz), 6.2 (1H, d, J 2 Hz); 6.6 (1H, d, J 8 Hz) |
| 58 | C | H | Cl | (4-isopropyl piperazin-o) | H |  | 1.2 (6H, d, J 7 Hz); 2.8-2.9 (4H, m); 2.9-3.0 (1H, m); 3.0-3.2 (4H, m); 3.5 (2H, bs); 6.5 (1H, dd, J 2 and 8 Hz); 6.7 (1H, d, J 2 Hz); 6.85 (1H, d J 8 Hz) |
| 59 | E | H | (2-dimethyl aminoeth-yl)sulfam-oyl) | H | H | 244 | 2.0 (6H, s); 2.2-2.3 (2H, m); 2.85-2.95 (2H, m); 6.65-6.75 (1H, m); 6.95-7.05 (2H, m); 7.05-7.15 (1H, m) |
| 60 | A | H | Cl | 2-(4-isopropyl piperazin-o)ethoxy | H | 298 | 1.3 (6H, d, J 7 Hz); 2.85-3.05 (10H, m); 3.15 (1H, sectuplet, J 7 Hz); 4.1 92H, t, J 7 Hz); 6.65 (1H, dd, J 2 and 8 Hz); 6.8 (1H, d, J 8 Hz); 6.85 (1H, d, J 8 Hz) |
| 61 | C | H | H | ((1,2-dimethyl) piperazin-4-yl | H | 206 | (dmso-d₆) 1.0 (3H, d, J 6 Hz); 2.05-2.15 (1H, m); 2.2 (3H, s); 2.15-2.25 (2H, m); 2.55-2.65 (1H, m); 2.7-2.8 (1H, m); 3.15-3.25 (2H, m); |

-continued

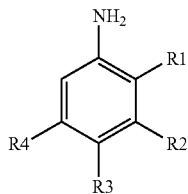

| Ex. | Method | R1 | R2 | R3 | R4 | MS | NMR |
|---|---|---|---|---|---|---|---|
| | | | | | | | 6.5 (2H, d, J 8 Hz); 6.7 (2H, d, J 8 Hz) |
| 62 | H | H | H | 1-methylpi-perid-4-yl | H | 191 | See specific example |
| 63 | H | H | H | 1-(isopropyl)pi-perid-4-yl | H | 219 | 1.1 (6H, d, J 7 Hz); 1.7-1.8 (2H, m); 11.8-1.9 (2H, m), 2.2-2.3 (2H, m); 2.35-2.45 (1H, m); 2.75-2.85 (1H, m); 3.0-3.1 (2H, m); 3.6 (2H, bs); 6.7 (2H, d, J 8 Hz); 7.05 (2H, d, J 8 Hz) |
| 64 | H | H | H | 1-(3-(N,N-dimethyl aminopropyl)piperid-4-yl | H | 262 | 1.7-1.9 (6H, m); 2.05-2.15 (2H, m); 2.3 (6H, s); 2.3-2.4 (2H, m); 2.4-2.5 (3H, m); 3.05-3.15 (2H, m); 3.6 (2H, bs), 6.65 (2H, d, J 8 Hz); 7.05 (2H, d, J 8 Hz) |
| 65 | I | H | OCH$_3$ | (4-methylpiperazino)methylcarbonylamino | H | 279 | See specific example |
| 66 | A | H | F | (3-(1-morpholino)propoxy | H | 255 | 1.9-2.0 (2H, m); 2.4-2.45 (4H, m); 2.5 (2H, t, J 7.5 Hz); 3.5 (2H, bs); 3.65-3.75 (4H, m); 4.0 (2H, t, J 7.5 Hz); 6.33-6.38 (1H, m); 6.45 (1H, dd, J 2.5 and 12.5); 6.8 (1H, t, J 9 Hz) |
| 67 | A | H | F | (3-(1-morpholino)ethoxy | H | 241 | (dmso-d$_6$) 2.4-2.5 (4H, m); 2.6 (2H, t, J 5.6 Hz); 3.54-3.6 (4H, m); 3.96 (2H, t, J 5.6 Hz); 6.27-6.35 (1H, m); 6.39 (1H, dd, J 2.5 and 13 Hz); 6.84 (1H, dd J 8.5 and 13 Hz) |
| 68 | A | H | F | 2-(1-pyrrolidino)ethoxy | H | 225 | (dmso-d$_6$) 1.6-1.7 (4H, m); 2.72 (2H, t, J 5.8 Hz), |

-continued

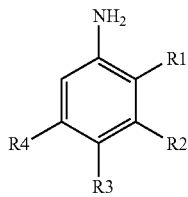

| Ex. | Method | R1 | R2 | R3 | R4 | MS | NMR |
|---|---|---|---|---|---|---|---|
| | | | | | | | 3.15-3.35 (2H, m); 3.45-3.55 (2H, m); 3.95 (2H, t, J 5.8 Hz); 6.25-6.3 (1H, m); 6.39 (1H, dd, J 2.5 and 13 Hz); 6.83 (1H, t, J 9.4 Hz) |
| 69 | J | H | F | (1-methylpi-peridin-3-yl)metho-xy | H | 239 | (MeOH-$d_4$) 1.05-1.15 (1H, m); 1.6-1.7 (1H, m); 1.7-1.8 (2H, m); 1.9-2.0 (1H, m); 2.0-2.15 (2H, m), 2.33 (3H, s); 2.85-2.95 (1H, m); 3.05-3.15 (1H, m); 3.75 (1H, dd, J 7.5 and 9.5); 3.84 (1H, dd, J 5.5 and 9.5); 6.40-6.45 (1H, m); 6.51 (1H, dd, J 2.5 and 13 Hz); 6.84 (1H, t, J 9.5 Hz) |
| 70 | A | H | F | 3-(1-pyrrolidi-no)propo-xy | H | 239 | 1.7-1.8 (4H, m); 1.95-2.05 (2H, m); 2.45-2.55 (4H, m), 2.6 (2H, t, J 7 Hz); 3.5 (2H, bs); 4.0 (2H, t, J 7 Hz); 6.33-6.37 (1H, m); 6.45 (1H, dd, J 2.5 and 13 Hz); 6.80 (1H, t, J 9 Hz) |
| 71 | J | H | F | (octahy-dro-2H-quinolizin-1-yl)metho-xy | H | 279 | (dmso-$d_6$) 1.1-1.8 (9H, m); 1.9-2.0 (3H, m); 2.7-2.8 (2H, m); 3.9-4.0 (1H, m); 4.05-4.15 (1H, m); 4.9 (1H, bs); 6.35-6.4 (1H, m); 6.45-6.5 (1H, m); 6.85-6.95 (1H, m) |
| 72 | J Boc deriv-ative | H | F | (1-(tert-butoxycar-bonyl)pi-peridin-3-yl)metho-xy | H | 225, 325 | (dmso-$d_6$) 1.5-1.6 (1H, m); 1.65-1.8 (2H, m); 2.75-2.85 (2H, m); 3.65-3.8 (4H, m); 3.8-4.05 (2H, m); 5.0 (2H, bs); 6.25-6.30 (1H, m); |

-continued

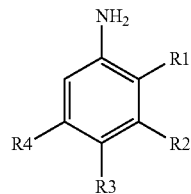

| Ex. | Method | R1 | R2 | R3 | R4 | MS | NMR |
|---|---|---|---|---|---|---|---|
| 73 | A | H | F | 2-(1-tert-butoxycarbonyl)piperazin-4-yl)ethoxy | H | 340 | 6.39 (1H, dd, J 2.5 and 13 Hz); 6.83 (1H, dd, J 9.1 and 9.8 Hz) (dmso-d₆) 1.45 (9H, s); 2.4-2.5 (4H, m); 2.65 (2H, t, J 6.5 Hz); 3.25-3.35 (4H, m), 4.0 (2H, t, J 6.5 Hz); 4.95 (2H, bs); 6.25-6.35 (1H, m); 6.4 (1H, dd, J 2.5 and 13 Hz); 6.85 (1H, t, J 9 Hz) |
| 74 | D | H | H | (4-(2-tert-butoxycarbonylamino)-ethyl)piperazin-1-yl | H | | See specific example |
| 75 | D | H | H | (4-(2-N-tert-butoxycarbonyl-N-ethylamino)ethyl)piperazin-1-yl | H | | See specific example |
| 76 | F | H | F | (N-tert-butoxycarbonylpyrrolidin-2-(R)-yl)methoxy | H | 311 | 1.45 (9H, s); 1.8-1.9 (1H, m), 1.9-2.1 (2H, m); 2.1-2.2 (1H, m); 3.25-3.45 (2H, m); 3.75-4 (1H, m); 4.0-4.2 (2H, m); 6.3-6.4 (1H, m); 6.4-6.5 (1H, m); 6.8-6.95 (1H, m) |
| 77 | F | H | F | (N-tert-butoxycarbonylpyrrolidin-2-(S)-yl)methoxy | H | 311 | 1.45 (9H, s); 1.8-1.9 (1H, m); 1.9-2.1 (2H, m); 2.1-2.2 (1H, m); 3.25-3.45 (2H, m); 3.55 (2H, bs); 3.75-4 (1H, m); 4.0-4.2 (2H, m); 6.3-6.4 (1H, m); 6.4-6.5 (1H, m); 6.8-6.95 (1H, m) |
| 78 | A | H | F | 4-(1-imidazol-yl)buthoxy | H | | 1.7-1.85 (2H, m); 1.95-2.1 (2H, m); 3.95 |

-continued

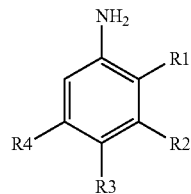

| Ex. | Method | R1 | R2 | R3 | R4 | MS | NMR |
|---|---|---|---|---|---|---|---|
| | | | | | | | (2H, t, J 7 Hz); 4.05 (2H, t, J 7 Hz); 6.45 (1H, m); 6.55 (1H, dd, J 2.5 and 13 Hz); 6.75 (1H, t, J 9.5 Hz); 6.9 (1H, s); 7.1 (1H, s); 7.5 (1H, s) |
| 79 | C | H | F | (1,2-dimethyl)piperazin-4-yl | H | 224 | See specific synthesis |
| 80 | C | H | F | (1,2,6-rimethyl)piperazin-4-yl | H | 238 | 1.15 (6H, d, II 7 Hz); 2.3 (3H, s); 2.4-2.5 (2H, m); 2.5-2.6 (2H, m); 3.1-3.2 (2H, m); 3.55 (2H, bs); 6.3-6.5 (2H, m), 6.8 (1H, t, J 9.5 Hz) |
| 81 | G | H | H | 2-(4-methylpiperazino)ethyl | H | | See specific synthesis |
| 82 | G | H | H | (4-methylpiperazino)carbonyl methyl | H | | See specific synthesis |
| 83 | G | H | H | 2-(1,2-dimethyl piperazi-4-yl)ethyl | H | 234 | 1.15 (3H, d, J 7.5 Hz); 1.85-1.95 (1H, m); 2.1-2.25 (1H, m); 2.25-2.4 (1H, m); 2.3-2.4 (1H, m) 2.5-2.6 (2H, m); 2.65-2.75 (2H, m); 2.8-2.9 (2H, m); 2.9-3.0 (2H, m); 3.6 (2H, bs); 6.65 (2H, d, J 8.5); 7.0 (2H, d, J 8.5) |
| 84 | G | H | H | (1,2-dimethyl piperazin-4-yl)carbonylmethyl | H | 248 | 0.95 and 1.05 (3H, two d, J 7 Hz); 1.9-2.1 (1H, m), 2.1-2.2 (1H, m); 2.2 (3H, s); 2.4-2.6 (1H, m); 2.7-3.0 (1H, m); 3.1-3.3 (1H, m); 3.6 (2H, s); 3.6-3.7 (1H, m), 4.3-4.45 (1H, m); 6.6 (2H, d, J 8.5 Hz); 7.0 (2H, d, J 8.5 Hz) |

-continued

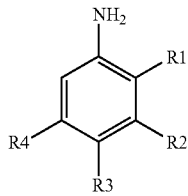

| Ex. | Method | R1 | R2 | R3 | R4 | MS | NMR |
|---|---|---|---|---|---|---|---|
| 85 | A | H | F | (4-(2-methoxyethyl)piperazino)-propoxy | H | | 1.9-2.0 (2H, m); 2.4-2.7 (12H, m); 3.4 (3H, s); 3.5-3.6 (4H, m), 3.95-4.1 (2H, m); 6.3-6.4 (1H, m); 6.45 (1H, dd, J 2.5 and 13 Hz); 6.8 (1H, t, J 9.5 Hz) |
| 86 | A | H | F | (4-(2-N,N-dimethylaminoethyl)piperazino)propoxy | H | | 1.9-2.0 (2H, m); 2.3 (6H, s); 2.4-2.7 (14H, m), 3.6 (2H, bs); 3.95-4.1 (2H, m); 6.3-6.4 (1H, m); 6.45 (1H, dd, J 2.5 and 13 Hz); 6.8 (1H, t, J 9.5 Hz) |

Method K

General method for the synthesis of 4-aminoanilines of type K.

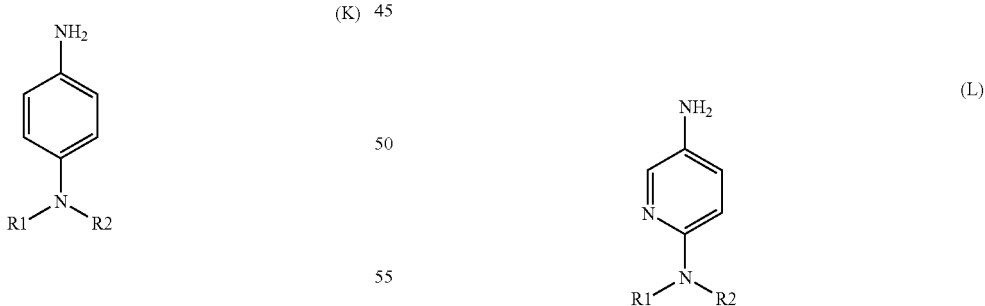

Step 1: A solution of 4-fluoronitrobenzene (1.41 g, 1.06 mL, 0.01 mol), N,N-diisopropylethylamine (1.1 equiv), and amine (1.1 equiv) in N,N-dimethylform-amide (8-10 mL) was heated at 100° C. for 48 h in a sealed tube. The reaction mixture was cooled to room temperature and concentrated. The residue was purified via column chromatography on silica gel (gradient elution with 0 to 10% methanol-dichloromethane) to afford the nitroaniline.

Step 2: 10% Palladium on carbon (0.05 g) was added to a solution of the nitroaniline (0.001 mol) in ethanol (50 mL) under a H$_2$(g) atmosphere (via balloon). The reaction mixture stirred at r.t. overnight and was then filtered through celite. The filtrate was concentrated to afford a dark yellow oil.

Method L

General method for the synthesis of 2,5-diaminopyridines of type L.

Step 1: A solution of 2-chloro-5-nitropyridine (0.317 g, 1.06 mL, 0.002 mol), N,N-diisopropylethylamine (1.1 equiv), and amine (1.1 equiv) in acetonitrile (40 mL) was refluxed for 24 h. The reaction mixture was cooled to room temperature and concentrated. The brown residue was used without purification.

Step 2: The diaminopyridine was prepared from the aminonitropyridine using the procedure in step 2 of method K.

Method M

General method for the synthesis of 4-aminoalkoxyanilines of type M.

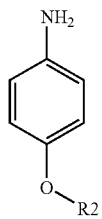
(M)

Step 1: A solution of 4-fluoronitrobenzene (0.141 g, 0.106 mL, 0.001 mol), aminoalcohol (1.1 equiv) in tetrahydrofuran (8-10 mL) was cooled to 0° C. in a sealed tube. A solution of KHMDS (0.5 M in toluene) was added dropwise, and the reaction mixture was allowed to reach room temperature. The mixture was partitioned between sat. aq. $K_2CO_3$ and ethylacetate. The organic layer was separated, dried over anhydrous $Na_2SO_4$, and concentrated. The residue was purified via column chromatography on silica gel (gradient elution with 0 to 10% methanol-dichloromethane) to afford the alkoxynitrobenzene.

Step 2: The alkoxyaniline was prepared from the alkoxynitrobenzene using the procedure in step 2 of method K.

Method N

General method for the synthesis of 4-[β-aminoalcohol]-alkoxyanilines of type N

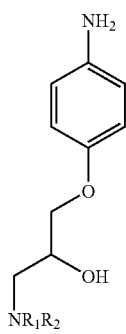
(N)

Step 1: A solution of 1,2-epoxy-3-(4-nitrophenoxy)propane (1.95 g, 0.01 mol), N,N-diisopropylethylamine (1.1 equiv), and amine (1.1 equiv) in methanol (60 mL) was refluxed for 24 h. The reaction mixture was cooled to room temperature and concentrated. The residue was purified via column chromatography on silica gel (gradient elution with 0 to 20% methanol-dichloromethane) to afford the aminoalkoxynitrobenzene.

Step 2: The aminoalkoxyaniline was prepared from the alkoxynitrobenzene using the procedure in step 2 of method K.

Table of anilines made.

| Aniline | MW | (MH+) | Method |
|---|---|---|---|
| | 176.26 | 177 | K |
| | 190.29 | 191 | K |
| | 205.31 | 206 | K |
| | 219.33 | 220 | K |

-continued

| Aniline | MW | (MH+) | Method |
|---|---|---|---|
| 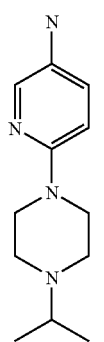 | 205.31 | 206 | K |
| 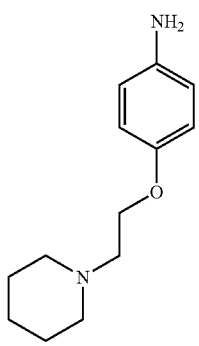 | 220.32 | 221 | L |
| 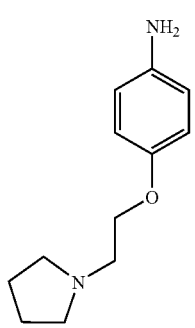 | 220.32 | 221 | M |
| 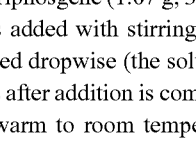 | 206.29 | 207 | M |

-continued

| Aniline | MW | (MH+) | Method |
|---|---|---|---|
| 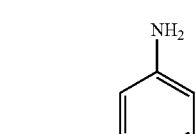 | 206.29 | 207 | M |
| 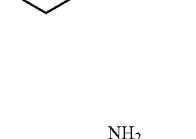 | 222.29 | 223 | M |
| 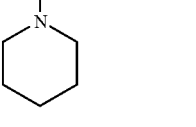 | 250.34 | 251 | N |

General Method for the Preparation of Chloroformates.

2,6-Dimethylphenylchloroformate

A solution of 2,6-dimethylphenol (1.2 g, 10 mmol) in dichloromethane (20 ml) was cooled to 0° C., and a solution of triphosgene (1.07 g, 3.6 mmol) in 15 mL dichloromethane was added with stirring. Pyridine (0.80 ml, 10 mmol) was added dropwise (the solution goes bright yellow then colorless after addition is complete), and the reaction was allowed to warm to room temperature overnight. The mixture was diluted with ethyl acetate and partitioned between ethyl acetate and 1 N HCl. The organic phase was separated and washed with 1 N HCl and brine, dried over anhydrous sodium sulfate, filtered, and concentrated to afford a yellow oil. The product was used without purification.

4-(3-Piperidin-1-yl-propoxy)-phenylamine 4-(3-piperidin-1-yl-propoxy)-phenylamine was prepared according to the method described in WO 03/018021.

Analytical Methods:

Unless otherwise indicated all HPLC analyses were run on an HP-1000 or HP-1050 system with an HP Zorbax SB-$C_{18}$ (5µ) reverse phase column (4.6×150 mm) run at 30° C. with a flow rate of 1.00 mL/min. The mobile phase used solvent A ($H_2O$/0.1% TFA) and solvent B ($CH_3CN$/0.1% TFA) with a 20 min gradient from 10% to 90% $CH_3CN$. The gradient was followed by a 2 min return to 10% $CH_3CN$ and a 3 min flush.

LC-MS Methods:

Method A:

Samples were run on an HP-1100 system with an HP Zorbax SB-$C_8$ (5µ) reverse phase column (4.6×50 mm) run at 30° C. with a flow rate of 0.75 ML/min. The mobile phase used solvent A ($H_2O$/0.1% AcOH) and solvent B ($CH_3CN$/0.1% AcOH) with a 10 min gradient from 10% to 90% $CH_3CN$. The gradient was followed by a 1 min return to 10% $CH_3CN$ and a 2 min flush.

Method B:

Samples were run on an HP-1100 system with an HP Zorbax SB-$C_8$ (5µ) reverse phase column (4.6×50 mm) run at 30° C. with a flow rate of 1.5 mL/min. The mobile phase used solvent A ($H_2O$/0.1% AcOH) and solvent B ($CH_3CN$/0.1% AcOH) with a 5 min gradient from 10% to 90% $CH_3CN$. The gradient was followed by a 0.5 min return to 10% $CH_3CN$ and a 1.5 min flush.

Proton NMR Spectra:

Unless otherwise indicated all $^1H$ NMR spectra were run on an Varian series Mercury 300 or 400 MHz instrument. All observed protons are reported as parts per million (ppm) downfield from tetramethylsilane (TMS) or other internal reference in the appropriate solvent indicated.

EXAMPLE 1

2,6-Dimethylphenyl 2-((4-((2-(dimethylamino)ethyl)oxy)phenyl)-amino)-4-pyrimidinyl(phenylmethyl)carbamate Step A: Benzyl-(2-chloropyrimidin-4-yl)amine A solution of 2,4-dichloropyrimidine (0.500 g, 3.36 mmol) in isopropanol (10 mL) was cooled to 0° C., and benzylamine (0.360 g, 0.37 mL, 3.36 mmol) was added. N,N-Diisopropylethylamine (0.434 g, 0.58 mL, 3.4 mmol) was added and the mixture was allowed to warm to room temperature over 15 h. The resulting white suspension was concentrated to afford a white solid. This material was purified via column chromatography on silica gel (gradient elution with 0-50% ethyl acetate-hexane) to afford benzyl-(2-chloropyrimidin-4-yl)amine as a white solid. MS ($MH^+$) 220.1; Calculated 219.68 for $C_{11}H_{10}ClN_3$.

Step B: Benzyl-(2-chloropyrimidin-4-yl)carbamic acid 2,6-dimethylphenyl ester

Benzyl-(2-chloropyrimidin-4-yl)amine (0.250 g, 1.14 mmol) was added to a solution of 2,6-dimethylphenylchloroformate (0.210 g, 1.14 mmol) in tetrahydrofuran (2 mL). N,N-Diisopropylethylamine (0.147 g, 0.20 mL, 1.1 mmol) was added and the mixture stirred at room temperature for 17 h. The resulting orange suspension was diluted with ethyl acetate and the mixture was partitioned between ethyl acetate and saturated sodium carbonate solution. The organic phase was separated and washed with brine, dried over anhydrous sodium sulfate, filtered, and concentrated to afford an orange oil. This oil was purified via column chromatography on silica gel (gradient elution with 0-25% ethyl acetate-hexane) to afford benzyl-(2-chloropyrimidin-4-yl)carbamic acid 2,6-dimethylphenyl ester as a white solid. MS ($MH^+$) 368; Calculated 367.84 for $C_{20}H_{18}ClN_3O_2$.

Step C: 2,6-dimethylphenyl 2-((4-((2-(dimethylamino)ethyl)oxy)phenyl)amino)-4-pyrimidinyl(phenylmethyl)carbmate A resealable tube was charged with the benzyl-(2-chloropyrimidin-4-yl)carbamic acid 2,6-dimethylphenyl ester (0.093 g, 0.253 mmol), 4-(2-dimethylaminoethoxy)-phenylamine (0.050 g, 0.278 mmol), and isopropanol (4 mL). Trifluoroacetic acid (0.072 g, 0.049 mL, 0.633 mmol) was added and the system was flushed with argon. The tube was sealed and the mixture was heated at 100° C. for 20 h. The reaction mixture was cooled to room temperature and concentrated to afford a pale purple oil. The oil was purified via column chromatography (gradient elution with 0-100% dichloromethane-(90: 10:1, dichloromethane/methanol/ammonium hydroxide)) to afford 2,6-dimethylphenyl 2-((4-((2-(dimethylamino)ethyl)oxy)phenyl)amino)-4-pyrimidinyl (phenylmethyl)carbamate as a white solid. MS ($MH^+$) 512.3; Calculated 511.62 for $C_{30}H_{33}N_5O_3$.

EXAMPLE 2

2,6-Dimethylphenyl(2,5-bis(methyloxy)phenyl)methyl(2-((4-((2-(dimethylamino)ethyl)oxy)phenyl)amino)-4-pyrimidinyl)carbamate Step A: (2-Chloropyrimidin-4-yl)-(2,5-dimethoxybenzyl) amine(2-Chloropyrimidin-4-yl)-(2,5-dimethoxybenzyl) amine was prepared as a white solid using the procedure outlined in the preparation of benzyl-(2-chloropyrimidin-4-yl)amine. MS (MH+) 280; Calculated 279.73 for $C_{13}H_{14}ClN_3O_2$.

Step B: (2-Chloropyrimidin-4-yl)-(2,5-dimethoxybenzyl) carbamic acid 2,6-dimethylphenyl ester (2-Chloropyrimidin-4-yl)-(2,5-dimethoxybenzyl)carbamic acid 2,6-dimethylphenyl ester was prepared as a white solid using the procedure outlined in the preparation of benzyl-(2-chloropyrimidin-4-yl)carbamic acid 2,6-dimethylphenyl ester. MS ($MH^+$) 428; Calculated 427.89 for $C_{22}H_{22}ClN_3O_4$.

Step C: 2,6-dimethylphenyl(2,5-bis(methyloxy)phenyl) methyl(2-((4-((2-(dimethylamino)ethyl)oxy)phenyl) amino)-4-pyrimidinyl)carbamate A resealable tube was charged with the (2-chloropyrimidin-4-yl)-(2,5-dimethoxybenzyl)carbamic acid 2,6-dimethylphenyl ester (0.200 g, 0.467 mmol), 4-(2-dimethylaminoethoxy)phenylamine (0.088 g, 0.490 mmol), tris(dibenzylidene-acetone)-di-palladium (0.017 g, 0.019 mmol), 4,5-bis-diphenylphosphanyl-9,9-dimethyl-9H-xanthene (0.032 g, 0.056 mmol), and sodium carbonate (0.069 g, 0.653 mmol). The system was flushed with argon and toluene (3 mL) was added followed by the addition of water (0.010 mL, 0.467 mmol) (with stirring). The tube was flushed with argon and sealed. The mixture was heated at 100° C. for 16 h and then cooled to room temperature. The reaction mixture was filtered, and the filtrate was concentrated to afford a brown oil. The oil was purified via column chromatography (gradient elution with 0-100% dichloromethane-(90:10:1, dichloromethane/methanol/ammonium hydroxide)) to afford 2,6-dimethylphenyl (2,5-bis(methyloxy)phenyl)methyl(2-((4-((2-(dimethylamino)ethyl)oxy)-phenyl)amino)-4-pyrimidinyl)carbamate as a yellow solid. MS (MH+) 572.3; Calculated 571.67 for $C_{32}H_{37}N_5O_5$.

EXAMPLES 3 TO 33

The following compounds were prepared using the procedure outlined above in Example 1, substituting the appropriate reagent amines and chloroformates.

EXAMPLE 3

2,6-Dimethylphenyl(2,4-bis(methyloxy)phenyl)methyl(2-((4-((2-(dimethylamino)ethyl)oxy)phenyl)amino)-4-pyrimidinyl)carbamate MS (MH$^+$) 572.3; Calculated 571.67 for $C_{32}H_{37}N_5O_5$.

EXAMPLE 4

2,6-Dimethylphenyl 2-((3,5-bis(methyloxy)-4-((3-(4-methyl-1-piperazinyl)propyl)oxy)phenyl)amino)-4-pyrimidinyl((2,5-bis(methyloxy)phenyl)-methyl)carbamate MS (MH$^+$) 701.3; Calculated 700.83 for $C_{38}H_{48}N_6O_7$.

EXAMPLE 5

2,6-Dimethylphenyl(2,5-bis(methyloxy)phenyl)methyl(2-((4-((3-(dimethylamino)propyl)oxy)phenyl)amino)-4-pyrimidinyl)carbamate MS (MH$^+$) 586.3; Calculated 585.70 for $C_{33}H_{39}N_5O_5$.

EXAMPLE 6

2,6-Dimethylphenyl(2,5-bis(methyloxy)phenyl)methyl(2-((3-(methyloxy)-4-((2-(4-methyl-1-piperazinyl)ethyl)oxy)phenyl)amino)-4-pyrimidinyl)carbamate MS (MH$^+$) 657.3; Calculated 656.78 for $C_{36}H_{44}N_6O_6$.

EXAMPLE 7

2,6-Dimethylphenyl(2,5-bis(methyloxy)phenyl)methyl(2-((3-(methyloxy)-4-((3-(4-methyl-1-piperazinyl)propyl)oxy)phenyl)amino)-4-pyrimidinyl)carbamate MS (MH$^+$) 671.3; Calculated 670.81 for $C_{37}H_{46}N_6O_6$.

EXAMPLE 8

2,6-Dimethylphenyl(2,5-bis(methyloxy)phenyl)methyl(2-((3-(methyl-oxy)-4-(4-methyl-1-piperazinyl)phenyl)amino)-4-pyrimidinyl)carbamate MS (MH$^+$) 613.3; Calculated 612.73 for $C_{34}H_{40}N_6O_5$.

EXAMPLE 9

2,6-Dimethylphenyl(2,5-bis(methyloxy)phenyl)methyl(2-((4-((3R)-3-(dimethylamino)-1-pyrrolidinyl)phenyl)amino)-4-pyrimidinyl)carbamate MS (MH$^+$) 597.3; Calculated 596.73 for $C_{34}H_{40}N_6O_4$.

EXAMPLE 10

2,6-Dimethylphenyl 2-((3,5-bis(methyloxy)-4-(4-methyl-1-piperazinyl)phenyl)amino)-4-pyrimidinyl((2,5-bis(methyloxy)phenyl)-methyl)carbamate MS (MH$^+$) 643.3; Calculated 642.75 for $C_{35}H_{42}N_6O_6$.

EXAMPLE 11

2,6-Dimethylphenyl 2-((4-((3R)-3-(dimethylamino)-1-pyrrolidinyl)-phenyl)amino)-4-pyrimidinyl((2-(methyloxy)phenyl)methyl)carbamate MS (MH$^+$) 567.3; Calculated 566.70 for $C_{33}H_{38}N_6O_3$.

EXAMPLE 12

2,6-Dimethylphenyl 2-((3-(methyloxy)-4-((2-(4-methyl-1-piperazinyl)ethyl)oxy)phenyl)amino)-4-pyrimidinyl((2-(methyloxy)-phenyl)methyl)carbamate MS (MH$^+$) 627.3; Calculated 626.75 for $C_{35}H_{42}N_6O_5$.

EXAMPLE 13

2,6-Dimethylphenyl 2-((3-(methyloxy)-4-((2-(4-methyl-1-piperazinyl)ethyl)oxy)phenyl)amino)-4-pyrimidinyl((3(methyloxy)phenyl)-methyl)carbamate MS (MH$^+$) 627.3; Calculated 626.75 for $C_{35}H_{42}N_6O_5$.

EXAMPLE 14

2,6-Dimethylphenyl 2-((3-(methyloxy)-4-((2-(4-methyl-1-piperazin-yl)ethyl)oxy)phenyl)amino)-4-pyrimidinyl((1R)-1-phenylethyl)carbamate MS (MH$^+$) 611.3; Calculated 610.76 for $C_{35}H_{42}N_6O_4$.

EXAMPLE 15

2,6-Dimethylphenyl 2-((3-(methyloxy)-4-((2-(4-methyl-1-piperazinyl)ethyl)oxy)phenyl)amino)-4-pyrimidinyl((1S)-1-phenylethyl)carbamate MS (MH$^+$) 611.3; Calculated 610.76 for $C_{35}H_{42}N_6O_4$.

EXAMPLE 16

2,6-Dimethylphenyl 2-((4-((2-(dimethylamino)ethyl)oxy)phenyl)-amino)-4-pyrimidinyl((1R)-1-phenylethyl)carbamate MS (MH$^+$) 526.3; Calculated 525.65 for $C_{31}H_{35}N_5O_3$.

EXAMPLE 17

2,6-Dimethylphenyl 2-((4-((2-(dimethylamino)ethyl)oxy)phenyl)-amino)-4-pyrimidinyl((1S)-1-phenylethyl)carbamate MS (MH$^+$) 526.3; Calculated 525.65 for $C_{31}H_{35}N_5O_3$.

EXAMPLE 18

2,6-Dimethylphenyl 2-((3-(methyloxy)-4-((2-(4-methyl-1-piperazinyl)ethyl)oxy)phenyl)amino)-4-pyrimidinyl((1R)-1-(3-(methyloxy)-phenyl)ethyl)carbamate MS (MH$^+$) 641.4; Calculated 640.78 for $C_{36}H_{44}N_6O_5$.

EXAMPLE 19

2,6-Dimethylphenyl 2-((3-(methyloxy)-4-((2-(4-methyl-1-piperazinyl)ethyl)oxy)phenyl)amino)-4-pyrimidinyl((1S)-1-(3-(methyloxy)phenyl)ethyl)carbamate MS (MH$^+$) 641.4; Calculated 640.78 for $C_{36}H_{44}N_6O_5$.

EXAMPLE 20

2,6-Dimethylphenyl 2-((3-(methyloxy)-4-((3-(4-methyl-1-piperazinyl)propyl)oxy)phenyl)amino)-4-pyrimidinyl((1R)-1-(3-(methyloxy)phenyl)ethyl)carbamate MS (MH$^+$) 655.4; Calculated 654.81 for $C_{37}H_{46}N_6O_5$.

EXAMPLE 21

2,6-Dimethylphenyl 2-((3-(methyloxy)-4-((3-(4-methyl-1-piperazinyl)propyl)oxy)phenyl)amino)-4-pyrimidinyl((1S)-1-(3(methyloxy)phenyl)ethyl)carbamate MS (MH$^+$) 655.4; Calculated 654.81 for $C_{37}H_{46}N_6O_5$.

EXAMPLE 22

2,6-Dimethylphenyl 2-((3,4-bis(methyloxy)-5-((3-(4-methyl-1-piperazinyl)propyl)oxy)phenyl)amino)-4-pyrimidinyl((1R)-1-phenylethyl)carbamate MS (MH$^+$) 655.3; Calculated 654.81 for $C_{37}H_{46}N_6O_5$.

EXAMPLE 23

2,6-Dimethylphenyl 2-((3,4-bis(methyloxy)-5-((3-(4-methyl-1-piperazinyl)propyl)oxy)phenyl)amino)-4-pyrimidinyl((1S)-1-phenylethyl)carbamate MS (MH$^+$) 655.3; Calculated 654.81 for $C_{37}H_{46}N_6O_5$.

EXAMPLE 24

2,4,6-Trimethylphenyl(2,5-bis(methyloxy)phenyl)methyl(2-((3-(methyloxy)-4-((2-(4-methyl-1-piperazinyl)ethyl)oxy)phenyl)amino)-4-pyrimidinyl)carbamate MS (MH$^+$) 671.3; Calculated 670.81 for $C_{37}H_{46}N_6O_6$.

EXAMPLE 25

2,4,6-Trimethylphenyl 2-((3,5-bis(methyloxy)-4-((3-(4-methyl-1-piperazinyl)propyl)oxy)phenyl)amino)-4-pyrimidinyl((2,5-bis(methyloxy)phenyl)methyl)carbamate MS (MH$^+$) 715.3; Calculated 714.86 for $C_{39}H_{50}N_6O_7$.

EXAMPLE 26

2,4,6-Trimethylphenyl(2,5-bis(methyloxy)phenyl)methyl(2-((3-(methyloxy)-4-((3-(4-methyl-1-piperazinyl)propyl)oxy)phenyl)amino)-4-pyrimidinyl)carbamate MS (MH$^+$) 685.3; Calculated 684.83 for $C_{38}H_{48}N_6O_6$.

EXAMPLE 27

2,4,6-Trimethylphenyl(2,5-bis(methyloxy)phenyl)methyl(2-((4-((3-(1-piperidinyl)propyl)oxy)phenyl)amino)-4-pyrimidinyl)carbamate MS (MH$^+$) 640.3; Calculated 639.79 for $C_{37}H_{45}N_5O_5$.

EXAMPLE 28

2,6-Dimethylphenyl 2-((3-(methyloxy)-4-((2-(4-methyl-1-piperazin-yl)ethyl)oxy)phenyl)amino)-4-pyrimidinyl(3-pyridinylmethyl)carbamate MS (MH$^+$) 598.3; Calculated 597.72 for $C_{33}H_{39}N_7O_4$.

EXAMPLE 29

2,6-Dimethylphenyl 2-((4-((2-(dimethylamino)ethyl)oxy)phenyl)-amino)-4-pyrimidinyl(3-pyridinylmethyl)carbamate MS (MH$^+$) 513.3; Calculated 512.61 for $C_{29}H_{32}N_6O_3$.

EXAMPLE 30

2,6-Dimethylphenyl 2-((4-((2-(dimethylamino)ethyl)oxy)phenyl)-amino)-4-pyrimidinyl((4-(methyloxy)phenyl)methyl)carbamate MS (MH$^+$) 542.3; Calculated 541 for $C_{31}H_{35}N_5O_4$.

EXAMPLE 31

2,6-Dimethylphenyl 2-((3-(methyloxy)-4-((2-(4-methyl-1-piperazinyl)ethyl)oxy)phenyl)amino)-4-pyrimidinyl((4-(methyloxy)phenyl)-methyl)carbamate MS (MH$^+$) 627.3; Calculated 626 for $C_{35}H_{42}N_6O_5$.

EXAMPLE 32

2,6-Dimethylphenyl(4-(methyloxy)phenyl)methyl(2-((4-((3-(1-piperidinyl)propyl)oxy)phenyl)amino)-4-pyrimidinyl)carbamate MS (MH$^+$) 596.3; Calculated 595 for $C_{35}H_{41}N_5O_4$.

EXAMPLE 33

2,6-Dimethylphenyl(2,5-bis(methyloxy)phenyl)methyl(2-((4-((3-(1-piperidinyl)propyl)oxy)phenyl)amino)-4-pyrimidinyl)carbamate MS (MH$^+$) 626.2; Calculated 625 for $C_{36}H_{43}N_5O_5$.

EXAMPLE 34

2,6-Dimethylphenyl 2-((2-((4-aminophenyl)oxy)ethyl)(methyl)-amino)-4-pyrimidinyl((2,5-bis(methyloxy)phenyl)methyl)carbamate 2,6-Dimethylphenyl 2-((2-((4-aminophenyl)oxy)ethyl)(methyl)amino)-4-pyrimidinyl((2,5-bis(methyloxy)phenyl)methyl)carbamate was prepared using the procedure outlined above for the preparation of 2,6-dimethylphenyl(2,5-bis(methyloxy)phenyl)methyl(2-((4-((2-(dimethylamino)ethyl)oxy)phenyl)amino)-4-pyrimidinyl)carbamate. MS (MH$^+$) 558.3; Calculated 557.64 for $C_{31}H_{35}N_5O_5$.

EXAMPLE 35

2,6-Dimethylphenyl(2-(methyloxy)phenyl)methyl(2-((3-(1-pyrrolidinyl)propyl)amino)-4-pyrimidinyl)carbamate Step A: (2-Chloropyrimidin-4-yl)-(2-methoxybenzyl)amine
(2-Chloropyrimidin-4-yl)-(2-methoxybenzyl)amine was prepared as an off-white solid using the procedure outlined in the preparation of benzyl-(2-chloropyrimidin-4-yl)amine. MS (MH$^+$) 250.1; Calculated 249.70 for $C_{12}H_{12}ClN_3O$.

Step B: (2-Chloropyrimidin-4-yl)-(2-methoxybenzyl)carbamic acid 2,6-dimethyl-phenyl ester (2-Chloropyrimidin-4-yl)-(2-methoxybenzyl)carbamic acid 2,6-dimethylphenyl ester was prepared as a pale orange solid using the procedure outlined in the preparation benzyl-(2-chloropyrimidin-4-yl)carbamic acid 2,6-dimethylphenyl ester. MS (MH$^+$) 398.1; Calculated 397.86 for $C_{21}H_{20}ClN_3O_3$.

Step C: 2,6-dimethylphenyl(2-(methyloxy)phenyl)methyl(2-((3-(1-pyrrolidinyl)propyl)amino)-4-pyrimidinyl)carbamate A resealable tube was charged with the (2-chloropyrimidin-4-yl)-(2-methoxy-benzyl)carbamic acid 2,6-dimethylphenyl ester (0.060 g, 0.151 mmol), 1-(3-aminopropyl)pyrrolidine (0.021 g, 0.166 mmol), and isopropanol (2 mL). N,N-Diisopropylethylamine (0.021 g, 0.029 mL, 1.1 mmol) was added and the system was flushed with argon. The tube was sealed and the mixture was heated at 85° C. for 12 h. The reaction mixture was cooled to room temperature and concentrated to afford an orange-brown oil. The oil was purified via preparative thin layer chromatography on silica gel plates (eluting with 90:10:1, dichloromethane/methanol/ammonium hydroxide) to afford 2,6-dimethylphenyl(2-(methyloxy)-phenyl)methyl(2-((3-(1-pyrrolidinyl)propyl)amino)-4-pyrimidinyl)carbamate as an off-white solid. MS (MH$^+$) 490.3; Calculated 489.62 for $C_{28}H_{35}N_5O_3$.

EXAMPLE 36

2,6-Dimethylphenyl 2-((3-(methyloxy)-4-((2-(4-methyl-1-piperazinyl)ethyl)oxy)phenyl)amino)-4-pyrimidinyl(2-(2-pyridinyl)ethyl)carbamate Step A: (2-Chloropyrimidin-4-yl)-(2-pyridin-2-yl-ethyl)amine 2,4-Dichloropyrimidine (1.43 g, 9.60 mmol) was added to a solution of 2-(2-aminoethyl)pyridine (1.00 g, 8.19 mmol) in isopropanol (10 mL). N,N-Diisopropyl-ethylamine (1.24 g, 1.67 mL, 9.59 mmol) was added and the mixture stirred at room temperature overnight. The resulting suspension was concentrated to afford an off-white solid. This material was purified via column chromatography on silica gel (gradient elution with 0-10% ethanol-dichloromethane) to afford (2-chloropyrim-idin-4-yl)-(2-pyridin-2-yl-ethyl)amine as an off-white solid. MS (MH$^+$) 235; Calculated 234.69 for $C_{11}H_{11}ClN_4$.

Step B: (2-Chloro-pyrimidin-4-yl)-(2-pyridin-2-yl-ethyl)carbamic acid 2,6-dimethylphenyl ester (2-Chloropyrimidin-4-yl)-(2-pyridin-2-yl-ethyl)carbamic acid 2,6-dimethylphenyl ester was prepared as a white solid using the procedure outlined in the preparation of benzyl-(2-chloropyrimidin-4-yl)carbamic acid 2,6-dimethylphenyl ester. MS (MH$^+$) 383.1; Calculated 382.85 for $C_{20}H_{19}ClN_4O_2$.

Step C. 2,6-dimethylphenyl 2-((3-(methyloxy)-4-((2-(4-methyl-1-piperazinyl)ethyl)-oxy)phenyl)amino)-4-pyrimidinyl(2-(2-pyridinyl)ethyl)carbamate 2,6-Dimethylphenyl 2-((3-(methyloxy)-4-((2-(4-methyl-1-piperazinyl)ethyl)oxy)-phenyl)amino)-4-pyrimidinyl(2-(2-pyridinyl)ethyl)carbamate was prepared as a white solid according to the procedure outlined in the preparation of 2,6-di-methylphenyl 2-((4-((2-(dimethylamino)ethyl)oxy)phenyl)amino)-4-pyrimidin-yl(phenylmethyl)carbamate. MS (MH$^+$) 612.3; Calculated 611.74 for $C_{34}H_{41}N_7O_4$.

EXAMPLES 37 TO 54

The following compounds were prepared using the procedure outlined above in Example 36 substituting the appropriate reagent amines and chloroformates.

EXAMPLE 37

2,6-Dimethylphenyl 2-((3-(methyloxy)-4-((3-(4-methyl-1-piperazinyl)propyl)oxy)phenyl)amino)-4-pyrimidinyl(2-(2-pyridinyl)ethyl)-carbamate MS (MH$^+$) 626.3; Calculated 625.77 for $C_{35}H_{43}N_7O_4$.

EXAMPLE 38

2,6-Dimethylphenyl 2-((3-(methyloxy)-4-((3-(4-methyl-1-piperazinyl)propyl)oxy)phenyl)amino)-4-pyrimidinyl(2-(3-pyridinyl)ethyl)-carbamate MS (MH$^+$) 626.3; Calculated 625.77 for $C_{35}H_{43}N_7O_4$.

EXAMPLE 39

2,4,6-Trimethylphenyl 2-((3-(methyloxy)-4-((3-(4-methyl-1-piperazinyl)propyl)oxy)phenyl)amino)-4-pyrimidinyl(2-(2-pyridinyl)ethyl)-carbamate MS (MH$^+$) 640.3; Calculated 639.80 for $C_{36}H_{45}N_7O_4$.

EXAMPLE 40

2,4,6-Trimethylphenyl 2-((3-(methyloxy)-4-((2-(4-methyl-1-piperazinyl)ethyl)oxy)phenyl)amino)-4-pyrimidinyl(2-(2-pyridinyl)ethyl)carbamate MS (MH$^+$) 626.3; Calculated 625.77 for $C_{35}H_{43}N_7O_4$.

EXAMPLE 41

2,4,6-Trimethylphenyl 2-((3,5-bis(methyloxy)-4-((3-(4-methyl-1-piperazinyl)propyl)oxy)phenyl)amino)-4-pyrimidinyl(2-(2-pyridinyl)ethyl)-carbamate MS (MH$^+$) 670.3; Calculated 669.82 for $C_{37}H_{47}N_7O_5$.

EXAMPLE 42

2,4,6-Trimethylphenyl 2-((4-((3-(1-piperidinyl)propyl)oxy)phenyl)-amino)-4-pyrimidinyl(2-(2-pyridinyl)ethyl)carbamate MS (MH$^+$) 595.3; Calculated 594.76 for $C_{35}H_{42}N_6O_3$.

EXAMPLE 43

2,4,6-Trimethylphenyl 2-((3,5-bis(methyloxy)-4-((3-(4-methyl-1-piperazinyl)propyl)oxy)phenyl)amino)-4-pyrimidinyl(2-(3-pyridinyl)ethyl)-carbamate MS (MH$^+$) 670.3; Calculated 669.82 for $C_{37}H_{47}N_7O_5$.

EXAMPLE 44

2,4,6-Trimethylphenyl 2-((4-((3-(1-piperidinyl)propyl)oxy)phenyl)-amino)-4-pyrimidinyl(2-(3-pyridinyl)ethyl)carbamate MS (MH$^+$) 595.3; Calculated 594.76 for $C_{35}H_{42}N_6O_3$.

EXAMPLE 45

2,4,6-Trimethylphenyl 2-((3-(methyloxy)-4-((3-(4-methyl-1-piperazinyl)propyl)oxy)phenyl)amino)-4-pyrimidinyl(2-(3-pyridinyl)ethyl)-carbamate MS (MH$^+$) 640.3; Calculated 639.80 for $C_{36}H_{45}N_7O_4$.

EXAMPLE 46

2,6-Dimethylphenyl 2-((4-((2-(dimethylamino)ethyl)oxy)phenyl)-amino)-4-pyrimidinyl(2-phenylethyl)carbamate MS (MH$^+$) 526.2; Calculated 525 for $C_{31}H_{35}N_5O_3$.

EXAMPLE 47

2,6-Dimethylphenyl 2-((3-(methyloxy)-4-((2-(4-methyl-1-piperazinyl)ethyl)oxy)phenyl)amino)-4-pyrimidinyl(2-phenylethyl)carbamate MS (MH$^+$) 611.3; Calculated 610 for $C_{35}H_{42}N_6O_4$.

EXAMPLE 48

2,6-Dimethylphenyl 2-phenylethyl(2-((4-((3-(1-piperidinyl)propyl)-oxy)phenyl)amino)-4-pyrimidinyl)carbamate MS (MH$^+$) 580.3; Calculated 579 for $C_{35}H_{41}N_5O_3$.

EXAMPLE 49

2,6-Dimethylphenyl 2-((4-((3-(dimethylamino)propyl)oxy)phenyl)-amino)-4-pyrimidinyl(2-phenylethyl)carbamate MS (MH$^+$) 540.3; Calculated 539 for $C_{32}H_{37}N_5O_3$.

EXAMPLE 50

2,6-Dimethylphenyl 2-((3-(methyloxy)-4-((3-(4-methyl-1-piperazinyl)propyl)oxy)phenyl)amino)-4-pyrimidinyl(2-phenylethyl)carbamate MS (MH$^+$) 625.3; Calculated 624 for $C_{36}H_{44}N_6O_4$.

EXAMPLE 51

2,6-Dimethylphenyl 2-((3,5-bis(methyloxy)-4-((3-(4-methyl-1-piperazinyl)propyl)oxy)phenyl)amino)-4-pyrimidinyl(2-phenylethyl)carbamate MS (MH$^+$) 655.3; Calculated 654 for $C_{37}H_{46}N_5O_3$.

EXAMPLE 52

2,6-Dimethylphenyl 2-((4-((2-(dimethylamino)ethyl)oxy)phenyl)-amino)-4-pyrimidinyl(3-phenylpropyl)carbamate MS (MH$^+$) 540.2; Calculated 539 for $C_{32}H_{37}N_5O_3$.

EXAMPLE 53

2,6-Dimethylphenyl 2-((4-((2-(dimethylamino)ethyl)oxy)phenyl)-amino)-4-pyrimidinyl(2-(2-(methyloxy)phenyl)ethyl)carbamate MS (MH$^+$) 556.2; Calculated 555 for $C_{32}H_{37}N_5O_4$.

EXAMPLE 54

2,6-Dimethylphenyl 2-((4-((2-(dimethylamino)ethyl)oxy)phenyl)-amino)-4-pyrimidinyl(2-(4-morpholinyl)ethyl)carbamate MS (MH$^+$) 535.2; Calculated 534 for $C_{29}H_{38}N_6O_4$.

EXAMPLE 55

2,6-Dimethylphenyl-4-(methyloxy)phenyl(2-((4-(4-methyl-1-piperazinyl)phenyl)amino)-4-pyrimidinyl)carbamate Step A: 2-Chloro-4-(4-methoxy)-anilinopyrimidine To a solution of 2,4-dichloropyrimidine (1.48 g, 0.01 mol) in isopropanol (20 mL), 4-methoxyaniline (1.23 g, 0.01 mol), and N,N-diisopropylethylamine (2.59 g, 3.50 mL, 0.02 mol) were added and the mixture was allowed to stir at room temperature for 48 h. The resulting suspension was partitioned between sat. aq. sodium carbonate and ethyl acetate. The organic phase was separated, dried over anhydrous sodium sulfate, filtered, and concentrated. The material was used without purification. MS (MH$^+$) 236; Calculated 235.67 for $C_{11}H_{10}ClN_3O$.

Step B: 2-Chloro-4-(N-2,6-dimethylphenoxycarbonyl-N-(4-methoxyanilino)aminopyrimidine 2-Chloro-4-(4-methoxyphenylaniline)aminopyrimidine (1.1 g, 5.4 mmol) was added to a solution of 2,6-dimethylphenylchloroformate (1 g, 5.4 mmol) in tetrahydrofuran (10 mL). N,N-Diisopropylethylamine (0.78 g, 1.05 mL, 6 mmol) was added and the mixture stirred at room temperature for 48 h. The resulting suspension was diluted with ethyl acetate and the mixture was partitioned between ethyl acetate and saturated sodium carbonate solution. The organic phase was separated and washed with brine, dried over anhydrous sodium sulfate, filtered, and concentrated to afford an orange oil. This oil was purified via column chromatography on silica gel (isocratic elution with dichloromethane) to afford 2-chloro-4-(N-2,6-dimethylphenoxycarbonyl-N-(4-methoxyanilino)aminopyrimidine as an off-white solid. MS (MH$^+$) 384; Calculated 383.84 for $C_{20}H_{18}ClN_3O_3$.

Step C: 2,6-Dimethylphenyl-4-(methyloxy)phenyl(2-((4-(4-methyl-1-piperazinyl)phenyl)amino)-4-pyrimidinyl)carbamate A resealable tube was charged with the 2-chloro-4-(N-2,6-dimethylphenoxycarbonyl-N-(4-methoxyanilino)aminopyrimidine (0.200 g, 0.0005 mmol), 4-(2-dimethylaminoethoxy)phenylamine (0.050 g, 0.278 mmol), and acetic acid (2 mL). The system was flushed with argon, and the tube was sealed. The mixture was heated at 100° C. for 20 h. The reaction mixture was cooled to room temperature and concentrated to afford a brown oil. The oil was diluted with ethyl acetate and partitioned between ethyl acetate and sat. aq. potassium carbonate. The organic layer was separated, dried over anhydrous sodium sulfate, and concentrated. The oil was purified via column chromatography (gradient elution with 0-10% methanol in dichloromethane) to afford 2,6-dimethylphenyl-4-(methyloxy)phenyl(2-((4-(4-methyl-1-piperazinyl)phenyl)amino)-4-pyrimidinyl)carbamate as a solid. MS (MH$^+$) 539; Calculated 538.66 for $C_{13}H_{34}N_6O_3$.

EXAMPLES 56-130

The following compounds were prepared using the procedures outlined above for the preparation of 2,6-dimethylphenyl-4-(methyloxy)phenyl(2-((4-(4-methyl-1-piperazinyl) phenyl)amino)-4-pyrimidinyl)carbamate. In cases where the anilines (from Step C) contained a tert-butoxycarbonyl protective group, an additional deprotection step was run in a solution of trifluoroacetic acid/dichloromethane (1:1) at room temperature for 20 h.

| No. | Formula | Name | MW | MH+ |
|---|---|---|---|---|
| 56 | $C_{32}H_{36}N_6O_4$ | 2,6-dimethylphenyl 2-((3-(methyloxy)-4-(4-methyl-1-piperazinyl)phenyl)amino)-4-pyrimidinyl(4-(methyloxy)phenyl)carbamate | 568.67 | 569 |
| 57 | $C_{31}H_{32}F_2N_6O_4$ | 2,6-dimethylphenyl 2-((3-((difluoromethyl)oxy)-4-(1-piperazinyl)phenyl)amino)-4-pyrimidinyl(4-(methyloxy)phenyl)carbamate | 590.63 | 591 |
| 58 | $C_{35}H_{40}N_6O_5$ | 1,1-dimethylethyl 4-(4-((4-(((((2,6-dimethylphenyl)oxy)carbonyl)(4-(methyloxy)phenyl)amino)-2-pyrimidinyl)amino)phenyl)-1-piperazinecarboxylate | 624.74 | 625 |
| 59 | $C_{30}H_{32}N_6O_3$ | 2,6-dimethylphenyl 4-(methyloxy)phenyl(2-((4-(1-piperazinyl)phenyl)amino)-4-pyrimidinyl)carbamate | 524.62 | 525 |
| 60 | $C_{34}H_{34}N_6O_2$ | 2,6-dimethylphenyl 2-((4-(4-methyl-1-piperazinyl)phenyl)amino)-4-pyrimidinyl(2-naphthalenyl)carbamate | 558.68 | 559 |
| 61 | $C_{35}H_{41}N_5O_6$ | 2,6-dimethylphenyl 2-((3,5-bis(methyloxy)-4-((2-(1-piperidinyl)ethyl)oxy)phenyl)amino)-4-pyrimidinyl(4-(methyloxy)phenyl)carbamate | 627.74 | 628 |
| 62 | $C_{33}H_{38}N_6O_4$ | 2,6-dimethylphenyl 4-(methyloxy)phenyl-(2-((4-((2-(4-methyl-1-piperazinyl)ethyl)-oxy)phenyl)amino)-4-pyrimidinyl)carbamate | 582.70 | 583 |
| 63 | $C_{25}H_{22}ClN_5O_3$ | 2,6-dimethylphenyl 2-((6-chloro-3-pyridinyl)amino)-4-pyrimidinyl(4-(methyloxy)phenyl)carbamate | 475.93 | 476 |
| 64 | $C_{28}H_{22}ClN_5O_2$ | 2,6-dimethylphenyl 2-((6-chloro-3-pyridinyl)amino)-4-pyrimidinyl(2-naphthalenyl)carbamate | 495.97 | 496 |
| 65 | $C_{34}H_{33}FN_6O_2$ | 2,6-dimethylphenyl 2-((3-fluoro-4-(4-methyl-1-piperazinyl)phenyl)amino)-4-pyrimidinyl(2-naphthalenyl)carbamate | 576.67 | 577 |
| 66 | $C_{37}H_{39}FN_6O_3$ | 2,6-dimethylphenyl 2-((3-fluoro-4-((3-(4-methyl-1-piperazinyl)propyl)oxy)phenyl)amino)-4-pyrimidinyl(2-naphthalenyl)carbamate | 634.75 | 635 |
| 67 | $C_{30}H_{33}N_7O_3$ | 2,6-dimethylphenyl 4-(methyloxy)phenyl(2-((6-(4-methyl-1-piperazinyl)-3-pyridinyl)amino)-4-pyrimidinyl)carbamate | 539.64 | 540 |
| 68 | $C_{33}H_{37}N_5O_4$ | 2,6-dimethylphenyl 4-(methyloxy)phenyl(2-((4-((2-(1-piperidinyl)ethyl)oxy)phenyl)amino)-4-pyrimidinyl)carbamate | 567.69 | 568 |
| 69 | $C_{30}H_{31}N_5O_4$ | 2,6-dimethylphenyl 4-(methyloxy)phenyl(2-((4-(4-morpholinyl)phenyl)amino)-4-pyrimidinyl)carbamate | 525.61 | 526 |
| 70 | $C_{27}H_{26}N_4O_4$ | 2,6-dimethylphenyl 4-(methyloxy)phenyl(2-((4-(methyloxy)phenyl)amino)-4-pyrimidinyl)carbamate | 470.53 | 471 |
| 71 | $C_{29}H_{30}N_4O_6$ | 2,6-dimethylphenyl 4-(methyloxy)phenyl(2-((3,4,5-tris(methyloxy)phenyl)amino)-4-pyrimidinyl)carbamate | 530.58 | 531 |
| 72 | $C_{29}H_{28}N_4O_5$ | 2,6-dimethylphenyl 2-(3,4-dihydro-2H-1,5-benzodioxepin-7-ylamino)-4-pyrimidinyl(4-(methyloxy)phenyl)carbamate | 512.56 | 513 |
| 73 | $C_{29}H_{30}N_6O_4$ | 2,6-dimethylphenyl 4-(methyloxy)phenyl(2-((6-(4-morpholinyl)-3-pyridinyl)amino)-4-pyrimidinyl)carbamate | 526.59 | 527 |
| 74 | $C_{33}H_{31}N_5O_3$ | 2,6-dimethylphenyl 2-((4-(4-morpholinyl)phenyl)amino)-4-pyrimidinyl(2-naphthalenyl)carbamate | 545.64 | 546 |
| 75 | $C_{35}H_{33}N_5O_3$ | 2,6-dimethylphenyl 1,1'-biphenyl-4-yl(2-((4-(4-morpholinyl)phenyl)amino)-4-pyrimidinyl)carbamate | 571.68 | 572 |

-continued

| No. | Formula | Name | MW | MH+ |
|---|---|---|---|---|
| 76 | $C_{36}H_{36}N_6O_2$ | 2,6-dimethylphenyl 1,1'-biphenyl-4-yl(2-((4-(4-methyl-1-piperazinyl)phenyl)-amino)-4-pyrimidinyl)carbamate | 584.72 | 585 |
| 77 | $C_{35}H_{32}ClN_5O_3$ | 2,6-dimethylphenyl 1,1'-biphenyl-4-yl(2-((3-chloro-4-(4-morpholinyl)phenyl)-amino)-4-pyrimidinyl)carbamate | 606.12 | 607 |
| 78 | $C_{32}H_{30}N_4O_5$ | 2,6-dimethylphenyl 2-naphthalenyl(2-((3,4,5-tris(methyloxy)phenyl)amino)-4-pyrimidinyl)carbamate | 550.61 | 551 |
| 79 | $C_{35}H_{37}N_7O_2$ | 2,6-dimethylphenyl 2-((6-(4-(1-methyl-ethyl)-1-piperazinyl)-3-pyridinyl)amino)-4-pyrimidinyl(2-naphthalenyl)carbamate | 587.72 | 588 |
| 80 | $C_{34}H_{32}N_4O_5$ | 2,6-dimethylphenyl 1,1'-biphenyl-4-yl(2-((3,4,5-tris(methyloxy)phenyl)amino)-4-pyrimidinyl)carbamate | 576.65 | 577 |
| 81 | $C_{37}H_{39}N_5O_3$ | 2,6-dimethylphenyl 2-naphthalenyl(2-((3-((3-(1-piperidinyl)propyl)oxy)phenyl)-amino)-4-pyrimidinyl)carbamate | 601.75 | 602 |
| 82 | $C_{36}H_{38}N_6O_2$ | 2,6-dimethylphenyl 2-((4-(4-(1-methyl-ethyl)-1-piperazinyl)phenyl)amino)-4-pyrimidinyl(2-naphthalenyl)carbamate | 586.74 | 587 |
| 83 | $C_{38}H_{40}N_6O_2$ | 2,6-dimethylphenyl 1,1'-biphenyl-4-yl(2-((4-(4-(1-methylethyl)-1-piperazinyl)-phenyl)amino)-4-pyrimidinyl)carbamate | 612.77 | 613 |
| 84 | $C_{30}H_{24}N_6O_2$ | 2,6-dimethylphenyl 2-(1H-indazol-5-ylamino)-4-pyrimidinyl(2-naphthalenyl)-carbamate | 500.56 | 501 |
| 85 | $C_{37}H_{40}N_6O_3$ | 2,6-dimethylphenyl 2-((3-((3-(4-methyl-1-piperazinyl)propyl)oxy)phenyl)amino)-4-pyrimidinyl(2-naphthalenyl)carbamate | 616.76 | 617 |
| 86 | $C_{36}H_{38}FN_5O_3$ | 2,6-dimethylphenyl 2-((4-((3-(diethyl-amino)propyl)oxy)-3-fluorophenyl)-amino)-4-pyrimidinyl(2-naphthalenyl)-carbamate | 607.73 | 608 |
| 87 | $C_{32}H_{36}N_6O_4$ | 2,6-dimethylphenyl 2,4-bis(methyloxy)-phenyl(2-((4-(4-methyl-1-piperazinyl)-phenyl)amino)-4-pyrimidinyl)carbamate | 568.67 | 569 |
| 88 | $C_{34}H_{40}N_6O_4$ | 2,6-dimethylphenyl 2,4-bis(methyloxy)-phenyl(2-((4-(4-(1-methylethyl)-1-piperazinyl)phenyl)amino)-4-pyrimidinyl)carbamate | 596.73 | 597 |
| 89 | $C_{33}H_{38}N_6O_4$ | 2,6-dimethylphenyl 2,4-bis(methyloxy)-phenyl(2-((4-(4-methyl-1,4-diazepan-1-yl)phenyl)amino)-4-pyrimidinyl)-carbamate | 582.70 | 583 |
| 90 | $C_{37}H_{38}N_6O_2$ | 2,6-dimethylphenyl 1,1'-biphenyl-4-yl(2-((4-(4-methyl-1,4-diazepan-1-yl)phenyl)-amino)-4-pyrimidinyl)carbamate | 598.75 | 599 |
| 91 | $C_{39}H_{41}N_5O_4$ | 2,6-dimethylphenyl 1,1'-biphenyl-4-yl(2-((4-((2-hydroxy-3-(1-piperidinyl)propyl)-oxy)phenyl)amino)-4-pyrimidinyl)-carbamate | 643.78 | 644 |
| 92 | $C_{35}H_{41}N_5O_6$ | 2,6-dimethylphenyl 2,4-bis(methyloxy)-phenyl(2-((4-((2-hydroxy-3-(1-piperidinyl)propyl)oxy)phenyl)amino)-4-pyrimidinyl)carbamate | 627.74 | 628 |
| 93 | $C_{37}H_{43}N_5O_7$ | 2-(4-((2-((2,4-bis(methyloxy)phenyl)-(((2,6-dimethylphenyl)oxy)carbonyl)-amino)-2-pyrimidinyl)amino)phenyl)-oxy)-1-(1-piperidinylmethyl)ethyl acetate | 669.78 | 670 |
| 94 | $C_{36}H_{36}N_6O_2$ | 2,6-dimethylphenyl 1,1'-biphenyl-3-yl(2-((4-(4-methyl-1-piperazinyl)phenyl)-amino)-4-pyrimidinyl)carbamate | 584.72 | 585 |
| 95 | $C_{38}H_{39}N_7O_2$ | 2,6-dimethylphenyl 9-ethyl-9H-carbazol-3-yl(2-((4-(4-methyl-1-piperazinyl)-phenyl)amino)-4-pyrimidinyl)carbamate | 625.77 | 626 |
| 96 | $C_{35}H_{41}N_5O_8$ | 2,6-dimethylphenyl 2-((3,5-bis(methyl-oxy)-4-((2-(4-morpholinyl)ethyl)oxy)-phenyl)amino)-4-pyrimidinyl(2,4-bis(methyloxy)phenyl)carbamate | 659.74 | 660 |
| 97 | $C_{35}H_{40}FN_5O_5$ | 2,6-dimethylphenyl 2,4-bis(methyloxy)-phenyl(2-((3-fluoro-4-((3-(1-piperidinyl)-propyl)oxy)phenyl)amino)-4-pyrimidinyl)carbamate | 629.73 | 630 |

-continued

| No. | Formula | Name | MW | MH+ |
|---|---|---|---|---|
| 98 | $C_{33}H_{38}N_6O_5$ | 2,6-dimethylphenyl 2,4-bis(methyloxy)-phenyl(2-((3-(methyloxy)-4-(4-methyl-1-piperazinyl)phenyl)amino)-4-pyrimidinyl)carbamate | 598.70 | 599 |
| 99 | $C_{35}H_{36}N_6O_3$ | 2,6-dimethylphenyl 2-((3-(methyloxy)-4-(4-methyl-1-piperazinyl)phenyl)amino)-4-pyrimidinyl(2-naphthalenyl)carbamate | 588.71 | 589 |
| 100 | $C_{35}H_{43}N_7O_4$ | 2,6-dimethylphenyl 2,4-bis(methyloxy)-phenyl(2-((4-(4-(2-(dimethylamino)-ethyl)-1-piperazinyl)phenyl)amino)-4-pyrimidinyl)carbamate | 625.77 | 626 |
| 101 | $C_{36}H_{45}N_7O_4$ | 2,6-dimethylphenyl 2,4-bis(methyloxy)-phenyl(2-((4-(4-(3-(dimethylamino)-propyl)-1-piperazinyl)phenyl)amino)-4-pyrimidinyl)carbamate | 639.80 | 640 |
| 102 | $C_{33}H_{37}N_7O_5$ | 2,6-dimethylphenyl 2-((4-(4-(2-amino-2-oxoethyl)-1-piperazinyl)phenyl)amino)-4-pyrimidinyl(2,4-bis(methyloxy)phenyl)-carbamate | 611.70 | 612 |
| 103 | $C_{42}H_{48}N_8O_2$ | 2,6-dimethylphenyl 2-((4-(4-(3-(dimethyl-amino)propyl)-1-piperazinyl)phenyl)-amino)-4-pyrimidinyl(9-ethyl-9H-carbazol-3-yl)carbamate | 696.90 | 697 |
| 104 | $C_{33}H_{38}N_6O_4$ | 2,6-dimethylphenyl 2,4-bis(methyloxy)-phenyl(2-((4-((3R)-3-(dimethylamino)-1-pyrrolidinyl)phenyl)amino)-4-pyrimidinyl)carbamate | 582.70 | 583 |
| 105 | $C_{36}H_{44}N_6O_6$ | 2,6-dimethylphenyl 2,4-bis(methyloxy)-phenyl(2-((3-(methyloxy)-4-((3-(4-methyl-1-piperazinyl)propyl)oxy)phenyl)-amino)-4-pyrimidinyl)carbamate | 656.78 | 657 |
| 106 | $C_{32}H_{36}N_6O_6$ | 2-(methyloxy)phenyl 2,4-bis(methyloxy)-phenyl(2-((3-(methyloxy)-4-(4-methyl-1-piperazinyl)phenyl)amino)-4-pyrimidinyl)carbamate | 600.67 | 601 |
| 107 | $C_{35}H_{42}N_6O_7$ | 2-(methyloxy)phenyl 2,4-bis(methyloxy)-phenyl(2-((3-(methyloxy)-4-((3-(4-methyl-1-piperazinyl)propyl)oxy)phenyl)-amino)-4-pyrimidinyl)carbamate | 658.75 | 659 |
| 108 | $C_{31}H_{34}N_6O_5$ | 2-(methyloxy)phenyl 2,4-bis(methyloxy)-phenyl(2-((4-(4-methyl-1-piperazinyl)-phenyl)amino)-4-pyrimidinyl)carbamate | 570.65 | 571 |
| 109 | $C_{37}H_{37}N_7O_3$ | 2,6-dimethylphenyl 2-((4-(4-(2-amino-2-oxoethyl)-1-piperazinyl)phenyl)amino)-4-pyrimidinyl(1,1'-biphenyl-3-yl)carbamate | 627.75 | 628 |
| 110 | $C_{32}H_{37}N_5O_5$ | 2,6-dimethylphenyl 2,4-bis(methyloxy)-phenyl(2-((4-((3-(dimethylamino)propyl)-oxy)phenyl)amino)-4-pyrimidinyl)-carbamate | 571.67 | 572 |
| 111 | $C_{35}H_{35}N_5O_3$ | 2,6-dimethylphenyl 1,1'-biphenyl-3-yl(2-((4-((2-(dimethylamino)ethyl)oxy)-phenyl)amino)-4-pyrimidinyl)carbamate | 573.69 | 574 |
| 112 | $C_{33}H_{39}N_5O_6$ | 2,6-dimethylphenyl 2,4-bis(methyloxy)-phenyl(2-((4-((2-((1-methylethyl)amino)-ethyl)oxy)-3-(methyloxy)phenyl)amino)-4-pyrimidinyl)carbamate | 601.70 | 602 |
| 113 | $C_{30}H_{33}N_5O_6$ | 2-(methyloxy)phenyl 2,4-bis(methyloxy)-phenyl(2-((4-((2-(dimethylamino)ethyl)-oxy)phenyl)amino)-4-pyrimidinyl)-carbamate | 559.62 | 560 |
| 114 | $C_{31}H_{35}N_5O_3$ | 2,6-dimethylphenyl 2-((4-((2-(dimethyl-amino)ethyl)oxy)phenyl)amino)-4-pyrim-idinyl(2,4-dimethylphenyl)carbamate | 525.65 | 526 |
| 115 | $C_{30}H_{33}N_5O_4$ | 2,6-dimethylphenyl 2-((4-((2-(dimethyl-amino)ethyl)oxy)phenyl)amino)-4-pyrimidinyl(2-(methyloxy)phenyl)-carbamate | 527.62 | 528 |
| 116 | $C_{29}H_{31}N_5O_4$ | 2,6-dimethylphenyl 2,4-bis(methyloxy)-phenyl(2-((4-(dimethylamino)phenyl)-amino)-4-pyrimidinyl)carbamate | 513.60 | 514 |
| 117 | $C_{29}H_{31}N_5O_4$ | 2,6-dimethylphenyl 2,4-bis(methyloxy)-phenyl(2-((3-(dimethylamino)phenyl)-amino)-4-pyrimidinyl)carbamate | 513.60 | 514 |
| 118 | $C_{31}H_{35}N_5O_4$ | 2,6-dimethylphenyl 2-((4-((3-(dimethyl-amino)propyl)oxy)phenyl)amino)-4-pyrimidinyl(2-(methyloxy)phenyl)-carbamate | 541.65 | 542 |

-continued

| No. | Formula | Name | MW | MH+ |
|---|---|---|---|---|
| 119 | $C_{33}H_{37}N_5O_5$ | 2,6-dimethylphenyl 2,4-bis(methyloxy)-phenyl(2-((4-((2-(1-pyrrolidinyl)ethyl)-oxy)phenyl)amino)-4-pyrimidinyl)-carbamate | 583.69 | 584 |
| 120 | $C_{35}H_{41}N_5O_5$ | 2,6-dimethylphenyl 2,4-bis(methyloxy)-phenyl(2-((3-((3-(1-piperidinyl)propyl)-oxy)phenyl)amino)-4-pyrimidinyl)-carbamate | 611.74 | 612 |
| 121 | $C_{36}H_{43}N_5O_6$ | 2,6-dimethylphenyl 2,4-bis(methyloxy)-phenyl(2-((4-((2-(methyloxy)-3-(1-piperidinyl)propyl)oxy)phenyl)amino)-4-pyrimidinyl)carbamate | 641.77 | 642 |
| 122 | $C_{34}H_{39}FN_6O_4$ | 2,6-dimethylphenyl 2,4-bis(methyloxy)-phenyl(2-((3-fluoro-4-(4-(1-methylethyl)-1-piperazinyl)phenyl)amino)-4-pyrimidinyl)carbamate | 614.72 | 615 |
| 123 | $C_{31}H_{33}N_5O_5$ | 2,6-dimethylphenyl 2,4-bis(methyloxy)-phenyl(2-((4-(4-morpholinyl)phenyl)-amino)-4-pyrimidinyl)carbamate | 555.63 | 556 |
| 124 | $C_{37}H_{38}N_6O_3$ | 2,6-dimethylphenyl 2-((4-((2-(dimethylamino)ethyl)oxy)phenyl)-amino)-4-pyrimidinyl(9-ethyl-9H-carbazol-3-yl)carbamate | 614.75 | 615 |
| 125 | $C_{38}H_{40}N_6O_3$ | 2,6-dimethylphenyl 2-((4-((3-(dimethyl-amino)propyl)oxy)phenyl)amino)-4-pyrimidinyl(9-ethyl-9H-carbazol-3-yl)-carbamate | 628.77 | 629 |
| 126 | $C_{34}H_{39}N_5O_5$ | 2,6-dimethylphenyl 2,4-bis(methyloxy)-phenyl(2-((4-((2-(1-piperidinyl)ethyl)-oxy)phenyl)amino)-4-pyrimidinyl)-carbamate | 597.71 | 598 |
| 127 | $C_{33}H_{37}N_5O_5$ | 2,6-dimethylphenyl 2,4-bis(methyloxy)-phenyl(2-((4-((1-methyl-4-piperidinyl)-oxy)phenyl)amino)-4-pyrimidinyl)-carbamate | 583.69 | 584 |
| 128 | $C_{33}H_{37}N_5O_6$ | 2,6-dimethylphenyl 2,4-bis(methyloxy)-phenyl(2-((4-((2-(4-morpholinyl)ethyl)-oxy)phenyl)amino)-4-pyrimidinyl)-carbamate | 599.68 | 600 |
| 129 | $C_{34}H_{40}N_6O_6$ | 2,6-dimethylphenyl 2-((3,5-bis(methyl-oxy)-4-(4-methyl-1-piperazinyl)phenyl)-amino)-4-pyrimidinyl(2,4-bis(methyl-oxy)phenyl)carbamate | 628.73 | 629 |
| 130 | $C_{33}H_{38}N_6O_5$ | 2,6-dimethylphenyl 2-((3,5-bis(methyl-oxy)-4-(4-methyl-1-piperazinyl)phenyl)-amino)-4-pyrimidinyl(2-(methyloxy)-phenyl)carbamate | 598.70 | 599 |

EXAMPLES 131-169

The following compounds were prepared using the procedures outlined above for the preparation of 2,6-dimethylphenyl-4-(methyloxy)phenyl(2-((4-(4-methyl-1-piperazinyl)phenyl)amino)-4-pyrimidinyl)carbamate with the following exception: In Step C, a solution of isopropanol/trifluoroacetic acid (10:1) was used in place of acetic acid.

| No. | Formula | Name | MW | MH+ |
|---|---|---|---|---|
| 131 | $C_{32}H_{37}N_5O_3$ | 2,6-dimethylphenyl 2-((4-((2-(dimethylamino)ethyl)oxy)phenyl)-amino)-4-pyrimidinyl(2-(1-methylethyl)-phenyl)carbamate | 539.68 | 540 |
| 132 | $C_{33}H_{39}N_5O_3$ | 2,6-dimethylphenyl 2-((4-((3-(dimethylamino)propyl)oxy)phenyl)-amino)-4-pyrimidinyl(2-(1-methylethyl)-phenyl)carbamate | 553.70 | 554 |
| 133 | $C_{31}H_{35}N_5O_5$ | 2,6-dimethylphenyl 2,4-bis(methyloxy)-phenyl(2-((4-((2-(dimethylamino)ethyl)-oxy)phenyl)amino)-4-pyrimidinyl)-carbamate | 557.65 | 558 |
| 134 | $C_{30}H_{31}F_2N_5O_4$ | 2,6-dimethylphenyl 2-((difluoromethyl)-oxy)phenyl(2-((4-((2-(dimethylamino)-ethyl)oxy)phenyl)amino)-4-pyrimidinyl)-carbamate | 563.60 | 564 |

-continued

| No. | Formula | Name | MW | MH+ |
|---|---|---|---|---|
| 135 | $C_{31}H_{33}F_2N_5O_4$ | 2,6-dimethylphenyl 2-((difluoromethyl)oxy)phenyl(2-((4-((3-(dimethylamino)propyl)oxy)phenyl)amino)-4-pyrimidinyl)carbamate | 577.63 | 578 |
| 136 | $C_{27}H_{27}N_5O_6S$ | 2,6-dimethylphenyl 2-((4-(aminosulfonyl)phenyl)amino)-4-pyrimidinyl(2,4-bis(methyloxy)phenyl)carbamate | 549.61 | 550 |
| 137 | $C_{32}H_{36}N_6O_3$ | 2,6-dimethylphenyl 2-((4-((3R)-3-(dimethylamino)-1-pyrrolidinyl)phenyl)amino)-4-pyrimidinyl(2-(methyloxy)phenyl)carbamate | 552.68 | 553 |
| 138 | $C_{32}H_{37}N_5O_5$ | 2,4,6-trimethylphenyl 2,4-bis(methyloxy)phenyl(2-((4-((2-(dimethylamino)ethyl)oxy)phenyl)amino)-4-pyrimidinyl)carbamate | 571.67 | 572 |
| 139 | $C_{33}H_{39}N_5O_5$ | 2,4,6-trimethylphenyl 2,4-bis(methyloxy)phenyl(2-((4-((3-(dimethylamino)propyl)oxy)phenyl)amino)-4-pyrimidinyl)carbamate | 585.70 | 586 |
| 140 | $C_{38}H_{48}N_6O_7$ | 2,4,6-trimethylphenyl 2-((3,5-bis(methyloxy)-4-((3-(4-methyl-1-piperazinyl)propyl)oxy)phenyl)amino)-4-pyrimidinyl(2,4-bis(methyloxy)phenyl)carbamate | 700.83 | 701 |
| 141 | $C_{34}H_{40}N_6O_5$ | 2,4,6-trimethylphenyl 2,4-bis(methyloxy)phenyl(2-((3-(methyloxy)-4-(4-methyl-1-piperazinyl)phenyl)amino)-4-pyrimidinyl)carbamate | 612.73 | 613 |
| 142 | $C_{31}H_{36}N_6O_6S$ | 2,6-dimethylphenyl 2,4-bis(methyloxy)phenyl(2-((4-(((2-(dimethylamino)ethyl)amino)sulfonyl)phenyl)amino)-4-pyrimidinyl)carbamate | 620.73 | 621 |
| 143 | $C_{32}H_{34}F_2N_6O_4$ | 2,6-dimethylphenyl 2-((difluoromethyl)oxy)phenyl(2-((3-(methyloxy)-4-(4-methyl-1-piperazinyl)phenyl)amino)-4-pyrimidinyl)carbamate | 604.66 | 605 |
| 144 | $C_{35}H_{40}F_2N_6O_5$ | 2,6-dimethylphenyl 2-((difluoromethyl)oxy)phenyl(2-((3-(methyloxy)-4-((3-(4-methyl-1-piperazinyl)propyl)oxy)phenyl)amino)-4-pyrimidinyl)carbamate | 662.73 | 663 |
| 145 | $C_{28}H_{29}N_5O_4$ | 2,6-dimethylphenyl 2-(((4-aminophenyl)methyl)amino)-4-pyrimidinyl(2,4-bis(methyloxy)phenyl)carbamate | 499.57 | 500 |
| 146 | $C_{28}H_{29}N_5O_4$ | 2,6-dimethylphenyl 2-((4-(aminomethyl)phenyl)amino)-4-pyrimidinyl(2,4-bis(methyloxy)phenyl)carbamate | 499.57 | 500 |
| 147 | $C_{34}H_{38}F_2N_6O_5$ | 2,6-dimethylphenyl 2-((difluoromethyl)oxy)phenyl(2-((3-(methyloxy)-4-((2-(4-methyl-1-piperazinyl)ethyl)oxy)phenyl)amino)-4-pyrimidinyl)carbamate | 648.71 | 649 |
| 148 | $C_{35}H_{40}F_2N_6O_6$ | 2,6-dimethylphenyl 2-((3,4-bis(methyloxy)-5-((2-(4-methyl-1-piperazinyl)ethyl)oxy)phenyl)amino)-4-pyrimidinyl(2-((difluoromethyl)oxy)phenyl)carbamate | 678.73 | 679 |
| 149 | $C_{34}H_{40}N_6O_5$ | 2,6-dimethylphenyl 2-((3-(methyloxy)-4-((2-(4-methyl-1-piperazinyl)ethyl)oxy)phenyl)amino)-4-pyrimidinyl(2-(methyloxy)phenyl)carbamate | 612.73 | 613 |
| 150 | $C_{35}H_{42}N_6O_6$ | 2,6-dimethylphenyl 2-((3,4-bis(methyloxy)-5-((2-(4-methyl-1-piperazinyl)ethyl)oxy)phenyl)amino)-4-pyrimidinyl(2-(methyloxy)phenyl)carbamate | 642.75 | 643 |
| 151 | $C_{30}H_{32}FN_5O_4$ | 2,6-dimethylphenyl 2-((4-((2-(dimethylamino)ethyl)oxy)-3-fluorophenyl)amino)-4-pyrimidinyl(2-(methyloxy)phenyl)carbamate | 545.61 | 546 |
| 152 | $C_{31}H_{34}FN_5O_5$ | 2,6-dimethylphenyl 2,4-bis(methyloxy)phenyl(2-((4-((2-(dimethylamino)ethyl)oxy)-3-fluorophenyl)amino)-4-pyrimidinyl)carbamate | 575.64 | 576 |
| 153 | $C_{32}H_{37}N_5O_6$ | 2,6-dimethylphenyl 2,4-bis(methyloxy)phenyl(2-((4-((2-(dimethylamino)ethyl)oxy)-3-(methyloxy)phenyl)amino)-4-pyrimidinyl)carbamate | 587.67 | 588 |

-continued

| No. | Formula | Name | MW | MH+ |
|---|---|---|---|---|
| 154 | $C_{31}H_{35}N_5O_4$ | 2,6-dimethylphenyl 2-((4-((2-(dimethyl-amino)ethyl)oxy)phenyl)amino)-4-pyrimidinyl(2-(ethyloxy)phenyl)-carbamate | 541.65 | 542 |
| 155 | $C_{32}H_{37}N_5O_4$ | 2,6-dimethylphenyl 2-((4-((3-(dimethyl-amino)propyl)oxy)phenyl)amino)-4-pyrimidinyl(2-(ethyloxy)phenyl)-carbamate | 555.68 | 556 |
| 156 | $C_{30}H_{33}N_5O_3S$ | 2,6-dimethylphenyl 2-((4-((2-(dimethyl-amino)ethyl)oxy)phenyl)amino)-4-pyrimidinyl(2-(methylsulfanyl)phenyl)-carbamate | 543.69 | 544 |
| 157 | $C_{31}H_{34}N_6O_3$ | 2,6-dimethylphenyl 2-(methyloxy)-phenyl(2-((4-(4-methyl-1-piperazinyl)-phenyl)amino)-4-pyrimidinyl)carbamate | 538.65 | 539 |
| 158 | $C_{31}H_{32}F_2N_6O_3$ | 2,6-dimethylphenyl 2-((difluoromethyl)-oxy)phenyl(2-((4-(4-methyl-1-piperazin-yl)phenyl)amino)-4-pyrimidinyl)-carbamate | 574.63 | 575 |
| 159 | $C_{37}H_{46}N_6O_7$ | 2,6-dimethylphenyl 2-((3,5-bis(methyl-oxy)-4-((3-(4-methyl-1-piperazinyl)-propyl)oxy)phenyl)amino)-4-pyrimidin-yl(2,4-bis(methyloxy)phenyl)carbamate | 686.81 | 687 |
| 160 | $C_{36}H_{44}N_6O_7$ | 2,6-dimethylphenyl 2-((3,5-bis(methyl-oxy)-4-((2-(4-methyl-1-piperazinyl)-ethyl)oxy)phenyl)amino)-4-pyrimidin-yl(2,4-bis(methyloxy)phenyl)carbamate | 672.78 | 673 |
| 161 | $C_{36}H_{43}N_5O_6$ | 2,4,6-trimethylphenyl 2,4-bis(methyl-oxy)phenyl(2-((4-((2-hydroxy-3-(1-piperidinyl)propyl)oxy)phenyl)amino)-4-pyrimidinyl)carbamate | 641.77 | 642 |
| 162 | $C_{37}H_{46}N_6O_7$ | 2,4,6-trimethylphenyl 2-((3,5-bis(methyl-oxy)-4-((2-(4-methyl-1-piperazinyl)-ethyl)oxy)phenyl)amino)-4-pyrimidin-yl(2,4-bis(methyloxy)phenyl)carbamate | 686.81 | 687 |
| 163 | $C_{36}H_{44}N_6O_6$ | 2,6-dimethylphenyl 2-((3,5-bis(methyl-oxy)-4-((2-(4-methyl-1-piperazinyl)-ethyl)oxy)phenyl)amino)-4-pyrimidin-yl(2-(ethyloxy)phenyl)carbamate | 656.78 | 657 |
| 164 | $C_{34}H_{40}N_6O_5$ | 2,6-dimethylphenyl 2,4-bis(methyloxy)-phenyl(2-((4-(((2-(diethylamino)ethyl)-amino)carbonyl)phenyl)amino)-4-pyrimidinyl)carbamate | 612.73 | 613 |
| 165 | $C_{37}H_{46}N_6O_6$ | 2,6-dimethylphenyl 2-((3,5-bis(methyl-oxy)-4-((3-(4-methyl-1-piperazinyl)-propyl)oxy)phenyl)amino)-4-pyrimidin-yl(2-(ethyloxy)phenyl)carbamate | 670.81 | 671 |
| 166 | $C_{35}H_{41}N_5O_4$ | 2,6-dimethylphenyl 2,4-dimethylphenyl-(2-((4-((2-hydroxy-3-(1-piperidinyl)-propyl)oxy)phenyl)amino)-4-pyrimidinyl)carbamate | 595.74 | 596 |
| 167 | $C_{35}H_{42}N_6O_4$ | 2,6-dimethylphenyl 2,4-dimethylphenyl-(2-((3-(methyloxy)-4-((2-(4-methyl-1-piperazinyl)ethyl)oxy)phenyl)amino)-4-pyrimidinyl)carbamate | 610.76 | 611 |
| 168 | $C_{37}H_{46}N_6O_6$ | 2,4,6-trimethylphenyl 2,4-bis(methyl-oxy)phenyl(2-((3-(methyloxy)-4-((3-(4-methyl-1-piperazinyl)propyl)oxy)-phenyl)amino)-4-pyrimidinyl)carbamate | 670.81 | 671 |
| 169 | $C_{36}H_{44}N_6O_6$ | 2,4,6-trimethylphenyl 2,4-bis(methyl-oxy)phenyl(2-((3-(methyloxy)-4-((2-(4-methyl-1-piperazinyl)ethyl)oxy)phenyl)-amino)-4-pyrimidinyl)carbamate | 656.78 | 657 |

EXAMPLES 170 TO 172

The following compounds were prepared using the procedures outlined above for the preparation of 2,6-dimethylphenyl-4-(methyloxy)phenyl(2-((4-(4-methyl-1-piperazinyl)phenyl)amino)-4-pyrimidinyl)carbamate with the following exception: In Step C the reactions were heated in isopropanol at 80° C. for 1-2 days with N,N-diisopropylethylamine and no acid catalyst. Concentration and chromatography afforded the final compounds.

EXAMPLE 170

2,6-Dimethylphenyl 2,4-bis(methyloxy)phenyl(2-((2-(4-morpholinyl)ethyl)amino)-4-pyrimidinyl)carbamate MS (MH$^+$) 508.2; Calculated 507 for $C_{27}H_{33}N_5O_5$.

EXAMPLE 171

2,6-Dimethylphenyl 2,4-bis(methyloxy)phenyl(2-((3-(1-pyrrolidinyl)propyl)amino)-4-pyrimidinyl)carbamate MS (MH$^+$) 506.2; Calculated 505 for $C_{28}H_{35}N_5O_4$.

EXAMPLE 172

2,6-Dimethylphenyl 2,4-bis(methyloxy)phenyl(2-((3-(4-methyl-1-piperazinyl)propyl)amino)-4-pyrimidinyl)carbamate MS (MH$^+$) 535.3; Calculated 534 for $C_{29}H_{38}N_6O_4$.

EXAMPLE 173

3-Pyridinylmethyl-2-((4-((2-(dimethylamino)ethyl)oxy)phenyl)amino)-4-pyrimidinyl(4-(methyloxy)phenyl)carbamate Step A: (4-Methoxyphenyl)-carbamic acid pyridin-3-ylmethyl ester A resealable tube was charged with 4-methoxyphenylisocyanate (1.00 g, 6.70 mmol), 3-pyridylcarbinol (0.800 g, 7.33 mmol), and toluene (4 mL). The tube was sealed and the mixture was heated at 100° C. for 20 h. The reaction mixture was cooled to room temperature. The resulting white solid was collected by suction filtration and washed with diethyl ether. The solid was dried under vacuum to give (4-methoxyphenyl)-carbamic acid pyridin-3-ylmethyl ester a white solid.

Step B: (2-Chloropyrimidin-4-yl)-(4-methoxyphenyl)carbamic acid pyridin-3-ylmethyl ester Sodium hydride (60% dispersion, 0.30 g, 0.75 mmol) was added to a solution of 2,4-dichloropyrimidine (0.75 g, 0.50 mmol) and (4-methoxyphenyl)-carbamic acid pyridin-3-ylmethyl ester (1.3 g, 0.50 mmol) in DMF (5 mL). The mixture was allowed to stir at room temperature for 2 h. The resulting solution was diluted with sat. aqueous ammonium chloride and ethyl acetate. The organic phase was separated and washed with brine, dried over anhydrous magnesium sulfate, filtered, and concentrated to afford a colorless oil. This oil was purified via column chromatography on silica gel (gradient elution with 0-5% methanol-dichloro-methane) to afford (2-chloropyrimidin-4-yl)-(4-methoxyphenyl)carbamic acid pyridin-3-ylmethyl ester as a tan solid. MS (MH$^+$) 371; Calculated 370.8 for $C_{18}H_{15}ClN_4O_3$.

Step C: 3-Pyridinylmethyl-2-((4-((2-(dimethylamino)ethyl)oxy)phenyl)amino)-4-pyrimidinyl(4-(methyloxy)phenyl)carbamate A resealable tube was charged with (2-chloropyrimidin-4-yl)-(4-methoxyphenyl)-carbamic acid pyridin-3-ylmethyl ester (0.100 g, 0.270 mmol), 4-(2-dimethylamino-ethoxy)-phenylamine (0.073 g, 0.405 mmol), and isopropanol (2 mL). Trifluoroacetic acid (0.148 g, 0.100 mL, 1.30 mmol) was added, the tube was sealed, and the mixture was heated at 100° C. for 20 h. The reaction mixture was cooled to room temperature and concentrated to afford a pale purple oil. The oil was purified via preparative reverse phase HPLC. The isolated fractions were partitioned between ethyl acetate and saturated sodium bicarbonate solution. The organic phase was separated, dried over anhydrous magnesium sulfate, filtered, and concentrated to afford 3-pyridinylmethyl-2-((4-((2-(dimethylamino)ethyl)oxy)phenyl)amino)-4-pyrimidinyl(4-(methyloxy)phenyl)carbamate as a white solid. MS (MH$^+$) 515; Calculated 514.59 for $C_{28}H_{30}N_6O_4$.

EXAMPLES 174 TO 178

The following compounds were prepared using the procedure outlined above for the synthesis of 3-pyridinylmethyl-2-((4-((2-(dimethylamino)ethyl)oxy)phenyl)amino)-4-pyrimidinyl(4-(methyloxy)phenyl)carbamate.

EXAMPLE 174

3-Pyridinylmethyl 2-((3-(methyloxy)-4-(4-methyl-1-piperazinyl)phenyl)amino)-4-pyrimidinyl(4-(methyloxy)phenyl)carbamate MS (MH$^+$) 556; Calculated 555.64 for $C_{30}H_{33}N_7O_4$.

EXAMPLE 175

(3S)-Tetrahydro-3-furanyl 2-((4-((2-(dimethylamino)ethyl)oxy)phenyl)amino)-4-pyrimidinyl(4-(methyloxy)phenyl)carbamate MS (MH$^+$) 494; Calculated 493.57 for $C_{26}H_{31}N_5O_5$.

EXAMPLE 176

(3S)-Tetrahydro-3-furanyl 2-((3-(methyloxy)-4-(4-methyl-1-piperazinyl)phenyl)amino)-4-pyrimidinyl(4-(methyloxy)phenyl)carbamate MS (MH$^+$) 535; Calculated 534.62 for $C_{28}H_{34}N_6O_5$.

EXAMPLE 177

2,6-Dimethylphenyl 2,4-bis(methyloxy)phenyl(2-((4-((3-(1-piperidinyl)propyl)oxy)phenyl)amino)-4-pyrimidinyl)carbamate MS (MH$^+$) 612; Calculated 611.74 for $C_{35}H_{41}N_5O_5$.

EXAMPLE 178

4-Pyridinylmethyl 4-(methyloxy)phenyl(2-((4-((3-(1-piperidinyl)-propyl)oxy)phenyl)amino)-4-pyrimidinyl)carbamate MS (MH$^+$) 569; Calculated 568.67 for $C_{32}H_{36}N_6O_4$.

EXAMPLE 179

2,6-Dimethylphenyl 4-(methyloxy)-2-(1,3-oxazol-5-yl)phenyl(2-((4-((3-(1-piperidinyl)propyl)oxy)phenyl)amino)-4-pyrimidinyl)carbamate Step A: 5-Methoxy-2-nitro-benzaldehyde To a suspension of 5-hydroxy-2-nitro-benzaldehyde (10 g, 59.8 mmol) and cesium carbonate (23 g, 70.6 mmol) in DMF (40 mL) was added iodomethane (8.8 mL, 141 mmol), and the mixture stirred at room temperature for 17 h. The resulting red-orange suspension was diluted with ethyl acetate and the mixture was partitioned between ethyl acetate and water. The organic phase was separated and washed with brine, dried over anhydrous magnesium sulfate, filtered, and concentrated to afford a thick yellow oil which solidified on standing to afford 5-methoxy-2-nitro-benzaldehyde.

Step B: 5-(5-Methoxy-2-nitrophenyl)oxazole

A suspension of 5-methoxy-2-nitro-benzaldehyde (3.5 g, 19.3 mmol), tosylmethyl-isocyanide (4.5 g, 23.05 mmol) and potassium carbonate (6.7 g, 48.5 mmol) in methanol (40 mL) was stirred at room temperature for 4 h. The resulting red-orange suspension was concentrated and the residue diluted with ethyl acetate. The mixture was partitioned between ethyl acetate and water. The organic phase was separated and washed with brine, dried over anhydrous magnesium sulfate, filtered, and concentrated to afford a yellow oil. This oil was purified via column chromatography on silica gel (gradient elution with 0-10% methanol-methylenechloride) to afford 5-(5-methoxy-2-nitrophenyl)oxazole.

Step C: 4-Methoxy-2-(oxazol-5-yl)phenylamine

A flask was charged with the 5% Pd/C (800 mg), (5-methoxy-2-nitrophenyl)oxazole. (2.5 g, 11.35 mmol) and ethanol (100 mL). The system was flushed with hydrogen and the mixture stirred under a hydrogen atmosphere for 17 h. The catalyst was removed via suction filtration and the organics concentrated to afford 4-methoxy-2-(oxazol-5-yl)phenylamine as a yellow-green solid.

Step D: (2-Chloropyrimidin-4-yl)-(4-methoxy-2-oxazol-5-yl-phenyl)-amine

Prepared using the procedure outlined for the preparation of 2-chloro-4-(4-methoxy)-anilinopyrimidine.

Step E: (2-Chloropyrimidin-4-yl)-(4-methoxy-2-(oxazol-5-yl)phenyl)carbamic acid 2,6-dimethylphenyl ester 2,6-Dimethylphenylchloroformate (0.200 g, 1.08 mmol) was added to a solution of (2-chloropyrimidin-4-yl)-(4-methoxy-2-oxazol-5-yl-phenyl)-amine (0.200 g, 0.661 mmol), 4-dimethylaminopyridine (0.050 g, 0.41 mmol) and N,N-diisopropylethyl-amine (0.551 g, 1.0 mL, 4.26 mmol) in tetrahydrofuran (2 mL). The mixture stirred at room temperature for 17 h. The resulting solution was diluted with ethyl acetate and the mixture was partitioned between ethyl acetate and saturated sodium bicarbonate solution. The organic phase was separated, dried over anhydrous magnesium sulfate, filtered, and concentrated to afford an oil. This oil was purified via column chromatography on silica gel (gradient elution with 0-50% ethyl acetate-hexane) to afford (2-chloropyrimidin-4-yl)-(4-methoxy-2-(oxazol-5-yl)phenyl)-carbamic acid 2,6-dimethylphenyl ester as a tan solid. MS (MH$^+$) 451; Calculated 450.89 for $C_{23}H_{19}ClN_4O_4$ Step F: 2,6-Dimethylphenyl 4-(methyloxy)-2-(1,3-oxazol-5-yl)phenyl(2-((4-((3-(1-piperidinyl)propyl)oxy)phenyl)amino)-4-pyrimidinyl)carbamate Prepared using the procedure outlined for the preparation of 2,6-dimethylphenyl 2-((4-((2-(dimethylamino)ethyl)oxy)phenyl)amino)-4-pyrimidinyl(phenylmethyl)-carbamate. MS (MH$^+$) 649; Calculated 648.77 for $C_{37}H_{40}N_6O_5$.

EXAMPLE 180

2,6-Dimethylphenyl 2,4-bis(methyloxy)phenyl(5-fluoro-2-((4-((3-(1-piperidinyl)propyl)oxy)phenyl)amino)-4-pyrimidinyl)carbamate Step A: (2-Chloro-5-fluoro-pyrimidin-4-yl)-(2,4-dimethoxy-phenyl)-amine 2,4-dimethoxyaniline (4.1 g, 24.6 mmol) was added to a solution of 2,4-dichloro-5-fluoropyrimidine (4.1 g, 24.6 mmol) in isopropanol (16 mL). N,N-Diisopropyl-ethylamine (6.30 g, 8.50 mL, 48.8 mmol) was added and the mixture was allowed to stir at room temperature for 24 h. The solution was partitioned between ethyl acetate and water. The organic phase was separated and washed with brine, dried over anhydrous magnesium sulfate, filtered, and concentrated to afford an oil. This oil was purified via column chromatography on silica gel (gradient elution with 0-10% methanol-methylenechloride) to afford (2-chloro-5-fluoro-pyrimidin-4-yl)-(2,4-dimethoxy-phenyl) amine. MS (MH$^+$) 284; Calculated 283.69 for $C_{12}H_{11}ClFN_3O_2$.

Step B: 2-Chloro-5-fluoro-pyrimidin-4-yl)-(2,4-dimethoxyphenyl)carbamic acid 2,6-dimethylphenyl ester 2,6-Dimethylphenylchloroformate (1.5 g, 8.1 mmol) was added to a solution of (2-chloro-5-fluoro-pyrimidin-4-yl)-(2,4-dimethoxy-phenyl) amine (1.0 g, 3.52 mmol), 4-dimethylaminopyridine (0.100 g, 0.82 mmol) and N,N-diisopropyl-ethylamine (1.82 g, 2.5 mL, 14.1 mmol) in tetrahydrofuran (15 mL). The mixture stirred at room temperature for 17 h. The resulting solution was diluted with ethyl acetate and the mixture was partitioned between ethyl acetate and saturated sodium bicarbonate solution. The organic phase was separated, dried over anhydrous magnesium sulfate, filtered, and concentrated to afford an oil. This oil was purified via column chromatography on silica gel (gradient elution with 0-100% ethyl acetate-hexane) to afford 2-chloro-5-fluoro-pyrimidin-4-yl)-(2,4-dimethoxyphenyl)carbamic acid 2,6-dimethylphenyl ester.

Step C. 2,6-dimethylphenyl 2,4-bis(methyloxy)phenyl(5-fluoro-2-((4-((3-(1-piperidinyl)propyl)oxy)phenyl)amino)-4-pyrimidinyl)carbamate Prepared using the procedure outlined for the preparation of 2,6-dimethylphenyl 2-((4-((2-(dimethylamino)ethyl)oxy)phenyl)amino)-4-pyrimidinyl(phenylmethyl)-carbamate. MS (MH$^+$) 630; Calculated 629.73 for $C_{35}H_{40}N_5O_5F$.

EXAMPLE 181

3-Pyridinylmethyl 2,4-bis(methyloxy)phenyl(2-((4-((3-(1-piperidinyl)propyl)oxy)phenyl)amino)-4-pyrimidinyl)carbamate Step A: (2-Chloro-pyrimidin-4-yl)-(2,4-dimethoxyphenyl)carbamic acid pyridin-3-ylmethyl ester ((3-Pyridinyl)methyl)-(4-nitrophenyl)carbonate (Ref. EP 0486948 A2) (7.70 g, 28.1 mmol) was added to a solution of (2-chloropyrimidin-4-yl)-(2,4-dimethoxy-phenyl)amine (5.0 g, 18.8 mmol), 4-dimethylaminopyridine (0.500 g, 3.28 mmol) and N,N-diisopropylethylamine (9.73 g, 13.0 mL, 75.3 mmol) in tetrahydrofuran (50 mL). The mixture stirred at room temperature for 72 h. The resulting solution was diluted with ethyl acetate and the mixture was partitioned between ethyl acetate and saturated sodium bicarbonate solution. The organic phase was separated, dried over anhydrous magnesium sulfate, filtered, and concentrated to afford an oil. This oil was purified via column chromatography on silica gel (gradient elution with 0-10% methanol-methylenechloride)

to afford (2-chloro-pyrimidin-4-yl)-(2,4-dimethoxyphenyl) carbamic acid pyridin-3-ylmethyl ester as a white solid. MS (MH$^+$) 401; Calculated 400.82 for $C_{19}H_{17}N_4O_4Cl$.

Step B: 3-Pyridinylmethyl 2,4-bis(methyloxy)phenyl(2-((4-((3-(1-piperidinyl)-propyl)oxy)phenyl)amino)-4-pyrimidinyl)carbamate Prepared using the procedure outlined for the preparation of 2,6-dimethylphenyl 2-((4-((2-(dimethylamino)ethyl)oxy) phenyl)amino)-4-pyrimidinyl(phenylmethyl)-carbamate. MS (MH$^+$) 599; Calculated 598.71 for $C_{33}H_{38}N_6O_5$.

EXAMPLE 182

3-Pyridinylmethyl 2,4-bis(methyloxy)phenyl(2-((3-(methyloxy)-4-(4-methyl-1-piperazinyl)phenyl) amino)-4-pyrimidinyl)carbamate A resealable tube was charged with (2-chloro-pyrimidin-4-yl)-(2,4-dimethoxy-phenyl)carbamic acid pyridin-3-ylmethyl ester (0.100 g, 0.249 mol), 3-(methyloxy)-4-(4-methyl-1-piperazinyl)aniline (0.100 g, 0.45 mmol), and isopropanol (2 mL). Trifluoroacetic acid (0.074 g, 0.050 mL, 0.65 mmol) was added. The tube was sealed and the mixture was heated at 60° C. for 20 h. The reaction mixture was cooled to room temperature and concentrated to afford a pale purple oil. The resulting solution was diluted with ethyl acetate and the mixture was partitioned between ethyl acetate and saturated sodium bicarbonate solution. The organic phase was separated, dried over anhydrous sodium sulfate, filtered, and concentrated to afford an oil. This oil was purified via column chromatography on silica gel (gradient elution with 0-100% dichloromethane-(90:10:1, dichloromethane/methanol/ammonium hydroxide)) to afford 3-pyridinylmethyl 2,4-bis(methyloxy)-phenyl(2-((3-(methyloxy)-4-(4-methyl-1-piperazinyl)phenyl)amino)-4-pyrimidinyl)-carbamate as an off-white solid. MS (MH$^+$) 586; Calculated 585.66 for $C_{31}H_{35}N_7O_5$.

EXAMPLE 183

3-Pyridinylmethyl 2,4-bis(methyloxy)phenyl(2-((4-((2-(dimethylamino)ethyl)oxy)phenyl)amino)-4-pyrimidinyl)carbamate A resealable tube was charged with (2-chloro-pyrimidin-4-yl)-(2,4-dimethoxy-phenyl)-carbamic acid pyridin-3-ylmethyl ester (0.100 g, 0.249 mol), 4-(2-dimethylamino-ethoxy)-phenylamine (0.100 g, 0.51 mmol), and isopropanol (2 mL). Trifluoroacetic acid (0.074 g, 0.050 mL, 0.65 mmol) was added. The tube was sealed and the mixture was heated at 60° C. for 20 h. The reaction mixture was cooled to room temperature and concentrated to afford a pale purple oil. The resulting solution was diluted with ethyl acetate and the mixture was partitioned between ethyl acetate and saturated sodium bicarbonate solution. The organic phase was separated, dried over anhydrous sodium sulfate, filtered, and concentrated to afford an oil. This oil was purified via column chromatography on silica gel (gradient elution with 0-100% dichloromethane-(90:10:1, dichloromethane/methanol/ammonium hydroxide)) to afford 3-pyridinylmethyl 2,4-bis(methyloxy)-phenyl(2-((4-((2-(dimethylamino)ethyl)oxy)phenyl)amino)-4-pyrimidinyl)-carbamate as a tan solid. MS (MH$^+$) 545; Calculated 544.61 for $C_{29}H_{32}N_6O_5$.

EXAMPLES 184 TO 187

The following compounds were prepared using the procedure outlined above for the preparation of in 2,6-dimethylphenyl-4-(methyloxy)phenyl(2-((4-(4-methyl-1-piperazinyl)phenyl)amino)-4-pyrimidinyl)carbamate, with the exception of the following. Step A: the reaction was performed using 2,4-dichloropyridine and 2,4-dimethoxyaniline.HCl in i-PrOH at 100° C. for 2-3 days. Step C: The reactions were heated from 7-19 days, concentrated, diluted with EtOAc, washed with saturated aqueous sodium bicarbonate and brine, dried, concentrated and purified by chromatography (SiO$_2$, CH$_2$Cl$_2$-MeOH elution systems) to afford the final compounds.

EXAMPLE 184

2,6-Dimethylphenyl 2,4-bis(methyloxy)phenyl(2-((4-((2-(dimethylamino)ethyl)oxy)phenyl)amino)-4-pyridinyl)carbamate MS (MH$^+$) 557.2; Calculated 556 for $C_{32}H_{36}N_4O_5$.

EXAMPLE 185

2,6-Dimethylphenyl 2,4-bis(methyloxy)phenyl(2-((4-((3-(dimethylamino)propyl)oxy)phenyl)amino)-4-pyridinyl)carbamate MS (MH$^+$) 571.2; Calculated 570 for $C_{33}H_{38}N_4O_5$.

EXAMPLE 186

2,6-Dimethylphenyl 2,4-bis(methyloxy)phenyl(2-((3-(methyloxy)-4-((2-(4-methyl-1-piperazinyl) ethyl)oxy)phenyl)amino)-4-pyridinyl)carbamate MS (MH$^+$) 642.3; Calculated 641 for $C_{36}H_{43}N_5O_6$.

EXAMPLE 187

2,6-Dimethylphenyl 2-((3,5-bis(methyloxy)-4-((3-(4-methyl-1-piperazinyl)propyl)oxy)phenyl)amino)-4-pyridinyl(2,4-bis(methyloxy)phenyl)-carbamate MS (MH$^+$) 686.3; Calculated 685 for $C_{38}H_{47}N_5O_7$.

The following additional exemplary compounds were synthesized in accordance with the methods described herein:

EXAMPLE 188

2,6-dimethylphenyl 2,4-bis(methyloxy)phenyl(2-((4-((2-(diethylamino)ethyl)oxy)phenyl)amino)-4-pyrimidinyl)carbamate;

EXAMPLE 189

2,6-dimethylphenyl 2,4-bis(methyloxy)phenyl(2-((3-chloro-4-((2-((1-methylethyl)amino)ethyl)oxy)phenyl)amino)-4-pyrimidinyl)carbamate;

EXAMPLE 190

2,6-dimethylphenyl 2,4-bis(methyloxy)phenyl(2-((4-(((2-(diethylamino)ethyl)(methyl)amino)carbonyl) phenyl)amino)-4-pyrimidinyl)carbamate;

EXAMPLE 191

2,6-dimethylphenyl 2-((3,4-bis(methyloxy)-5-((3-(4-methyl-1-piperazinyl)propyl)oxy)phenyl)amino)-4-pyrimidinyl(2,4-dimethylphenyl)carbamate;

EXAMPLE 192

2,4,6-trimethylphenyl 2,4-bis(methyloxy)phenyl(2-((4-(4-methyl-1-piperazinyl)phenyl)amino)-4-pyrimidinyl)carbamate;

EXAMPLE 193

2,6-dimethylphenyl 2,4-bis(methyloxy)phenyl(2-((3,5-difluoro-4-((2-(1-piperidinyl)ethyl)oxy)phenyl)amino)-4-pyrimidinyl)carbamate;

EXAMPLE 194

2,4,6-trimethylphenyl 2-((4-((2-(dimethylamino)ethyl)oxy)phenyl)amino)-4-pyrimidinyl(2-(2-(methyloxy)phenyl)ethyl)carbamate;

EXAMPLE 195

2,4,6-trimethylphenyl 2-((4-((2-(dimethylamino)ethyl)oxy)phenyl)amino)-4-pyrimidinyl(3-phenylpropyl)carbamate;

EXAMPLE 196

2,4,6-trimethylphenyl 2-((4-((2-(dimethylamino)ethyl)oxy)phenyl)amino)-4-pyrimidinyl(2-(4-morpholinyl)ethyl)carbamate;

EXAMPLE 197

2,4,6-trimethylphenyl 2-((4-((3-(1-piperidinyl)propyl)oxy)phenyl)amino)-4-pyrimidinyl((2-((trifluoromethyl)oxy)phenyl)methyl)carbamate;

EXAMPLE 198

2,4,6-trimethylphenyl 2-((3-(methyloxy)-4-((3-(4-methyl-1-piperazinyl)propyl)oxy)phenyl)amino)-4-pyrimidinyl((2-((trifluoromethyl)oxy)phenyl)methyl)carbamate;

EXAMPLE 199

2,4,6-trimethylphenyl 2-((3-(methyloxy)-4-((2-(4-methyl-1-piperazinyl)ethyl)oxy)phenyl)amino)-4-pyrimidinyl((2-((trifluoromethyl)oxy)phenyl)methyl)carbamate;

EXAMPLE 200

2,4,6-trimethylphenyl 2-((3,5-bis(methyloxy)-4-((3-(4-methyl-1-piperazinyl)propyl)oxy)phenyl)amino)-4-pyrimidinyl((2((trifluoromethyl)oxy)phenyl)methyl)carbamate;

EXAMPLE 201

2,6-dimethylphenyl 2-((4-(4-amino-1-piperidinyl)phenyl)amino)-4-pyrimidinyl(2,4-bis(methyloxy)phenyl)carbamate;

EXAMPLE 202

2,6-dimethylphenyl 2-((3,4-bis(methyloxy)-5-((2-(4-methyl-1-piperazinyl)ethyl)oxy)phenyl)amino)-4-pyrimidinyl(2-(ethyloxy)phenyl)carbamate;

EXAMPLE 203

2,6-dimethylphenyl 2-((4-((2-(dimethylamino)ethyl)oxy)phenyl)amino)-4-pyrimidinyl(4-fluoro-2-((1-methylethyl)oxy)phenyl)carbamate;

EXAMPLE 204

2,6-dimethylphenyl 2-((3,4-bis(methyloxy)-5-((3-(4-methyl-1-piperazinyl)propyl)oxy)phenyl)amino)-4-pyrimidinyl(2-(ethyloxy)phenyl)carbamate;

EXAMPLE 205

2,6-dimethylphenyl 2-((3,5-bis(methyloxy)-4-((3-(4-methyl-1-piperazinyl)propyl)oxy)phenyl)amino)-4-pyrimidinyl(4-fluoro-2-((1-methylethyl)oxy)phenyl)carbamate;

EXAMPLE 206

2,6-dimethylphenyl 2-(ethyloxy)phenyl(2-((4-(4-methyl-1-piperazinyl)phenyl)amino)-4-pyrimidinyl)carbamate;

EXAMPLE 207

2,6-dimethylphenyl 4-fluoro-2-((1-methylethyl)oxy)phenyl(2-((4-(4-methyl-1-piperazinyl)phenyl)amino)-4-pyrimidinyl)carbamate;

EXAMPLE 208

2,4,6-trimethylphenyl(2,5-dichlorophenyl)methyl(2-((4-((3-(1-piperidinyl)propyl)oxy)phenyl)amino)-4-pyrimidinyl)carbamate;

EXAMPLE 209

2,4,6-trimethylphenyl(2,5-dichlorophenyl)methyl(2-((3-(methyloxy)-4-((3-(4-methyl-1-piperazinyl)propyl)oxy)phenyl)amino)-4-pyrimidinyl)carbamate;

EXAMPLE 210

2,4,6-trimethylphenyl(2,5-dichlorophenyl)methyl(2-((3-fluoro-4-((3-(1-piperidinyl)propyl)oxy)phenyl)amino)-4-pyrimidinyl)carbamate;

EXAMPLE 211

2,4,6-trimethylphenyl(2,5-dimethylphenyl)methyl(2-((4-((3-(1-piperidinyl)propyl)oxy)phenyl)amino)-4-pyrimidinyl)carbamate;

EXAMPLE 212

2,4,6-trimethylphenyl(2,5-dimethylphenyl)methyl(2-((3-(methyloxy)-4-((3-(4-methyl-1-piperazinyl)propyl)oxy)phenyl)amino)-4-pyrimidinyl)carbamate;

EXAMPLE 213

2,4,6-trimethylphenyl(2,5-dimethylphenyl)methyl(2-((3-fluoro-4-((3-(1-piperidinyl)propyl)oxy)phenyl)amino)-4-pyrimidinyl)carbamate;

EXAMPLE 214

2,6-dimethylphenyl 2-(ethyloxy)phenyl(2-((3-(methyloxy)-4-((2-(4-methyl-1-piperazinyl)ethyl)oxy)phenyl)amino)-4-pyrimidinyl)carbamate;

EXAMPLE 215

2,6-dimethylphenyl 2-((3-aminophenyl)amino)-4-pyrimidinyl(1,1'-biphenyl-3-yl)carbamate;

EXAMPLE 216

2,6-dimethylphenyl 2-((3-aminophenyl)amino)-4-pyrimidinyl(2-(ethyloxy)phenyl)carbamate;

EXAMPLE 217

2,4,6-trimethylphenyl(2,5-bis(methyloxy)phenyl)methyl(2-((4-(((2-(dimethylamino)ethyl)amino)carbonyl)phenyl)amino)-4-pyrimidinyl)carbamate;

EXAMPLE 218

2,6-dimethylphenyl 2-((3,5-bis(methyloxy)-4-((2-(4-methyl-1-piperazinyl)ethyl)oxy)phenyl)amino)-4-pyrimidinyl(4-fluoro-2-((1-methylethyl)oxy)phenyl)carbamate;

EXAMPLE 219

2,6-dimethylphenyl 2-((3,4-bis(methyloxy)-5-((3-(4-methyl-1-piperazinyl)propyl)oxy)phenyl)amino)-4-pyrimidinyl(4-fluoro-2-((1-methylethyl)oxy)phenyl)carbamate;

EXAMPLE 220

2,6-dimethylphenyl 4-fluoro-2-((1-methylethyl)oxy)phenyl(2-((3-(methyloxy)-4-((3-(4-methyl-1-piperazinyl)propyl)oxy)phenyl)amino)-4-pyrimidinyl)carbamate;

EXAMPLE 221

2,6-dimethylphenyl 4-fluoro-2-((1-methylethyl)oxy)phenyl(2-((3-(methyloxy)-4-((2-(4-methyl-1-piperazinyl)ethyl)oxy)phenyl)amino)-4-pyrimidinyl)carbamate;

EXAMPLE 222

2,6-dimethylphenyl 2-((4-(aminocarbonyl)phenyl)amino)-4-pyrimidinyl(1,1'-biphenyl-3-yl)carbamate;

EXAMPLE 223

2-chlorophenyl 2,4-bis(methyloxy)phenyl(2-((4-((3-(1-piperidinyl)propyl)oxy)phenyl)amino)-4-pyrimidinyl)carbamate;

EXAMPLE 224

2-chlorophenyl 2,4-bis(methyloxy)phenyl(2-((3-(methyloxy)-4-(4-methyl-1-piperazinyl)phenyl)amino)-4-pyrimidinyl)carbamate;

EXAMPLE 225

2,6-dimethylphenyl 2-ethyl-4-(methyloxy)phenyl(2-((4-((3-(1-piperidinyl)propyl)oxy)phenyl)amino)-4-pyrimidinyl)carbamate;

EXAMPLE 226

2,6-dimethylphenyl 2-(1,3-oxazol-5-yl)phenyl(2-((4-((3-(1-piperidinyl)propyl)oxy)phenyl)amino)-4-pyrimidinyl)carbamate;

EXAMPLE 227

2,6-difluorophenyl 2,4-bis(methyloxy)phenyl(2-((4-((3-(1-piperidinyl)propyl)oxy)phenyl)amino)-4-pyrimidinyl)carbamate;

EXAMPLE 228

2,4,6-trimethylphenyl 2-((4-(((2-(dimethylamino)ethyl)amino)carbonyl)phenyl)amino)-4-pyrimidinyl(2-(methyloxy)phenyl)carbamate;

EXAMPLE 229

2,4,6-trimethylphenyl 2-((4-(((2-(diethylamino)ethyl)amino)carbonyl)phenyl)amino)-4-pyrimidinyl(2-(methyloxy)phenyl)carbamate;

EXAMPLE 230

2,4,6-trimethylphenyl 2-((2-(aminomethyl)phenyl)amino)-4-pyrimidinyl(2-(methyloxy)phenyl)carbamate;

EXAMPLE 231

2,4,6-trimethylphenyl(5-chloro-2-methylphenyl)methyl(2-((3-(methyloxy)-4-((3-(4-methyl-1-piperazinyl)propyl)oxy)phenyl)amino)-4-pyrimidinyl)carbamate;

EXAMPLE 232

2,4,6-trimethylphenyl(5-chloro-2-methylphenyl)methyl(2-((3-fluoro-4-((3-(1-piperidinyl)propyl)oxy)phenyl)amino)-4-pyrimidinyl)carbamate;

EXAMPLE 233

2,4,6-trimethylphenyl(2-chloro-5-(trifluoromethyl) phenyl)methyl(2-((3-(methyloxy)-4-((3-(4-methyl-1-piperazinyl)propyl)oxy)phenyl)amino)-4-pyrimidinyl)carbamate;

EXAMPLE 234

2,4,6-trimethylphenyl(2-chloro-5-(trifluoromethyl) phenyl)methyl(2-((3-fluoro-4-((3-(1-piperidinyl) propyl)oxy)phenyl)amino)-4-pyrimidinyl)carbamate;

EXAMPLE 235

2,6-dimethylphenyl(2,5-bis(methyloxy)phenyl)methyl(2-((4-(4-methyl-1-piperazinyl)phenyl)amino)-4-pyrimidinyl)carbamate;

EXAMPLE 236

2,6-dimethylphenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 237

2,6-dimethylphenyl(2,5-bis(methyloxy)phenyl)methyl(2-((3-fluoro-4-((3-(1-piperidinyl)propyl)oxy) phenyl)amino)-4-pyrimidinyl)carbamate;

EXAMPLE 238

2,6-dimethylphenyl(2,5-bis(methyloxy)phenyl)methyl(2-((3-fluoro-4-(4-methyl-1-piperazinyl)phenyl) amino)-4-pyrimidinyl)carbamate;

EXAMPLE 239

2,6-dimethylphenyl(2,5-bis(methyloxy)phenyl)methyl(2-((4-(4-(1-methylethyl)-1-piperazinyl)phenyl) amino)-4-pyrimidinyl)carbamate;

EXAMPLE 240

2,6-dimethylphenyl(2,5-bis(methyloxy)phenyl)methyl(2-((3-((difluoromethyl)oxy)-4-(4-methyl-1-piperazinyl)phenyl)amino)-4-pyrimidinyl)carbamate;

EXAMPLE 241

2,6-dimethylphenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 242

2,6-dimethylphenyl(2,5-bis(methyloxy)phenyl)methyl(2-((4-(2-(3,4-dimethyl-1-piperazinyl)ethyl)phenyl)amino)-4-pyrimidinyl)carbamate;

EXAMPLE 243

2,6-dimethylphenyl(2,5-bis(methyloxy)phenyl)methyl(2-((4-(3,4-dimethyl-1-piperazinyl)-3-fluorophenyl)amino)-4-pyrimidinyl)carbamate;

EXAMPLE 244

2,6-dimethylphenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 245

2,6-dimethylphenyl(2,5-bis(methyloxy)phenyl)methyl(2-((4-(((2-(diethylamino)ethyl)(methyl)amino) carbonyl)phenyl)amino)-4-pyrimidinyl)carbamate;

EXAMPLE 246

2,6-dimethylphenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 247

2,6-dimethylphenyl(2,5-bis(methyloxy)phenyl)methyl(2-((4-(4-(3-(dimethylamino)propyl)-1-piperazinyl)phenyl)amino)-4-pyrimidinyl)carbamate;

EXAMPLE 248

2,6-dimethylphenyl(2,5-bis(methyloxy)phenyl)methyl(2-((3-fluoro-4-((2-(4-methyl-1-piperazinyl) ethyl)oxy)phenyl)amino)-4-pyrimidinyl)carbamate;

EXAMPLE 249

2,6-dimethylphenyl(2,5-bis(methyloxy)phenyl)methyl(2-((3-(((2-(diethylamino)ethyl)(methyl)amino) carbonyl)phenyl)amino)-4-pyrimidinyl)carbamate;

EXAMPLE 250

2,6-dimethylphenyl(2,5-bis(methyloxy)phenyl)methyl(2-((4-(3,4-dimethyl-1-piperazinyl)phenyl) amino)-4-pyrimidinyl)carbamate;

EXAMPLE 251

2,6-dimethylphenyl(2,5-bis(methyloxy)phenyl)methyl(2-((4-((3R,5S)-3,4,5-trimethyl-1-piperazinyl) phenyl)amino)-4-pyrimidinyl)carbamate;

EXAMPLE 252

2,6-dimethylphenyl(2,5-bis(methyloxy)phenyl)methyl(2-((3-(4-methyl-1-piperazinyl)phenyl)amino)-4-pyrimidinyl)carbamate;

EXAMPLE 253

2,4,6-trimethylphenyl 2-((3-aminophenyl)amino)-4-pyrimidinyl(2-(methyloxy)phenyl)carbamate;

EXAMPLE 254

2,6-dimethylphenyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 255

2,6-dimethylphenyl 2,4-bis(methyloxy)phenyl(2-((3-fluoro-4-(4-methyl-1-piperazinyl)phenyl)amino)-4-pyrimidinyl)carbamate;

EXAMPLE 256

2,6-dimethylphenyl 2,4-bis(methyloxy)phenyl(2-((3-((difluoromethyl)oxy)-4-(4-methyl-1-piperazinyl)phenyl)amino)-4-pyrimidinyl)carbamate;

EXAMPLE 257

2,6-dimethylphenyl 2,4-bis(methyloxy)phenyl(2-((3-chloro-4-(4-(1-methylethyl)-1-piperazinyl)phenyl)amino)-4-pyrimidinyl)carbamate;

EXAMPLE 258

2,6-dimethylphenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 259

2,6-dimethylphenyl 2,4-bis(methyloxy)phenyl(2-((4-(3,4-dimethyl-1-piperazinyl)-3-fluorophenyl)amino)-4-pyrimidinyl)carbamate;

EXAMPLE 260

2,6-dimethylphenyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 261

2,6-dimethylphenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 262

2,6-dimethylphenyl 2,4-bis(methyloxy)phenyl(2-((3-fluoro-4-((2-(4-methyl-1-piperazinyl)ethyl)oxy)phenyl)amino)-4-pyrimidinyl)carbamate;

EXAMPLE 263

2,6-dimethylphenyl 2,4-bis(methyloxy)phenyl(2-((3-(4-methyl-1-piperazinyl)phenyl)amino)-4-pyrimidinyl)carbamate;

EXAMPLE 264

2,6-dimethylphenyl 2,4-bis(methyloxy)phenyl(2-((3-fluoro-4-((3R,5S)-3,4,5-trimethyl-1-piperazinyl)phenyl) amino)-4-pyrimidinyl)carbamate;

EXAMPLE 265

2,6-dimethylphenyl 2-((3,5-bis(methyloxy)-4-((2-(4-methyl-1-piperazinyl)ethyl)oxy)phenyl)amino)-4-pyrimidinyl((2,5-bis(methyloxy)phenyl)methyl)carbamate;

EXAMPLE 266

2,6-dimethylphenyl(2,5-bis(methyloxy)phenyl)methyl(2-((4-(4-(2-(dimethylamino)ethyl)-1-piperazinyl)phenyl)amino)-4-pyrimidinyl)carbamate;

EXAMPLE 267

2,6-dimethylphenyl 2,4-bis(methyloxy)phenyl(2-((4-(2-(3,4-dimethyl-1-piperazinyl)ethyl)phenyl)amino)-4-pyrimidinyl)carbamate;

EXAMPLE 268

2,6-dimethylphenyl 2-((2-(aminomethyl)phenyl)amino)-4-pyrimidinyl(1,1'-biphenyl-3-yl)carbamate;

EXAMPLE 269

2,4,6-trimethylphenyl 2-((3-(acetylamino)phenyl)amino)-4-pyrimidinyl(2-(methyloxy)phenyl)carbamate;

EXAMPLE 270

4-chloro-2-(methyloxy)phenyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 271

4-chloro-2-(methyloxy)phenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 272

4-chloro-2-(methyloxy)phenyl 2,4-bis(methyloxy)phenyl(2-((3-fluoro-4-((3-(1-piperidinyl)propyl)oxy)phenyl)amino)-4-pyrimidinyl)carbamate;

EXAMPLE 273

2,6-dimethylphenyl 2,4-bis(methyloxy)phenyl(2-((4-(3,4-dimethyl-1-piperazinyl)phenyl)amino)-4-pyrimidinyl)carbamate;

EXAMPLE 274

2,6-dimethylphenyl 2,4-bis(methyloxy)phenyl(2-((4-(((6-(dimethylamino)hexyl)amino)carbonyl)phenyl)amino)-4-pyrimidinyl)carbamate;

EXAMPLE 275

2,6-dimethylphenyl 2,4-bis(methyloxy)phenyl(2-((4-(((4-(diethylamino)butyl)amino)carbonyl)phenyl)amino)-4-pyrimidinyl)carbamate;

EXAMPLE 276

2,6-dimethylphenyl 2,4-bis(methyloxy)phenyl(2-((3-(((6-(dimethylamino)hexyl)amino)carbonyl)phenyl)amino)-4-pyrimidinyl)carbamate;

EXAMPLE 277

2-methyl-6-(2-propenyl)phenyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 278

2-methyl-6-(2-propenyl)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 279

2-methyl-6-(2-propenyl)phenyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 280

2-methyl-6-(2-propenyl)phenyl 2,4-bis(methyloxy)phenyl(2-((3-((3-(1-piperidinyl)propyl)oxy)phenyl)amino)-4-pyrimidinyl)carbamate;

EXAMPLE 281

2-methyl-6-(2-propenyl)phenyl 2,4-bis(methyloxy)phenyl(2-((3-fluoro-4-((3-(1-piperidinyl)propyl)oxy)phenyl)amino)-4-pyrimidinyl)carbamate;

EXAMPLE 282

2-methyl-6-(2-propenyl)phenyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 283

2-methyl-6-(2-propenyl)phenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 284

2,6-dimethylphenyl(2,5-bis(methyloxy)phenyl)methyl(2-((4-(((6-(dimethylamino)hexyl)amino)carbonyl)phenyl)amino)-4-pyrimidinyl)carbamate;

EXAMPLE 285

2,6-dimethylphenyl(2,5-bis(methyloxy)phenyl)methyl(2-((4-(((4-(diethylamino)butyl)amino)carbonyl)phenyl)amino)-4-pyrimidinyl)carbamate;

EXAMPLE 286

2,6-dimethylphenyl(2,5-bis(methyloxy)phenyl)methyl(2-((3-(((4-(diethylamino)butyl)amino)carbonyl)phenyl)amino)-4-pyrimidinyl)carbamate;

EXAMPLE 287

2,6-dimethylphenyl(2,5-bis(methyloxy)phenyl)methyl(2-((3-(((6-(dimethylamino)hexyl)amino)carbonyl)phenyl)amino)-4-pyrimidinyl)carbamate;

EXAMPLE 288

2,6-dimethylphenyl(2,5-bis(methyloxy)phenyl)methyl(2-((3-(((3-(diethylamino)propyl)amino)carbonyl)phenyl)amino)-4-pyrimidinyl)carbamate;

EXAMPLE 289

2,6-dimethylphenyl(2,5-bis(methyloxy)phenyl)methyl(2-((3-(methyloxy)-4-(((2S)-2-pyrrolidinylmethyl)oxy)phenyl)amino)-4-pyrimidinyl)carbamate;

EXAMPLE 290

2,6-bis(methyloxy)phenyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 291

2,6-bis(methyloxy)phenyl 2,4-bis(methyloxy)phenyl(2-((3-fluoro-4-((3-(1-piperidinyl)propyl)oxy)phenyl)amino)-4-pyrimidinyl)carbamate;

EXAMPLE 292

2,6-bis(methyloxy)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 293

2,6-bis(methyloxy)phenyl 2,4-bis(methyloxy)phenyl(2-((4-(3,4-dimethyl-1-piperazinyl)-3-fluorophenyl)amino)-4-pyrimidinyl)carbamate;

EXAMPLE 294

2,6-difluorophenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 295

2,6-difluorophenyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 296

2,6-difluorophenyl 2,4-bis(methyloxy)phenyl(2-((3-fluoro-4-((3-(1-piperidinyl)propyl)oxy)phenyl)amino)-4-pyrimidinyl)carbamate;

EXAMPLE 297

2,6-difluorophenyl 2,4-bis(methyloxy)phenyl(2-((3-((3-(1-piperidinyl)propyl)oxy)phenyl)amino)-4-pyrimidinyl)carbamate;

EXAMPLE 298

2,6-difluorophenyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 299

2,6-difluorophenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 300

2,6-difluorophenyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 301

2,6-difluorophenyl 2,4-bis(methyloxy)phenyl(2-((4-(3,4-dimethyl-1-piperazinyl)-3-fluorophenyl)amino)-4-pyrimidinyl)carbamate;

EXAMPLE 302

4-chloro-2-(methyloxy)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 303

4-chloro-2-(methyloxy)phenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 304

4-chloro-2-(methyloxy)phenyl(2,5-bis(methyloxy)phenyl)methyl(2((3-fluoro-4-((3-(1-piperidinyl)propyl)oxy)phenyl)amino)-4-pyrimidinyl)carbamate;

EXAMPLE 305

4-chloro-2-(methyloxy)phenyl(2,5-bis(methyloxy)phenyl)methyl(2-((3-((3-(1-piperidinyl)propyl)oxy)phenyl)amino)-4-pyrimidinyl)carbamate;

EXAMPLE 306

4-chloro-2-(methyloxy)phenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 307

4-chloro-2-(methyloxy)phenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 308

4-chloro-2-(methyloxy)phenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 309

4-chloro-2-(methyloxy)phenyl(2,5-bis(methyloxy)phenyl)methyl(2-((4-(3,4-dimethyl-1-piperazinyl)-3-fluorophenyl)amino)-4-pyrimidinyl)carbamate;

EXAMPLE 310

2,6-dimethylcyclohexyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 311

2,6-dimethylphenyl 2,4-bis(methyloxy)phenyl(2-((3-(((4-(diethylamino)butyl)amino)carbonyl)phenyl)amino)-4-pyrimidinyl)carbamate;

EXAMPLE 312

2,6-dimethylphenyl 2,4-bis(methyloxy)phenyl(2-((3-(((3-(diethylamino)propyl)amino)carbonyl)phenyl)amino)-4-pyrimidinyl)carbamate;

EXAMPLE 313

2,6-dimethylphenyl 2-chlorophenyl(2-((3-fluoro-4-((3-(4-methyl-1-piperazinyl)propyl)oxy)phenyl)amino)-4-pyrimidinyl)carbamate;

EXAMPLE 314

2,6-dimethylphenyl 2-((3,4-bis(methyloxy)-5-((3-(4-methyl-1-piperazinyl)propyl)oxy)phenyl)amino)-4-pyrimidinyl(2-chlorophenyl)carbamate;

EXAMPLE 315

2,4,6-trimethylphenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 316

2,4,6-trimethylphenyl 2,4-bis(methyloxy)phenyl(2-((3-fluoro-4-((3-(4-methyl-1-piperazinyl)propyl)oxy)phenyl) amino)-4-pyrimidinyl)carbamate;

EXAMPLE 317

2,4,6-trimethylphenyl 2,4-bis(methyloxy)phenyl(2-((3-fluoro-4-((3-(1-piperidinyl)propyl)oxy)phenyl)amino)-4-pyrimidinyl)carbamate;

EXAMPLE 318

2,4,6-trimethylphenyl 2,4-bis(methyloxy)phenyl(2-((3-((3-(1-piperidinyl)propyl)oxy)phenyl)amino)-4-pyrimidinyl)carbamate;

EXAMPLE 319

2,4,6-trimethylphenyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 320

2,4,6-trimethylphenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 321

2,4,6-trimethylphenyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 322

2,4,6-trimethylphenyl 2,4-bis(methyloxy)phenyl(2-((4-(3,4-dimethyl-1-piperazinyl)-3-fluorophenyl)amino)-4-pyrimidinyl)carbamate;

EXAMPLE 323

2,4,6-trimethylphenyl(2,5-bis(methyloxy)phenyl)methyl(2-((4-(4-methyl-1-piperazinyl)phenyl)amino)-4-pyrimidinyl)carbamate;

EXAMPLE 324

2,4,6-trimethylphenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 325

2,4,6-trimethylphenyl(2,5-bis(methyloxy)phenyl)methyl(2-((3-fluoro-4-(4-methyl-1-piperazinyl)phenyl)amino)-4-pyrimidinyl)carbamate;

EXAMPLE 326

2,4,6-trimethylphenyl(2,5-bis(methyloxy)phenyl)methyl(2-((3-((difluoromethyl)oxy)-4-(4-methyl-1-piperazinyl)phenyl)amino)-4-pyrimidinyl)carbamate;

EXAMPLE 327

2,4,6-trimethylphenyl(2,5-bis(methyloxy)phenyl)methyl(2-((3-chloro-4-(4-(1-methylethyl)-1-piperazinyl)phenyl)amino)-4-pyrimidinyl)carbamate;

EXAMPLE 328

2,4,6-trimethylphenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 329

2,4,6-trimethylphenyl(2,5-bis(methyloxy)phenyl)methyl(2-((4-((3-(4-(1-methylethyl)-1-piperazinyl)propyl)oxy)-3-(methyloxy)phenyl)amino)-4-pyrimidinyl)carbamate;

EXAMPLE 330

2,4,6-trimethylphenyl(2,5-bis(methyloxy)phenyl)methyl(2-((4-(3,4-dimethyl-1-piperazinyl)-3-fluorophenyl)amino)-4-pyrimidinyl)carbamate;

EXAMPLE 331

2,4,6-trimethylphenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 332

2,4,6-trimethylphenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 333

2,4,6-trimethylphenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 334

2,4,6-trimethylphenyl 2-((3,5-bis(methyloxy)-4-((2-(4-methyl-1-piperazinyl)ethyl)oxy)phenyl)amino)-4-pyrimidinyl((2,5-bis(methyloxy)phenyl)methyl)carbamate;

EXAMPLE 335

2,4,6-trimethylphenyl(2,5-bis(methyloxy)phenyl)methyl(2-((3-fluoro-4-((2-(4-methyl-1-piperazinyl)ethyl)oxy)phenyl)amino)-4-pyrimidinyl)carbamate;

EXAMPLE 336

2,4,6-trimethylphenyl(2,5-bis(methyloxy)phenyl)methyl(2-((3-(4-methyl-1-piperazinyl)phenyl)amino)-4-pyrimidinyl)carbamate;

EXAMPLE 337

2,4,6-trimethylphenyl(2,5-bis(methyloxy)phenyl)methyl(2-((3-(((2-(diethylamino)ethyl)(methyl)amino)carbonyl)phenyl)amino)-4-pyrimidinyl)carbamate;

EXAMPLE 338

2,4,6-trimethylphenyl(2,5-bis(methyloxy)phenyl)methyl(2-((4-(3,4-dimethyl-1-piperazinyl)phenyl)amino)-4-pyrimidinyl)carbamate;

EXAMPLE 339

2,4,6-trimethylphenyl(2,5-bis(methyloxy)phenyl)methyl(2-((3-fluoro-4-((3R,5S)-3,4,5-trimethyl-1-piperazinyl)phenyl)amino)-4-pyrimidinyl)carbamate;

EXAMPLE 340

2-((methyloxy)methyl)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 341

2-((methyloxy)methyl)phenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 342

2-((methyloxy)methyl)phenyl(2,5-bis(methyloxy)phenyl)methyl(2-((3-fluoro-4-((3-(1-piperidinyl)propyl)oxy)phenyl)amino)-4-pyrimidinyl)carbamate;

EXAMPLE 343

2-((methyloxy)methyl)phenyl(2,5-bis(methyloxy)phenyl)methyl(2-((3-((3-(1-piperidinyl)propyl)oxy)phenyl)amino)-4-pyrimidinyl)carbamate;

EXAMPLE 344

2-((methyloxy)methyl)phenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 345

2-((methyloxy)methyl)phenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 346

2-((methyloxy)methyl)phenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 347

2-((methyloxy)methyl)phenyl(2,5-bis(methyloxy)phenyl)methyl(2-((4-(3,4-dimethyl-1-piperazinyl)-3-fluorophenyl)amino)-4-pyrimidinyl)carbamate;

EXAMPLE 348

2-((methyloxy)methyl)phenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 349

2-((methyloxy)methyl)phenyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 350

2-((methyloxy)methyl)phenyl 2,4-bis(methyloxy)phenyl(2-((3-fluoro-4-((3-(1-piperidinyl)propyl)oxy)phenyl)amino)-4-pyrimidinyl)carbamate;

EXAMPLE 351

2-((methyloxy)methyl)phenyl 2,4-bis(methyloxy)phenyl(2-((3-((3-(1-piperidinyl)propyl)oxy)phenyl)amino)-4-pyrimidinyl)carbamate;

EXAMPLE 352

2-((methyloxy)methyl)phenyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 353

2-((methyloxy)methyl)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 354

2-((methyloxy)methyl)phenyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 355

2-((methyloxy)methyl)phenyl 2,4-bis(methyloxy)phenyl(2-((4-(3,4-dimethyl-1-piperazinyl)-3-fluorophenyl)amino)-4-pyrimidinyl)carbamate;

EXAMPLE 356

5-methyl-2-(methyloxy)phenyl 2,4-bis(methyloxy)phenyl(2-((4-(3,4-dimethyl-1-piperazinyl)-3-fluorophenyl)amino)-4-pyrimidinyl)carbamate;

EXAMPLE 357

5-methyl-2-(methyloxy)phenyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 358

2,6-dimethylphenyl 2,4-bis(methyloxy)phenyl(2-((4-(((3-(diethylamino)propyl)amino)carbonyl)phenyl)amino)-4-pyrimidinyl)carbamate;

EXAMPLE 359

2,6-dimethylphenyl 2,4-bis(methyloxy)phenyl(2-((3-(((2-(diethylamino)ethyl)amino)carbonyl)phenyl)amino)-4-pyrimidinyl)carbamate;

EXAMPLE 360

2,6-dimethylphenyl(2,5-bis(methyloxy)phenyl)methyl(2-((4-(((2-(diethylamino)ethyl)amino)carbonyl)phenyl)amino)-4-pyrimidinyl)carbamate;

EXAMPLE 361

2,6-dimethylphenyl(2,5-bis(methyloxy)phenyl)methyl(2-((3-(((2-(diethylamino)ethyl)amino)carbonyl)phenyl)amino)-4-pyrimidinyl)carbamate;

EXAMPLE 362

2,6-dimethylphenyl 2,4-bis(methyloxy)phenyl(2-((4-(((2-(diethylamino)ethyl)amino)carbonyl)-3-fluorophenyl)amino)-4-pyrimidinyl)carbamate;

EXAMPLE 363

2,4,6-trimethylphenyl(3,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 364

2,4,6-trimethylphenyl(3,5-bis(methyloxy)phenyl)methyl(2-((3-fluoro-4-((3-(1-piperidinyl)propyl)oxy)phenyl)amino)-4-pyrimidinyl)carbamate;

EXAMPLE 365

2,4,6-trimethylphenyl(3,5-bis(methyloxy)phenyl)methyl(2-((3-((3-(1-piperidinyl)propyl)oxy)phenyl)amino)-4-pyrimidinyl)carbamate;

EXAMPLE 366

2,4,6-trimethylphenyl(3,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 367

2,4,6-trimethylphenyl(3,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 368

2,4,6-trimethylphenyl(3,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 369

2,4,6-trimethylphenyl(3,5-bis(methyloxy)phenyl)methyl(2-((4-(3,4-dimethyl-1-piperazinyl)-3-fluorophenyl)amino)-4-pyrimidinyl)carbamate;

EXAMPLE 370

2,6-dimethylphenyl 2-chlorophenyl(2-((3-fluoro-4-((3-(1-piperidinyl)propyl)oxy)phenyl)amino)-4-pyrimidinyl)carbamate;

EXAMPLE 371

2,6-dimethylphenyl 2-chlorophenyl(2-((3-((3-(1-piperidinyl)propyl)oxy)phenyl)amino)-4-pyrimidinyl)carbamate;

EXAMPLE 372

2,6-dimethylphenyl 2-chlorophenyl(2-((4-(((2-(diethylamino)ethyl)(methyl)amino)carbonyl)phenyl)amino)-4-pyrimidinyl)carbamate;

EXAMPLE 373

2,6-dimethylphenyl 2-chlorophenyl(2-((3-fluoro-4-((2-(4-(1-methylethyl)-1-piperazinyl)ethyl)oxy)phenyl)amino)-4-pyrimidinyl)carbamate;

EXAMPLE 374

2,6-dimethylphenyl 2-chlorophenyl(2-((3-fluoro-4-(((1-methyl-3-piperidinyl)methyl)oxy)phenyl)amino)-4-pyrimidinyl)carbamate;

EXAMPLE 375

2,6-dimethylphenyl 2-chlorophenyl(2-((4-(3,4-dimethyl-1-piperazinyl)-3-fluorophenyl)amino)-4-pyrimidinyl)carbamate;

EXAMPLE 376

5-methyl-2-(methyloxy)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 377

5-methyl-2-(methyloxy)phenyl 2,4-bis(methyloxy)phenyl(2-((3-((3-(1-piperidinyl)propyl)oxy)phenyl)amino)-4-pyrimidinyl)carbamate;

EXAMPLE 378

2,6-dimethylphenyl cyclohexyl(2-((3-fluoro-4-((3-(1-piperidinyl)propyl)oxy)phenyl)amino)-4-pyrimidinyl)carbamate;

EXAMPLE 379

2-(methylsulfanyl)phenyl 2,4-bis(methyloxy)phenyl (2-((4-(3,4-dimethyl-1-piperazinyl)-3-fluorophenyl)amino)-4-pyrimidinyl)carbamate;

EXAMPLE 380

2-(methylsulfanyl)phenyl 2,4-bis(methyloxy)phenyl (2-((3-fluoro-4-((2-(4-(1-methylethyl)-1-piperazinyl)ethyl)oxy)phenyl)amino)-4-pyrimidinyl)carbamate;

EXAMPLE 381

2,4,6-trimethylphenyl(2,5-dichlorophenyl)methyl(2-((4-(((4-(diethylamino)butyl)amino)carbonyl)phenyl)amino)-4-pyrimidinyl)carbamate;

EXAMPLE 382

2,4,6-trimethylphenyl(2,5-dichlorophenyl)methyl(2-((4-(((6-(dimethylamino)hexyl)amino)carbonyl)phenyl)amino)-4-pyrimidinyl)carbamate;

EXAMPLE 383

2,4,6-trimethylphenyl(2,5-dichlorophenyl)methyl(2-((3-(((4-(diethylamino)butyl)amino)carbonyl)phenyl)amino)-4-pyrimidinyl)carbamate;

EXAMPLE 384

2,4,6-trimethylphenyl(2,5-dichlorophenyl)methyl(2-((3-(((6-(dimethylamino)hexyl)amino)carbonyl)phenyl)amino)-4-pyrimidinyl)carbamate;

EXAMPLE 385

2,4,6-trimethylphenyl(2,5-dichlorophenyl)methyl(2-((3-(((2-(diethylamino)ethyl)amino)carbonyl)phenyl)amino)-4-pyrimidinyl)carbamate;

EXAMPLE 386

2,4,6-trimethylphenyl(2,5-dichlorophenyl)methyl(2-((3-(((3-(diethylamino)propyl)amino)carbonyl)phenyl)amino)-4-pyrimidinyl)carbamate;

EXAMPLE 387

2,4,6-trimethylphenyl(2,5-dichlorophenyl)methyl(2-((4-(((3-(diethylamino)propyl)amino)carbonyl)phenyl)amino)-4-pyrimidinyl)carbamate;

EXAMPLE 388

2,4,6-trimethylphenyl(2,5-dichlorophenyl)methyl(2-((4-(((2-(diethylamino)ethyl)amino)carbonyl)phenyl)amino)-4-pyrimidinyl)carbamate;

EXAMPLE 389

2,6-dimethylphenyl cyclohexyl(2-((3-fluoro-4-((2-(4-(1-methylethyl)-1-piperazinyl)ethyl)oxy)phenyl)amino)-4-pyrimidinyl)carbamate;

EXAMPLE 390

2,6-dimethylphenyl cyclohexyl(2-((3-fluoro-4-(((1-methyl-3-piperidinyl)methyl)oxy)phenyl)amino)-4-pyrimidinyl)carbamate;

EXAMPLE 391

2,6-dimethylphenyl cyclohexyl(2-((3-fluoro-4-((3-(4-methyl-1-piperazinyl)propyl)oxy)phenyl)amino)-4-pyrimidinyl)carbamate;

EXAMPLE 392

2,6-dimethylphenyl cyclohexyl(2-((4-(((2-(diethylamino)ethyl)(methyl)amino)carbonyl)phenyl)amino)-4-pyrimidinyl)carbamate;

EXAMPLE 393

2,6-dimethylphenyl(2,5-bis(methyloxy)phenyl)methyl(2-((4-(((6-(dimethylamino)hexyl)amino)carbonyl)-3-fluorophenyl)amino)-4-pyrimidinyl)carbamate;

EXAMPLE 394

2,6-dimethylcyclohexyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 395

2,6-dimethylcyclohexyl 2,4-bis(methyloxy)phenyl(2-((3-fluoro-4-((3-(1-piperidinyl)propyl)oxy)phenyl)amino)-4-pyrimidinyl)carbamate;

EXAMPLE 396

2,6-dimethylcyclohexyl 2,4-bis(methyloxy)phenyl(2-((3-((3-(1-piperidinyl)propyl)oxy)phenyl)amino)-4-pyrimidinyl)carbamate;

EXAMPLE 397

2,6-dimethylcyclohexyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 398

2,6-dimethylcyclohexyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 399

2,6-dimethylcyclohexyl 2,4-bis(methyloxy)phenyl(2-((4-(3,4-dimethyl-1-piperazinyl)-3-fluorophenyl)amino)-4-pyrimidinyl)carbamate;

EXAMPLE 400

2-methyl-1-(1-methylethyl)propyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 401

2-methyl-1-(1-methylethyl)propyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 402

2-methyl-1-(1-methylethyl)propyl 2,4-bis(methyloxy)phenyl(2-((3-fluoro-4-((3-(1-piperidinyl)propyl)oxy)phenyl)amino)-4-pyrimidinyl)carbamate;

EXAMPLE 403

2-methyl-1-(1-methylethyl)propyl 2,4-bis(methyloxy)phenyl(2-((3-((3-(1-piperidinyl)propyl)oxy)phenyl)amino)-4-pyrimidinyl)carbamate;

EXAMPLE 404

2-methyl-1-(1-methylethyl)propyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 405

2-methyl-1-(1-methylethyl)propyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 406

2-methyl-1-(1-methylethyl)propyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 407

2-methyl-1-(1-methylethyl)propyl 2,4-bis(methyloxy)phenyl(2-((4-(3,4-dimethyl-1-piperazinyl)-3-fluorophenyl)amino)-4-pyrimidinyl)carbamate;

EXAMPLE 408

2-methyl-1-(1-methylethyl)butyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 409

2-methyl-1-(1-methylethyl)butyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 410

2-methyl-1-(1-methylethyl)butyl 2,4-bis(methyloxy)phenyl(2-((3-fluoro-4-((3-(1-piperidinyl)propyl)oxy)phenyl)amino)-4-pyrimidinyl)carbamate;

EXAMPLE 411

2-methyl-1-(1-methylethyl)butyl 2,4-bis(methyloxy)phenyl(2-((3-((3-(1-piperidinyl)propyl)oxy)phenyl)amino)-4-pyrimidinyl)carbamate;

EXAMPLE 412

2-methyl-1-(1-methylethyl)butyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 413

2-methyl-1-(1-methylethyl)butyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 414

2-methyl-1-(1-methylethyl)butyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 415

2-methyl-1-(1-methylethyl)butyl 2,4-bis(methyloxy)phenyl(2-((4-(3,4-dimethyl-1-piperazinyl)-3-fluorophenyl)amino)-4-pyrimidinyl)carbamate;

EXAMPLE 416

(1S)-1-phenylethyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 417

(1S)-1-phenylethyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 418

(1S)-1-phenylethyl 2,4-bis(methyloxy)phenyl(2-((3-fluoro-4-((3-(1-piperidinyl)propyl)oxy)phenyl)amino)-4-pyrimidinyl)carbamate;

EXAMPLE 419

(1S)-1-phenylethyl 2,4-bis(methyloxy)phenyl(2-((3-((3-(1-piperidinyl)propyl)oxy)phenyl)amino)-4-pyrimidinyl)carbamate;

EXAMPLE 420

(1S)-1-phenylethyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 421

(1S)-1-phenylethyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 422

(1S)-1-phenylethyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 423

(1S)-1-phenylethyl 2,4-bis(methyloxy)phenyl(2-((4-(3,4-dimethyl-1-piperazinyl)-3-fluorophenyl)amino)-4-pyrimidinyl)carbamate;

EXAMPLE 424

2,4,6-trimethylphenyl 2-((3,4-bis(methyloxy)-5-((3-(4-methyl-1-piperazinyl)propyl)oxy)phenyl)amino)-4-pyrimidinyl((2,3-bis(methyloxy)phenyl)methyl)carbamate;

EXAMPLE 425

2,4,6-trimethylphenyl(2,3-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 426

2,4,6-trimethylphenyl(2,3-bis(methyloxy)phenyl)methyl(2-((3-fluoro-4-((3-(1-piperidinyl)propyl)oxy)phenyl)amino)-4-pyrimidinyl)carbmate;

EXAMPLE 427

2,4,6-trimethylphenyl(2,3-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 428

2,4,6-trimethylphenyl(2,3-bis(methyloxy)phenyl)methyl(2-((4-(3,4-dimethyl-1-piperazinyl)-3-fluorophenyl)amino)-4-pyrimidinyl)carbamate;

EXAMPLE 429

2,4,6-trimethylphenyl(2,5-dichlorophenyl)methyl(2-((4-(4-methyl-1-piperazinyl)phenyl)amino)-4-pyrimidinyl)carbamate;

EXAMPLE 430

2,4,6-trimethylphenyl(2,5-dichlorophenyl)methyl(2-((3-fluoro-4-((3-(4-methyl-1-piperazinyl)propyl)oxy)phenyl)amino)-4-pyrimidinyl)carbamate;

EXAMPLE 431

2,4,6-trimethylphenyl(2,5-dichlorophenyl)methyl(2-((3-fluoro-4-(4-methyl-1-piperazinyl)phenyl)amino)-4-pyrimidinyl)carbamate;

EXAMPLE 432

2,4,6-trimethylphenyl(2,5-dichlorophenyl)methyl(2-((3-((difluoromethyl)oxy)-4-(4-methyl-1-piperazinyl)phenyl)amino)-4-pyrimidinyl)carbamate;

EXAMPLE 433

2,4,6-trimethylphenyl(2,5-dichlorophenyl)methyl(2-((3-fluoro-4-((2-(4-(1-methylethyl)-1-piperazinyl)ethyl)oxy)phenyl)amino)-4-pyrimidinyl)carbamate;

EXAMPLE 434

2,4,6-trimethylphenyl(2,5-dichlorophenyl)methyl(2-((4-((3-(4-(1-methylethyl)-1-piperazinyl)propyl)oxy)-3-(methyloxy)phenyl)amino)-4-pyrimidinyl)carbamate;

EXAMPLE 435

2,4,6-trimethylphenyl(2,5-dichlorophenyl)methyl(2-((4-((3-(4-(2-(dimethylamino)ethyl)-1-piperazinyl)propyl)oxy)-3-fluorophenyl)amino)-4-pyrimidinyl)carbamate;

EXAMPLE 436

2,4,6-trimethylphenyl(2,5-dichlorophenyl)methyl(2-((4-(3,4-dimethyl-1-piperazinyl)-3-fluorophenyl)amino)-4-pyrimidinyl)carbamate;

EXAMPLE 437

2,4,6-trimethylphenyl(2,5-dichlorophenyl)methyl(2-((3-fluoro-4-(((1-methyl-3-piperidinyl)methyl)oxy)phenyl)amino)-4-pyrimidinyl)carbamate;

EXAMPLE 438

2,4,6-trimethylphenyl(2,5-dichlorophenyl)methyl(2-((4-(((2-(diethylamino)ethyl)(methyl)amino)carbonyl)phenyl)amino)-4-pyrimidinyl)carbamate;

EXAMPLE 439

2,4,6-trimethylphenyl(2,5-dichlorophenyl)methyl(2-((3-fluoro-4-((2-(4-methyl-1-piperazinyl)ethyl)oxy)phenyl)amino)-4-pyrimidinyl)carbamate;

EXAMPLE 440

2,4,6-trimethylphenyl(2,5-dichlorophenyl)methyl(2-((4-(3,4-dimethyl-1-piperazinyl)phenyl)amino)-4-pyrimidinyl)carbamate;

EXAMPLE 441 methyl 2-((((2-((3,4-bis(methyloxy)-5-((3-(4-methyl-1-piperazinyl)propyl)oxy)phenyl)amino)-4-pyrimidinyl)((2,5-bis(methyloxy)phenyl)methyl)amino)carbonyl)oxy)benzoate;

EXAMPLE 442 methyl 2-(((((2,5-bis(methyloxy)phenyl)methyl)(2-((3-fluoro-4-((3-(4-methyl-1-piperazinyl)propyl)oxy)phenyl)amino)-4-pyrimidinyl)amino)carbonyl)oxy)benzoate;

EXAMPLE 443 methyl 2-(((((2,5-bis(methyloxy)phenyl)methyl)(2-((3-fluoro-4-((3-(1-piperidinyl)propyl)oxy)phenyl)amino)-4-pyrimidinyl)amino)carbonyl)oxy)benzoate;

EXAMPLE 444 methyl 2-(((((2,5-bis(methyloxy)phenyl)methyl)(2-((3-((3-(1-piperidinyl)propyl)oxy)phenyl)amino)-4-pyrimidinyl)amino)carbonyl)oxy)benzoate;

EXAMPLE 445 methyl 2-(((((2,5-bis(methyloxy)phenyl)methyl)(2-((4-(((2-(diethylamino)ethyl)(methyl)amino)carbonyl)phenyl)amino)-4-pyrimidinyl)amino)carbonyl)oxy)benzoate;

EXAMPLE 446 methyl 2-(((((2,5-bis(methyloxy)phenyl)methyl)(2-((3-fluoro-4-((2-(4-(1-methylethyl)-1-piperazinyl)ethyl)oxy)phenyl)amino)-4-pyrimidinyl)amino)carbonyl)oxy)benzoate;

EXAMPLE 447 methyl 2-(((((2,5-bis(methyloxy)phenyl)methyl)(2-((3-fluoro-4-(((1-methyl-3-piperidinyl)methyl)oxy)phenyl)amino)-4-pyrimidinyl)amino)carbonyl)oxy)benzoate;

EXAMPLE 448 methyl 2-(((((2,5-bis(methyloxy)phenyl)methyl)(2-((4-(3,4-dimethyl-1-piperazinyl)-3-fluorophenyl)amino)-4-pyrimidinyl)amino)carbonyl)oxy)benzoate;

EXAMPLE 449 methyl 2-((((2-((3,4-bis(methyloxy)-5-((3-(4-methyl-1-piperazinyl)propyl)oxy)phenyl)amino)-4-pyrimidinyl)(2,4-bis(methyloxy)phenyl)amino)carbonyl)oxy)benzoate;

EXAMPLE 450 methyl 2-(((((2,4-bis(methyloxy)phenyl)(2-((3-fluoro-4-((3-(4-methyl-1-piperazinyl)propyl)oxy)phenyl)amino)-4-pyrimidinyl)amino)carbonyl)oxy)benzoate;

EXAMPLE 451 methyl 2-(((((2,4-bis(methyloxy)phenyl)(2-((3-fluoro-4-((3-(1-piperidinyl)propyl)oxy)phenyl)amino)-4-pyrimidinyl)amino)carbonyl)oxy)benzoate;

EXAMPLE 452 methyl 2-(((((2,4-bis(methyloxy)phenyl)(2-((3-((3-(1-piperidinyl)propyl)oxy)phenyl)amino)-4-pyrimidinyl)amino)carbonyl)oxy)benzoate;

EXAMPLE 453 methyl 2-(((((2,4-bis(methyloxy)phenyl)(2-((4-(((2-(diethylamino)ethyl)(methyl)amino)carbonyl)phenyl)amino)-4-pyrimidinyl)amino)carbonyl)oxy)benzoate;

EXAMPLE 454 methyl 2-(((((2,4-bis(methyloxy)phenyl)(2-((3-fluoro-4-((2-(4-(1-methylethyl)-1-piperazinyl)ethyl)oxy)phenyl)amino)-4-pyrimidinyl)amino)carbonyl)oxy)benzoate;

EXAMPLE 455 methyl 2-(((((2,4-bis(methyloxy)phenyl)(2-((3-fluoro-4-(((1-methyl-3-piperidinyl)methyl)oxy)phenyl)amino)-4-pyrimidinyl)amino)carbonyl)oxy)benzoate;

EXAMPLE 456 methyl 2-(((((2,4-bis(methyloxy)phenyl)(2-((4-(3,4-dimethyl-1-piperazinyl)-3-fluorophenyl)amino)-4-pyrimidinyl)amino)carbonyl)oxy)benzoate;

EXAMPLE 457

2,6-bis(methyloxy)phenyl 2-((3,4-bis(methyloxy)-5-((3-(4-methyl-1-piperazinyl)propyl)oxy)phenyl)amino)-4-pyrimidinyl(((2,5-bis(methyloxy)phenyl)methyl)carbamate;

EXAMPLE 458

2,6-bis(methyloxy)phenyl(2,5-bis(methyloxy)phenyl)methyl(2-((3-fluoro-4-((3-(1-piperidinyl)propyl)oxy)phenyl)amino)-4-pyrimidinyl)carbamate;

EXAMPLE 459

2,6-bis(methyloxy)phenyl(2,5-bis(methyloxy)phenyl)methyl(2-((3-((3-(1-piperidinyl)propyl)oxy)phenyl)amino)-4-pyrimidinyl)carbamate;

EXAMPLE 460

2,6-bis(methyloxy)phenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 461

2,6-difluorophenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 462

2,6-difluorophenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 463

2,6-difluorophenyl(2,5-bis(methyloxy)phenyl)methyl(2-((3-fluoro-4-((3-(1-piperidinyl)propyl)oxy)phenyl)amino)-4-pyrimidinyl)carbamate;

EXAMPLE 464

2,6-difluorophenyl(2,5-bis(methyloxy)phenyl)methyl(2-((3-((3-(1-piperidinyl)propyl)oxy)phenyl)amino)-4-pyrimidinyl)carbamate;

EXAMPLE 465

5-methyl-2-(methyloxy)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 466

5-methyl-2-(methyloxy)phenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 467

5-methyl-2-(methyloxy)phenyl(2,5-bis(methyloxy)phenyl)methyl(2-((3-fluoro-4-((3-(1-piperidinyl)propyl)oxy)phenyl)amino)-4-pyrimidinyl)carbamate;

EXAMPLE 468

5-methyl-2-(methyloxy)phenyl(2,5-bis(methyloxy)phenyl)methyl(2-((3-((3-(1-piperidinyl)propyl)oxy)phenyl)amino)-4-pyrimidinyl)carbamate;

EXAMPLE 469

5-methyl-2-(methyloxy)phenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 470

5-methyl-2-(methyloxy)phenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 471

5-methyl-2-(methyloxy)phenyl(2,5-bis(methyloxy)phenyl)methyl(2-((3-fluoro-4-((((1-methyl-3-piperidinyl)methyl)oxy)phenyl)amino)-4-pyrimidinyl)carbamate;

EXAMPLE 472

2,6-dimethylphenyl 2-((3,4-bis(methyloxy)-5-((3-(4-methyl-1-piperazinyl)propyl)oxy)phenyl)amino)-4-pyrimidinyl(2,5-bis(methyloxy)phenyl)carbamate;

EXAMPLE 473

2,6-dimethylphenyl 2,5-bis(methyloxy)phenyl(2-((3-fluoro-4-((3-(4-methyl-1-piperazinyl)propyl)oxy)phenyl)amino)-4-pyrimidinyl)carbamate;

EXAMPLE 474

2,6-dimethylphenyl 2,5-bis(methyloxy)phenyl(2-((3-fluoro-4-((3-(1-piperidinyl)propyl)oxy)phenyl)amino)-4-pyrimidinyl)carbamate;

EXAMPLE 475

2,6-dimethylphenyl 2,5-bis(methyloxy)phenyl(2-((3-((3-(1-piperidinyl)propyl)oxy)phenyl)amino)-4-pyrimidinyl)carbamate;

EXAMPLE 476

2,6-dimethylphenyl 2,5-bis(methyloxy)phenyl(2-((4-(((2-(diethylamino)ethyl)(methyl)amino)carbonyl)phenyl)amino)-4-pyrimidinyl)carbamate;

EXAMPLE 477

2,6-dimethylphenyl 2,5-bis(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 478

2,6-dimethylphenyl 2,5-bis(methyloxy)phenyl(2-((3-fluoro-4-(((1-methyl-3-piperidinyl)methyl)oxy)phenyl)amino)-4-pyrimidinyl)carbamate;

EXAMPLE 479

2,6-dimethylphenyl 2,5-bis(methyloxy)phenyl(2-((4-(3,4-dimethyl-1-piperazinyl)-3-fluorophenyl)amino)-4-pyrimidinyl)carbamate;

EXAMPLE 480

2,4,6-trimethylphenyl 2-((3,4-bis(methyloxy)-5-((3-(4-methyl-1-piperazinyl)propyl)oxy)phenyl)amino)-4-pyrimidinyl((3,5-bis(methyloxy)phenyl)methyl)carbamate;

EXAMPLE 481

2,4,6-trimethylphenyl 2-((3,4-bis(methyloxy)-5-((3-(4-methyl-1-piperazinyl)propyl)oxy)phenyl)amino)-4-pyrimidinyl((5-chloro-2-fluorophenyl)methyl)carbamate;

EXAMPLE 482

2,4,6-trimethylphenyl(5-chloro-2-fluorophenyl)methyl(2-((3-fluoro-4-((3-(4-methyl-1-piperazinyl)propyl)oxy)phenyl)amino)-4-pyrimidinyl)carbamate;

EXAMPLE 483

2,4,6-trimethylphenyl(5-chloro-2-fluorophenyl)methyl(2-((3-((3-(1-piperidinyl)propyl)oxy)phenyl)amino)-4-pyrimidinyl)carbamate;

EXAMPLE 484

2,4,6-trimethylphenyl(2,5-bis(methyloxy)phenyl)methyl(2-((6-((3-(4-methyl-1-piperazinyl)propyl)oxy)-3-pyridinyl)amino)-4-pyrimidinyl)carbamate;

EXAMPLE 485

2,4,6-trimethylphenyl(2-chloro-5-(trifluoromethyl)phenyl)methyl(2-((6-((3-(4-methyl-1-piperazinyl)propyl)oxy)-3-pyridinyl)amino)-4-pyrimidinyl)carbamate;

EXAMPLE 486

2,4,6-trimethylphenyl(5-chloro-2-methylphenyl)methyl(2-((6-((3-(4-methyl-1-piperazinyl)propyl)oxy)-3-pyridinyl)amino)-4-pyrimidinyl)carbamate;

EXAMPLE 487

2,4,6-trimethylphenyl 2-((3,4-bis(methyloxy)-5-((3-(4-methyl-1-piperazinyl)propyl)oxy)phenyl)amino)-4-pyrimidinyl((3,5-dichlorophenyl)methyl)carbamate;

EXAMPLE 488

2,4,6-trimethylphenyl(3,5-dichlorophenyl)methyl(2-((3-fluoro-4-((3-(4-methyl-1-piperazinyl)propyl)oxy)phenyl)amino)-4-pyrimidinyl)carbamate;

EXAMPLE 489

2,4,6-trimethylphenyl(3,5-dichlorophenyl)methyl(2-((3-((3-(1-piperidinyl)propyl)oxy)phenyl)amino)-4-pyrimidinyl)carbamate;

EXAMPLE 490

2,4,6-trimethylphenyl(3,5-dichlorophenyl)methyl(2-((4-(((2-(diethylamino)ethyl)(methyl)amino)carbonyl)phenyl)amino)-4-pyrimidinyl)carbamate;

EXAMPLE 491

2,4,6-trimethylphenyl(3,5-dichlorophenyl)methyl(2-((3-fluoro-4-((2-(4-(1-methylethyl)-1-piperazinyl)ethyl)oxy)phenyl)amino)-4-pyrimidinyl)carbamate;

EXAMPLE 492

2,4,6-trimethylphenyl(3,5-dichlorophenyl)methyl(2-((3-fluoro-4-(((1-methyl-3-piperidinyl)methyl)oxy)phenyl)amino)-4-pyrimidinyl)carbamate;

EXAMPLE 493

2-methyl-6-(2-propenyl)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 494

2-methyl-6-(2-propenyl)phenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 495

2-methyl-6-(2-propenyl)phenyl(2,5-bis(methyloxy)phenyl)methyl(2-((3-fluoro-4-((3-(1-piperidinyl)propyl)oxy)phenyl)amino)-4-pyrimidinyl)carbamate;

EXAMPLE 496

2-methyl-6-(2-propenyl)phenyl(2,5-bis(methyloxy)phenyl)methyl(2-((3-((3-(1-piperidinyl)propyl)oxy)phenyl)amino)-4-pyrimidinyl)carbamate;

EXAMPLE 497

2-methyl-6-(2-propenyl)phenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 498

2-methyl-6-(2-propenyl)phenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 499

2-methyl-6-(2-propenyl)phenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 500

2-methyl-6-(2-propenyl)phenyl(2,5-bis(methyloxy)phenyl)methyl(2-((4-(3,4-dimethyl-1-piperazinyl)-3-fluorophenyl)amino)-4-pyrimidinyl)carbamate;

EXAMPLE 501

2,6-dimethylphenyl 2-((4-(((2-(diethylamino)ethyl)(methyl)amino)carbonyl)phenyl)amino)-4-pyrimidinyl(2-(methyloxy)-4-(2-((1-methylpropyl)amino)-2-oxoethyl)phenyl)carbamate;

EXAMPLE 502

2,6-dimethylphenyl 2-((3-fluoro-4-((3-(1-piperidinyl)propyl)oxy)phenyl)amino)-4-pyrimidinyl(2-(methyloxy)-4-(2-((1-methylpropyl)amino)-2-oxoethyl)phenyl)carbamate;

EXAMPLE 503

2,6-dimethylphenyl 2-((3-fluoro-4-((2-(4-(1-methylethyl)-1-piperazinyl)ethyl)oxy)phenyl)amino)-4-pyrimidinyl(2-(methyloxy)-4-(2-((1-methylpropyl)amino)-2-oxoethyl)phenyl)carbamate;

EXAMPLE 504

2,6-dimethylphenyl 4-(2-(diethylamino)-2-oxoethyl)-2-(methyloxy)phenyl(2-((3-fluoro-4-((3-(4-methyl-1-piperazinyl)propyl)oxy)phenyl)amino)-4-pyrimidinyl)carbamate;

EXAMPLE 505

2,6-dimethylphenyl 4-(2-(diethylamino)-2-oxoethyl)-2-(methyloxy)phenyl(2-((3-fluoro-4-((3-(1-piperidinyl)propyl)oxy)phenyl)amino)-4-pyrimidinyl)carbamate;

EXAMPLE 506

2,4,6-trimethylphenyl(3-chlorophenyl)methyl(2-((4-(((2-(diethylamino)ethyl)(methyl)amino)carbonyl)phenyl)amino)-4-pyrimidinyl)carbamate;

EXAMPLE 507

2,4,6-trimethylphenyl(3-chlorophenyl)methyl(2-((3-fluoro-4-((3-(4-methyl-1-piperazinyl)propyl)oxy)phenyl)amino)-4-pyrimidinyl)carbamate;

EXAMPLE 508

2,4,6-trimethylphenyl 2-((3,4-bis(methyloxy)-5-((3-(4-methyl-1-piperazinyl)propyl)oxy)phenyl)amino)-4-pyrimidinyl((3-chlorophenyl)methyl)carbamate;

EXAMPLE 509

2,4,6-trimethylphenyl(3-chlorophenyl)methyl(2-((3-fluoro-4-(((1-methyl-3-piperidinyl)methyl)oxy)phenyl)amino)-4-pyrimidinyl)carbamate;

EXAMPLE 510

2,4,6-trimethylphenyl(3-chlorophenyl)methyl(2-((3-fluoro-4-((2-(4-(1-methylethyl)-1-piperazinyl)ethyl)oxy)phenyl)amino)-4-pyrimidinyl)carbamate;

EXAMPLE 511

2-(methylsulfanyl)phenyl 2,4-bis(methyloxy)phenyl(2-((3-fluoro-4-(((1-methyl-3-piperidinyl)methyl)oxy)phenyl)amino)-4-pyrimidinyl)carbamate;

EXAMPLE 512

2-(methylsulfanyl)phenyl 2,4-bis(methyloxy)phenyl(2-((3-((3-(1-piperidinyl)propyl)oxy)phenyl)amino)-4-pyrimidinyl)carbamate;

EXAMPLE 513

2-(methylsulfanyl)phenyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 514

2,4,6-trimethylphenyl(2-chloro-5-(trifluoromethyl)phenyl)methyl(2-((3-((difluoromethyl)oxy)-4-(4-methyl-1-piperazinyl)phenyl)amino)-4-pyrimidinyl)carbamate;

EXAMPLE 515

2,4,6-trimethylphenyl(2,5-dichlorophenyl)methyl(2-((3-(4-methyl-1-piperazinyl)phenyl)amino)-4-pyrimidinyl)carbamate;

EXAMPLE 516

2,4,6-trimethylphenyl(2-chloro-5-(trifluoromethyl)phenyl)methyl(2-((3-fluoro-4-(4-methyl-1-piperazinyl)phenyl)amino)-4-pyrimidinyl)carbamate;

EXAMPLE 517

2,4,6-trimethylphenyl(2,5-dichlorophenyl)methyl(2-((3-(((2-(diethylamino)ethyl)(methyl)amino)carbonyl)phenyl)amino)-4-pyrimidinyl)carbamate;

EXAMPLE 518

2,4,6-trimethylphenyl(2,5-dichlorophenyl)methyl(2-((3-fluoro-4-((3R,5S)-3,4,5-trimethyl-1-piperazinyl)phenyl)amino)-4-pyrimidinyl)carbamate;

EXAMPLE 519

2,4,6-trimethylphenyl(2-chloro-5-(trifluoromethyl)phenyl)methyl(2-((4-(4-methyl-1-piperazinyl)phenyl)amino)-4-pyrimidinyl)carbamate;

EXAMPLE 520

2,4,6-trimethylphenyl 2-((3,5-bis(methyloxy)-4-((2-(4-methyl-1-piperazinyl)ethyl)oxy)phenyl)amino)-4-pyrimidinyl((2,5-dichlorophenyl)methyl)carbamate;

EXAMPLE 521

2,4,6-trimethylphenyl(2-chloro-5-(trifluoromethyl)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 522

2,4,6-trimethylphenyl 2-((3,4-bis(methyloxy)-5-((3-(4-methyl-1-piperazinyl)propyl)oxy)phenyl)amino)-4-pyrimidinyl((2,5-dichlorophenyl)methyl)carbamate;

EXAMPLE 523

2,4,6-trimethylphenyl 2-((3-chloro-4-(4-(1-methylethyl)-1-piperazinyl)phenyl)amino)-4-pyrimidinyl((2-chloro-5-(trifluoromethyl)phenyl)methyl)carbamate;

EXAMPLE 524

2,4,6-trimethylphenyl(2,3-bis(methyloxy)phenyl)methyl(2-((3-((3-(1-piperidinyl)propyl)oxy)phenyl)amino)-4-pyrimidinyl)carbamate;

EXAMPLE 525

2,6-dimethylphenyl 2-((3,4-bis(methyloxy)-5-((3-(4-methyl-1-piperazinyl)propyl)oxy)phenyl)amino)-4-pyrimidinyl(3-(3-((1-methylpropyl)amino)-3-oxopropyl)phenyl)carbamate;

EXAMPLE 526

2,6-dimethylphenyl 2-((3-fluoro-4-((3-(4-methyl-1-piperazinyl)propyl)oxy)phenyl)amino)-4-pyrimidinyl(3-(3-((1-methylpropyl)amino)-3-oxopropyl)phenyl)carbamate;

EXAMPLE 527

2,6-dimethylphenyl 2-((3-fluoro-4-((3-(1-piperidinyl)propyl)oxy)phenyl)amino)-4-pyrimidinyl(3-(3-((1-methylpropyl)amino)-3-oxopropyl)phenyl)carbamate;

EXAMPLE 528

2,6-dimethylphenyl 2-((4-(((2-(diethylamino)ethyl)(methyl)amino)carbonyl)phenyl)amino)-4-pyrimidinyl(3-(3-((1-methylpropyl)amino)-3-oxopropyl)phenyl)carbamate;

EXAMPLE 529

2,6-bis(methyloxy)phenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 530

2,6-difluorophenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 531

2,6-bis(methyloxy)phenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 532

2,6-difluorophenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 533

5-methyl-2-(methyloxy)phenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

EXAMPLE 534

5-methyl-2-(methyloxy)phenyl 2,4-bis(methyloxy)phenyl(2-((3-fluoro-4-((3-(4-methyl-1-piperazinyl)propyl)oxy)phenyl)amino)-4-pyrimidinyl)carbamate;

EXAMPLE 535

5-methyl-2-(methyloxy)phenyl 2,4-bis(methyloxy)phenyl(2-((3-fluoro-4-((3-(1-piperidinyl)propyl)oxy)phenyl)amino)-4-pyrimidinyl)carbamate;

EXAMPLE 536

5-methyl-2-(methyloxy)phenyl 2,4-bis(methyloxy)phenyl(2-((4-(((2-(diethylamino)ethyl)(methyl)amino)carbonyl)phenyl)amino)-4-pyrimidinyl)carbamate;

EXAMPLE 537

2,6-bis(methyloxy)phenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 538

2,6-difluorophenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 539

2,6-difluorophenyl(2,5-bis(methyloxy)phenyl)methyl(2-((4-(3,4-dimethyl-1-piperazinyl)-3-fluorophenyl)amino)-4-pyrimidinyl)carbamate;

EXAMPLE 540

2,4,6-trimethylphenyl(2,5-dichlorophenyl)methyl(2-((6-((3-(4-methyl-1-piperazinyl)propyl)oxy)-3-pyridinyl)amino)-4-pyrimidinyl)carbamate;

EXAMPLE 541

2-methyl-1-(1-methylethyl)propyl 2-((3,4-bis(methyloxy)-5-((3-(4-methyl-1-piperazinyl)propyl)oxy)phenyl)amino)-4-pyrimidinyl((3-(methyloxy)phenyl)methyl)carbamate;

EXAMPLE 542

2-methyl-1-(1-methylethyl)propyl 2-((3-fluoro-4-((3-(4-methyl-1-piperazinyl)propyl)oxy)phenyl)amino)-4-pyrimidinyl((3-(methyloxy)phenyl)methyl)carbamate;

EXAMPLE 543

2-methyl-1-(1-methylethyl)propyl 2-((3-fluoro-4-((3-(1-piperidinyl)propyl)oxy)phenyl)amino)-4-pyrimidinyl((3-(methyloxy)phenyl)methyl)carbamate;

EXAMPLE 544

2-methyl-1-(1-methylethyl)propyl (3-(methyloxy)phenyl)methyl(2-((3-((3-(1-piperidinyl)propyl)oxy)phenyl)amino)-4-pyrimidinyl)carbamate;

EXAMPLE 545

2-methyl-1-(1-methylethyl)propyl 2-((4-(((2-(diethylamino)ethyl)(methyl)amino)carbonyl)phenyl)amino)-4-pyrimidinyl((3-(methyloxy)phenyl)methyl)carbamate;

EXAMPLE 546

2-methyl-1-(1-methylethyl)propyl 2-((3-fluoro-4-((2-(4-(1-methylethyl)-1-piperazinyl)ethyl)oxy)phenyl)amino)-4-pyrimidinyl((3-(methyloxy)phenyl)methyl)carbamate;

EXAMPLE 547

2-methyl-1-(1-methylethyl)propyl 2-((3-fluoro-4-(((1-methyl-3-piperidinyl)methyl)oxy)phenyl)amino)-4-pyrimidinyl((3-(methyloxy)phenyl)methyl)carbamate;

EXAMPLE 548

2-methyl-1-(1-methylethyl)butyl 2-((3,4-bis(methyloxy)-5-((3-(4-methyl-1-piperazinyl)propyl)oxy)phenyl)amino)-4-pyrimidinyl((3-(methyloxy)phenyl)methyl)carbamate;

EXAMPLE 549

2-methyl-1-(1-methylethyl)butyl 2-((3-fluoro-4-((3-(4-methyl-1-piperazinyl)propyl)oxy)phenyl)amino)-4-pyrimidinyl((3-(methyloxy)phenyl)methyl)carbamate;

EXAMPLE 550

2-methyl-1-(1-methylethyl)butyl 2-((3-fluoro-4-((3-(1-piperidinyl)propyl)oxy)phenyl)amino)-4-pyrimidinyl((3-(methyloxy)phenyl)methyl)carbamate;

EXAMPLE 551

2-methyl-1-(1-methylethyl)butyl (3-(methyloxy)phenyl)methyl(2-((3-((3-(1-piperidinyl)propyl)oxy)phenyl)amino)-4-pyrimidinyl)carbamate;

EXAMPLE 552

2-methyl-1-(1-methylethyl)butyl 2-((4-(((2-(diethylamino)ethyl)(methyl)amino)carbonyl)phenyl)amino)-4-pyrimidinyl((3-(methyloxy)phenyl)methyl)carbamate;

EXAMPLE 553

2-methyl-1-(1-methylethyl)butyl 2-((3-fluoro-4-((2-(4-(1-methylethyl)-1-piperazinyl)ethyl)oxy)phenyl)amino)-4-pyrimidinyl((3-(methyloxy)phenyl)methyl)carbamate;

EXAMPLE 554

2-methyl-1-(1-methylethyl)butyl 2-((3-fluoro-4-(((1-methyl-3-piperidinyl)methyl)oxy)phenyl)amino)-4-pyrimidinyl((3-(methyloxy)phenyl)methyl)carbamate;

EXAMPLE 555

2,6-dimethylcyclohexyl 2-((3,4-bis(methyloxy)-5-((3-(4-methyl-1-piperazinyl)propyl)oxy)phenyl)amino)-4-pyrimidinyl((3-(methyloxy)phenyl)methyl)carbamate;

EXAMPLE 556

2,4,6-trimethylphenyl(3,5-dichlorophenyl)methyl(2-((3-fluoro-4-((3-(1-piperidinyl)propyl)oxy)phenyl)amino)-4-pyrimidinyl)carbamate;

EXAMPLE 557

2,4,6-trimethylphenyl(3,5-dichlorophenyl)methyl(2-((4-(3,4-dimethyl-1-piperazinyl)-3-fluorophenyl)amino)-4-pyrimidinyl)carbamate;

EXAMPLE 558

2,4,6-trimethylphenyl 2-((3,4-bis(methyloxy)-5-((3-(4-methyl-1-piperazinyl)propyl)oxy)phenyl)amino)-4-pyrimidinyl((3,5-dimethylphenyl)methyl)carbamate;

EXAMPLE 559

2,4,6-trimethylphenyl(3,5-dimethylphenyl)methyl(2-((3-fluoro-4-((3-(4-methyl-1-piperazinyl)propyl)oxy)phenyl)amino)-4-pyrimidinyl)carbamate;

EXAMPLE 560

2,4,6-trimethylphenyl(3,5-dimethylphenyl)methyl(2-((3-fluoro-4-((3-(1-piperidinyl)propyl)oxy)phenyl)amino)-4-pyrimidinyl)carbamate;

EXAMPLE 561

2,4,6-trimethylphenyl(3,5-dimethylphenyl)methyl(2-((3-((3-(1-piperidinyl)propyl)oxy)phenyl)amino)-4-pyrimidinyl)carbamate;

EXAMPLE 562

2,4,6-trimethylphenyl 2-((4-(((2-(diethylamino)ethyl)(methyl)amino)carbonyl)phenyl)amino)-4-pyrimidinyl((3,5-dimethylphenyl)methyl)carbamate;

EXAMPLE 563

2,4,6-trimethylphenyl(3,5-dimethylphenyl)methyl(2-((3-fluoro-4-((2-(4-(1-methylethyl)-1-piperazinyl)ethyl)oxy)phenyl)amino)-4-pyrimidinyl)carbamate;

EXAMPLE 564

2,4,6-trimethylphenyl(3,5-dimethylphenyl)methyl(2-((3-fluoro-4-(((1-methyl-3-piperidinyl)methyl)oxy)phenyl)amino)-4-pyrimidinyl)carbamate;

EXAMPLE 565

2,6-dimethylphenyl cyclohexyl(2-((3-((3-(1-piperidinyl)propyl)oxy)phenyl)amino)-4-pyrimidinyl)carbamate;

EXAMPLE 566

2,4,6-trimethylphenyl(3-chlorophenyl)methyl(2-((3-((3-(1-piperidinyl)propyl)oxy)phenyl)amino)-4-pyrimidinyl)carbamate;

EXAMPLE 567

2,6-dimethylphenyl 2-((3,4-bis(methyloxy)-5-((3-(4-methyl-1-piperazinyl)propyl)oxy)phenyl)amino)-4-pyrimidinyl(4-methyl-2-(methyloxy)phenyl)carbamate;

EXAMPLE 568

2,6-dimethylphenyl 2-((3-fluoro-4-((3-(4-methyl-1-piperazinyl)propyl)oxy)phenyl)amino)-4-pyrimidinyl(4-methyl-2-(methyloxy)phenyl)carbamate;

EXAMPLE 569

2,6-dimethylphenyl 2-((3-fluoro-4-((3-(1-piperidinyl)propyl)oxy)phenyl)amino)-4-pyrimidinyl(4-methyl-2-(methyloxy)phenyl)carbamate;

EXAMPLE 570

2,6-dimethylphenyl 4-methyl-2-(methyloxy)phenyl(2-((3-((3-(1-piperidinyl)propyl)oxy)phenyl)amino)-4-pyrimidinyl)carbamate;

EXAMPLE 571

2,6-dimethylphenyl 2-((4-(((2-(diethylamino)ethyl)(methyl)amino)carbonyl)phenyl)amino)-4-pyrimidinyl(4-methyl-2-(methyloxy)phenyl)carbamate;

EXAMPLE 572

2,6-dimethylphenyl 2-((3-fluoro-4-((2-(4-(1-methylethyl)-1-piperazinyl)ethyl)oxy)phenyl)amino)-4-pyrimidinyl(4-methyl-2-(methyloxy)phenyl)carbamate;

EXAMPLE 573

2,6-dimethylphenyl 2-((3-fluoro-4-(((1-methyl-3-piperidinyl)methyl)oxy)phenyl)amino)-4-pyrimidinyl(4-methyl-2-(methyloxy)phenyl)carbamate;

EXAMPLE 574

2,6-dimethylphenyl 2-((4-(3,4-dimethyl-1-piperazinyl)-3-fluorophenyl)amino)-4-pyrimidinyl(4-methyl-2-(methyloxy)phenyl)carbamate;

EXAMPLE 575

2,4,6-trimethylphenyl(5-chloro-2-fluorophenyl)methyl(2-((3-fluoro-4-((3-(1-piperidinyl)propyl)oxy)phenyl)amino)-4-pyrimidinyl)carbamate;

EXAMPLE 576

2,4,6-trimethylphenyl(5-chloro-2-fluorophenyl)methyl(2-((4-(((2-(diethylamino)ethyl)(methyl)amino)carbonyl)phenyl)amino)-4-pyrimidinyl)carbamate;

EXAMPLE 577

2,4,6-trimethylphenyl(5-chloro-2-fluorophenyl)methyl(2-((3-fluoro-4-((2-(4-(1-methylethyl)-1-piperazinyl)ethyl)oxy)phenyl)amino)-4-pyrimidinyl)carbamate;

EXAMPLE 578

2,4,6-trimethylphenyl(5-chloro-2-fluorophenyl)methyl(2-((3-fluoro-4-(((1-methyl-3-piperidinyl)methyl)oxy)phenyl)amino)-4-pyrimidinyl)carbamate;

EXAMPLE 579

2,4,6-trimethylphenyl(5-chloro-2-fluorophenyl)methyl(2-((4-(3,4-dimethyl-1-piperazinyl)-3-fluorophenyl)amino)-4-pyrimidinyl)carbamate;

EXAMPLE 580

2,6-dimethylphenyl 2-((4-(((2-(diethylamino)ethyl)(methyl)amino)carbonyl)phenyl)amino)-4-pyrimidinyl(4-(2-(diethylamino)-2-oxoethyl)-2-(methyloxy)phenyl)carbamate;

EXAMPLE 581

2,6-dimethylphenyl 4-(2-(diethylamino)-2-oxoethyl)-2-(methyloxy)phenyl(2-((4-(3,4-dimethyl-1-piperazinyl)-3-fluorophenyl)amino)-4-pyrimidinyl)carbamate;

EXAMPLE 582

2,6-dimethylphenyl 2-((3,4-bis(methyloxy)-5-((3-(4-methyl-1-piperazinyl)propyl)oxy)phenyl)amino)-4-pyrimidinyl(4-(2-(diethylamino)-2-oxoethyl)-2-(methyloxy)phenyl)carbamate;

EXAMPLE 583

2,6-dimethylphenyl 4-(2-(diethylamino)-2-oxoethyl)-2-(methyloxy)phenyl(2-((3-fluoro-4-(((1-methyl-3-piperidinyl)methyl)oxy)phenyl)amino)-4-pyrimidinyl)carbamate;

EXAMPLE 584

2,6-dimethylphenyl 4-(2-(diethylamino)-2-oxoethyl)-2-(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 585

2,6-dimethylphenyl 4-(2-(diethylamino)-2-oxoethyl)-2-(methyloxy)phenyl(2-((3-((3-(1-piperidinyl)propyl)oxy)phenyl)amino)-4-pyrimidinyl)carbamate;

EXAMPLE 586

2,4,6-trimethylphenyl 2-((4-(((2-(diethylamino)ethyl)(methyl)amino)carbonyl)phenyl)amino)-4-pyrimidinyl(2-(4-(methyloxy)phenyl)ethyl)carbamate;

EXAMPLE 587

2,4,6-trimethylphenyl 2-((3-fluoro-4-((3-(4-methyl-1-piperazinyl)propyl)oxy)phenyl)amino)-4-pyrimidinyl(2-(4-(methyloxy)phenyl)ethyl)carbamate;

EXAMPLE 588

2,4,6-trimethylphenyl 2-((3-fluoro-4-((3-(1-piperidinyl)propyl)oxy)phenyl)amino)-4-pyrimidinyl(2-(4-(methyloxy)phenyl)ethyl)carbamate;

EXAMPLE 589

2,4,6-trimethylphenyl 2-((4-(3,4-dimethyl-1-piperazinyl)-3-fluorophenyl)amino)-4-pyrimidinyl(2-(4-(methyloxy)phenyl)ethyl)carbamate;

EXAMPLE 590

2,4,6-trimethylphenyl 2-((3,4-bis(methyloxy)-5-((3-(4-methyl-1-piperazinyl)propyl)oxy)phenyl)amino)-4-pyrimidinyl(2-(4-(methyloxy)phenyl)ethyl)carbamate;

EXAMPLE 591

2,4,6-trimethylphenyl 2-((3-fluoro-4-(((1-methyl-3-piperidinyl)methyl)oxy)phenyl)amino)-4-pyrimidinyl(2-(4-(methyloxy)phenyl)ethyl)carbamate;

EXAMPLE 592

2,4,6-trimethylphenyl 2-((3-fluoro-4-((2-(4-(1-methylethyl)-1-piperazinyl)ethyl)oxy)phenyl)amino)-4-pyrimidinyl(2-(4-(methyloxy)phenyl)ethyl)carbamate;

EXAMPLE 593

2,4,6-trimethylphenyl 2-(4-(methyloxy)phenyl)ethyl(2-((3-((3-(1-piperidinyl)propyl)oxy)phenyl)amino)-4-pyrimidinyl)carbamate;

EXAMPLE 594

2,4,6-trimethylphenyl 2-((4-(((2-(diethylamino)ethyl)(methyl)amino)carbonyl)phenyl)amino)-4-pyrimidinyl((3,5-difluorophenyl)methyl)carbamate;

EXAMPLE 595

2,4,6-trimethylphenyl(3,5-difluorophenyl)methyl(2-((3-fluoro-4-((3-(4-methyl-1-piperazinyl)propyl)oxy)phenyl)amino)-4-pyrimidinyl)carbamate;

EXAMPLE 596

2,4,6-trimethylphenyl(3,5-difluorophenyl)methyl(2-((3-fluoro-4-((3-(1-piperidinyl)propyl)oxy)phenyl)amino)-4-pyrimidinyl)carbamate;

EXAMPLE 597

2,4,6-trimethylphenyl(3,5-difluorophenyl)methyl(2-((4-(3,4-dimethyl-1-piperazinyl)-3-fluorophenyl)amino)-4-pyrimidinyl)carbamate;

EXAMPLE 598

2,4,6-trimethylphenyl 2-((3,4-bis(methyloxy)-5-((3-(4-methyl-1-piperazinyl)propyl)oxy)phenyl)amino)-4-pyrimidinyl((3,5-difluorophenyl)methyl)carbamate;

EXAMPLE 599

2,4,6-trimethylphenyl(3,5-difluorophenyl)methyl(2-((3-fluoro-4-(((1-methyl-3-piperidinyl)methyl)oxy)phenyl)amino)-4-pyrimidinyl)carbamate;

EXAMPLE 600

2,4,6-trimethylphenyl(3,5-difluorophenyl)methyl(2-((3-fluoro-4-((2-(4-(1-methylethyl)-1-piperazinyl)ethyl)oxy)phenyl)amino)-4-pyrimidinyl)carbamate;

EXAMPLE 601

2,6-dimethylphenyl 2-((3,4-bis(methyloxy)-5-((3-(4-methyl-1-piperazinyl)propyl)oxy)phenyl)amino)-4-pyrimidinyl(3-(3-((2-(methyloxy)ethyl)amino)-3-oxopropyl)phenyl)carbamate;

EXAMPLE 602

2,6-dimethylphenyl 2-((3-fluoro-4-((3-(4-methyl-1-piperazinyl)propyl)oxy)phenyl)amino)-4-pyrimidinyl(3-(3-((2-(methyloxy)ethyl)amino)-3-oxopropyl)phenyl)carbamate;

EXAMPLE 603

2,6-dimethylphenyl 2-((3-fluoro-4-((3-(1-piperidinyl)propyl)oxy)phenyl)amino)-4-pyrimidinyl(3-(3-((2-(methyloxy)ethyl)amino)-3-oxopropyl)phenyl)carbamate;

EXAMPLE 604

2,6-dimethylphenyl 3-(3-((2-(methyloxy)ethyl)amino)-3-oxopropyl)phenyl(2-((3-((3-(1-piperidinyl)propyl)oxy)phenyl)amino)-4-pyrimidinyl)carbamate;

EXAMPLE 605

2,4,6-trimethylphenyl(2-chloro-5-(trifluoromethyl)phenyl)methyl(2-((4-((3-(4-(1-methylethyl)-1-piperazinyl)propyl)oxy)-3-(methyloxy)phenyl)amino)-4-pyrimidinyl)carbamate;

EXAMPLE 606

2,4,6-trimethylphenyl(2-chloro-5-(trifluoromethyl)phenyl)methyl(2-((3-fluoro-4-(((1-methyl-3-piperidinyl)methyl)oxy)phenyl)amino)-4-pyrimidinyl)carbamate;

EXAMPLE 607

2,4,6-trimethylphenyl(2-chloro-5-(trifluoromethyl)phenyl)methyl(2-((4-(((2-(diethylamino)ethyl)(methyl)amino)carbonyl)phenyl)amino)-4-pyrimidinyl)carbamate;

EXAMPLE 608

2,4,6-trimethylphenyl 2-((3,4-bis(methyloxy)-5-((3-(4-methyl-1-piperazinyl)propyl)oxy)phenyl)amino)-4-pyrimidinyl((2-chloro-5-(trifluoromethyl)phenyl)methyl)carbamate;

EXAMPLE 609

2,4,6-trimethylphenyl 2-((3,5-bis(methyloxy)-4-((2-(4-methyl-1-piperazinyl)ethyl)oxy)phenyl)amino)-4-pyrimidinyl((2-chloro-5-(trifluoromethyl)phenyl)methyl)carbamate;

EXAMPLE 610

2,4,6-trimethylphenyl(2-chloro-5-(trifluoromethyl)phenyl)methyl(2-((3-fluoro-4-((2-(4-methyl-1-piperazinyl)ethyl)oxy)phenyl)amino)-4-pyrimidinyl)carbamate;

EXAMPLE 611

2,4,6-trimethylphenyl(2-chloro-5-(trifluoromethyl)phenyl)methyl(2-((3-(4-methyl-1-piperazinyl)phenyl)amino)-4-pyrimidinyl)carbamate;

EXAMPLE 612

2,4,6-trimethylphenyl(2-chloro-5-(trifluoromethyl)phenyl)methyl(2-((3-(((2-(diethylamino)ethyl)(methyl)amino)carbonyl)phenyl)amino)-4-pyrimidinyl)carbamate;

EXAMPLE 613

2,4,6-trimethylphenyl(2-chloro-5-(trifluoromethyl)phenyl)methyl(2-((4-(3,4-dimethyl-1-piperazinyl)phenyl)amino)-4-pyrimidinyl)carbamate;

EXAMPLE 614

2,4,6-trimethylphenyl(2-chloro-5-(trifluoromethyl)phenyl)methyl(2-((3-fluoro-4-((3R,5S)-3,4,5-trimethyl-1-piperazinyl)phenyl)amino)-4-pyrimidinyl)carbamate;

EXAMPLE 615

2,4,6-trimethylphenyl(5-chloro-2-methylphenyl)methyl(2-((4-(4-methyl-1-piperazinyl)phenyl)amino)-4-pyrimidinyl)carbamate;

EXAMPLE 616

2,4,6-trimethylphenyl(5-chloro-2-methylphenyl)methyl(2-((3-fluoro-4-((3-(4-methyl-1-piperazinyl)propyl)oxy)phenyl)amino)-4-pyrimidinyl)carbamate;

EXAMPLE 617

2,4,6-trimethylphenyl(5-chloro-2-methylphenyl)methyl(2-((3-fluoro-4-(4-methyl-1-piperazinyl)phenyl)amino)-4-pyrimidinyl)carbamate;

EXAMPLE 618

2,4,6-trimethylphenyl 2-((3-chloro-4-(4-(1-methylethyl)-1-piperazinyl)phenyl)amino)-4-pyrimidinyl((5-chloro-2-methylphenyl)methyl)carbamate;

EXAMPLE 619

2,4,6-trimethylphenyl(5-chloro-2-methylphenyl)methyl(2-((3-fluoro-4-((2-(4-(1-methylethyl)-1-piperazinyl)ethyl)oxy)phenyl)amino)-4-pyrimidinyl)carbamate;

EXAMPLE 620

2,4,6-trimethylphenyl(5-chloro-2-methylphenyl)methyl(2-((4-((3-(4-(1-methylethyl)-1-piperazinyl)propyl)oxy)-3-(methyloxy)phenyl)amino)-4-pyrimidinyl)carbamate;

EXAMPLE 621

2,4,6-trimethylphenyl(5-chloro-2-methylphenyl)methyl(2-((4-(2-(4-methyl-1-piperazinyl)ethyl)phenyl)amino)-4-pyrimidinyl)carbamate;

EXAMPLE 622

2,4,6-trimethylphenyl(5-chloro-2-methylphenyl)methyl(2-((3-fluoro-4-(((1-methyl-3-piperidinyl)methyl)oxy)phenyl)amino)-4-pyrimidinyl)carbamate;

EXAMPLE 623

2,4,6-trimethylphenyl(5-chloro-2-methylphenyl)methyl(2-((4-(((2-(diethylamino)ethyl)(methyl)amino)carbonyl)phenyl)amino)-4-pyrimidinyl)carbamate;

EXAMPLE 624

2,4,6-trimethylphenyl 2-((3,4-bis(methyloxy)-5-((3-(4-methyl-1-piperazinyl)propyl)oxy)phenyl)amino)-4-pyrimidinyl((5-chloro-2-methylphenyl)methyl)carbamate;

EXAMPLE 625

2,4,6-trimethylphenyl 2-((3,5-bis(methyloxy)-4-((2-(4-methyl-1-piperazinyl)ethyl)oxy)phenyl)amino)-4-pyrimidinyl((5-chloro-2-methylphenyl)methyl)carbamate;

EXAMPLE 626

2,4,6-trimethylphenyl(5-chloro-2-methylphenyl)methyl(2-((3-(4-methyl-1-piperazinyl)phenyl)amino)-4-pyrimidinyl)carbamate;

EXAMPLE 627

2,4,6-trimethylphenyl(5-chloro-2-methylphenyl)methyl(2-((3-(((2-(diethylamino)ethyl)(methyl)amino)carbonyl)phenyl)amino)-4-pyrimidinyl)carbamate;

EXAMPLE 628

2,4,6-trimethylphenyl(5-chloro-2-methylphenyl)methyl(2-((4-(3,4-dimethyl-1-piperazinyl)phenyl)amino)-4-pyrimidinyl)carbamate;

EXAMPLE 629

2,4,6-trimethylphenyl(5-chloro-2-methylphenyl)methyl(2-((3-fluoro-4-((3R,5S)-3,4,5-trimethyl-1-piperazinyl)phenyl)amino)-4-pyrimidinyl)carbamate;

EXAMPLE 630

2,4,6-trimethylphenyl(5-chloro-2-methylphenyl)methyl(2-((3-((difluoromethyl)oxy)-4-(4-methyl-1-piperazinyl)phenyl)amino)-4-pyrimidinyl)carbamate;

EXAMPLE 631

2,4,6-trimethylphenyl(5-chloro-2-methylphenyl)methyl(2-((3-fluoro-4-((2-(4-methyl-1-piperazinyl)ethyl)oxy)phenyl)amino)-4-pyrimidinyl)carbamate;

EXAMPLE 632

2,6-dimethylphenyl 2-((3-fluoro-4-((3-(4-methyl-1-piperazinyl)propyl)oxy)phenyl)amino)-4-pyrimidinyl(3-(2-(3-methyl-1,2,4-oxadiazol-5-yl)ethyl)phenyl)carbamate;

EXAMPLE 633

2,6-dimethylphenyl 2-((3-fluoro-4-((3-(1-piperidinyl)propyl)oxy)phenyl)amino)-4-pyrimidinyl(3-(2-(3-methyl-1,2,4-oxadiazol-5-yl)ethyl)phenyl)carbamate;

EXAMPLE 634

2,6-dimethylphenyl 3-(2-(3-methyl-1,2,4-oxadiazol-5-yl)ethyl)phenyl(2-((3-((3-(1-piperidinyl)propyl)oxy)phenyl)amino)-4-pyrimidinyl)carbamate;

EXAMPLE 635

2,6-dimethylphenyl 2-((4-(((2-(diethylamino)ethyl)(methyl)amino)carbonyl)phenyl)amino)-4-pyrimidinyl(3-(2-(3-methyl-1,2,4-oxadiazol-5-yl)ethyl)phenyl)carbamate;

EXAMPLE 636

2,6-dimethylphenyl 2-((3-fluoro-4-((2-(4-(1-methylethyl)-1-piperazinyl)ethyl)oxy)phenyl)amino)-4-pyrimidinyl(3-(2-(3-methyl-1,2,4-oxadiazol-5-yl)ethyl)phenyl)carbamate;

EXAMPLE 637

2,6-dimethylphenyl 2-((3-fluoro-4-(((1-methyl-3-piperidinyl)methyl)oxy)phenyl)amino)-4-pyrimidinyl(3-(2-(3-methyl-1,2,4-oxadiazol-5-yl)ethyl)phenyl)carbamate;

EXAMPLE 638

2,4,6-trimethylphenyl 2-((3,4-bis(methyloxy)-5-((3-(4-methyl-1-piperazinyl)propyl)oxy)phenyl)amino)-4-pyrimidinyl((2,5-difluorophenyl)methyl)carbamate;

EXAMPLE 639

2,4,6-trimethylphenyl(2,5-difluorophenyl)methyl(2-((3-fluoro-4-((3-(4-methyl-1-piperazinyl)propyl)oxy)phenyl)amino)-4-pyrimidinyl)carbamate;

EXAMPLE 640

2,4,6-trimethylphenyl(2,5-difluorophenyl)methyl(2-((3-fluoro-4-((3-(1-piperidinyl)propyl)oxy)phenyl)amino)-4-pyrimidinyl)carbamate;

EXAMPLE 641

2,4,6-trimethylphenyl(2,5-difluorophenyl)methyl(2-((3-((3-(1-piperidinyl)propyl)oxy)phenyl)amino)-4-pyrimidinyl)carbamate;

EXAMPLE 642

2,4,6-trimethylphenyl 2-((4-(((2-(diethylamino)ethyl)(methyl)amino)carbonyl)phenyl)amino)-4-pyrimidinyl((2,5-difluorophenyl)methyl)carbamate;

EXAMPLE 643

2,4,6-trimethylphenyl(2,5-difluorophenyl)methyl(2-((3-fluoro-4-((2-(4-(1-methylethyl)-1-piperazinyl)ethyl)oxy)phenyl)amino)-4-pyrimidinyl)carbamate;

EXAMPLE 644

2,4,6-trimethylphenyl(2,5-difluorophenyl)methyl(2-((3-fluoro-4-(((1-methyl-3-piperidinyl)methyl)oxy)phenyl)amino)-4-pyrimidinyl)carbamate;

EXAMPLE 645

2,4,6-trimethylphenyl(2,5-difluorophenyl)methyl(2-((4-(3,4-dimethyl-1-piperazinyl)-3-fluorophenyl)amino)-4-pyrimidinyl)carbamate;

EXAMPLE 646

2,4,6-trimethylphenyl(3,5-bis(trifluoromethyl)phenyl)methyl(2-((4-(((2-(diethylamino)ethyl)(methyl)amino)carbonyl)phenyl)amino)-4-pyrimidinyl)carbamate;

EXAMPLE 647

2,4,6-trimethylphenyl(3,5-bis(trifluoromethyl)phenyl)methyl(2-((3-fluoro-4-((3-(4-methyl-1-piperazinyl)propyl)oxy)phenyl)amino)-4-pyrimidinyl)carbamate;

EXAMPLE 648

2,4,6-trimethylphenyl(3,5-bis(trifluoromethyl)phenyl)methyl(2-((3-fluoro-4-((3-(1-piperidinyl)propyl)oxy)phenyl)amino)-4-pyrimidinyl)carbamate;

EXAMPLE 649

2,4,6-trimethylphenyl(3,5-bis(trifluoromethyl)phenyl)methyl(2-((4-(3,4-dimethyl-1-piperazinyl)-3-fluorophenyl)amino)-4-pyrimidinyl)carbamate;

EXAMPLE 650

2,4,6-trimethylphenyl 2-((3,4-bis(methyloxy)-5-((3-(4-methyl-1-piperazinyl)propyl)oxy)phenyl)amino)-4-pyrimidinyl((3,5-bis(trifluoromethyl)phenyl)methyl)carbamate;

EXAMPLE 651

2,4,6-trimethylphenyl(3,5-bis(trifluoromethyl)phenyl)methyl(2-((3-fluoro-4-(((1-methyl-3-piperidinyl)methyl)oxy)phenyl)amino)-4-pyrimidinyl)carbamate;

EXAMPLE 652

2,4,6-trimethylphenyl(3,5-bis(trifluoromethyl)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 653

2,4,6-trimethylphenyl(3-chlorophenyl)methyl(2-((4-(3,4-dimethyl-1-piperazinyl)-3-fluorophenyl)amino)-4-pyrimidinyl)carbamate;

EXAMPLE 654

2,4,6-trimethylphenyl(3,5-difluorophenyl)methyl(2-((3-((3-(1-piperidinyl)propyl)oxy)phenyl)amino)-4-pyrimidinyl)carbamate;

EXAMPLE 655

(1S)-1-phenylethyl 2-((3,4-bis(methyloxy)-5-((3-(4-methyl-1-piperazinyl)propyl)oxy)phenyl)amino)-4-pyrimidinyl((3-(methyloxy)phenyl)methyl)carbamate;

EXAMPLE 656

(1S)-1-phenylethyl 2-((3-fluoro-4-((3-(4-methyl-1-piperazinyl)propyl)oxy)phenyl)amino)-4-pyrimidinyl((3-(methyloxy)phenyl)methyl)carbamate;

EXAMPLE 657

(1S)-1-phenylethyl 2-((3-fluoro-4-((3-(1-piperidinyl)propyl)oxy)phenyl)amino)-4-pyrimidinyl((3-(methyloxy)phenyl)methyl)carbamate;

EXAMPLE 658

(1S)-1-phenylethyl (3-(methyloxy)phenyl)methyl(2-((3-((3-(1-piperidinyl)propyl)oxy)phenyl)amino)-4-pyrimidinyl)carbamate;

EXAMPLE 659

(1S)-1-phenylethyl 2-((4-(((2-(diethylamino)ethyl)(methyl)amino)carbonyl)phenyl)amino)-4-pyrimidinyl((3-(methyloxy)phenyl)methyl)carbamate;

EXAMPLE 660

(1S)-1-phenylethyl 2-((3-fluoro-4-((2-(4-(1-methylethyl)-1-piperazinyl)ethyl)oxy)phenyl)amino)-4-pyrimidinyl((3-(methyloxy)phenyl)methyl)carbamate;

EXAMPLE 661

(1S)-1-phenylethyl 2-((3-fluoro-4-(((1-methyl-3-piperidinyl)methyl)oxy)phenyl)amino)-4-pyrimidinyl((3-(methyloxy)phenyl)methyl)carbamate;

EXAMPLE 662

(1S)-1-phenylethyl 2-((4-(3,4-dimethyl-1-piperazinyl)-3-fluorophenyl)amino)-4-pyrimidinyl((3-(methyloxy)phenyl)methyl)carbamate;

EXAMPLE 663

2,6-dimethylcyclohexyl 2-((3-fluoro-4-((3-(4-methyl-1-piperazinyl)propyl)oxy)phenyl)amino)-4-pyrimidinyl((3-(methyloxy)phenyl)methyl)carbamate;

EXAMPLE 664

2,6-dimethylcyclohexyl 2-((3-fluoro-4-((3-(1-piperidinyl)propyl)oxy)phenyl)amino)-4-pyrimidinyl((3-(methyloxy)phenyl)methyl)carbamate;

EXAMPLE 665

2,6-dimethylcyclohexyl (3-(methyloxy)phenyl)methyl(2-((3-((3-(1-piperidinyl)propyl)oxy)phenyl)amino)-4-pyrimidinyl)carbamate;

EXAMPLE 666

2,6-dimethylcyclohexyl 2-((4-(((2-(diethylamino)ethyl)(methyl)amino)carbonyl)phenyl)amino)-4-pyrimidinyl((3-(methyloxy)phenyl)methyl)carbamate;

EXAMPLE 667

2,6-dimethylcyclohexyl 2-((3-fluoro-4-((2-(4-(1-methylethyl)-1-piperazinyl)ethyl)oxy)phenyl)amino)-4-pyrimidinyl((3-(methyloxy)phenyl)methyl)carbamate;

EXAMPLE 668

2,6-dimethylcyclohexyl 2-((3-fluoro-4-(((1-methyl-3-piperidinyl)methyl)oxy)phenyl)amino)-4-pyrimidinyl((3-(methyloxy)phenyl)methyl)carbamate;

EXAMPLE 669

2,6-dimethylcyclohexyl 2-((4-(3,4-dimethyl-1-piperazinyl)-3-fluorophenyl)amino)-4-pyrimidinyl((3-(methyloxy)phenyl)methyl)carbamate;

EXAMPLE 670

2-(methylsulfanyl)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 671

2-(methylsulfanyl)phenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 672

2-(methylsulfanyl)phenyl(2,5-bis(methyloxy)phenyl)methyl(2-((3-fluoro-4-((3-(1-piperidinyl)propyl)oxy)phenyl)amino)-4-pyrimidinyl)carbamate;

EXAMPLE 673

2-(methylsulfanyl)phenyl(2,5-bis(methyloxy)phenyl)methyl(2-((3-((3-(1-piperidinyl)propyl)oxy)phenyl)amino)-4-pyrimidinyl)carbamate;

EXAMPLE 674

2-(methylsulfanyl)phenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 675

2-(methylsulfanyl)phenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 676

2-(methylsulfanyl)phenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 677

2,4,6-trimethylphenyl 2-((3,4-bis(methyloxy)-5-((3-(4-methyl-1-piperazinyl)propyl)oxy)phenyl)amino)-4-pyrimidinyl((2-phenyl-1,3-thiazol-4-yl)methyl)carbamate;

EXAMPLE 678

2,4,6-trimethylphenyl 2-((3-fluoro-4-((3-(4-methyl-1-piperazinyl)propyl)oxy)phenyl)amino)-4-pyrimidinyl((2-phenyl-1,3-thiazol-4-yl)methyl)carbamate;

EXAMPLE 679

2,4,6-trimethylphenyl 2-((3-fluoro-4-((3-(1-piperidinyl)propyl)oxy)phenyl)amino)-4-pyrimidinyl((2-phenyl-1,3-thiazol-4-yl)methyl)carbamate;

EXAMPLE 680

2,4,6-trimethylphenyl(2-phenyl-1,3-thiazol-4-yl)methyl(2-((3-((3-(1-piperidinyl)propyl)oxy)phenyl)amino)-4-pyrimidinyl)carbamate;

EXAMPLE 681

2,4,6-trimethylphenyl 2-((4-(((2-(diethylamino)ethyl)(methyl)amino)carbonyl)phenyl)amino)-4-pyrimidinyl((2-phenyl-1,3-thiazol-4-yl)methyl)carbamate;

EXAMPLE 682

2,4,6-trimethylphenyl 2-((3-fluoro-4-((2-(4-(1-methylethyl)-1-piperazinyl)ethyl)oxy)phenyl)amino)-4-pyrimidinyl((2-phenyl-1,3-thiazol-4-yl)methyl)carbamate;

EXAMPLE 683

2,4,6-trimethylphenyl 2-((3-fluoro-4-(((1-methyl-3-piperidinyl)methyl)oxy)phenyl)amino)-4-pyrimidinyl((2-phenyl-1,3-thiazol-4-yl)methyl)carbamate;

EXAMPLE 684

2,4,6-trimethylphenyl 2-((4-(3,4-dimethyl-1-piperazinyl)-3-fluorophenyl)amino)-4-pyrimidinyl((2-phenyl-1,3-thiazol-4-yl)methyl)carbamate;

EXAMPLE 685

2,4,6-trimethylphenyl(2-chloro-5-(trifluoromethyl)phenyl)methyl(2-((4-(2-(4-methyl-1-piperazinyl)ethyl)phenyl)amino)-4-pyrimidinyl)carbamate;

EXAMPLE 686

2,6-dimethylphenyl 2-ethylimidazo[1,2-a]pyridin-8-yl(2-((3-fluoro-4-((3-(4-methyl-1-piperazinyl)propyl)oxy)phenyl)amino)-4-pyrimidinyl)carbamate;

EXAMPLE 687

2,6-dimethylphenyl 2-ethylimidazo[1,2-a]pyridin-8-yl(2-((3-fluoro-4-((3-(1-piperidinyl)propyl)oxy)phenyl)amino)-4-pyrimidinyl)carbamate;

EXAMPLE 688

2,6-dimethylphenyl 2-ethylimidazo[1,2-a]pyridin-8-yl(2-((3-((3-(1-piperidinyl)propyl)oxy)phenyl)amino)-4-pyrimidinyl)carbamate;

EXAMPLE 689

2,6-dimethylphenyl 2-((4-(((2-(diethylamino)ethyl)(methyl)amino)carbonyl)phenyl)amino)-4-pyrimidinyl(2-ethylimidazo[1,2-a]pyridin-8-yl)carbamate;

EXAMPLE 690

2,4,6-trimethylphenyl 2-((3,4-bis(methyloxy)-5-((3-(4-methyl-1-piperazinyl)propyl)oxy)phenyl)amino)-4-pyrimidinyl((3-(2-((1-methylpropyl)amino)-2-oxoethyl)phenyl)methyl)carbamate;

EXAMPLE 691

2,4,6-trimethylphenyl 2-((3-fluoro-4-((3-(4-methyl-1-piperazinyl)propyl)oxy)phenyl)amino)-4-pyrimidinyl((3-(2-((1-methylpropyl)amino)-2-oxoethyl)phenyl)methyl)carbamate;

EXAMPLE 692

2,4,6-trimethylphenyl 2-((3-fluoro-4-((3-(1-piperidinyl)propyl)oxy)phenyl)amino)-4-pyrimidinyl((3-(2-((1-methylpropyl)amino)-2-oxoethyl)phenyl)methyl)carbamate;

EXAMPLE 693

2,4,6-trimethylphenyl(3-(2-((1-methylpropyl)amino)-2-oxoethyl)phenyl)methyl(2-((3-((3-(1-piperidinyl)propyl)oxy)phenyl)amino)-4-pyrimidinyl)carbamate;

EXAMPLE 694

2,4,6-trimethylphenyl(2-chloro-3,6-difluorophenyl)methyl(2-((4-(((2-(diethylamino)ethyl)(methyl)amino)carbonyl)phenyl)amino)-4-pyrimidinyl)carbamate;

EXAMPLE 695

2,4,6-trimethylphenyl(2-chloro-3,6-difluorophenyl)methyl(2-((3-fluoro-4-((3-(4-methyl-1-piperazinyl)propyl)oxy)phenyl)amino)-4-pyrimidinyl)carbamate;

EXAMPLE 696

2,4,6-trimethylphenyl(2-chloro-3,6-difluorophenyl)methyl(2-((3-fluoro-4-((3-(1-piperidinyl)propyl)oxy)phenyl)amino)-4-pyrimidinyl)carbamate;

EXAMPLE 697

2,4,6-trimethylphenyl(2-chloro-3,6-difluorophenyl)methyl(2-((4-(3,4-dimethyl-1-piperazinyl)-3-fluorophenyl)amino)-4-pyrimidinyl)carbamate;

EXAMPLE 698

2,4,6-trimethylphenyl 2-((3,4-bis(methyloxy)-5-((3-(4-methyl-1-piperazinyl)propyl)oxy)phenyl)amino)-4-pyrimidinyl((2-chloro-3,6-difluorophenyl)methyl)carbamate;

EXAMPLE 699

2,4,6-trimethylphenyl(2-chloro-3,6-difluorophenyl)methyl(2-((3-fluoro-4-(((1-methyl-3-piperidinyl)methyl)oxy)phenyl)amino)-4-pyrimidinyl)carbamate;

EXAMPLE 700

2,4,6-trimethylphenyl(2-chloro-3,6-difluorophenyl)methyl(2-((3-fluoro-4-((2-(4-(1-methylethyl)-1-piperazinyl)ethyl)oxy)phenyl)amino)-4-pyrimidinyl)carbamate;

EXAMPLE 701

2,4,6-trimethylphenyl(2-chloro-3,6-difluorophenyl)methyl(2-((3-((3-(1-piperidinyl)propyl)oxy)phenyl)amino)-4-pyrimidinyl)carbamate;

EXAMPLE 702

2,6-dimethylphenyl 3-(3-((1-methylpropyl)amino)-3-oxopropyl)phenyl(2-((3-((3-(1-piperidinyl)propyl)oxy)phenyl)amino)-4-pyrimidinyl)carbamate;

EXAMPLE 703

2,6-dimethylphenyl 2-((3-fluoro-4-((2-(4-(1-methylethyl)-1-piperazinyl)ethyl)oxy)phenyl)amino)-4-pyrimidinyl(3-(3-((1-methylpropyl)amino)-3-oxopropyl)phenyl)carbamate;

EXAMPLE 704

2,6-dimethylphenyl 2-((3-fluoro-4-(((1-methyl-3-piperidinyl)methyl)oxy)phenyl)amino)-4-pyrimidinyl(3-(3-((1-methylpropyl)amino)-3-oxopropyl)phenyl)carbamate;

EXAMPLE 705

2,6-dimethylphenyl 2-((4-(3,4-dimethyl-1-piperazinyl)-3-fluorophenyl)amino)-4-pyrimidinyl(3-(3-((1-methylpropyl)amino)-3-oxopropyl)phenyl)carbamate;

EXAMPLE 706

2,6-dimethylphenyl 2-((4-(((2-(diethylamino)ethyl)(methyl)amino)carbonyl)phenyl)amino)-4-pyrimidinyl(3-(3-((2-(methyloxy)ethyl)amino)-3-oxopropyl)phenyl)carbamate;

EXAMPLE 707

2,6-dimethylphenyl 2-((3-fluoro-4-((2-(4-(1-methylethyl)-1-piperazinyl)ethyl)oxy)phenyl)amino)-4-pyrimidinyl(3-(3-((2-(methyloxy)ethyl)amino)-3-oxopropyl)phenyl)carbamate;

EXAMPLE 708

2,6-dimethylphenyl 2-((3-fluoro-4-(((1-methyl-3-piperidinyl)methyl)oxy)phenyl)amino)-4-pyrimidinyl(3-(3-((2-(methyloxy)ethyl)amino)-3-oxopropyl)phenyl)carbamate;

EXAMPLE 709

2,6-dimethylphenyl 2-((4-(3,4-dimethyl-1-piperazinyl)-3-fluorophenyl)amino)-4-pyrimidinyl(3-(3-((2-(methyloxy)ethyl)amino)-3-oxopropyl)phenyl)carbamate;

EXAMPLE 710

2,6-dimethylphenyl 2-((3,4-bis(methyloxy)-5-((3-(4-methyl-1-piperazinyl)propyl)oxy)phenyl)amino)-4-pyrimidinyl(3-(3-(diethylamino)-3-oxopropyl)phenyl)carbamate;

EXAMPLE 711

2,6-dimethylphenyl 3-(3-(diethylamino)-3-oxopropyl)phenyl(2-((3-fluoro-4-((3-(4-methyl-1-piperazinyl)propyl)oxy)phenyl)amino)-4-pyrimidinyl)carbamate;

EXAMPLE 712

2,6-dimethylphenyl 3-(3-(diethylamino)-3-oxopropyl)phenyl(2-((3-fluoro-4-((3-(1-piperidinyl)propyl)oxy)phenyl)amino)-4-pyrimidinyl)carbamate;

EXAMPLE 713

2,6-dimethylphenyl 3-(3-(diethylamino)-3-oxopropyl)phenyl(2-((3-((3-(1-piperidinyl)propyl)oxy)phenyl)amino)-4-pyrimidinyl)carbamate;

EXAMPLE 714

2,6-dimethylphenyl 2-((4-(((2-(diethylamino)ethyl)(methyl)amino)carbonyl)phenyl)amino)-4-pyrimidinyl(3-(3-(diethylamino)-3-oxopropyl)phenyl)carbamate;

EXAMPLE 715

2,6-dimethylphenyl 3-(3-(diethylamino)-3-oxopropyl)phenyl(2-((3-fluoro-4-((2-(4-(1-methylethyl)-1-piperazinyl)ethyl)oxy)phenyl)amino)-4-pyrimidinyl)carbamate;

EXAMPLE 716

2,6-dimethylphenyl 3-(3-(diethylamino)-3-oxopropyl)phenyl(2-((3-fluoro-4-(((1-methyl-3-piperidinyl)methyl)oxy)phenyl)amino)-4-pyrimidinyl)carbamate;

EXAMPLE 717

2,6-dimethylphenyl 3-(3-(diethylamino)-3-oxopropyl)phenyl(2-((4-(3,4-dimethyl-1-piperazinyl)-3-fluorophenyl)amino)-4-pyrimidinyl)carbamate;

EXAMPLE 718

2,6-dimethylphenyl 2-((3,4-bis(methyloxy)-5-((3-(4-methyl-1-piperazinyl)propyl)oxy)phenyl)amino)-4-pyrimidinyl(2-(methyloxy)-4-(((1-methylpropyl)amino)carbonyl)phenyl)carbamate;

EXAMPLE 719

2,6-dimethylphenyl 2-((3-fluoro-4-((3-(4-methyl-1-piperazinyl)propyl)oxy)phenyl)amino)-4-pyrimidinyl(2-(methyloxy)-4-(((1-methylpropyl)amino)carbonyl)phenyl)carbamate;

EXAMPLE 720

2,6-dimethylphenyl 2-((3-fluoro-4-((3-(1-piperidinyl)propyl)oxy)phenyl)amino)-4-pyrimidinyl(2-(methyloxy)-4-(((1-methylpropyl)amino)carbonyl)phenyl)carbamate;

EXAMPLE 721

2,6-dimethylphenyl 2-((3-fluoro-4-((2-(4-(1-methylethyl)-1-piperazinyl)ethyl)oxy)phenyl)amino)-4-pyrimidinyl(2-(methyloxy)-4-(((1-methylpropyl)amino)carbonyl)phenyl)carbamate;

EXAMPLE 722

2,6-dimethylphenyl 2-((3,4-bis(methyloxy)-5-((3-(4-methyl-1-piperazinyl)propyl)oxy)phenyl)amino)-4-pyrimidinyl(4-butyl-2-(methyloxy)phenyl)carbamate;

EXAMPLE 723

2,6-dimethylphenyl 4-butyl-2-(methyloxy)phenyl(2-((3-fluoro-4-((3-(4-methyl-1-piperazinyl)propyl)oxy)phenyl)amino)-4-pyrimidinyl)carbamate;

EXAMPLE 724

2,6-dimethylphenyl 4-butyl-2-(methyloxy)phenyl(2-((3-fluoro-4-((3-(1-piperidinyl)propyl)oxy)phenyl)amino)-4-pyrimidinyl)carbamate;

EXAMPLE 725

2,6-dimethylphenyl 4-butyl-2-(methyloxy)phenyl(2-((4-(((2-(diethylamino)ethyl)(methyl)amino)carbonyl)phenyl)amino)-4-pyrimidinyl)carbamate;

EXAMPLE 726

2,6-dimethylphenyl 4-butyl-2-(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 727

2,6-dimethylphenyl 4-butyl-2-(methyloxy)phenyl(2-((3-fluoro-4-(((1-methyl-3-piperidinyl)methyl)oxy)phenyl)amino)-4-pyrimidinyl)carbamate;

EXAMPLE 728

2,4,6-trimethylphenyl 1,3-benzodioxol-5-ylmethyl(2-((3,4-bis(methyloxy)-5-((3-(4-methyl-1-piperazinyl)propyl)oxy)phenyl)amino)-4-pyrimidinyl)carbamate;

EXAMPLE 729

2,4,6-trimethylphenyl 1,3-benzodioxol-5-ylmethyl(2-((3-fluoro-4-((3-(4-methyl-1-piperazinyl)propyl)oxy)phenyl)amino)-4-pyrimidinyl)carbamate;

EXAMPLE 730

2,4,6-trimethylphenyl 1,3-benzodioxol-5-ylmethyl(2-((3-fluoro-4-((3-(1-piperidinyl)propyl)oxy)phenyl)amino)-4-pyrimidinyl)carbamate;

EXAMPLE 731

2,4,6-trimethylphenyl 1,3-benzodioxol-5-ylmethyl(2-((3-((3-(1-piperidinyl)propyl)oxy)phenyl)amino)-4-pyrimidinyl)carbamate;

EXAMPLE 732

2,4,6-trimethylphenyl 1,3-benzodioxol-5-ylmethyl(2-((4-(((2-(diethylamino)ethyl)(methyl)amino)carbonyl)phenyl)amino)-4-pyrimidinyl)carbamate;

EXAMPLE 733

2,4,6-trimethylphenyl 1,3-benzodioxol-5-ylmethyl(2-((3-fluoro-4-((2-(4-(1-methylethyl)-1-piperazinyl)ethyl)oxy)phenyl)amino)-4-pyrimidinyl)carbamate;

EXAMPLE 734

2,4,6-trimethylphenyl 1,3-benzodioxol-5-ylmethyl(2-((3-fluoro-4-(((1-methyl-3-piperidinyl)methyl)oxy)phenyl)amino)-4-pyrimidinyl)carbamate;

EXAMPLE 735

2,4,6-trimethylphenyl 1,3-benzodioxol-5-ylmethyl(2-((4-(3,4-dimethyl-1-piperazinyl)-3-fluorophenyl)amino)-4-pyrimidinyl)carbamate;

EXAMPLE 736

2,4,6-trimethylphenyl 2-((3,4-bis(methyloxy)-5-((3-(4-methyl-1-piperazinyl)propyl)oxy)phenyl)amino)-4-pyrimidinyl((3,4-difluorophenyl)methyl)carbamate;

EXAMPLE 737

2,4,6-trimethylphenyl(3,4-difluorophenyl)methyl(2-((3-fluoro-4-((3-(4-methyl-1-piperazinyl)propyl)oxy)phenyl)amino)-4-pyrimidinyl)carbamate;

EXAMPLE 738

2,4,6-trimethylphenyl(3,4-difluorophenyl)methyl(2-((3-fluoro-4-((3-(1-piperidinyl)propyl)oxy)phenyl)amino)-4-pyrimidinyl)carbamate;

EXAMPLE 739

2,4,6-trimethylphenyl(3,4-difluorophenyl)methyl(2-((3-((3-(1-piperidinyl)propyl)oxy)phenyl)amino)-4-pyrimidinyl)carbamate;

EXAMPLE 740

2,4,6-trimethylphenyl 2-((4-(((2-(diethylamino)ethyl)(methyl)amino)carbonyl)phenyl)amino)-4-pyrimidinyl((3,4-difluorophenyl)methyl)carbamate;

EXAMPLE 741

2,4,6-trimethylphenyl(3,4-difluorophenyl)methyl(2-((3-fluoro-4-((2-(4-(1-methylethyl)-1-piperazinyl)ethyl)oxy)phenyl)amino)-4-pyrimidinyl)carbamate;

EXAMPLE 742

2,4,6-trimethylphenyl(3,4-difluorophenyl)methyl(2-((3-fluoro-4-(((1-methyl-3-piperidinyl)methyl)oxy)phenyl)amino)-4-pyrimidinyl)carbamate;

EXAMPLE 743

2,4,6-trimethylphenyl(3,4-difluorophenyl)methyl(2-((4-(3,4-dimethyl-1-piperazinyl)-3-fluorophenyl)amino)-4-pyrimidinyl)carbamate;

EXAMPLE 744

2,4,6-trimethylphenyl(6-fluoro-4H-1,3-benzodioxin-8-yl)methyl(2-((3-fluoro-4-((3-(4-methyl-1-piperazinyl)propyl)oxy)phenyl)amino)-4-pyrimidinyl)carbamate;

EXAMPLE 745

2,4,6-trimethylphenyl(6-fluoro-4H-1,3-benzodioxin-8-yl)methyl(2-((3-fluoro-4-((3-(1-piperidinyl)propyl)oxy)phenyl)amino)-4-pyrimidinyl)carbamate;

EXAMPLE 746

2,4,6-trimethylphenyl 2-((4-(((2-(diethylamino)ethyl)(methyl)amino)carbonyl)phenyl)amino)-4-pyrimidinyl((6-fluoro-4H-1,3-benzodioxin-8-yl)methyl)carbamate;

EXAMPLE 747

2,4,6-trimethylphenyl(6-fluoro-4H-1,3-benzodioxin-8-yl)methyl(2-((3-fluoro-4-((2-(4-(1-methylethyl)-1-piperazinyl)ethyl)oxy)phenyl)amino)-4-pyrimidinyl)carbamate;

EXAMPLE 748

2,4,6-trimethylphenyl 2-((3-fluoro-4-((3-(4-methyl-1-piperazinyl)propyl)oxy)phenyl)amino)-4-pyrimidinyl((3-(1H-pyrazol-1-ylmethyl)phenyl)methyl)carbamate;

EXAMPLE 749

2,4,6-trimethylphenyl 2-((3-fluoro-4-((3-(1-piperidinyl)propyl)oxy)phenyl)amino)-4-pyrimidinyl((3-(1H-pyrazol-1-ylmethyl)phenyl)methyl)carbamate;

EXAMPLE 750

2,4,6-trimethylphenyl 2-((3-((3-(1-piperidinyl)propyl)oxy)phenyl)amino)-4-pyrimidinyl((3-(1H-pyrazol-1-ylmethyl)phenyl)methyl)carbamate;

EXAMPLE 751

2,4,6-trimethylphenyl 2-((4-(((2-(diethylamino)ethyl)(methyl)amino)carbonyl)phenyl)amino)-4-pyrimidinyl((3-(1H-pyrazol-1-ylmethyl)phenyl)methyl)carbamate;

EXAMPLE 752

2,4,6-trimethylphenyl 2-((3-fluoro-4-((2-(4-(1-methylethyl)-1-piperazinyl)ethyl)oxy)phenyl)amino)-4-pyrimidinyl((3-(1H-pyrazol-1-ylmethyl)phenyl)methyl)carbamate;

EXAMPLE 753

2,4,6-trimethylphenyl 2-((3-fluoro-4-(((1-methyl-3-piperidinyl)methyl)oxy)phenyl)amino)-4-pyrimidinyl((3-(1H-pyrazol-1-ylmethyl)phenyl)methyl)carbamate;

EXAMPLE 754

2,4,6-trimethylphenyl 2-((4-(3,4-dimethyl-1-piperazinyl)-3-fluorophenyl)amino)-4-pyrimidinyl((3-(1H-pyrazol-1-ylmethyl)phenyl)methyl)carbamate;

EXAMPLE 755

2,4,6-trimethylphenyl 4-(3-(diethylamino)-2-methyl-3-oxopropyl)-2-(methyloxy)phenyl(2-((3-fluoro-4-((3-(4-methyl 1-piperazinyl)propyl)oxy)phenyl)amino)-4-pyrimidinyl)carbamate;

EXAMPLE 756

2,4,6-trimethylphenyl 4-(3-(diethylamino)-2-methyl-3-oxopropyl)-2-(methyloxy)phenyl(2-((3-fluoro-4-((3-(1-piperidinyl)propyl)oxy)phenyl)amino)-4-pyrimidinyl)carbamate;

EXAMPLE 757

2,4,6-trimethylphenyl 4-(3-(diethylamino)-2-methyl-3-oxopropyl)-2-(methyloxy)phenyl(2-((3-((3-(1-piperidinyl)propyl)oxy)phenyl)amino)-4-pyrimidinyl)carbamate;

EXAMPLE 758

2,4,6-trimethylphenyl 2-((4-(((2-(diethylamino)ethyl)(methyl)amino)carbonyl)phenyl)amino)-4-pyrimidinyl(4-(3-(diethylamino)-2-methyl-3-oxopropyl)-2-(methyloxy)phenyl)carbamate;

EXAMPLE 759

2,4,6-trimethylphenyl 4-(3-(diethylamino)-2-methyl-3-oxopropyl)-2-(methyloxy)phenyl(2-((3-fluoro-4-((2-(4-(1-methylethyl)-1-piperazinyl)ethyl)oxy)phenyl)amino)-4-pyrimidinyl)carbamate;

EXAMPLE 760

2,4,6-trimethylphenyl 4-(3-(diethylamino)-2-methyl-3-oxopropyl)-2-(methyloxy)phenyl(2-((3-fluoro-4-(((1-methyl-3-piperidinyl)methyl)oxy)phenyl)amino)-4-pyrimidinyl)carbamate;

EXAMPLE 761

2,4,6-trimethylphenyl 4-(3-(diethylamino)-2-methyl-3-oxopropyl)-2-(methyloxy)phenyl(2-((4-(3,4-dimethyl-1-piperazinyl)-3-fluorophenyl)amino)-4-pyrimidinyl)carbamate;

EXAMPLE 762

2,6-dimethylphenyl 2-((3-fluoro-4-((3-(4-methyl-1-piperazinyl)propyl)oxy)phenyl)amino)-4-pyrimidinyl(2-(methyloxy)-4-(3-((1-methylpropyl)amino)-3-oxopropyl)phenyl)carbamate;

EXAMPLE 763

2,6-dimethylphenyl 2-((3-fluoro-4-((3-(1-piperidinyl)propyl)oxy)phenyl)amino)-4-pyrimidinyl(2-(methyloxy)-4-(3-(1-methylpropyl)amino)-3-oxopropyl)phenyl)carbamate;

EXAMPLE 764

2,6-dimethylphenyl 2-(methyloxy)-4-(3-((1-methylpropyl)amino)-3-oxopropyl)phenyl(2-((3-((3-(1-piperidinyl)propyl)oxy)phenyl)amino)-4-pyrimidinyl)carbamate;

EXAMPLE 765

2,6-dimethylphenyl 2-((4-(((2-(diethylamino)ethyl)(methyl)amino)carbonyl)phenyl)amino)-4-pyrimidinyl(2-(methyloxy)-4-(3-((1-methylpropyl)amino)-3-oxopropyl)phenyl)carbamate;

EXAMPLE 766

2,6-dimethylphenyl 2-((3-fluoro-4-((2-(4-(1-methylethyl)-1-piperazinyl)ethyl)oxy)phenyl)amino)-4-pyrimidinyl(2-(methyloxy)-4-(3-((1-methylpropyl)amino)-3-oxopropyl)phenyl)carbamate;

EXAMPLE 767

2,6-dimethylphenyl 2-((3-fluoro-4-(((1-methyl-3-piperidinyl)methyl)oxy)phenyl)amino)-4-pyrimidinyl(2-(methyloxy)-4-(3-((1-methylpropyl)amino)-3-oxopropyl)phenyl)carbamate;

EXAMPLE 768

2,6-dimethylphenyl 2-((3,4-bis(methyloxy)-5-((3-(4-methyl-1-piperazinyl)propyl)oxy)phenyl)amino)-4-pyrimidinyl(2-(methyloxy)-4-(1H-pyrazol-1-yl)phenyl)carbamate;

EXAMPLE 769

2,6-dimethylphenyl 2-((3-fluoro-4-((3-(4-methyl-1-piperazinyl)propyl)oxy)phenyl)amino)-4-pyrimidinyl(2-(methyloxy)-4-(1H-pyrazol-1-yl)phenyl)carbamate;

EXAMPLE 770

2,6-dimethylphenyl 2-((3-fluoro-4-((3-(1-piperidinyl)propyl)oxy)phenyl)amino)-4-pyrimidinyl(2-(methyloxy)-4-(1H-pyrazol-1-yl)phenyl)carbamate;

EXAMPLE 771

2,6-dimethylphenyl 2-(methyloxy)-4-(1H-pyrazol-1-yl)phenyl(2-((3-((3-(1-piperidinyl)propyl)oxy)phenyl)amino)-4-pyrimidinyl)carbamate;

EXAMPLE 772

2,6-dimethylphenyl 2-((4-(((2-(diethylamino)ethyl)(methyl)amino)carbonyl)phenyl)amino)-4-pyrimidinyl(2-(methyloxy)-4-(1H-pyrazol-1-yl)phenyl)carbamate;

EXAMPLE 773

2,6-dimethylphenyl 2-((3-fluoro-4-(((1-methyl-3-piperidinyl)methyl)oxy)phenyl)amino)-4-pyrimidinyl(2-(methyloxy)-4-(1H-pyrazol-1-yl)phenyl)carbamate;

EXAMPLE 774

2,6-dimethylphenyl 2-((4-(3,4-dimethyl-1-piperazinyl)-3-fluorophenyl)amino)-4-pyrimidinyl(2-(methyloxy)-4-(1H-pyrazol-1-yl)phenyl)carbamate;

EXAMPLE 775

4-fluoro-2,6-dimethylphenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

EXAMPLE 776

4-fluoro-2,6-dimethylphenyl(2,5-bis(methyloxy)phenyl)methyl(2-((3-fluoro-4-((3-(4-methyl-1-piperazinyl)propyl)oxy)phenyl)amino)-4-pyrimidinyl)carbamate;

EXAMPLE 777

4-fluoro-2,6-dimethylphenyl(2,5-bis(methyloxy)phenyl)methyl(2-((3-fluoro-4-((3-(1-piperidinyl)propyl)oxy)phenyl)amino)-4-pyrimidinyl)carbamate;

EXAMPLE 778

4-fluoro-2,6-dimethylphenyl(2,5-bis(methyloxy)phenyl)methyl(2-((3-((3-(1-piperidinyl)propyl)oxy)phenyl)amino)-4-pyrimidinyl)carbamate;

EXAMPLE 779

4-fluoro-2,6-dimethylphenyl(2,5-bis(methyloxy)phenyl)methyl(2-((4-(((2-(diethylamino)ethyl)(methyl)amino)carbonyl)phenyl)amino)-4-pyrimidinyl)carbamate;

EXAMPLE 780

4-fluoro-2,6-dimethylphenyl(2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

EXAMPLE 781

4-fluoro-2,6-dimethylphenyl(2,5-bis(methyloxy)phenyl)methyl(2-((3-fluoro-4-(((1-methyl-3-piperidinyl)methyl)oxy)phenyl)amino)-4-pyrimidinyl)carbamate;

EXAMPLE 782

4-fluoro-2,6-dimethylphenyl(2,5-bis(methyloxy)phenyl)methyl(2-((4-(3,4-dimethyl-1-piperazinyl)-3-fluorophenyl)amino)-4-pyrimidinyl)carbamate;

EXAMPLE 783

2,6-dimethylphenyl 2-((3,5-bis(methyloxy)-4-((3-(4-methyl-1-piperazinyl)propyl)oxy)phenyl)amino)-4-pyrimidinyl(4-((E)-2-(3-methyl-1,2,4-oxadiazol-5-yl)ethenyl)-2-(methyloxy)phenyl)carbamate;

EXAMPLE 784

2,6-dimethylphenyl 2-((3-fluoro-4-((3-(4-methyl-1-piperazinyl)propyl)oxy)phenyl)amino)-4-pyrimidinyl(4-((E)-2-(3-methyl-1,2,4-oxadiazol-5-yl)ethenyl)-2-(methyloxy)phenyl)carbamate;

EXAMPLE 785

2,6-dimethylphenyl 2-((3-fluoro-4-((3-(1-piperidinyl)propyl)oxy)phenyl)amino)-4-pyrimidinyl(4-((E)-2-(3-methyl-1,2,4-oxadiazol-5-yl)ethenyl)-2-(methyloxy)phenyl)carbamate;

EXAMPLE 786

2,6-dimethylphenyl 2-((3-fluoro-4-((2-(4-(1-methylethyl)-1-piperazinyl)ethyl)oxy)phenyl)amino)-4-pyrimidinyl(4-((E)-2-(3-methyl-1,2,4-oxadiazol-5-yl)ethenyl)-2-(methyloxy)phenyl)carbamate;

EXAMPLE 787

2,4,6-trimethylphenyl 2-((4-(((2-(diethylamino)ethyl)(methyl)amino)carbonyl)phenyl)amino)-4-pyrimidinyl(2,3-dihydro-1H-inden-1-yl)carbamate;

EXAMPLE 788

2,4,6-trimethylphenyl 2,3-dihydro-1H-inden-1-yl(2-((3-fluoro-4-((3-(4-methyl-1-piperazinyl)propyl)oxy)phenyl)amino)-4-pyrimidinyl)carbamate;

EXAMPLE 789

2,4,6-trimethylphenyl 2,3-dihydro-1H-inden-1-yl(2-((3-fluoro-4-((3-(1-piperidinyl)propyl)oxy)phenyl)amino)-4-pyrimidinyl)carbamate;

EXAMPLE 790

2,4,6-trimethylphenyl 2,3-dihydro-1H-inden-1-yl(2-((4-(3,4-dimethyl-1-piperazinyl)-3-fluorophenyl)amino)-4-pyrimidinyl)carbamate;

EXAMPLE 791

2,4,6-trimethylphenyl 2,3-dihydro-1H-inden-1-yl(2-((3-fluoro-4-(((1-methyl-3-piperidinyl)methyl)oxy)phenyl)amino)-4-pyrimidinyl)carbamate;

EXAMPLE 792

2,4,6-trimethylphenyl 2,3-dihydro-1H-inden-1-yl(2-((3-fluoro-4-((2-(4-(1-methylethyl)-1-piperazinyl)ethyl)oxy)phenyl)amino)-4-pyrimidinyl)carbamate;

EXAMPLE 793

2,4,6-trimethylphenyl 2,3-dihydro-1H-inden-1-yl(2-((3-((3-(1-piperidinyl)propyl)oxy)phenyl)amino)-4-pyrimidinyl)carbamate;

EXAMPLE 794

2,4,6-trimethylphenyl 2-((4-(((2-(diethylamino)ethyl)(methyl)amino)carbonyl)phenyl)amino)-4-pyrimidinyl((4-(1H-1,2,4-triazol-1-ylmethyl)phenyl)methyl)carbamate;

EXAMPLE 795

2,4,6-trimethylphenyl 2-((3-fluoro-4-((3-(1-piperidinyl)propyl)oxy)phenyl)amino)-4-pyrimidinyl((4-(1H-1,2,4-triazol-1-ylmethyl)phenyl)methyl)carbamate;

EXAMPLE 796

2,4,6-trimethylphenyl 2-((3,4-bis(methyloxy)-5-((3-(4-methyl-1-piperazinyl)propyl)oxy)phenyl)amino)-4-pyrimidinyl((4-(1H-1,2,4-triazol-1-ylmethyl)phenyl)methyl)carbamate;

EXAMPLE 797

2,4,6-trimethylphenyl 2-((3-fluoro-4-(((1-methyl-3-piperidinyl)methyl)oxy)phenyl)amino)-4-pyrimidinyl((4-(1H-1,2,4-triazol-1-ylmethyl)phenyl)methyl)carbamate;

EXAMPLE 798

2,4,6-trimethylphenyl 2-((3-fluoro-4-((2-(4-(1-methylethyl)-1-piperazinyl)ethyl)oxy)phenyl)amino)-4-pyrimidinyl((4-(1H-1,2,4-triazol-1-ylmethyl)phenyl)methyl)carbamate;

EXAMPLE 799

2,4,6-trimethylphenyl 2-((4-(((2-(diethylamino)ethyl)(methyl)amino)carbonyl)phenyl)amino)-4-pyrimidinyl(2,3-dihydro-1,4-benzodioxin-6-ylmethyl)carbamate;

EXAMPLE 800

2,4,6-trimethylphenyl 2,3-dihydro-1,4-benzodioxin-6-ylmethyl(2-((3-fluoro-4-((3-(4-methyl-1-piperazinyl)propyl)oxy)phenyl)amino)-4-pyrimidinyl)carbamate;

EXAMPLE 801

2,4,6-trimethylphenyl 2,3-dihydro-1,4-benzodioxin-6-ylmethyl(2-((3-fluoro-4-((3-(1-piperidinyl)propyl)oxy)phenyl)amino)-4-pyrimidinyl)carbamate;

EXAMPLE 802

2,4,6-trimethylphenyl 2-((3,4-bis(methyloxy)-5-((3-(4-methyl-1-piperazinyl)propyl)oxy)phenyl)amino)-4-pyrimidinyl(2,3-dihydro-1,4-benzodioxin-6-ylmethyl)carbamate;

EXAMPLE 803

2,4,6-trimethylphenyl 2,3-dihydro-1,4-benzodioxin-6-ylmethyl(2-((3-fluoro-4-(((1-methyl-3-piperidinyl)methyl)oxy)phenyl)amino)-4-pyrimidinyl)carbamate;

EXAMPLE 804

2,4,6-trimethylphenyl 2,3-dihydro-1,4-benzodioxin-6-ylmethyl(2-((3-fluoro-4-((2-(4-(1-methylethyl)-1-piperazinyl)ethyl)oxy)phenyl)amino)-4-pyrimidinyl)carbamate;

EXAMPLE 805

2,4,6-trimethylphenyl 2-((3,5-bis(methyloxy)-4-((2-(4-methyl-1-piperazinyl)ethyl)oxy)phenyl)amino)-4-pyrimidinyl((5-chloro-2-fluorophenyl)methyl)carbamate;

EXAMPLE 806

2,4,6-trimethylphenyl(5-chloro-2-fluorophenyl)methyl(2-((3-fluoro-4-(4-methyl-1-piperazinyl)phenyl)amino)-4-pyrimidinyl)carbamate;

EXAMPLE 807

2,4,6-trimethylphenyl(5-chloro-2-fluorophenyl)methyl(2-((3-fluoro-4-((2-(4-methyl-1-piperazinyl)ethyl)oxy)phenyl)amino)-4-pyrimidinyl)carbamate;

EXAMPLE 808

2,4,6-trimethylphenyl(5-chloro-2-fluorophenyl)methyl(2-((3-((difluoromethyl)oxy)-4-(4-methyl-1-piperazinyl)phenyl)amino)-4-pyrimidinyl)carbamate;

EXAMPLE 809

2,4,6-trimethylphenyl(5-chloro-2-fluorophenyl)methyl(2-((3-chloro-4-(4-(1-methylethyl)-1-piperazinyl)phenyl)amino)-4-pyrimidinyl)carbamate;

EXAMPLE 810

2,4,6-trimethylphenyl(5-chloro-2-fluorophenyl)methyl(2-((3-(4-methyl-1-piperazinyl)phenyl)amino)-4-pyrimidinyl)carbamate;

EXAMPLE 811

2,4,6-trimethylphenyl(5-chloro-2-fluorophenyl)methyl(2-((3-(((2-(diethylamino)ethyl)(methyl)amino)carbonyl)phenyl)amino)-4-pyrimidinyl)carbamate;

EXAMPLE 812

2,4,6-trimethylphenyl(5-chloro-2-fluorophenyl)methyl(2-((4-((3-(4-(1-methylethyl)-1-piperazinyl)propyl)oxy)-3-(methyloxy)phenyl)amino)-4-pyrimidinyl)carbamate;

EXAMPLE 813

2,4,6-trimethylphenyl(5-chloro-2-fluorophenyl)methyl(2-((4-(3,4-dimethyl-1-piperazinyl)phenyl)amino)-4-pyrimidinyl)carbamate;

EXAMPLE 814

2,4,6-trimethylphenyl(5-chloro-2-fluorophenyl)methyl(2-((3-fluoro-4-((3R,5S)-3,4,5-trimethyl-1-piperazinyl)phenyl)amino)-4-pyrimidinyl)carbamate;

EXAMPLE 815

2,4,6-trimethylphenyl(5-chloro-2-fluorophenyl)methyl(2-((4-(2-(4-methyl-1-piperazinyl)ethyl)phenyl)amino)-4-pyrimidinyl)carbamate;

EXAMPLE 816

2,4,6-trimethylphenyl 2-((3-fluoro-4-((3-(4-methyl-1-piperazinyl)propyl)oxy)phenyl)amino)-4-pyrimidinyl((3-(5-methyl-1,2,4-oxadiazol-3-yl)phenyl)methyl)carbamate;

EXAMPLE 817

2,4,6-trimethylphenyl 2-((4-(3,4-dimethyl-1-piperazinyl)-3-fluorophenyl)amino)-4-pyrimidinyl((3-(5-methyl-1,2,4-oxadiazol-3-yl)phenyl)methyl)carbamate;

EXAMPLE 818

2,4,6-trimethylphenyl 2-((3,4-bis(methyloxy)-5-((3-(4-methyl-1-piperazinyl)propyl)oxy)phenyl)amino)-4-pyrimidinyl((4-(5-methyl-1,2,4-oxadiazol-3-yl)phenyl)methyl)carbamate;

EXAMPLE 819

2,4,6-trimethylphenyl 2-((3-fluoro-4-((3-(4-methyl-1-piperazinyl)propyl)oxy)phenyl)amino)-4-pyrimidinyl((4-(5-methyl-1,2,4-oxadiazol-3-yl)phenyl)methyl)carbamate;

EXAMPLE 820

2,4,6-trimethylphenyl 2-((3-fluoro-4-((3-(1-piperidinyl)propyl)oxy)phenyl)amino)-4-pyrimidinyl((4-(5-methyl-1,2,4-oxadiazol-3-yl)phenyl)methyl)carbamate;

EXAMPLE 821

2,4,6-trimethylphenyl(4-(5-methyl-1,2,4-oxadiazol-3-yl)phenyl)methyl(2-((3-((3-(1-piperidinyl)propyl)oxy)phenyl)amino)-4-pyrimidinyl)carbamate;

EXAMPLE 822

2,4,6-trimethylphenyl 2-((4-(((2-(diethylamino)ethyl)(methyl)amino)carbonyl)phenyl)amino)-4-pyrimidinyl((4-(5-methyl-1,2,4-oxadiazol-3-yl)phenyl)methyl)carbamate;

EXAMPLE 823

2,4,6-trimethylphenyl 2-((3-fluoro-4-((2-(4-(1-methylethyl)-1-piperazinyl)ethyl)oxy)phenyl)amino)-4-pyrimidinyl((4-(5-methyl-1,2,4-oxadiazol-3-yl)phenyl)methyl)carbamate;

EXAMPLE 824

2,4,6-trimethylphenyl 2-((3-fluoro-4-(((1-methyl-3-piperidinyl)methyl)oxy)phenyl)amino)-4-pyrimidinyl((4-(5-methyl-1,2,4-oxadiazol-3-yl)phenyl)methyl)carbamate;

EXAMPLE 825

2,4,6-trimethylphenyl 2-((4-(3,4-dimethyl-1-piperazinyl)-3-fluorophenyl)amino)-4-pyrimidinyl((4-(5-methyl-1,2,4-oxadiazol-3-yl)phenyl)methyl)carbamate;

EXAMPLE 826

2,4,6-trimethylphenyl 2-((3,4-bis(methyloxy)-5-((3-(4-methyl-1-piperazinyl)propyl)oxy)phenyl)amino)-4-pyrimidinyl((6-fluoro-4H-1,3-benzodioxin-8-yl)methyl)carbamate; and

EXAMPLE 827 mesityl 4-(3-(diethylamino)-2-methyl-3-oxopropyl)-2-methoxyphenyl(2-(3,5-dimethoxy-4-(3-(4-methylpiperazin-1-yl)propoxy)phenylamino)pyrimidin-4-yl)carbamate.

Biological Assays

The following assays can be employed to determine the degree of activity of a compound as a protein kinase inhibitor. Compounds described herein have been tested in one or more of these assays, and have shown activity. Representative compounds of the invention were tested and found to exhibit $IC_{50}$ values of at least <10 μM in any one of the described assays, thereby demonstrating and confirming the utility of the compounds of the invention as protein kinase inhibitors and in the prophylaxis and treatment of immune diseases, hyperproliferative disorders, etc.

LCK-Homogeneous Time Resolved Fluorescent (HTRF) Kinase Assay:

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 μL of compound in 100% DMSO, 15 μL of ATP and biotinylated Gastrin, and 15 μL of LCK KD GST (225-509) for a final volume of 40 μL. The final concentration of gastrin is 1.2 μM. The final concentration of ATP is 0.5 μM (Km app=0.6 μM+/−0.1) and the final concentration of LCK is 250 pM. Buffer conditions are as follows: 50 mM HEPES pH 7.5, 50 mM NaCl, 20 mM $MgCl$, 5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Assays for other kinases are done in a similar way as described above, varying the concentrations of enzyme, peptide substrate, and ATP added to the reaction, depending on the specific activity of the kinase and measured Km's for the substrates.

A vast majority of the exemplary compounds 1-828 exhibited an average $IC_{50}$ value of 10 uM or less in a human HTRF assay, for the inhibition of the Lck kinase enzyme. Each of exemplary compounds 188-216, 218-231 and 233-828 exhibited an average $IC_{50}$ value of 1 uM or less in the human HTFR assay for the inhibition of the Lck kinase enzyme.

Human Mixed Lymphocyte Reaction (huMLR):

The purpose of this assay is to test the potency of T cell activation inhibitors in an in vitro model of allogeneic T cell stimulation. Human peripheral blood lymphocytes (hPBL; $2\times10^5$/well) are incubated with mitomycin C-treated B lymphoblastoid cells (JY cell line; $1\times10^5$/well) as allogeneic stimulators in the presence or absence of dilutions of potential inhibitor compound in 96-well round-bottom tissue culture plates. These cultures are incubated at 37° C. in 5% $CO_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter.

Jurkat Proliferation/Survival Assay:

The purpose of this assay is to test the general anti-proliferative/cytotoxic effect of compounds on the Jurkat human T cell line. Jurkat cells ($1\times10^5$/well) are plated in 96-well flat-bottom tissue culture plates with or without compound dilutions and cultured for 72 h at 37° C. in 5% $CO_2$. Viable cell number is determined during the last 4 h of culture by adding 10 μL/well WST-1 dye. WST-1 dye conversion relies on active mitochondrial electron transport for reduction of the tetrazolium dye. The dye conversion is read by OD at 450-600 nm.

Anti-CD3/CD28-Induced T Cell IL-2 Secretion and Proliferation Assay:

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates ($1\times10^5$ T cells/well). Cells are cultured for ~20 h at 37° C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and $^3$H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

Methods of Use

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

For the treatment of Lck-mediated diseases and other diseases listed above, the compounds of the present invention may be administered orally, parenterally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) believed to be in need of preventative treatment, such as, for example, pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients and the like as described herein. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The dosage regimen for treating Lck-mediated diseases and other diseases listed above with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0. 1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula I

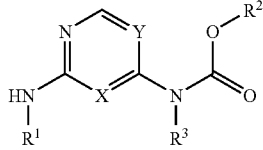

I or a pharmaceutically-acceptable salt thereof, wherein
one of X and Y is N and the other of X an Y is CH;
$R^1$ is selected from —$R^{11}$, —$R^{11}$—$R^{12}$, —$R^{11}$—$R^{14}$, —$R^{12}$—$R^{14}$, —$R^{11}$—$R^{12}$—$R^{14}$, —$R^{11}$—$R^{13}$—$R^{14}$, —$R^{12}$—$R^{13}$—$R^{14}$, —$R^{11}$—$R^{13}$—$R^{12}$—$R^{14}$ and —$R^{11}$—$R^{12}$—$R^{13}$—$R^{14}$, any of which is substituted by 0, 1, 2, 3 or 4 substituents independently selected from $R^c$;
$R^3$ is selected from —$R^{31}$, —$R^{31}$—$R^{32}$, —$R^{31}$—$R^{34}$, —$R^{32}$—$R^{34}$, —$R^{31}$—$R^{32}$—$R^{34}$, —$R^{31}$—$R^{33}$—$R^{34}$, —$R^{32}$—$R^{33}$—$R^{34}$, —$R^{31}$—$R^{33}$—$R^{32}$—$R^{34}$ and —$R^{31}$—$R^{32}$—$R^{33}$—$R^{34}$, any of which is substituted by 0, 1, 2, 3 or 4 substituents independently selected from $R^c$;
$R^{11}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{12}$ is, independently at each instance, $C_{1-8}$alkyl;
$R^{13}$ is, independently at each instance, —C(═O)—, —C(═O)O—, —C(═O)NR$^a$—, —C(═NR$^a$)NR$^a$—, —O—, —OC(═O)—, —OC(═O)NR$^a$—, —OC(═O)N(R$^a$)S(═O)$_2$—, —OC$_{2-6}$alkylNR$^a$—, —OC$_{2-6}$alkylO—, —S—, —S(═O)—, —S(═O)$_2$—, —S(═O)$_2$NR$^a$—, —S(═O)$_2$N(R$^a$)C(═O)—, —S(═O)$_2$N(R$^a$)C(═O)O—, —S(═O)$_2$N(R$^a$)C(═O)NR$^a$—, —N(R$^a$)—, —N(R$^a$)C(═O)—, —N(R$^a$)C(═O)O—, —N(R$^a$)C(═O)N(R$^a$)—, —N(R$^a$)C(═NR$^a$)N(R$^a$)—, —N(R$^a$)S(═O)$_2$—, —N(R$^a$)S(═O)$_2$ N(R$^a$)—, —NR$^a$C$_{2-6}$alkylN(R$^a$)— or —NR$^a$C$_{2-6}$ alkylO—;
$R^{14}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;
$R^{21}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;
$R^{22}$ is, independently at each instance, $C_{1-8}$alkyl;
$R^{23}$ is, independently at each instance, —C(═O)—, —C(═O)O—, —C(═O)NR$^a$—, —C(═NR$^a$)NR$^a$—, —O—, —OC(═O)—, —OC(═O)NR$^a$—, —OC(═O)N(R$^a$)S(═O)$_2$—, —OC$_{2-6}$alkylNR$^a$—, —OC$_{2-6}$alkylO—, —S—, —S(═O)—, —S(═O)$_2$—, —S(═O)$_2$NR$^a$—, —S(═O)$_2$N(R$^a$)C(═O)—, —S(═O)$_2$N(R$^a$)C(═O)O—, —S(═O)$_2$N(R$^a$)C(═O)NR$^a$—, —N(R$^a$)—, —N(R$^a$)C(═O)—, —N(R$^a$)C(═O)O—, —N(R$^a$)C(═O)N(R$^a$)—, —N(R$^a$)C(═NR$^a$)N(R$^a$)—, —N(R$^a$)S(═O)$_2$—, —N(R$^a$)S(═O)$_2$ N(R$^a$)—, —NR$^a$C$_{2-6}$alkylN(R$^a$)— or —NR$^a$C$_{2-6}$ alkylO—;
$R^{24}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;
$R^{32}$ is, independently at each instance, $C_{1-8}$alkyl;
$R^{33}$ is, independently at each instance, —C(═O)—, —C(═O)O—, —C(═O)NR$^a$—, —C(═NR$^a$)NR$^a$—, —O—, —OC(═O)—, —OC(═O)NR$^a$—, —OC(═O)N(R$^a$)S(═O)$_2$—, —OC$_{2-6}$alkylNR$^a$—, —OC$_{2-6}$alkylO—, —S—, —S(═O)—, —S(═O)$_2$—, —S(═O)$_2$NR$^a$—, —S(═O)$_2$N(R$^a$)C(═O)—, —S(═O)$_2$N(R$^a$)C(═O)O—, —S(═O)$_2$N(R$^a$)C(═O)NR$^a$—, —N(R$^a$)—, —N(R$^a$)C(═O)—, —N(R$^a$)C(═O)O—, —N(R$^a$)C(═O)N(R$^a$)—, —N(R$^a$)C(═NR$^a$)N(R$^a$)—, —N(R$^a$)S(═O)$_2$—, —N(R$^a$)S(═O)$_2$ N(R$^a$)—, —NR$^a$C$_{2-6}$alkylN(R$^a$)— or —NR$^a$C$_{2-6}$ alkylO—;
$R^{34}$ is, independently at each instance, a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^a$ is, independently at each instance, H or $R^b$;
$R^b$ is, independently at each instance, $C_{1-8}$alkyl, phenyl, or benzyl; and
$R^c$ is, independently at each instance, $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$,OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$,—S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$.

2. A compound according to claim 1 wherein X is N and Y is CH.

3. A compound according to claim 1 wherein $R^{11}$ is phenyl or pyridine, either of which is substituted by 0, 1, 2, 3 or 4 substituents independently selected from $R^c$.

4. A compound according to claim 1 wherein $R^{21}$ is phenyl, which is substituted by 0, 1, 2, 3 or 4 substituents independently selected from $R^c$.

5. A compound according to claim 1 wherein
$R^{11}$ is phenyl or pyridine;
$R^{13}$ is, independently at each instance, —C(=O)N$R^a$, —O—, —OC$_{2-6}$alkylN$R^a$, —OC$_{2-6}$alkylO—, —S—, —S(=O)$_2$N$R^a$—, —N($R^a$)—, —N($R^a$)C(=O)—, —N($R^a$)S(=O)$_2$—, —N($R^a$)S(=O)$_2$N($R^a$)—, —N$R^aC_{2-6}$alkylN($R^a$)— or —N$R^aC_{2-6}$alkylO—; and
$R^{14}$ is, independently at each instance, a saturated or unsaturated 5-, 6- or 7-membered monocyclic ring containing 0, 1, 2, 3 or 4 atoms selected from N, O and S.

6. A compound according to claim 1 wherein
$R^1$ is selected from 3,4-bismethoxy-5-(3-(4-methyl-1-piperizinyl) propyl)oxy phenyl, 3-fluoro-4-(1-methyl-3-piperidinyl)methyloxy phenyl, 3-fluoro-4-(4-(1-methylethyl)-1-piperizinyl)ethyloxy phenyl, 3-chloro-4-(4-(1-methylethyl)-1-piperizinyl)phenyl, 3-methoxy-4-(4-(1-methylethyl)-1-piperizinyl)propyloxyphenyl, 4-(2-diethylamino) ethyl)-(N-methyl)aminocarbonyl phenyl, 4-(2-diethylamino)ethyl)-aminocarbonyl phenyl, 3-(2-diethylamino)ethyl)-aminocarbonyl phenyl, 4-(2-dimethylamino)ethyl)- aminocarbonyl phenyl, 4-(2-diethylamino)propyl)-aminocarbonyl phenyl, 3-(2-diethylamino) propyl)-aminocarbonyl phenyl, 3-(2-dimethylamino)hexyl)-aminocarbonyl phenyl, 4-(2-dimethylamino)hexyl)-aminocarbonyl phenyl, 3-(2-diethylamino)butyl)-aminocarbonyl phenyl, 3-(2-diethylamino)butyl)-aminocarbonyl phenyl, 3-(1-piperidinyl)propyloxy phenyl, 3- fluoro-4-(1-piperidinyl) propyloxy phenyl, 3-fluoro-4-(1-methyl-3-piperidinyl)propyloxy phenyl, 3-(1-piperidinyl) propyloxy phenyl, 3-fluoro-4-(1-piperidinyl)propyloxy phenyl, 4-(4-amino-1- piperidinyl) phenyl, 3,5-difluoro-4-(2-(1-piperidinyl)ethyl)oxy phenyl, 3-fluoro-4-(4-methyl-1- piperizinyl)propyloxy phenyl, 4-(3,4-dimethyl-1-piperizinyl)-3-fluorophenyl, 4-(4-methyl-1-piperizinyl) ethylphenyl, 3-fluoro-4-(3,4,5-trimethyl-1-piperizinyl) phenyl, 4-(3,4-dimethyl-1- piperizinyl) phenyl, 3-(4-methyl-1-piperizinyl)phenyl, 4-(3-dimethylaminopropyl-1-piperizinyl) phenyl, 3-difluoromethoxy-4-(4-methyl-1-piperizinyl)phenyl, 3,5-bismethoxy-4-(4- methyl-1-piperizinyl)ethyloxy phenyl, 3-(4-methyl-1-piperizinyl)propyloxy pyridine, 3- methoxy -4-(2-pyrrolinidyl)methyloxy phenyl, 3-acetylaminophenyl and 2-aminomethyiphenyl, 3-aminophenyl.

7. A compound according to claim 1 wherein
$R^2$ is selected from 2-methylphenyl, 3-methylphenyl, 4-methylphenyl, 2-methoxyphenyl, 3-methoxyphenyl, 4-methoxyphenyl, 2-chlorophenyl, 2,5-dimethylphenyl, 2,6-dimethylphenyl, 2,4-dimethylphenyl, 3,5-dimethylphenyl, 2,5-dimethoxyphenyl, 2,4-dimethoxyphenyl, 2,6-dimethoxyphenyl, 3,5-dimethoxyphenyl, 2,6-difluorophenyl, 2,5-difluorophenyl, 2,4-difluorophenyl, 3,5-difluorophenyl, 4-fluoro-2,6-dimethylphenyl, 2,4,6-trimethyiphenyl, 2,4,6-trimethoxyphenyl, 2-(methoxy)methylphenyl, 3-(methoxy)methylphenyl, 4-(methoxy)methylphenyl, 2-(methoxy)methyl-5-methylphenyl, 2-methylsulfanylphenyl, 3-methylsulfanylphenyl, 4-methylsulfanylphenyl, 2,6-dimethylcyclohexyl, 2,5-dimethylcyclohexyl, 2,4-dimethylcyclohexyl, 3,5-dimethylcyclohexyl, 3,5-dimethoxycyclohexyl, 2-methyl-1-(1-methylethyl)propyl, 1-isopropyl-2-methylbutyl, 1-phenylethyl, 2-methanoylphenyl, 2-methyl-6-(2-propenyl)phenyl, 5-methyl-2-methyloxyphenyl and 4-chloro-2-methoxyphenyl.

8. A compound according to claim 1 wherein
$R^3$ is selected from 2,4-dimethoxyphenyl, 2,4-dimethylphenyl, 2-(2-methoxyphenyl) ethyl, 3-phenylpropyl, 2-(4-morpholinyl)ethyl, (2-(trifluoromethyloxy)phenyl) methyl, 2-ethyloxyphenyl, 4-fluoro-2-(1-methylethyloxy)phenyl, 2,5-dichlorophenyl methyl, 3,5-dichlorophenyl methyl, 3,5-difluorophenyl methyl, 3,4-difluorophenyl methyl, 2-chloro-3,6-difluorophenyl methyl, 3,5-(bis)trifluoromethylphenyl methyl, 2,5-dimethylphenyl methyl, 3,5-dimethylphenyl methyl, 2,5-dimethoxyphenyl methyl, 2,3-dimethoxyphenyl methyl, 1,1'-biphenyl, 2-ethyl-4-methoxyphenyl, 4-methyl-2-methoxyphenyl, 4-butyl-2-methoxyphenyl, 2-(1, 3-oxazole) phenyl, (5-chloro-2-methylphenyl)methyl, 2-chloro-5-trifluoromethyl phenyl methyl, 5-chloro-2-fluorophenyl methyl, 2-chlorophenyl, 3-chlorophenyl methyl, 3-methoxyphenyl methyl, cyclohexyl, 2-methoxy-4-(2-(1-methylpropylamino) 2-oxoethyl) phenyl, 2-methoxy-4-(2-(diethylamino)2-oxoethyl)phenyl, 3-(2- (1-methylpropylamino) 3-oxopropyl)phenyl, 3-(3-(2-methyloxyethylamino)-3-oxopropyl)phenyl, 3-(2-(diethylamino)3-oxopropyl)phenyl, 2-methoxy-4-(2-(diethylamino)--2-methyl-3-oxopropyl) phenyl, 2-methoxy-4-(1-methylpropylamino)carbonyl phenyl, 4-methoxyphenyl ethyl, 3-(2-(3-methyl-1,2,4-oxodiazole-5-yl)ethyl)phenyl, 3-(5-methyl-1,2,4-oxodiazole-3-yl)phenyl methyl, 4-(5-methyl-1,2,4-oxodiazole-3-yl) phenyl methyl, 2-phenyl-1,3-thiazole-4-yl methyl, 2-ethyl-[1,2-a]imidazole, benzodioxo-5-yl-methyl, 6-fluoro-4H-1,3-benzodioxin-8-yl methyl, (3-(1H-pyrazole-1-yl)methyl)phenyl methyl, 2-methoxy-4-(1H-pyrazole-1-yl) phenyl, 2,3-dihydro-1H-inden-1-yl, 4-(1H-1,2,4-triazole-1-yl)methyl)phenyl methyl and 2,3-dihydro-1,4-benzodioxin-6-yl methyl.

9. A compound according to claim 1, of Formula I

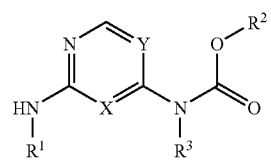

or a pharmaceutically-acceptable salt thereof, wherein
X is N and Y is CH;

R₁ is selected from 3,4-bismethoxy-5-(3-(4-methyl-1-piperizinyl) propyl)oxy phenyl, 3-fluoro-4-(1-methyl-3-piperidinyl)methyloxy phenyl, 3-fluoro-4-(4-(1-methylethyl)-1-piperizinyl) ethyloxy phenyl, 3-chloro-4-(4-(1-methylethyl)-1-piperizinyl) phenyl, 3-methoxy-4-(4-(1-methylethyl)-1-piperizinyl)propyloxyphenyl, 4-(2-diethylamino) ethyl)-(N-methyl)aminocarbonyl phenyl, 4-(2-diethylamino)ethyl)-aminocarbonyl phenyl, 3-(2-diethylamino)ethyl)-aminocarbonyl phenyl, 4-(2-dimethylamino)ethyl)-aminocarbonyl phenyl, 4-(2-diethylamino)propyl)-aminocarbonyl phenyl, 3-(2-diethylamino) propyl)-aminocarbonyl phenyl, 3-(2-dimethylamino)hexyl)-aminocarbonyl phenyl, 4-(2-dimethylamino)hexyl)-aminocarbonyl phenyl, 3-(2-diethylamino)butyl)-aminocarbonyl phenyl, 3-(2-diethylamino)butyl)-aminocarbonyl phenyl, 3-(1-piperidinyl)propyloxy phenyl, 3-fluoro-4-(1-piperidinyl)propyloxy phenyl, 3-fluoro-4-(1-methyl-3-piperidinyl)propyloxy phenyl, 3-(1-piperidinyl)propyloxy phenyl, 3-fluoro-4-(1-piperidinyl)propyloxy phenyl, 4-(4-amino-1- piperidinyl) phenyl, 3,5-difluoro-4-(2-(1-piperidinyl)ethyl)oxy phenyl, 3-fluoro-4-(4-methyl-1-piperizinyl) propyloxy phenyl, 4-(3,4-dimethyl-1-piperizinyl)-3-fluorophenyl, 4-(4-methyl-1-piperizinyl) ethylphenyl, 3-fluoro-4-(3,4,5-trimethyl-1-piperizinyl) phenyl, 4-(3,4-dimethyl-1-piperizinyl) phenyl, 3-(4-methyl-1-piperizinyl)phenyl, 4-(3-dimethylaminopropyl-1-piperizinyl) phenyl, 3-difluoromethoxy-4-(4-methyl-1-piperizinyl)phenyl, 3,5-bismethoxy-4-(4-methyl-1-piperizinyl) ethyloxy phenyl, 3-(4-methyl-1-piperizinyl)propyloxy pyridine, 3-methoxy-4-(2-pyrrolinidyl) methyloxy phenyl, 3-acetylaminophenyl and 2-aminomethyiphenyl, 3-aminophenyl;

R² is selected from 2-methylphenyl, 3-methylphenyl, 4-methylphenyl, 2-methoxyphenyl, 3-methoxyphenyl, 4-methoxyphenyl, 2-chlorophenyl, 2,5-dimethylphenyl, 2,6-dimethylphenyl, 2,4-dimethylphenyl, 3,5-dimethylphenyl, 2,5-dimethoxyphenyl, 2,4-dimethoxyphenyl, 2,6-dimethoxyphenyl, 3,5-dimethoxyphenyl, 2,6-difluorophenyl, 2,5-difluorophenyl, 2,4-difluorophenyl, 3,5-difluorophenyl, 4-fluoro-2,6-dimethylphenyl, 2,4,6-trimethylphenyl, 2,4,6-trimethoxyphenyl, 2-(methoxy) methylphenyl, 3-(methoxy)methylphenyl, 4-(methoxy) methylphenyl, 2-(methoxy)methyl-5-methylphenyl, 2-methylsulfanylphenyl, 3-methylsulfanylphenyl, 4-methylsulfanylphenyl, 2,6-dimethylcyclohexyl, 2,5-dimethylcyclohexyl, 2,4-dimethylcyclohexyl, 3,5-dimethylcyclohexyl, 3,5-dimethoxycyclohexyl, 2-methyl-1-(1-methylethyl)propyl, 1-isopropyl-2-methylbutyl, 1-phenylethyl, 2-methanoylphenyl, 2-methyl-6-(2-propenyl)phenyl, 5-methyl-2-methyloxyphenyl and 4-chloro-2-methoxyphenyl; and R³ is selected from 2,4-dimethoxyphenyl, 2,4-dimethylphenyl, 2-(2-methoxyphenyl) ethyl, 3-phenylpropyl, 2-(4-morpholinyl)ethyl, (2-(trifluoromethyloxy)phenyl) methyl, 2-ethyloxyphenyl, 4-fluoro-2-(1-methylethyloxy)phenyl, 2,5-dichlorophenyl methyl, 3,5-dichlorophenyl methyl, 3,5-difluorophenyl methyl, 3,4-difluorophenyl methyl, 2-chloro-3,6-difluorophenyl methyl, 3,5-(bis)trifluoromethylphenyl methyl, 2,5-dimethylphenyl methyl, 3,5-dimethylphenyl methyl, 2,5-dimethoxyphenyl methyl, 2,3-dimethoxyphenyl methyl, 1,1'-biphenyl, 2-ethyl-4-methoxyphenyl, 4-methyl-2-methoxyphenyl, 4-butyl-2-methoxyphenyl, 2-(1, 3-oxazole) phenyl, (5-chloro-2-methylphenyl)methyl, 2-chloro-5-trifluoromethyl phenyl methyl, 5-chloro-2-fluorophenyl methyl, 2-chlorophenyl, 3-chlorophenyl methyl, 3- methoxyphenyl methyl, cyclohexyl, 2-methoxy-4-(2-(1-methylpropylamino) 2-oxoethyl) phenyl, 2-methoxy-4-(2-(diethylamino)2-oxoethyl)phenyl, 3-(2-(1-methylpropylamino) 3-oxopropyl)phenyl, 3-(3-(2-methyloxyethylamino)-3-oxopropyl)phenyl, 3-(2-(diethylamino)3-oxopropyl)phenyl, 2-methoxy-4-(2-(diethylamino)2-methyl-3-oxopropyl) phenyl, 2-methoxy-4-(1-methylpropylamino)carbonyl phenyl, 4-methoxyphenyl ethyl, 3-(2-(3-methyl-1,2,4-oxodiazole-5-yl)ethyl)phenyl, 3-(5-methyl-1,2,4-oxodiazole-3-yl)phenyl methyl, 4-(5-methyl-1,2,4-oxodiazole-3-yl) phenyl methyl, 2-phenyl-1,3-thiazole-4-yl methyl, 2-ethyl-[1,2-a]imidazole, benzodioxo-5-yl-methyl, 6-fluoro-4H-1,3-benzodioxin-8-yl methyl, (3-(1H-pyrazole-1-yl)methyl)phenyl methyl, 2-methoxy-4-(1H-pyrazole-1-yl) phenyl, 2,3-dihydro-1H-inden-1-yl, 4-(1H-1,2,4-triazole-1-yl)methyl)phenyl methyl and 2,3-dihydro-1,4-benzodioxin-6-yl methyl.

10. A method for making a compound according to claim 1, the method comprising the steps of:

reacting a compound having the structure

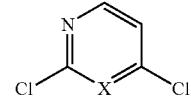

wherein X is N, with R³NH₂ to form a chloroaniline of

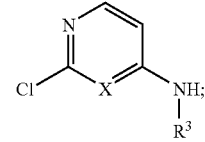

structure reacting the chloroaniline with R²O(C=O)Cl to form a carbamate of structure

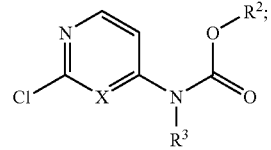

and reacting the carbamate with R¹NH₂ in the presence of an acid to form a compound of structure:

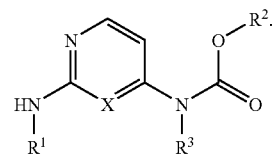

11. A pharmaceutical composition comprising a compound according to claim 1 and a pharmaceutically acceptable carrier.

12. A method of treatment of arthritis, rheumatoid arthritis, psoriatic arthritis, or osteoarthritis in a mammal comprising administering to the mammal a therapeutically-effective amount of a compound according to claim 1.

* * * * *